United States Patent
Hosmane et al.

(10) Patent No.: US 8,518,901 B2
(45) Date of Patent: Aug. 27, 2013

(54) FUSED DIIMIDAZODIAZEPINE COMPOUNDS AND METHODS OF USE AND MANUFACTURE THEREOF

(75) Inventors: Ramachandra S. Hosmane, Columbia, MD (US); Venu Raman, Ellicott City, MD (US); Raj Kumar, Haryana (IN)

(73) Assignee: The Johns Hopkins University, Baltimore, MD (US)

( * ) Notice: Subject to any disclaimer, the term of this patent is extended or adjusted under 35 U.S.C. 154(b) by 170 days.

(21) Appl. No.: 13/061,612

(22) PCT Filed: Sep. 23, 2009

(86) PCT No.: PCT/US2009/005273
§ 371 (c)(1),
(2), (4) Date: Jul. 25, 2011

(87) PCT Pub. No.: WO2010/039187
PCT Pub. Date: Apr. 8, 2010

(65) Prior Publication Data
US 2011/0275588 A1  Nov. 10, 2011

Related U.S. Application Data

(60) Provisional application No. 61/099,324, filed on Sep. 23, 2008.

(51) Int. Cl.
*A01N 43/04* (2006.01)
*A61K 31/70* (2006.01)
*C07H 19/00* (2006.01)
*C07H 19/22* (2006.01)
*C07D 491/00* (2006.01)

(52) U.S. Cl.
USPC ............... 514/43; 514/22; 536/27.1; 540/557

(58) Field of Classification Search
USPC ................ 514/22, 43; 536/27.1; 540/557
See application file for complete search history.

(56) References Cited

U.S. PATENT DOCUMENTS 5,387,585 A    2/1995   Borer et al.
5,698,155 A   12/1997   Grosswald et al.

OTHER PUBLICATIONS

Sun, Z.; Hosmane, R.S. Synth. Commun. 2001, 31, 549.
Yahya-Zadeh, A.; Booth, B. L. Synth. Commun. 2001, 31, 3225.
Dias, A.M.; Cabral, I.; Proenca, M.F.; Booth, B.L. J. Org. Chem. 2002, 67, 5546.
Langer, 1990, Science 249: 1527-1533.
Buchwald et al., 1980, Surgery 88:507.
Saudek et al., 1989 N. Engl. J. Med. 321:574.
Langer and Peppas, 1983, J. Macromol. Sci. Rev. Macromol. Chem. 23:61.
Levy et al., 1985, Science 228:190.
During et al., 1989, Ann. Neurol. 25:351.
Howard et al., 1989, J. Neurosurg. 71:105.
Kumar et al., 2008, *Organic Letters*, 10(20), 4681-4684.
International Search Report, issued in counterpart International Application No. PCT/US2009/005273, dated Apr. 23, 2010.
European Search Report issued in counterpart International Application No. PCT/US2009/005273, dated May 24, 2012.

*Primary Examiner* — Eric S Olson
*Assistant Examiner* — Zhengfu Wang
(74) *Attorney, Agent, or Firm* — Venable LLP; Keith G. Haddaway

(57) ABSTRACT

The invention encompasses novel compounds and pharmaceutically acceptable salts thereof and compositions including therapeutically or prophylactically effective amounts of such compounds or pharmaceutically acceptable salts thereof. The invention also encompasses methods for treating or preventing diseases and disorders associated abnormal cell growth, for example, treating or preventing cancer or tumor growth, which methods include administering to a mammal in need thereof a composition comprising a therapeutically or prophylactically effective amount of a compound of the invention or a pharmaceutically acceptable salt thereof.

37 Claims, 55 Drawing Sheets

$^1$H NMR ($\delta$, DMSO-d$_6$, $J$ IN Hz IN PARENTHESES) DATA OF COMPOUNDS 3 AND 11-14$^a$

| COMPD | H-2 | H-5 | H-12 | H-14 & H-18 | H-1' | H-3' & H-7' | H-9 (N) | H-2" & H-6" |
|---|---|---|---|---|---|---|---|---|
| 3 | 8.92 s | 8.75 s | 5.51 s | 7.33 d (8.7) | 5.08 s | 7.29 d (8.7) | -- | -- |
| 11 | 7.87 s | 7.53 s | -- | -- | 4.63 dd (15.1, 18.3) | 7.19d (8.6) | 9.82s | 6.68d (8.6) |
| 12 (CDCl$_3$) | 7.69 s | 7.65 s | 5.13 q (14.2) | 7.08 d (8.6) | 4.72s | 7.33d (8.6) | 9.47s | 6.72d (8.6) |
| 13 | 7.83 s | 7.50 s | -- | -- | 4.62 dd (15.1, 18.3) | 7.20 d (8.72) | 9.68s | 6.56d (9.2) |
| 14 | 7.85 s | 7.50 s | -- | -- | 4.60dd (15.1, 18.3) | 7.22d (8.72) | 9.4s | 5.80d (H-2") (8.72) |

$^a$DATA ARE BASED ON DEPT, HMQC AND HMBC EXPERIMENTS.

*FIG. 1*

$^{13}$C NMR ($\delta$, DMSO-d$_6$) DATA OF COMPOUNDS 3 AND 11-14$^\alpha$

| C | 3 | 11 | 12 | 13 | 14 |
|---|---|---|---|---|---|
| | | | (CDCl$_3$) | | |
| C-2 | 148.9 | 137.5 | 138.3 | 137.2 | 137.2 |
| C-5 | 150.3 | 145.9 | 146.6 | 145.9 | 146.0 |
| C-6a | 160.2 | 154.3 | 154.6 | 154.7 | 154.2 |
| C-8 | 166.3 | 155.8 | 156.2 | 155.8 | 156.6 |
| C-9a | -- | 64.6 | 64.2 | 64.7 | 63.4 |
| C-10 | -- | 121.0 | 121.0 | 121.3 | 122.0 |
| C-11 | -- | 134.8 | 134.4 | 134.7 | 134.9 |
| C-12 | 47.0 | -- | 46.9 | -- | -- |
| C-14 & C-18 | 129.8 | -- | 129.0 | -- | -- |
| C-1' | 43.4 | 40.6 | 43.4 | 42.8 | 42.9 |
| C-3' & C-7' | 129.7 | 129.4 | 129.9 | 129.4 | 129.9 |
| C-2" & C-6" | -- | 127.7 | 127.4 | 127.1 | 122.8 (C-2") |

$^\alpha$DATA ARE BASED ON DEPT, HMQC AND HMBC EXPERIMENTS.

*FIG. 2*

THREE-BOND $^1$H-C$^{13}$ COUPLING (HMBC) IN COMPOUNDS 3 AND 11-14

| H | 3 | 11 | 12 | 13 | 14 |
|---|---|---|---|---|---|
| H-2 & C-11 | C-12 | C-10 & C-11 | C-10 & C-11 | C-10 & C-11 | C-10 & C- |
| H-5 & C-11 | C-6a | C-6a & C-11 | C-6a & C-11 | C-6a & C-11 | C-6A & C- |
| H-12 | C-2, C-14, & C-18 | -- | C-2, C-14, & C-18 | -- | -- |
| H-14 & C-18 | C-12 | -- | C-12 | -- | -- |
| H-1' & C-7' H-3' & H-7' & C-1' | C-6A, C-8, C-3' & C-7' C-1' | C-8, C-3' & C-7' C-1' | C-8, C-3' & C-7' C-1' | C-8, C-3' & C-7' C-1' | C-8, C-3' |
| H-9(N 9a*) | -- | C-8*, C-9a* | C-8*, C-9a* | C-8*, C-9a* | C-8*, C- |
| H-2" & H-6" (2") | -- | C-9a | C-9a | C-9a | C-9a (H- |

*TWO-BOND COUPLING ENHANCEMENT OBSERVED.

*FIG. 3*

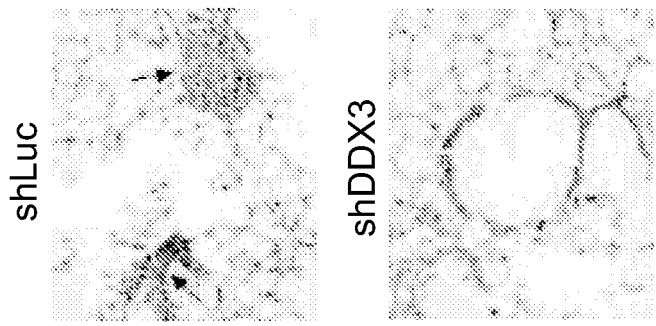
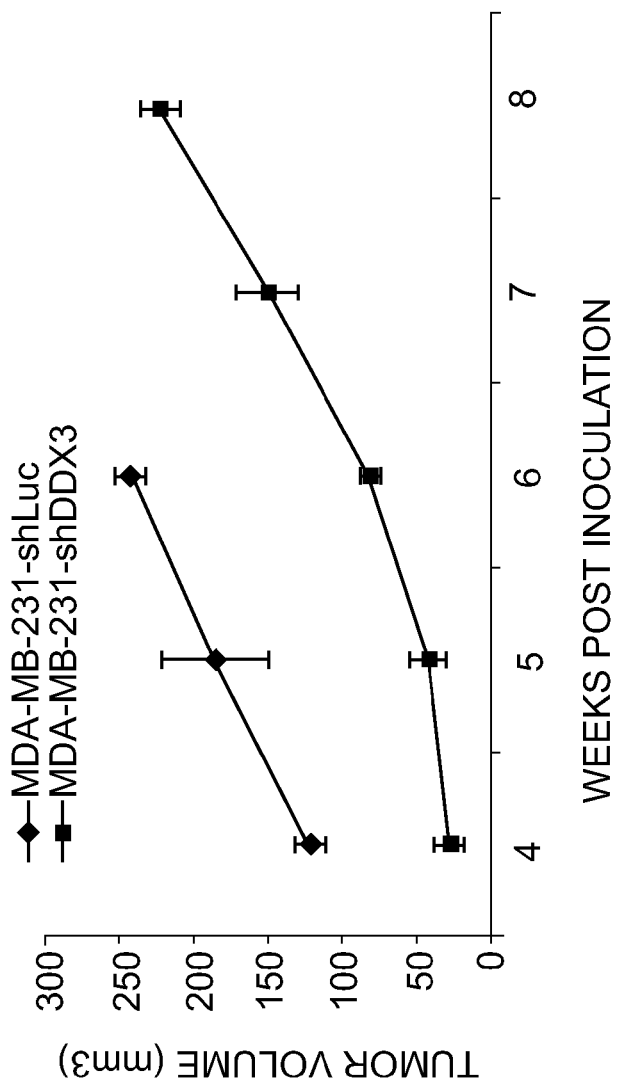
FIG. 42B
FIG. 42A

RED (PINK) AND WHITE (BLUE) PULP SIMILAR PATTERNS IN BOTH GROUPS

A-MONOCYTES, B-PLATELET, C-NEUTROPHILS, D-RBC

SIMILAR PATTERNS, CELL NUMBERS AND TYPES IN BOTH BLOOD SMEARS

FUSED DIIMIDAZODIAZEPINE COMPOUNDS AND METHODS OF USE AND MANUFACTURE THEREOF

RELATED APPLICATIONS

The present application is a U.S. National Phase Application of International Application No. PCT/US2009/005273, filed Sep. 23, 2009, which claims the benefit of U.S. Provisional Application No. 61/099,324, filed Sep. 23, 2008, all of which are hereby incorporated by reference in their entireties.

GOVERNMENT SUPPORT

This Invention was made with Government support under grant no. AI 071802 awarded by the National Institutes of Health. The Government has certain rights in this invention.

FIELD OF THE INVENTION

The invention encompasses novel compounds and pharmaceutically acceptable salts thereof and compositions including therapeutically or prophylactically effective amounts of such compounds or pharmaceutically acceptable salts thereof. The invention also encompasses methods for treating or preventing diseases and disorders associated abnormal cell growth, for example, treating or preventing cancer or tumor growth, which methods include administering to a mammal in need thereof a composition comprising a therapeutically or prophylactically effective amount of a compound of the invention or a pharmaceutically acceptable salt thereof.

BACKGROUND OF THE INVENTION

Treatment of cancer varies based on the type of cancer and its stage. The stage of a cancer refers to how much it has grown and whether the tumor has spread from its original location. If the cancer is confined to one location and has not spread, the most common goals for treatment are surgery and cure. This is often the case with skin cancers, as well as cancers of the lung, breast, and colon.

If the tumor has spread to local lymph nodes only, sometimes these can also be removed. If surgery cannot remove all of the cancer, the options for treatment include radiation, chemotherapy, or both. Some cancers require a combination of surgery, radiation, and chemotherapy.

Although current radiotherapeutic agents, chemotherapeutic agents and biological toxins are potent cytotoxins, they do not discriminate between normal and malignant cells, producing adverse effects and dose-limiting toxicities. There remains a need for lung cancer specific cancer markers.

The present inventors have identified novel compounds that are effective in discriminately inhibiting the growth of cancer and tumor cells while allowing healthy "normal" cells to remain unaffected.

Surprisingly, the methods and compositions of the invention fulfill the needs and satisfy other objects and advantages that will become apparent from the description which follows

SUMMARY OF THE INVENTION

The invention encompasses compounds and compositions and methods comprising the compounds of Formulas I-V that are useful for treating or preventing a disease or disorder including, but not limited to, conditions caused by uncontrolled cell growth, hyperproliferation of cells, tumor growth, and cancers.

The invention also encompasses methods for treating or preventing lung cancer, pancreatic cancer, leukemia, breast cancer, liver cancer, kidney cancer, ovarian cancer, human glioblastoma and prostate cancer, which comprises administering to a mammal in need of such treatment or prevention a therapeutically or prophylactically effective amount of a composition comprising a compound of Formula I-V, or a pharmaceutically acceptable salt or prodrug thereof, and a pharmaceutically acceptable vehicle.

In certain embodiments, a composition or formulation comprising a compound of Formula I-V is useful in treating or preventing conditions caused by uncontrolled cell growth.

In certain embodiments, a composition or formulation comprising a compound of Formula I-V is useful in killing abnormal or cancerous cells while simultaneously not affecting healthy or normal cells.

In certain embodiments, a composition or formulation comprising a compound of Formula I-V act as cytotoxic agents.

In certain embodiments, a composition or formulation comprising a compound of Formula I-V act as apoptotic agents.

As described herein, the compositions that are useful in the methods of the invention encompass compounds of Formulas I-V.

In one embodiment, the invention encompasses compositions and formulations for treating or preventing diseases or disorders comprising a compound of Formula (I):

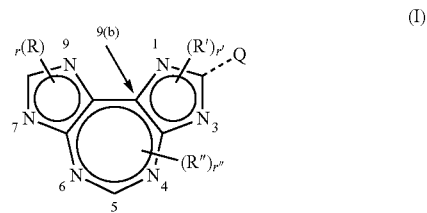

or pharmaceutically acceptable salts and prodrugs thereof, wherein:

R, R', and R'' are each independently a hydrogen, hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)$R^3$; —C(S)$R^3$; —S(O)$R^3$; —S(O)$_2$$R^3$; —C(O)N$R^4$$R^5$; —C(S)N$R^3$$R^4$; —C(X)Y$R^5$$R^6$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens;

R, R', and R'' can also form a ring with one or more C, S, O, N atoms such that, for example, R and R' together include:

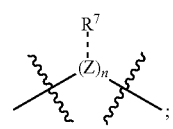

$R^7$ is a hydrogen; hydroxyl; substituted and unsubstituted: cyclic and acyclic alkyl group, group, alkenyl group, alkynyl group, aryl group, aryloxy group, alkylary group, aryalkyl group, heteroaryl group, heterocycloalkyl group;

—C(O)alkyl; —C(O)alkenyl; —C(O)alkynyl; —C(O)aryl; —C(O)benzyl; —C(O)NR³R⁴; —C(S)alkyl; —C(S)alkenyl; —C(S)alkynyl; —C(S)aryl; —C(S)benzyl; —C(S)NR³R⁴; —C(X)YR¹R²;

wherein

Q is O, NH, or S;

X is O, N, or S;

Y is O, CH₂, NH, or S;

Z is CH, N, P, or C;

------ is a single bond or double bond; wherein if ------ is a double bond, R² or R⁷ is independently O, S, or NH;

n is 1, 2, 3, or 4; and r, r', and r" are each independently an integer from 1 to about 3.

In certain illustrative embodiments, R, R', and R" are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO₂, triazolyl.

In another embodiment, the invention encompasses compositions and formulations for treating or preventing diseases or disorders comprising a compound of Formula (II):

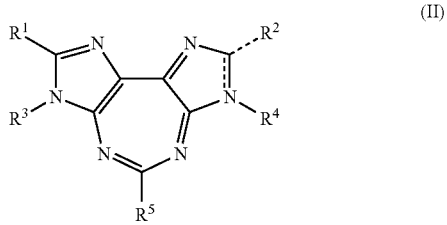

(II)

or pharmaceutically acceptable salts and prodrugs thereof, wherein

R¹, R², R³, R⁴, and R⁵ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)R³; —C(S)R³; —S(O)R³; —S(O)₂R³; —C(O)NR⁴R⁵; —C(S)NR³R⁴; —C(X)YR⁵R⁶; -β-D-ribosyl; -α-D-ribosyl; -β-L-ribosyl; -α-L-ribosyl; 2'-deoxy-β-D-ribosyl; 2'-deoxy-α-D-ribosyl; 2'-deoxy-α-L-ribosyl; and ribose or deoxyribose sugars substituted with one or more halogens;

R¹ and R³ or R² and R⁴ can also form a ring with one or more C, S, O, N atoms such that R¹ and R³ or R² and R⁴ together include

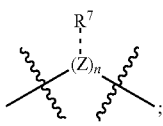

;

R⁷ is a hydrogen; hydroxyl; substituted and unsubstituted: cyclic and acyclic alkyl group, group, alkenyl group, alkynyl group, aryl group, aryloxy group, alkylary group, arylalkyl group, heteroaryl group, heterocycloalkyl group; —C(O)alkyl; —C(O)alkenyl; —C(O)alkynyl; —C(O)aryl; —C(O)benzyl; —C(O)NR³R⁴; —C(S)alkyl; —C(S)alkenyl; —C(S)alkynyl; —C(S)aryl; —C(S)benzyl; —C(S)NR³R⁴; —C(X)YR¹R²;

wherein

X is O, N, or S;

Y is O, CH₂, NH, or S;

Z is CH, N, P, or C;

------ is a single bond or double bond; wherein if ------ is a double bond, R² or R⁷ is independently O, S, or NH; and n is 1, 2, 3, or 4.

In certain illustrative embodiments, R¹, R², R³, R⁴, and R⁵ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO₂, triazolyl.

In another embodiment, the invention encompasses compositions and formulations for treating or preventing diseases or disorders comprising a compound of Formula (III):

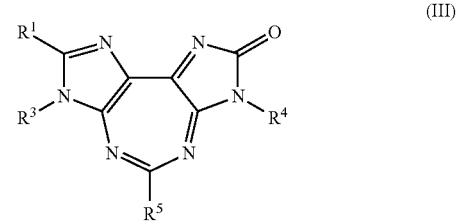

(III)

or pharmaceutically acceptable salts and prodrugs thereof, wherein

R¹, R³, R⁴, and R⁵ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)R³; —C(S)R³; —S(O)R³; —S(O)₂R³; —C(O)NR⁴R⁵; —C(S)NR³R⁴; —C(X)YR⁵R⁶; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens;

R¹ and R³ can also form a ring with one or more C, S, O, N atoms such that R¹ and R³ together include

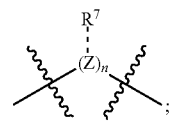

;

R⁷ is a hydrogen; hydroxyl; substituted and unsubstituted: cyclic and acyclic alkyl group, group, alkenyl group, alkynyl group, aryl group, aryloxy group, alkylary group, arylalkyl group, heteroaryl group, heterocycloalkyl group; —C(O)alkyl; —C(O)alkenyl; —C(O)alkynyl; —C(O)aryl; —C(O)benzyl; —C(O)NR³R⁴; —C(S)alkyl; —C(S)alkenyl; —C(S)alkynyl; —C(S)aryl; —C(S)benzyl; —C(S)NR³R⁴; —C(X)YR¹R²;

wherein

X is O, N, or S;

Y is O, CH$_2$, NH, or S;

Z is CH, N, P, or C;

------- is a single bond or double bond; wherein if ------- is a double bond, R$^2$ or R$^7$ is independently O, S, or NH; and n is 1, 2, 3, or 4.

In certain illustrative embodiments, R$^1$, R$^3$, R$^4$, and R$^5$ are not all hydrogen.

In certain illustrative embodiments, R$^1$, R$^3$, R$^4$, and R$^5$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO$_2$, triazolyl.

In another embodiment, the invention encompasses compositions and formulations for treating or preventing diseases or disorders comprising a compound of Formula (IV):

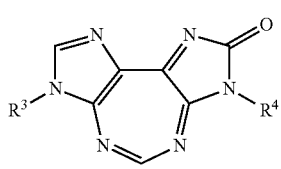

(IV)

or pharmaceutically acceptable salts and prodrugs thereof, wherein

R$^3$ and R$^4$ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)R$^3$; —C(S)R$^3$; —S(O)R$^3$; —S(O)$_2$R$^3$; —C(O)NR$^4$R$^5$; —C(S)NR$^3$R$^4$; —C(X)YR$^5$R$^6$; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens.

In certain illustrative embodiments, R$^3$ and R$^4$ are both not hydrogen.

In certain illustrative embodiments, R$^3$ and R$^4$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO$_2$, triazolyl.

In another embodiment, the invention encompasses compositions and formulations for treating or preventing diseases or disorders comprising a compound of Formula (V):

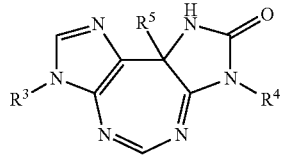

(V)

or pharmaceutically acceptable salts and prodrugs thereof, wherein

R$^3$, R$^4$, and R$^5$ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)R$^3$; —C(S)R$^3$; —S(O)R$^3$; —S(O)$_2$R$^3$; —C(O)NR$^4$R$^5$; —C(S)NR$^3$R$^4$; —C(X)YR$^5$R$^6$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens.

In certain illustrative embodiments, R$^3$, R$^4$, and R$^5$ are not each hydrogen.

In certain illustrative embodiments, R$^3$, R$^4$, and R$^5$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO$_2$, triazolyl.

In various other illustrative embodiments of the invention, the compounds of the invention can be encompassed by the following illustrative embodiments.

The present invention may be understood more fully by reference to the figures, detailed description, and examples, which are intended to exemplify non-limiting embodiments of the invention.

BRIEF DESCRIPTION OF THE DRAWINGS

FIG. 1 illustrates $^1$H NMR (δ, DMSO-d$_6$, J in Hz in parentheses) data of illustrative compounds 3 and 11-14a.

FIG. 2 illustrates $^{13}$C NMR (δ, DMSO-d$_6$) data of illustrative compounds 3 and 11-14.

FIG. 3 illustrates a three-Bond $^1$H—C$^{13}$ Coupling (HMBC) in illustrative compounds 3 and 11-14.

FIG. 42: A) Tumor growth rate in the mammary fat pad of SCID mice (preclinical breast cancer model) using wild type and DDX3 knockdown MDA-MB-231 cells. B) Cross section of lungs of animals injected orthotopically (mammary fat pad) with MDA-MB-231 and MDAMB-231-shDDX3 cells. Note that the lungs from MDA-MB-231-shDDX3 injected animals showed no tumor formation as compared to the wild type cells (black arrows points to lung metastasis).

Figure 4:
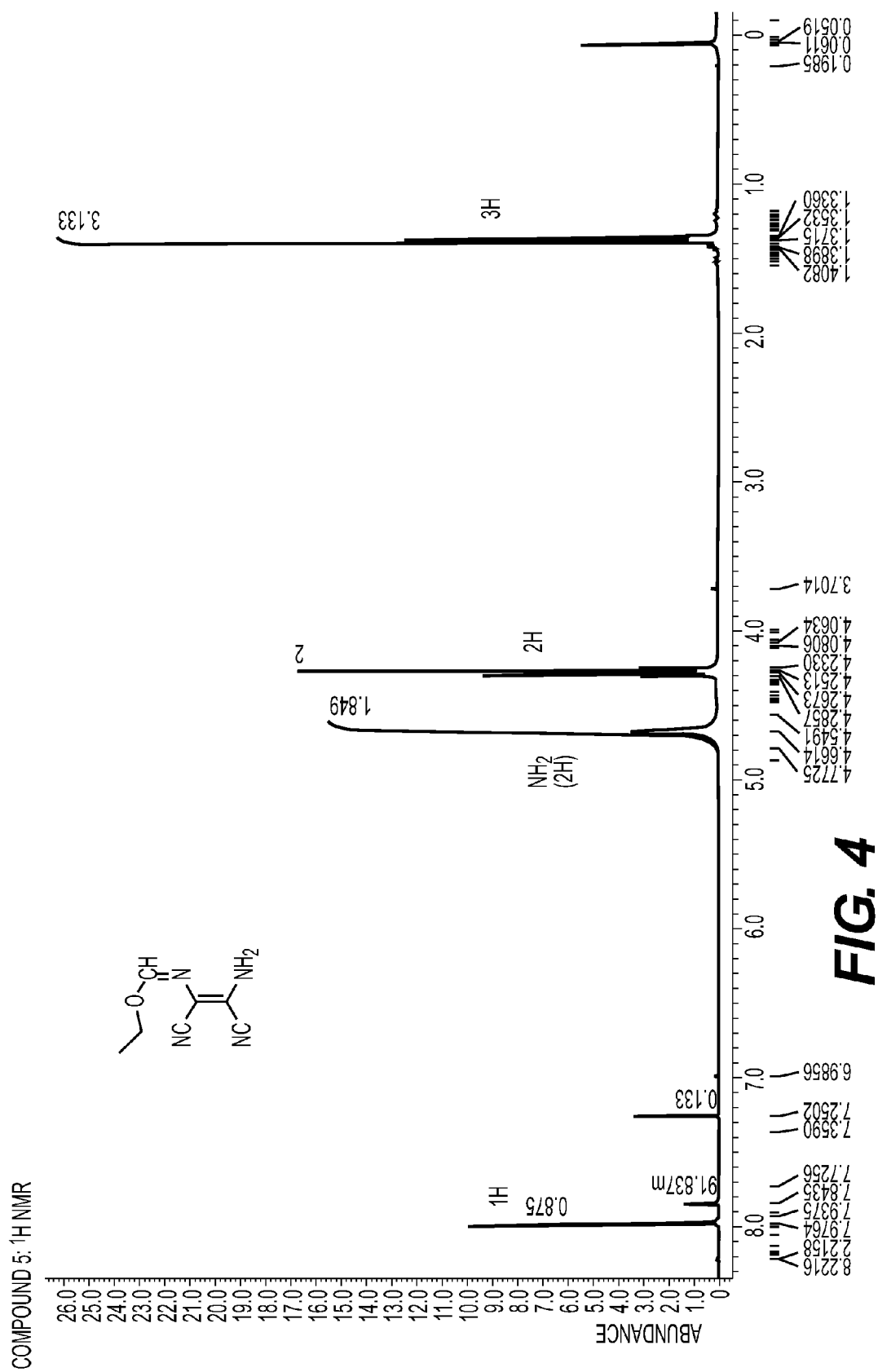
FIG. 4 illustrates $^1$H NMR (δ, DMSO-d$_6$, J in Hz in parentheses) data of compound 5.

DETAILED DESCRIPTION OF THE INVENTION 5.1. Definitions

As used herein and unless otherwise indicated, the term "alkoxy group" means an —O-alkyl group, wherein alkyl is as defined herein. An alkoxy group can be unsubstituted or substituted with one or two suitable substituents. Preferably, the alkyl chain of an alkyloxy group is from 1 to 6 carbon atoms in length, referred to herein, for example, as "($C_1$-$C_{10}$) alkoxy."

As used herein and unless otherwise indicated, the term "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to ($C_2$-$C_8$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein and unless otherwise indicated, the term "alkylalkoxy" or "alkyloxyalkyl group" means a saturated, monovalent unbranched or branched hydrocarbon chain covalently bonded to an oxygen and covalently bonded to a second a saturated, monovalent unbranched or branched hydrocarbon chain (e.g., -alkyl-O-alkyl).

As used herein and unless otherwise indicated, the term "alkyl" or "alkyl group" means a substituted or unsubstituted, saturated, monovalent unbranched or branched hydrocarbon chain. Examples of alkyl groups include, but are not limited to, ($C_1$-$C_{10}$)alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein and unless otherwise indicated, the term "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein and unless otherwise indicated, the term "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "($C_6$)aryl."

As used herein and unless otherwise indicated, the term "aryloxy group" means an —O-aryl group, wherein aryl is as defined herein. An aryloxy group can be unsubstituted or substituted with one or two suitable substituents. Preferably, the aryl ring of an aryloxy group is a monocyclic ring, wherein the ring comprises 6 carbon atoms, referred to herein as "($C_6$)aryloxy."

As used herein, the term "benzyl" means —$CH_2$-phenyl.

As used herein, the term "carbonyl" group is a divalent group of the formula —C(O)—.

As used herein and unless otherwise indicated, the term "compounds of the invention" means, collectively, the compounds of formulas I, II, III, IV, and V and pharmaceutically acceptable salts thereof as well as compounds depicted herein including Compounds 3, 11, 12, 13, 14, 21, 23, 25, 27, and 101-193. The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

As used herein and unless otherwise indicated, the term "cyclic alkyl" and "cycloalkyl group" are used synonymously and each means a monocyclic or polycyclic saturated ring comprising carbon and hydrogen atoms and having no carbon-carbon multiple bonds. Examples of cycloalkyl groups include, but are not limited to, ($C_3$-$C_7$)cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

As used herein and unless otherwise indicated, the term "halogen" means fluorine, chlorine, bromine, or iodine. Correspondingly, the meaning of the terms "halo" and "Hal" encompass fluoro, chloro, bromo, and iodo.

As used-herein and unless otherwise indicated, the term "formulation" refers to a composition comprising a compound of the invention that is described in a particular dosage form (e.g., tablet) or with a particular dosage amount (e.g., 30 mg/kg).

As used herein and unless otherwise indicated, the term "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, furyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "($C_2$-$C_5$) heteroaryl."

As used herein and unless otherwise indicated, the term "heterocycloalkyl group" means a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 7 carbon atoms and form 1 to 3 heteroatoms, referred to herein as ($C_1$-$C_7$)heterocycloalkyl.

As used herein and unless otherwise indicated, the term "heterocyclic radical" or "heterocyclic ring" means a heterocycloalkyl group or a heteroaryl group.

As used herein and unless otherwise indicated, the term "hydrocarbyl group" means a monovalent group selected from ($C_1$-$C_8$)alkyl, ($C_2$-$C_8$)alkenyl, and ($C_2$-$C_8$)alkynyl, optionally substituted with one or two suitable substituents. Preferably, the hydrocarbon chain of a hydrocarbyl group is from 1 to 6 carbon atoms in length, referred to herein as "($C_1$-$C_6$)hydrocarbyl."

When administered to a mammal (e.g., to an animal for veterinary use or to a human for clinical use), the compounds of the invention can be optionally administered in isolated form. As used herein, "isolated" means that the compounds of the invention are separated from other components of either (a) a natural source, such as a plant or cell, preferably bacterial culture, or (b) a synthetic organic chemical reaction mixture, preferably, via conventional techniques, the compounds of the invention are purified. As used herein, "purified" means that when isolated, the isolate contains at least 80% preferably at least 90%, more preferably at least 95%, and most preferably at least 99% of a compound of the invention by weight of the isolate.

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds, included in the present compositions, that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "pharmaceutically acceptable prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise oligonucleotides, peptides, lipids, aliphatic and aromatic groups, or NO, $NO_2$, ONO, and $ONO_2$ moieties. Prodrugs can typically be prepared using well known methods, such as those described in Burger's Medicinal Chemistry and Drug Discovery, pp. 172, 178, 949, 982 (Manfred E. Wolff ed., 5th ed. 1995), and Design of Prodrugs (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxy-methyl, pivaloyloxymethyl, and pivaloyloxyethyl esters), lactonyl esters (such as phthalidyl and thiophthalidyl esters), lower alkoxyacyloxyalkyl esters (such as methoxycarbonyloxy-methyl, ethoxycarbonyloxy-ethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, a amino acid amides, alkoxyacyl amides, and alkylaminoalkyl-carbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "phenyl" means —$C_6H_5$. A phenyl group can be unsubstituted or substituted with one or two suitable substituents.

As used herein and unless otherwise indicated, the terms "substituted" and "a suitable substituent" means a group that does not nullify the synthetic or pharmaceutical utility of the compounds of the invention or the intermediates useful for preparing them. Examples of substituted groups or suitable substituents include, but are not limited to: ($C_1$-$C_8$)alkyl; ($C_1$-$C_8$)alkenyl; ($C_1$-$C_8$)alkynyl; ($C_6$)aryl; ($C_3$-$C_5$)heteroaryl; ($C_3$-$C_7$)cycloalkyl; ($C_1$-$C_8$)alkoxy; ($C_6$)aryloxy; —CN; —OH; SH, oxo; halo, —$NO_2$, —$CO_2H$; —$NH_2$; —NHOH, —NH(($C_1$-$C_8$)alkyl); —N(($C_1$-$C_8$)alkyl)$_2$; —NH(($C_6$)aryl); —NHO(($C_1$-$C_8$)alkyl); —N(O($C_1$-$C_8$)alkyl)$_2$; —NH(O($C_6$)aryl); —S(($C_1$-$C_8$)alkyl); —S(($C_1$-$C_8$)alkyl)$_2$; —S(($C_6$)aryl); (=O); C(S), —N(($C_6$)aryl)$_2$; —CHO; —C(O)(($C_1$-$C_8$)alkyl); —C(O)(($C_6$)aryl); —$CO_2$(($C_1$-$C_8$)alkyl); and —$CO_2$(($C_6$)aryl), —C(S)(($C_1$-$C_8$)alkyl); —C(S)(($C_6$)aryl); —$SO_2$(($C_1$-$C_8$)alkyl); —$SO_2$(($C_6$)aryl), and —$SO_3H$, —C(S)O(($C_1$-$C_8$)alkyl); —C(S)(O)(($C_6$)aryl). In certain illustrative embodiments, the substituents can be one or more than one suitable groups, such as, but not limited to, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —$NO_2$, triazolyl. One of skill in art can readily choose a suitable substituent based on the stability and pharmacological and synthetic activity of the compound of the invention.

As used herein and unless otherwise indicated, the phrase "therapeutically effective amount" of a composition of the invention is measured by the therapeutic effectiveness of a compound of the invention, wherein at least one adverse effect of a disorder is ameliorated or alleviated.

The terms "treating or preventing" are intended to include preventing, eradicating, or inhibiting the resulting increase of undesired physiological activity associated with a disorder, for example, in the context of the therapeutic or prophylactic methods of the invention. In another embodiment, the term treating or preventing includes antagonistic effects, e.g., diminishment of the activity or production of mediators of a disorder.

5.2 Compounds of the Invention

As set forth herein, the invention includes, but is not limited to, compounds, compositions and formulations for treating or preventing treating or preventing a disease or disorder including, but not limited to, conditions caused by uncontrolled cell growth, hyperproliferation of cells, tumor growth, and cancers, for example, lung cancer, pancreatic cancer, leukemia, breast cancer, liver cancer, kidney cancer, ovarian cancer, human glioblastoma and prostate cancer, which comprises administering to a mammal in need of such treatment or prevention a therapeutically or prophylactically effective amount of a composition comprising a compound of Formula I-V, or a pharmaceutically acceptable salt or prodrug thereof, and a pharmaceutically acceptable vehicle. In certain embodiments, a composition or formulation comprising a compound of Formula I-V is useful in treating or preventing conditions caused by uncontrolled cell growth. In certain embodiments, a composition or formulation comprising a compound of Formula I-V is useful in killing abnormal or cancerous cells while simultaneously not affecting healthy or normal cells. In certain embodiments, a composition or formulation comprising a compound of Formula I-V act as cytotoxic agents. In certain embodiments, a composition or formulation comprising a compound of Formula I-V act as apoptotic agents.

The invention encompasses methods of treating or preventing diseases and disorders described herein by administering a composition or formulation comprising a compound of Formulas I-V or a pharmaceutically acceptable salt or prodrug thereof.

As described herein, the compositions that are useful in the methods of the invention encompass compounds of Formulas I-V.

In one embodiment, the invention encompasses compounds and compositions and formulations for treating or preventing diseases or disorders comprising a compound of Formula (I):

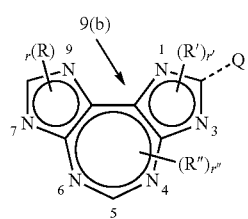

(I)

or pharmaceutically acceptable salts and prodrugs thereof, wherein:

R, R', and R" are each independently a hydrogen, hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)R³; —C(S)R³; —S(O)R³; —S(O)₂R³; —C(O)NR⁴R⁵; —C(S)NR³R⁴; —C(X)YR⁵R⁶; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens;

R, R', and R" can also form a ring with one or more C, S, O, N atoms such that, for example, R and R' together include:

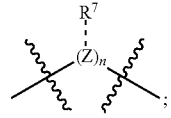

R⁷ is a hydrogen; hydroxyl; substituted and unsubstituted: cyclic and acyclic alkyl group, group, alkenyl group, alkynyl group, aryl group, aryloxy group, alkylary group, aryalkyl group, heteroaryl group, heterocycloalkyl group; —C(O)alkyl; —C(O)alkenyl; —C(O)alkynyl; —C(O)aryl; —C(O)benzyl; —C(O)NR³R⁴; —C(S)alkyl; —C(S)alkenyl; —C(S)alkynyl; —C(S)aryl; —C(S)benzyl; —C(S)NR³R⁴; —C(X)YR¹R²;

wherein

Q is O, NH, or S;

X is O, N, or S;

Y is O, CH₂, NH, or S;

Z is CH, N, P, or C;

------- is a single bond or double bond; wherein if ------- is a double bond, R² or R⁷ is independently O, S, or NH;

n is 1, 2, 3, or 4; and r, r', and r" are each independently an integer from 1 to about 3.

In certain illustrative embodiments, R, R', and R" are each independently are a substituted benzyl, alkyl, aryl, cycloalkyl, heteroaryl, or heterocycloalkyl with one or more substituents, such as, but not limited to, —H, —F, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO₂, triazolyl.

In certain illustrative embodiments, the compounds of the invention do not include compounds where both R, R', and R" are all hydrogen.

In certain illustrative embodiments, the substituents can be one or more than one suitable groups, such as, but not limited to, —F, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO₂, triazolyl.

In one embodiment, R is hydrogen. In another embodiment, R is an alkyl group. In another embodiment, R is an alkoxy group. In another embodiment, R is an alkylalkoxy group.

In another embodiment, R is an alkenyl group. In another embodiment, R is alkynyl group. In another embodiment, R is an aryl group. In another embodiment, R is aryloxy group. In another embodiment, R is benzyl group. In another embodiment, R is heteroaryl group. In another embodiment, R is heterocycloalkyl group. In another embodiment, R is a cycloalkyl group. In another embodiment, R is a benzyl group.

In certain illustrative embodiments, R is a benzyl group substituted with one or more —F groups.

In certain illustrative embodiments, R is a benzyl group substituted with one or more —Cl groups.

In certain illustrative embodiments, R is a benzyl group substituted with one or more —Br groups.

In certain illustrative embodiments, R is a benzyl group substituted with one or more —I groups.

In certain illustrative embodiments, R is a benzyl group substituted with one or more OH groups.

In certain illustrative embodiments, R is a benzyl group substituted with one or more azido groups.

In certain illustrative embodiments, R is a benzyl group substituted with one or more —SH groups.

In certain illustrative embodiments, R is a benzyl group substituted with one or more alkyl.

In certain illustrative embodiments, R is a benzyl group substituted with one or more aryl groups.

In certain illustrative embodiments, R is a benzyl group substituted with one or more heteroalkyl groups.

In certain illustrative embodiments, R is a benzyl group substituted with one or more alkyloxyl groups.

In certain illustrative embodiments, R is a benzyl group substituted with one or more alkylthiol groups.

In certain illustrative embodiments, R is a benzyl group substituted with one or more amino groups.

In certain illustrative embodiments, R is a benzyl group substituted with one or more hydroxylamino groups.

In certain illustrative embodiments, R is a benzyl group substituted with one or more N-alkylamino groups.

In certain illustrative embodiments, R is a benzyl group substituted with one or more —N,N-dialkylamino groups.

In certain illustrative embodiments, R is a benzyl group substituted with one or more N,N-dimethylamino groups.

In certain illustrative embodiments, R is a benzyl group substituted with one or more acyl groups.

In certain illustrative embodiments, R is a benzyl group substituted with one or more alkyloxycarbonyl groups. groups In certain illustrative embodiments, R is a benzyl group substituted with one or more sulfonyl groups.

In certain illustrative embodiments, R is a benzyl group substituted with one or more urea groups.

In certain illustrative embodiments, R is a benzyl group substituted with one or more —NO$_2$ groups.

In certain illustrative embodiments, R is a benzyl group substituted with one or more triazolyl groups.

In one embodiment, R' is hydrogen. In another embodiment, R' is an alkyl group. In another embodiment, R' is an alkoxy group. In another embodiment, R' is an alkylalkoxy group.

In another embodiment, R' is an alkenyl group. In another embodiment, R' is alkynyl group. In another embodiment, R' is an aryl group. In another embodiment, R' is aryloxy group. In another embodiment, R' is benzyl group. In another embodiment, R' is heteroaryl group. In another embodiment, R' is heterocycloalkyl group. In another embodiment, R' is a cycloalkyl group. In another embodiment, R' is a benzyl group.

In certain illustrative embodiments, R' is a benzyl group substituted with one or more —F groups.

In certain illustrative embodiments, R' is a benzyl group substituted with one or more —Cl groups.

In certain illustrative embodiments, R' is a benzyl group substituted with one or more —Br groups.

In certain illustrative embodiments, R' is a benzyl group substituted with one or more —I groups.

In certain illustrative embodiments, R' is a benzyl group substituted with one or more OH groups.

In certain illustrative embodiments, R' is a benzyl group substituted with one or more azido groups.

In certain illustrative embodiments, R' is a benzyl group substituted with one or more —SH groups.

In certain illustrative embodiments, R' is a benzyl group substituted with one or more alkyl.

In certain illustrative embodiments, R' is a benzyl group substituted with one or more aryl groups.

In certain illustrative embodiments, R' is a benzyl group substituted with one or more heteroalkyl groups.

In certain illustrative embodiments, R' is a benzyl group substituted with one or more alkyloxyl groups.

In certain illustrative embodiments, R' is a benzyl group substituted with one or more alkylthiol groups.

In certain illustrative embodiments, R' is a benzyl group substituted with one or more amino groups.

In certain illustrative embodiments, R' is a benzyl group substituted with one or more hydroxylamino groups.

In certain illustrative embodiments, R' is a benzyl group substituted with one or more N-alkylamino groups.

In certain illustrative embodiments, R' is a benzyl group substituted with one or more —N,N-dialkylamino groups.

In certain illustrative embodiments, R' is a benzyl group substituted with one or more —N,N-dimethylamino groups.

In certain illustrative embodiments, R' is a benzyl group substituted with one or more acyl groups.

In certain illustrative embodiments, R' is a benzyl group substituted with one or more alkyloxycarbonyl groups. groups In certain illustrative embodiments, R' is a benzyl group substituted with one or more sulfonyl groups.

In certain illustrative embodiments, R' is a benzyl group substituted with one or more urea groups.

In certain illustrative embodiments, R' is a benzyl group substituted with one or more —NO$_2$ groups.

In certain illustrative embodiments, R' is a benzyl group substituted with one or more triazolyl groups.

In another embodiment, R" is hydrogen. In another embodiment, R" is an alkyl group.

In another embodiment, R" is an alkoxy group. In another embodiment, R" is an alkylalkoxy group. In another embodiment, R" is an alkenyl group. In another embodiment, R" is alkynyl group. In another embodiment, R" is an aryl group. In another embodiment, R" is aryloxy group. In another embodiment, R" is benzyl group. In another embodiment, R" is heteroaryl group. In another embodiment, R" is heterocycloalkyl group. In another embodiment, R" is a cycloalkyl group. In another embodiment, R" is a benzyl group.

In certain illustrative embodiments, R" is a benzyl group substituted with one or more —F groups.

In certain illustrative embodiments, R" is a benzyl group substituted with one or more —Cl groups.

In certain illustrative embodiments, R" is a benzyl group substituted with one or more —Br groups.

In certain illustrative embodiments, R" is a benzyl group substituted with one or more —I groups.

In certain illustrative embodiments, R" is a benzyl group substituted with one or more OH groups.

In certain illustrative embodiments, R" is a benzyl group substituted with one or more azido groups.

In certain illustrative embodiments, R" is a benzyl group substituted with one or more —SH groups.

In certain illustrative embodiments, R" is a benzyl group substituted with one or more alkyl.

In certain illustrative embodiments, R" is a benzyl group substituted with one or more aryl groups.

In certain illustrative embodiments, R" is a benzyl group substituted with one or more heteroalkyl groups.

In certain illustrative embodiments, R" is a benzyl group substituted with one or more alkyloxyl groups.

In certain illustrative embodiments, R" is a benzyl group substituted with one or more alkylthiol groups.

In certain illustrative embodiments, R" is a benzyl group substituted with one or more amino groups.

In certain illustrative embodiments, R" is a benzyl group substituted with one or more hydroxylamino groups.

In certain illustrative embodiments, R" is a benzyl group substituted with one or more N-alkylamino groups.

In certain illustrative embodiments, R" is a benzyl group substituted with one or more —N,N-dialkylamino groups.

In certain illustrative embodiments, R" is a benzyl group substituted with one or more —N,N-dimethylamino groups.

In certain illustrative embodiments, R" is a benzyl group substituted with one or more acyl groups.

In certain illustrative embodiments, R" is a benzyl group substituted with one or more alkyloxycarbonyl groups. groups In certain illustrative embodiments, R" is a benzyl group substituted with one or more sulfonyl groups.

In certain illustrative embodiments, R" is a benzyl group substituted with one or more urea groups.

In certain illustrative embodiments, R" is a benzyl group substituted with one or more —$NO_2$ groups.

In certain illustrative embodiments, R" is a benzyl group substituted with one or more triazolyl groups.

In another embodiment, the invention encompasses compositions and formulations for treating or preventing diseases or disorders comprising a compound of Formula (II):

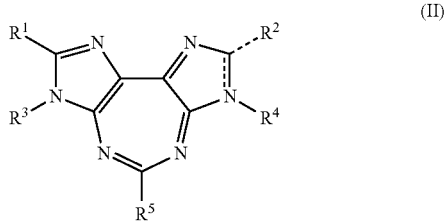

(II)

or pharmaceutically acceptable salts and prodrugs thereof, wherein $R^1$, $R^2$, $R^3$, $R^4$, and $R^5$ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)$R^3$; —C(S)$R^3$; —S(O)$R^3$; —S(O)$_2R^3$; —C(O)NR$^4R^5$; —C(S)NR$^3R^4$; —C(X)YR$^5R^6$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens; $R^1$ and $R^3$ or $R^2$ and $R^4$ can also form a ring with one or more C, S, O, N atoms such that R' and $R^3$ or $R^2$ and $R^4$ together include

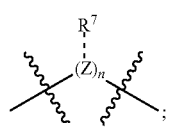

$R^7$ is a hydrogen; hydroxyl; substituted and unsubstituted: cyclic and acyclic alkyl group, group, alkenyl group, alkynyl group, aryl group, aryloxy group, alkylary group, aryalkyl group, heteroaryl group, heterocycloalkyl group; —C(O)alkyl; —C(O)alkenyl; —C(O)alkynyl; —C(O)aryl; —C(O)benzyl; —C(O)NR$^3R^4$; —C(S)alkyl; —C(S)alkenyl; —C(S)alkynyl; —C(S)aryl; —C(S)benzyl; —C(S)NR$^3R^4$; —C(X)YR$^1R^2$;

wherein

X is O, N, or S;

Y is O, $CH_2$, NH, or S;

Z is CH, N, P, or C;

------- is a single bond or double bond; wherein if ------- is a double bond, $R^2$ or $R^7$ is independently O, S, or NH; and n is 1, 2, 3, or 4.

In certain illustrative embodiments, R', $R^2$, $R^3$, $R^4$, and $R^5$ are each independently a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —$NO_2$, triazolyl.

In one embodiment, $R^1$ is hydrogen. In another embodiment, $R^1$ is an alkyl group. In another embodiment, $R^1$ is an alkoxy group. In another embodiment, $R^1$ is an alkylalkoxy group. In another embodiment, $R^1$ is an alkenyl group. In another embodiment, $R^1$ is alkynyl group. In another embodiment, $R^1$ is an aryl group. In another embodiment, $R^1$ is aryloxy group. In another embodiment, $R^1$ is benzyl group. In another embodiment, $R^1$ is heteroaryl group. In another embodiment, $R^1$ is heterocycloalkyl group. In another embodiment, $R^1$ is a cycloalkyl group. In another embodiment, $R^1$ is a benzyl group.

In certain illustrative embodiments, $R^1$ is a benzyl group substituted with one or more —F groups.

In certain illustrative embodiments, $R^1$ is a benzyl group substituted with one or more —Cl groups.

In certain illustrative embodiments, $R^1$ is a benzyl group substituted with one or more —Br groups.

In certain illustrative embodiments, $R^1$ is a benzyl group substituted with one or more —I groups.

In certain illustrative embodiments, $R^1$ is a benzyl group substituted with one or more OH groups.

In certain illustrative embodiments, $R^1$ is a benzyl group substituted with one or more azido groups.

In certain illustrative embodiments, $R^1$ is a benzyl group substituted with one or more —SH groups.

In certain illustrative embodiments, $R^1$ is a benzyl group substituted with one or more alkyl.

In certain illustrative embodiments, $R^1$ is a benzyl group substituted with one or more aryl groups.

In certain illustrative embodiments, $R^1$ is a benzyl group substituted with one or more heteroalkyl groups.

In certain illustrative embodiments, $R^1$ is a benzyl group substituted with one or more alkyloxyl groups.

In certain illustrative embodiments, $R^1$ is a benzyl group substituted with one or more alkylthiol groups.

In certain illustrative embodiments, $R^1$ is a benzyl group substituted with one or more amino groups.

In certain illustrative embodiments, $R^1$ is a benzyl group substituted with one or more hydroxylamino groups.

In certain illustrative embodiments, $R^1$ is a benzyl group substituted with one or more N-alkylamino groups.

In certain illustrative embodiments, $R^1$ is a benzyl group substituted with one or more —N,N-dialkylamino groups.

In certain illustrative embodiments, $R^1$ is a benzyl group substituted with one or more —N,N-dimethylamino groups.

In certain illustrative embodiments, $R^1$ is a benzyl group substituted with one or more acyl groups.

In certain illustrative embodiments, $R^1$ is a benzyl group substituted with one or more alkyloxycarbonyl groups. groups In certain illustrative embodiments, $R^1$ is a benzyl group substituted with one or more sulfonyl groups.

In certain illustrative embodiments, $R^1$ is a benzyl group substituted with one or more urea groups.

In certain illustrative embodiments, $R^1$ is a benzyl group substituted with one or more —$NO_2$ groups.

In certain illustrative embodiments, $R^1$ is a benzyl group substituted with one or more triazolyl groups.

In one embodiment, $R^2$ is hydrogen. In another embodiment, $R^2$ is an alkyl group. In another embodiment, $R^2$ is an alkoxy group. In another embodiment, $R^2$ is an alkylalkoxy group. In another embodiment, $R^2$ is an alkenyl group. In another embodiment, $R^2$ is alkynyl group. In another embodiment, $R^2$ is an aryl group. In another embodiment, $R^2$ is aryloxy group. In another embodiment, $R^2$ is benzyl group. In another embodiment, $R^2$ is heteroaryl group. In another embodiment, $R^2$ is heterocycloalkyl group. In another embodiment, $R^2$ is a cycloalkyl group. In another embodiment, $R^2$ is a benzyl group.

In certain illustrative embodiments, $R^2$ is a benzyl group substituted with one or more —F groups.

In certain illustrative embodiments, $R^2$ is a benzyl group substituted with one or more —Cl groups.

In certain illustrative embodiments, $R^2$ is a benzyl group substituted with one or more —Br groups.

In certain illustrative embodiments, $R^2$ is a benzyl group substituted with one or more —I groups.

In certain illustrative embodiments, $R^2$ is a benzyl group substituted with one or more OH groups.

In certain illustrative embodiments, $R^2$ is a benzyl group substituted with one or more azido groups.

In, certain illustrative embodiments, $R^2$ is a benzyl group substituted with one or more —SH groups.

In certain illustrative embodiments, $R^2$ is a benzyl group substituted with one or more alkyl.

In certain illustrative embodiments, $R^2$ is a benzyl group substituted with one or more aryl groups.

In certain illustrative embodiments, $R^2$ is a benzyl group substituted with one or more heteroalkyl groups.

In certain illustrative embodiments, $R^2$ is a benzyl group substituted with one or more alkyloxyl groups.

In certain illustrative embodiments, $R^2$ is a benzyl group substituted with one or more alkylthiol groups.

In certain illustrative embodiments, $R^2$ is a benzyl group substituted with one or more amino groups.

In certain illustrative embodiments, $R^2$ is a benzyl group substituted with one or more hydroxylamino groups.

In certain illustrative embodiments, $R^2$ is a benzyl group substituted with one or more N-alkylamino groups.

In certain illustrative embodiments, $R^2$ is a benzyl group substituted with one or more —N,N-dialkylamino groups.

In certain illustrative embodiments, $R^2$ is a benzyl group substituted with one or more —N,N-dimethylamino groups.

In certain illustrative embodiments, $R^2$ is a benzyl group substituted with one or more acyl groups.

In certain illustrative embodiments, $R^2$ is a benzyl group substituted with one or more alkyloxycarbonyl groups. groups In certain illustrative embodiments, $R^2$ is a benzyl group substituted with one or more sulfonyl groups.

In certain illustrative embodiments, $R^2$ is a benzyl group substituted with one or more urea groups.

In certain illustrative embodiments, $R^2$ is a benzyl group substituted with one or more —$NO_2$ groups.

In certain illustrative embodiments, $R^2$ is a benzyl group substituted with one or more triazolyl groups.

In one embodiment, $R^3$ is hydrogen. In another embodiment, $R^3$ is an alkyl group. In another embodiment, $R^3$ is an alkoxy group. In another embodiment, $R^3$ is an alkylalkoxy group. In another embodiment, $R^3$ is an alkenyl group. In another embodiment, $R^3$ is alkynyl group. In another embodiment, $R^3$ is an aryl group. In another embodiment, $R^3$ is aryloxy group. In another embodiment, $R^3$ is benzyl group. In another embodiment, $R^3$ is heteroaryl group. In another embodiment, $R^3$ is heterocycloalkyl group. In another embodiment, $R^3$ is a cycloalkyl group. In another embodiment, $R^3$ is a benzyl group.

In certain illustrative embodiments, $R^3$ is a benzyl group substituted with one or more —F groups.

In certain illustrative embodiments, $R^3$ is a benzyl group substituted with one or more —Cl groups.

In certain illustrative embodiments, $R^3$ is a benzyl group substituted with one or more —Br groups.

In certain illustrative embodiments, $R^3$ is a benzyl group substituted with one or more —I groups.

In certain illustrative embodiments, $R^3$ is a benzyl group substituted with one or more OH groups.

In certain illustrative embodiments, $R^3$ is a benzyl group substituted with one or more azido groups.

In certain illustrative embodiments, $R^3$ is a benzyl group substituted with one or more —SH groups.

In certain illustrative embodiments, $R^3$ is a benzyl group substituted with one or more alkyl.

In certain illustrative embodiments, $R^3$ is a benzyl group substituted with one or more aryl groups.

In certain illustrative embodiments, $R^3$ is a benzyl group substituted with one or more heteroalkyl groups.

In certain illustrative embodiments, $R^3$ is a benzyl group substituted with one or more alkyloxyl groups.

In certain illustrative embodiments, $R^3$ is a benzyl group substituted with one or more alkylthiol groups.

In certain illustrative embodiments, $R^3$ is a benzyl group substituted with one or more amino groups.

In certain illustrative embodiments, $R^3$ is a benzyl group substituted with one or more hydroxylamino groups.

In certain illustrative embodiments, $R^3$ is a benzyl group substituted with one or more N-alkylamino groups.

In certain illustrative embodiments, $R^3$ is a benzyl group substituted with one or more —N,N-dialkylamino groups.

In certain illustrative embodiments, $R^3$ is a benzyl group substituted with one or more —N,N-dimethylamino groups.

In certain illustrative embodiments, $R^3$ is a benzyl group substituted with one or more acyl groups.

In certain illustrative embodiments, $R^3$ is a benzyl group substituted with one or more alkyloxycarbonyl groups. groups In certain illustrative embodiments, $R^3$ is a benzyl group substituted with one or more sulfonyl groups.

In certain illustrative embodiments, $R^3$ is a benzyl group substituted with one or more urea groups.

In certain illustrative embodiments, $R^3$ is a benzyl group substituted with one or more —$NO_2$ groups.

In certain illustrative embodiments, $R^3$ is a benzyl group substituted with one or more triazolyl groups.

In one embodiment, $R^4$ is hydrogen. In another embodiment, $R^4$ is an alkyl group. In another embodiment, $R^4$ is an alkoxy group. In another embodiment, $R^4$ is an alkylalkoxy group. In another embodiment, $R^4$ is an alkenyl group. In another embodiment, $R^4$ is alkynyl group. In another embodiment, $R^4$ is an aryl group. In another embodiment, $R^4$ is aryloxy group. In another embodiment, $R^4$ is benzyl group. In another embodiment, $R^4$ is heteroaryl group. In another embodiment, $R^4$ is heterocycloalkyl group. In another embodiment, $R^4$ is a cycloalkyl group. In another embodiment, $R^4$ is a benzyl group.

In certain illustrative embodiments, $R^4$ is a benzyl group substituted with one or more —F groups.

In certain illustrative embodiments, $R^4$ is a benzyl group substituted with one or more —Cl groups.

In certain illustrative embodiments, $R^4$ is a benzyl group substituted with one or more —Br groups.

In certain illustrative embodiments, $R^4$ is a benzyl group substituted with one or more —I groups.

In certain illustrative embodiments, $R^4$ is a benzyl group substituted with one or more OH groups.

In certain illustrative embodiments, $R^4$ is a benzyl group substituted with one or more azido groups.

In certain illustrative embodiments, $R^4$ is a benzyl group substituted with one or more —SH groups.

In certain illustrative embodiments, $R^4$ is a benzyl group substituted with one or more alkyl.

In certain illustrative embodiments, $R^4$ is a benzyl group substituted with one or more aryl groups.

In certain illustrative embodiments, $R^4$ is a benzyl group substituted with one or more heteroalkyl groups.

In certain illustrative embodiments, $R^4$ is a benzyl group substituted with one or more alkyloxyl groups.

In certain illustrative embodiments, $R^4$ is a benzyl group substituted with one or more alkylthiol groups.

In certain illustrative embodiments, $R^4$ is a benzyl group substituted with one or more amino groups.

In certain illustrative embodiments, $R^4$ is a benzyl group substituted with one or more hydroxylamino groups.

In certain illustrative embodiments, $R^4$ is a benzyl group substituted with one or more N-alkylamino groups.

In certain illustrative embodiments, $R^4$ is a benzyl group substituted with one or more —N,N-dialkylamino groups.

In certain illustrative embodiments, $R^4$ is a benzyl group substituted with one or more —N,N-dimethylamino groups.

In certain illustrative embodiments, $R^4$ is a benzyl group substituted with one or more acyl groups.

In certain illustrative embodiments, $R^4$ is a benzyl group substituted with one or more alkyloxycarbonyl groups. groups In certain illustrative embodiments, $R^4$ is a benzyl group substituted with one or more sulfonyl groups.

In certain illustrative embodiments, $R^4$ is a benzyl group substituted with one or more urea groups.

In certain illustrative embodiments, $R^4$ is a benzyl group substituted with one or more —NO$_2$ groups.

In certain illustrative embodiments, $R^4$ is a benzyl group substituted with one or more triazolyl groups.

In one embodiment, $R^5$ is hydrogen. In another embodiment, $R^5$ is an alkyl group. In another embodiment, $R^5$ is an alkoxy group. In another embodiment, $R^5$ is an alkylalkoxy group. In another embodiment, $R^5$ is an alkenyl group. In another embodiment, $R^5$ is alkynyl group. In another embodiment, $R^5$ is an aryl group. In another embodiment, $R^5$ is aryloxy group. In another embodiment, $R^5$ is benzyl group. In another embodiment, $R^5$ is heteroaryl group. In another embodiment, $R^5$ is heterocycloalkyl group. In another embodiment, $R^5$ is a cycloalkyl group. In another embodiment, $R^5$ is a benzyl group.

In certain illustrative embodiments, $R^5$ is a benzyl group substituted with one or more —F groups.

In certain illustrative embodiments, $R^5$ is a benzyl group substituted with one or more —Cl groups.

In certain illustrative embodiments, $R^5$ is a benzyl group substituted with one or more —Br groups.

In certain illustrative embodiments, $R^5$ is a benzyl group substituted with one or more —I groups.

In certain illustrative embodiments, $R^5$ is a benzyl group substituted with one or more OH groups.

In certain illustrative embodiments, $R^5$ is a benzyl group substituted with one or more azido groups.

In certain illustrative embodiments, $R^5$ is a benzyl group substituted with one or more —SH groups.

In certain illustrative embodiments, $R^5$ is a benzyl group substituted with one or more alkyl.

In certain illustrative embodiments, $R^5$ is a benzyl group substituted with one or more aryl groups.

In certain illustrative embodiments, $R^5$ is a benzyl group substituted with one or more heteroalkyl groups.

In certain illustrative embodiments, $R^5$ is a benzyl group substituted with one or more alkyloxyl groups.

In certain illustrative embodiments, $R^5$ is a benzyl group substituted with one or more alkylthiol groups.

In certain illustrative embodiments, $R^5$ is a benzyl group substituted with one or more amino groups.

In certain illustrative embodiments, $R^5$ is a benzyl group substituted with one or more hydroxylamino groups.

In certain illustrative embodiments, $R^5$ is a benzyl group substituted with one or more N-alkylamino groups.

In certain illustrative embodiments, $R^5$ is a benzyl group substituted with one or more —N,N-dialkylamino groups.

In certain illustrative embodiments, $R^5$ is a benzyl group substituted with one or more —N,N-dimethylamino groups.

In certain illustrative embodiments, $R^5$ is a benzyl group substituted with one or more acyl groups.

In certain illustrative embodiments, $R^5$ is a benzyl group substituted with one or more alkyloxycarbonyl groups. groups In certain illustrative embodiments, $R^5$ is a benzyl group substituted with one or more sulfonyl groups.

In certain illustrative embodiments, $R^5$ is a benzyl group substituted with one or more urea groups.

In certain illustrative embodiments, $R^5$ is a benzyl group substituted with one or more —NO$_2$ groups.

In certain illustrative embodiments, $R^5$ is a benzyl group substituted with one or more triazolyl groups.

In another embodiment, the invention encompasses compositions and formulations for treating or preventing diseases or disorders comprising a compound of Formula (III):

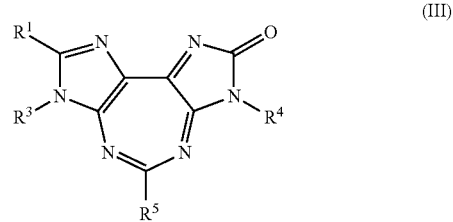

(III)

or pharmaceutically acceptable salts and prodrugs thereof, wherein
$R^1$, $R^3$, $R^4$, and $R^5$ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)R³; —C(S)R³; —S(O)R³; —S(O)₂R³; —C(O)NR⁴R⁵; —C(S)NR³R⁴; —C(X)YR⁵R⁶; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens; R¹ and R³ can also form a ring with one or more C, S, O, N atoms such that R' and R³ together include

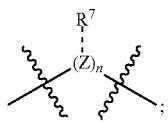

R⁷ is a hydrogen; hydroxyl; substituted and unsubstituted: cyclic and acyclic alkyl group, group, alkenyl group, alkynyl group, aryl group, aryloxy group, alkylary group, aryalkyl group, heteroaryl group, heterocycloalkyl group; —C(O)alkyl; —C(O)alkenyl; —C(O)alkynyl; —C(O)aryl; —C(O)benzyl; —C(O)NR³R⁴; —C(S)alkyl; —C(S)alkenyl; —C(S)alkynyl; —C(S)aryl; —C(S)benzyl; —C(S)NR³R⁴; —C(X)YR¹R²;

wherein

X is O, N, or S;

Y is O, CH₂, NH, or S;

Z is CH, N, P, or C;

_____ is a single bond or double bond; wherein if _____ is a double bond, R² or R⁷ is independently O, S, or NH; and n is 1, 2, 3, or 4.

In certain illustrative embodiments, R¹, R³, R⁴, and R⁵ are not all hydrogen.

In certain illustrative embodiments, R¹, R³, R⁴, and R⁵ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO₂, triazolyl.

In one embodiment, R¹ is hydrogen. In another embodiment, R¹ is an alkyl group. In another embodiment, R¹ is an alkoxy group. In another embodiment, R¹ is an alkylalkoxy group.

In another embodiment, R¹ is an alkenyl group. In another embodiment, R¹ is alkynyl group. In another embodiment, R¹ is an aryl group. In another embodiment, R¹ is aryloxy group. In another embodiment, R¹ is benzyl group. In another embodiment, R¹ is heteroaryl group. In another embodiment, R¹ is heterocycloalkyl group. In another embodiment, R¹ is a cycloalkyl group. In another embodiment, R¹ is a benzyl group.

In certain illustrative embodiments, R¹ is a benzyl group substituted with one or more —F groups.

In certain illustrative embodiments, R¹ is a benzyl group substituted with one or more —Cl groups.

In certain illustrative embodiments, R¹ is a benzyl group substituted with one or more —Br groups.

In certain illustrative embodiments, R¹ is a benzyl group substituted with one or more —I groups.

In certain illustrative embodiments, R¹ is a benzyl group substituted with one or more OH groups.

In certain illustrative embodiments, R¹ is a benzyl group substituted with one or more azido groups.

In certain illustrative embodiments, R¹ is a benzyl group substituted with one or more —SH groups.

In certain illustrative embodiments, R¹ is a benzyl group substituted with one or more alkyl.

In certain illustrative embodiments, R¹ is a benzyl group substituted with one or more aryl groups.

In certain illustrative embodiments, R¹ is a benzyl group substituted with one or more heteroalkyl groups.

In certain illustrative embodiments, R¹ is a benzyl group substituted with one or more alkyloxyl groups.

In certain illustrative embodiments, R¹ is a benzyl group substituted with one or more alkylthiol groups.

In certain illustrative embodiments, R¹ is a benzyl group substituted with one or more amino groups.

In certain illustrative embodiments, R¹ is a benzyl group substituted with one or more hydroxylamino groups.

In certain illustrative embodiments, R¹ is a benzyl group substituted with one or more N-alkylamino groups.

In certain illustrative embodiments, R¹ is a benzyl group substituted with one or more —N,N-dialkylamino groups.

In certain illustrative embodiments, R¹ is a benzyl group substituted with one or more —N,N-dimethylamino groups.

In certain illustrative embodiments, R¹ is a benzyl group substituted with one or more acyl groups.

In certain illustrative embodiments, R¹ is a benzyl group substituted with one or more alkyloxycarbonyl groups. groups In certain illustrative embodiments, R¹ is a benzyl group substituted with one or more sulfonyl groups.

In certain illustrative embodiments, R¹ is a benzyl group substituted with one or more urea groups.

In certain illustrative embodiments, R¹ is a benzyl group substituted with one or more —NO₂ groups.

In certain illustrative embodiments, R¹ is a benzyl group substituted with one or more triazolyl groups.

In one embodiment, R³ is hydrogen. In another embodiment, R³ is an alkyl group. In another embodiment, R³ is an alkoxy group. In another embodiment, R³ is an alkylalkoxy group. In another embodiment, R³ is an alkenyl group. In another embodiment, R³ is alkynyl group. In another embodiment, R³ is an aryl group. In another embodiment, R³ is aryloxy group. In another embodiment, R³ is benzyl group. In another embodiment, R³ is heteroaryl group. In another embodiment, R³ is heterocycloalkyl group. In another embodiment, R³ is a cycloalkyl group. In another embodiment, R³ is a benzyl group.

In certain illustrative embodiments, R³ is a benzyl group substituted with one or more —F groups.

In certain illustrative embodiments, R³ is a benzyl group substituted with one or more —Cl groups.

In certain illustrative embodiments, R³ is a benzyl group substituted with one or more —Br groups.

In certain illustrative embodiments, R³ is a benzyl group substituted with one or more —I groups.

In certain illustrative embodiments, R³ is a benzyl group substituted with one or more OH groups.

In certain illustrative embodiments, R³ is a benzyl group substituted with one or more azido groups.

In certain illustrative embodiments, R³ is a benzyl group substituted with one or more —SH groups.

In certain illustrative embodiments, R³ is a benzyl group substituted with one or more alkyl.

In certain illustrative embodiments, R³ is a benzyl group substituted with one or more aryl groups.

In certain illustrative embodiments, $R^3$ is a benzyl group substituted with one or more heteroalkyl groups.

In certain illustrative embodiments, $R^3$ is a benzyl group substituted with one or more alkyloxyl groups.

In certain illustrative embodiments, $R^3$ is a benzyl group substituted with one or more alkylthiol groups.

In certain illustrative embodiments, $R^3$ is a benzyl group substituted with one or more amino groups.

In certain illustrative embodiments, $R^3$ is a benzyl group substituted with one or more hydroxylamino groups.

In certain illustrative embodiments, $R^3$ is a benzyl group substituted with one or more N-alkylamino groups.

In certain illustrative embodiments, $R^3$ is a benzyl group substituted with one or more —N,N-dialkylamino groups.

In certain illustrative embodiments, $R^3$ is a benzyl group substituted with one or more —N,N-dimethylamino groups.

In certain illustrative embodiments, $R^3$ is a benzyl group substituted with one or more acyl groups.

In certain illustrative embodiments, $R^3$ is a benzyl group substituted with one or more alkyloxycarbonyl groups. groups In certain illustrative embodiments, $R^3$ is a benzyl group substituted with one or more sulfonyl groups.

In certain illustrative embodiments, $R^3$ is a benzyl group substituted with one or more urea groups.

In certain illustrative embodiments, $R^3$ is a benzyl group substituted with one or more —NO$_2$ groups.

In certain illustrative embodiments, $R^3$ is a benzyl group substituted with one or more triazolyl groups.

In one embodiment, $R^4$ is hydrogen. In another embodiment, $R^4$ is an alkyl group. In another embodiment, $R^4$ is an alkoxy group. In another embodiment, $R^4$ is an alkylalkoxy group. In another embodiment, $R^4$ is an alkenyl group. In another embodiment, $R^4$ is alkynyl group. In another embodiment, $R^4$ is an aryl group. In another embodiment, $R^4$ is aryloxy group. In another embodiment, $R^4$ is benzyl group. In another embodiment, $R^4$ is heteroaryl group. In another embodiment, $R^4$ is heterocycloalkyl group. In another embodiment, $R^4$ is a cycloalkyl group. In another embodiment, $R^4$ is a benzyl group.

In certain illustrative embodiments, $R^4$ is a benzyl group substituted with one or more —F groups.

In certain illustrative embodiments, $R^4$ is a benzyl group substituted with one or more —Cl groups.

In certain illustrative embodiments, $R^4$ is a benzyl group substituted with one or more —Br groups.

In certain illustrative embodiments, $R^4$ is a benzyl group substituted with one or more —I groups.

In certain illustrative embodiments, $R^4$ is a benzyl group substituted with one or more OH groups.

In certain illustrative embodiments, $R^4$ is a benzyl group substituted with one or more azido groups.

In certain illustrative embodiments, $R^4$ is a benzyl group substituted with one or more —SH groups.

In certain illustrative embodiments, $R^4$ is a benzyl group substituted with one or more alkyl.

In certain illustrative embodiments, $R^4$ is a benzyl group substituted with one or more aryl groups.

In certain illustrative embodiments, $R^4$ is a benzyl group substituted with one or more heteroalkyl groups.

In certain illustrative embodiments, $R^4$ is a benzyl group substituted with one or more alkyloxyl groups.

In certain illustrative embodiments, $R^4$ is a benzyl group substituted with one or more alkylthiol groups.

In certain illustrative embodiments, $R^4$ is a benzyl group substituted with one or more amino groups.

In certain illustrative embodiments, $R^4$ is a benzyl group substituted with one or more hydroxylamino groups.

In certain illustrative embodiments, $R^4$ is a benzyl group substituted with one or more N-alkylamino groups.

In certain illustrative embodiments, $R^4$ is a benzyl group substituted with one or more —N,N-dialkylamino groups.

In certain illustrative embodiments, $R^4$ is a benzyl group substituted with one or more —N,N-dimethylamino groups.

In certain illustrative embodiments, $R^4$ is a benzyl group substituted with one or more acyl groups.

In certain illustrative embodiments, $R^4$ is a benzyl group substituted with one or more alkyloxycarbonyl groups. groups In certain illustrative embodiments, $R^4$ is a benzyl group substituted with one or more sulfonyl groups.

In certain illustrative embodiments, $R^4$ is a benzyl group substituted with one or more urea groups.

In certain illustrative embodiments, $R^4$ is a benzyl group substituted with one or more —NO$_2$ groups.

In certain illustrative embodiments, $R^4$ is a benzyl group substituted with one or more triazolyl groups.

In one embodiment, $R^5$ is hydrogen. In another embodiment, $R^5$ is an alkyl group. In another embodiment, $R^5$ is an alkoxy group. In another embodiment, $R^5$ is an alkylalkoxy group. In another embodiment, $R^5$ is an alkenyl group. In another embodiment, $R^5$ is alkynyl group. In another embodiment, $R^5$ is an aryl group. In another embodiment, $R^5$ is aryloxy group. In another embodiment, $R^5$ is benzyl group. In another embodiment, $R^5$ is heteroaryl group. In another embodiment, $R^5$ is heterocycloalkyl group. In another embodiment, $R^5$ is a cycloalkyl group. In another embodiment, $R^5$ is a benzyl group.

In certain illustrative embodiments, $R^5$ is a benzyl group substituted with one or more —F groups.

In certain illustrative embodiments, $R^5$ is a benzyl group substituted with one or more —Cl groups.

In certain illustrative embodiments, $R^5$ is a benzyl group substituted with one or more —Br groups.

In certain illustrative embodiments, $R^5$ is a benzyl group substituted with one or more —I groups.

In certain illustrative embodiments, $R^5$ is a benzyl group substituted with one or more OH groups.

In certain illustrative embodiments, $R^5$ is a benzyl group substituted with one or more azido groups.

In certain illustrative embodiments, $R^5$ is a benzyl group substituted with one or more —SH groups.

In certain illustrative embodiments, $R^5$ is a benzyl group substituted with one or more alkyl.

In certain illustrative embodiments, $R^5$ is a benzyl group substituted with one or more aryl groups.

In certain illustrative embodiments, $R^5$ is a benzyl group substituted with one or more heteroalkyl groups.

In certain illustrative embodiments, $R^5$ is a benzyl group substituted with one or more alkyloxyl groups.

In certain illustrative embodiments, $R^5$ is a benzyl group substituted with one or more alkylthiol groups.

In certain illustrative embodiments, $R^5$ is a benzyl group substituted with one or more amino groups.

In certain illustrative embodiments, $R^5$ is a benzyl group substituted with one or more hydroxylamino groups.

In certain illustrative embodiments, $R^5$ is a benzyl group substituted with one or more N-alkylamino groups.

In certain illustrative embodiments, $R^5$ is a benzyl group substituted with one or more —N,N-dialkylamino groups.

In certain illustrative embodiments, $R^5$ is a benzyl group substituted with one or more —N,N-dimethylamino groups.

In certain illustrative embodiments, R⁵ is a benzyl group substituted with one or more acyl groups.

In certain illustrative embodiments, R⁵ is a benzyl group substituted with one or more alkyloxycarbonyl groups. groups In certain illustrative embodiments, R⁵ is a benzyl group substituted with one or more sulfonyl groups.

In certain illustrative embodiments, R⁵ is a benzyl group substituted with one or more urea groups.

In certain illustrative embodiments, R⁵ is a benzyl group substituted with one or more —NO₂ groups.

In certain illustrative embodiments, R⁵ is a benzyl group substituted with one or more triazolyl groups.

In another embodiment, the invention encompasses compositions and formulations for treating or preventing diseases or disorders comprising a compound of Formula (IV):

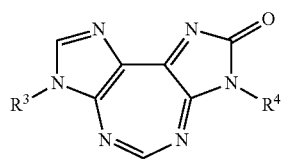

(IV)

or pharmaceutically acceptable salts and prodrugs thereof, wherein

R³ and R⁴ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)R³; —C(S)R³; —S(O)R³; —S(O)₂R³; —C(O)NR⁴R⁵; —C(S)NR³R⁴; —C(X)YR⁵R⁶; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens.

In certain illustrative embodiments, R³ and R⁴ are both not hydrogen.

In certain illustrative embodiments, R³ and R⁴ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO₂, triazolyl.

In one embodiment, R³ is hydrogen. In another embodiment, R³ is an alkyl group. In another embodiment, R³ is an alkoxy group. In another embodiment, R³ is an alkylalkoxy group. In another embodiment, R³ is an alkenyl group. In another embodiment, R³ is alkynyl group. In another embodiment, R³ is an aryl group. In another embodiment, R³ is aryloxy group. In another embodiment, R³ is benzyl group. In another embodiment, R³ is heteroaryl group. In another embodiment, R³ is heterocycloalkyl group. In another embodiment, R³ is a cycloalkyl group. In another embodiment, R³ is a benzyl group.

In certain illustrative embodiments, R³ is a benzyl group substituted with one or more —F groups.

In certain illustrative embodiments, R³ is a benzyl group substituted with one or more —Cl groups.

In certain illustrative embodiments, R³ is a benzyl group substituted with one or more —Br groups.

In certain illustrative embodiments, R³ is a benzyl group substituted with one or more —I groups.

In certain illustrative embodiments, R³ is a benzyl group substituted with one or more OH groups.

In certain illustrative embodiments, R³ is a benzyl group substituted with one or more azido groups.

In certain illustrative embodiments, R³ is a benzyl group substituted with one or more —SH groups.

In certain illustrative embodiments, R³ is a benzyl group substituted with one or more alkyl.

In certain illustrative embodiments, R³ is a benzyl group substituted with one or more aryl groups.

In certain illustrative embodiments, R³ is a benzyl group substituted with one or more heteroalkyl groups.

In certain illustrative embodiments, R³ is a benzyl group substituted with one or more alkyloxyl groups.

In certain illustrative embodiments, R³ is a benzyl group substituted with one or more alkylthiol groups.

In certain illustrative embodiments, R³ is a benzyl group substituted with one or more amino groups.

In certain illustrative embodiments, R³ is a benzyl group substituted with one or more hydroxylamino groups.

In certain illustrative embodiments, R³ is a benzyl group substituted with one or more N-alkylamino groups.

In certain illustrative embodiments, R³ is a benzyl group substituted with one or more —N,N-dialkylamino groups.

In certain illustrative embodiments, R³ is a benzyl group substituted with one or more —N,N-dimethylamino groups.

In certain illustrative embodiments, R³ is a benzyl group substituted with one or more acyl groups.

In certain illustrative embodiments, R³ is a benzyl group substituted with one or more alkyloxycarbonyl groups. groups In certain illustrative embodiments, R³ is a benzyl group substituted with one or more sulfonyl groups.

In certain illustrative embodiments, R³ is a benzyl group substituted with one or more urea groups.

In certain illustrative embodiments, R³ is a benzyl group substituted with one or more —NO₂ groups.

In certain illustrative embodiments, R³ is a benzyl group substituted with one or more triazolyl groups.

In one embodiment, R⁴ is hydrogen. In another embodiment, R⁴ is an alkyl group. In another embodiment, R⁴ is an alkoxy group. In another embodiment, R⁴ is an alkylalkoxy group. In another embodiment, R⁴ is an alkenyl group. In another embodiment, R⁴ is alkynyl group. In another embodiment, R⁴ is an aryl group. In another embodiment, R⁴ is aryloxy group. In another embodiment, R⁴ is benzyl group. In another embodiment, R⁴ is heteroaryl group. In another embodiment, R⁴ is heterocycloalkyl group. In another embodiment, R⁴ is a cycloalkyl group. In another embodiment, R⁴ is a benzyl group.

In certain illustrative embodiments, R⁴ is a benzyl group substituted with one or more —F groups.

In certain illustrative embodiments, R⁴ is a benzyl group substituted with one or more —Cl groups.

In certain illustrative embodiments, R⁴ is a benzyl group substituted with one or more —Br groups.

In certain illustrative embodiments, R⁴ is a benzyl group substituted with one or more —I groups.

In certain illustrative embodiments, R⁴ is a benzyl group substituted with one or more OH groups.

In certain illustrative embodiments, R⁴ is a benzyl group substituted with one or more azido groups.

In certain illustrative embodiments, R⁴ is a benzyl group substituted with one or more —SH groups.

In certain illustrative embodiments, R⁴ is a benzyl group substituted with one or more alkyl.

In certain illustrative embodiments, R⁴ is a benzyl group substituted with one or more aryl groups.

In certain illustrative embodiments, R⁴ is a benzyl group substituted with one or more heteroalkyl groups.

In certain illustrative embodiments, R⁴ is a benzyl group substituted with one or more alkyloxyl groups.

In certain illustrative embodiments, R⁴ is a benzyl group substituted with one or more alkylthiol groups.

In certain illustrative embodiments, R⁴ is a benzyl group substituted with one or more amino groups.

In certain illustrative embodiments, R⁴ is a benzyl group substituted with one or more hydroxylamino groups.

In certain illustrative embodiments, R⁴ is a benzyl group substituted with one or more N-alkylamino groups.

In certain illustrative embodiments, R⁴ is a benzyl group substituted with one or more —N,N-dialkylamino groups.

In certain illustrative embodiments, R⁴ is a benzyl group substituted with one or more —N,N-dimethylamino groups.

In certain illustrative embodiments, R⁴ is a benzyl group substituted with one or more acyl groups.

In certain illustrative embodiments, R⁴ is a benzyl group substituted with one or more alkyloxycarbonyl groups. groups In certain illustrative embodiments, R⁴ is a benzyl group substituted with one or more sulfonyl groups.

In certain illustrative embodiments, R⁴ is a benzyl group substituted with one or more urea groups.

In certain illustrative embodiments, R⁴ is a benzyl group substituted with one or more —NO₂ groups.

In certain illustrative embodiments, R⁴ is a benzyl group substituted with one or more triazolyl groups.

In another embodiment, the invention encompasses compositions and formulations for treating or preventing diseases or disorders comprising a compound of Formula (V):

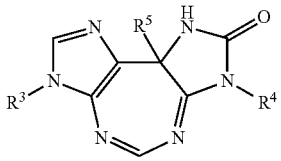

(V)

or pharmaceutically acceptable salts and prodrugs thereof, wherein

R³, R⁴, and R⁵ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)R³; —C(S)R³; —S(O)R³; —S(O)₂R³; —C(O)NR⁴R⁵; —C(S)NR³R⁴; —C(X)YR⁵R⁶; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens.

In certain illustrative embodiments, R³, R⁴, and R⁵ are not each hydrogen.

In certain illustrative embodiments, R³, R⁴, and R⁵ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO₂, triazolyl.

In one embodiment, R³ is hydrogen. In another embodiment, R³ is an alkyl group. In another embodiment, R³ is an alkoxy group. In another embodiment, R³ is an alkylalkoxy group. In another embodiment, R³ is an alkenyl group. In another embodiment, R³ is alkynyl group. In another embodiment, R³ is an aryl group. In another embodiment, R³ is aryloxy group. In another embodiment, R³ is benzyl group. In another embodiment, R³ is heteroaryl group. In another embodiment, R³ is heterocycloalkyl group. In another embodiment, R³ is a cycloalkyl group. In another embodiment, R³ is a benzyl group.

In certain illustrative embodiments, R³ is a benzyl group substituted with one or more —F groups.

In certain illustrative embodiments, R³ is a benzyl group substituted with one or more —Cl groups.

In certain illustrative embodiments, R³ is a benzyl group substituted with one or more —Br groups.

In certain illustrative embodiments, R³ is a benzyl group substituted with one or more —I groups.

In certain illustrative embodiments, R³ is a benzyl group substituted with one or more OH groups.

In certain illustrative embodiments, R³ is a benzyl group substituted with one or more azido groups.

In certain illustrative embodiments, R³ is a benzyl group substituted with one or more —SH groups.

In certain illustrative embodiments, R³ is a benzyl group substituted with one or more alkyl.

In certain illustrative embodiments, R³ is a benzyl group substituted with one or more aryl groups.

In certain illustrative embodiments, R³ is a benzyl group substituted with one or more heteroalkyl groups.

In certain illustrative embodiments, R³ is a benzyl group substituted with one or more alkyloxyl groups.

In certain illustrative embodiments, R³ is a benzyl group substituted with one or more alkylthiol groups.

In certain illustrative embodiments, R³ is a benzyl group substituted with one or more amino groups.

In certain illustrative embodiments, R³ is a benzyl group substituted with one or more hydroxylamino groups.

In certain illustrative embodiments, R³ is a benzyl group substituted with one or more N-alkylamino groups.

In certain illustrative embodiments, R³ is a benzyl group substituted with one or more —N,N-dialkylamino groups.

In certain illustrative embodiments, R³ is a benzyl group substituted with one or more —N,N-dimethylamino groups.

In certain illustrative embodiments, R³ is a benzyl group substituted with one or more acyl groups.

In certain illustrative embodiments, R³ is a benzyl group substituted with one or more alkyloxycarbonyl groups. groups In certain illustrative embodiments, R³ is a benzyl group substituted with one or more sulfonyl groups.

In certain illustrative embodiments, R³ is a benzyl group substituted with one or more urea groups.

In certain illustrative embodiments, R³ is a benzyl group substituted with one or more —NO₂ groups.

In certain illustrative embodiments, R³ is a benzyl group substituted with one or more triazolyl groups.

In one embodiment, R⁴ is hydrogen. In another embodiment, R⁴ is an alkyl group. In another embodiment, R⁴ is an alkoxy group. In another embodiment, R⁴ is an alkylalkoxy group. In another embodiment, R⁴ is an alkenyl group. In another embodiment, R⁴ is alkynyl group. In another embodiment, R⁴ is an aryl group. In another embodiment, R⁴ is aryloxy group. In another embodiment, $R^4$ is benzyl group. In another embodiment, $R^4$ is heteroaryl group. In another embodiment, $R^4$ is heterocycloalkyl group. In another embodiment, $R^4$ is a cycloalkyl group. In another embodiment, $R^4$ is a benzyl group.

In certain illustrative embodiments, $R^4$ is a benzyl group substituted with one or more —F groups.

In certain illustrative embodiments, $R^4$ is a benzyl group substituted with one or more —Cl groups.

In certain illustrative embodiments, $R^4$ is a benzyl group substituted with one or more —Br groups.

In certain illustrative embodiments, $R^4$ is a benzyl group substituted with one or more —I groups.

In certain illustrative embodiments, $R^4$ is a benzyl group substituted with one or more —OH groups.

In certain illustrative embodiments, $R^4$ is a benzyl group substituted with one or more azido groups.

In certain illustrative embodiments, $R^4$ is a benzyl group substituted with one or more —SH groups.

In certain illustrative embodiments, $R^4$ is a benzyl group substituted with one or more alkyl.

In certain illustrative embodiments, $R^4$ is a benzyl group substituted with one or more aryl groups.

In certain illustrative embodiments, $R^4$ is a benzyl group substituted with one or more heteroalkyl groups.

In certain illustrative embodiments, $R^4$ is a benzyl group substituted with one or more alkyloxyl groups.

In certain illustrative embodiments, $R^4$ is a benzyl group substituted with one or more alkylthiol groups.

In certain illustrative embodiments, $R^4$ is a benzyl group substituted with one or more amino groups.

In certain illustrative embodiments, $R^4$ is a benzyl group substituted with one or more hydroxylamino groups.

In certain illustrative embodiments, $R^4$ is a benzyl group substituted with one or more N-alkylamino groups.

In certain illustrative embodiments; $R^4$ is a benzyl group substituted with one or more —N,N-dialkylamino groups.

In certain illustrative embodiments, $R^4$ is a benzyl group substituted with one or more —N,N-dimethylamino groups.

In certain illustrative embodiments, $R^4$ is a benzyl group substituted with one or more acyl groups.

In certain illustrative embodiments, $R^4$ is a benzyl group substituted with one or more alkyloxycarbonyl groups. groups In certain illustrative embodiments, $R^4$ is a benzyl group substituted with one or more sulfonyl groups.

In certain illustrative embodiments, $R^4$ is a benzyl group substituted with one or more urea groups.

In certain illustrative embodiments, $R^4$ is a benzyl group substituted with one or more —$NO_2$ groups.

In certain illustrative embodiments, $R^4$ is a benzyl group substituted with one or more triazolyl groups.

In one embodiment, $R^5$ is hydrogen. In another embodiment, $R^5$ is an alkyl group. In another embodiment, $R^5$ is an alkoxy group. In another embodiment, $R^5$ is an alkylalkoxy group.

In another embodiment, $R^5$ is an alkenyl group. In another embodiment, $R^5$ is alkynyl group. In another embodiment, $R^5$ is an aryl group. In another embodiment, $R^5$ is aryloxy group. In another embodiment, $R^5$ is benzyl group. In another embodiment, $R^5$ is heteroaryl group. In another embodiment, $R^5$ is heterocycloalkyl group. In another embodiment, $R^5$ is a cycloalkyl group. In another embodiment, $R^5$ is a benzyl group.

In certain illustrative embodiments, $R^5$ is a phenyl or a benzyl group substituted with one or more —F groups.

In certain illustrative embodiments, $R^5$ is a phenyl or a benzyl group substituted with one or more —Cl groups.

In certain illustrative embodiments, $R^5$ is a phenyl or a benzyl group substituted with one or more —Br groups.

In certain illustrative embodiments, $R^5$ is a phenyl or a benzyl group substituted with one or more —I groups.

In certain illustrative embodiments, $R^5$ is a phenyl or a benzyl group substituted with one or more OH groups.

In certain illustrative embodiments, $R^5$ is a phenyl or a benzyl group substituted with one or more azido groups.

In certain illustrative embodiments, $R^5$ is a phenyl or a benzyl group substituted with one or more —SH groups.

In certain illustrative embodiments, $R^5$ is a phenyl or a benzyl group substituted with one or more alkyl.

In certain illustrative embodiments, $R^5$ is a phenyl or a benzyl group substituted with one or more aryl groups.

In certain illustrative embodiments, $R^5$ is a phenyl or a benzyl group substituted with one or more heteroalkyl groups.

In certain illustrative embodiments, $R^5$ is a phenyl or a benzyl group substituted with one or more alkyloxyl groups.

In certain illustrative embodiments, $R^5$ is a phenyl or a benzyl group substituted with one or more alkylthiol groups.

In certain illustrative embodiments, $R^5$ is a phenyl or a benzyl group substituted with one or more amino groups.

In certain illustrative embodiments, $R^5$ is a phenyl or a benzyl group substituted with one or more hydroxylamino groups.

In certain illustrative embodiments, $R^5$ is a phenyl or a benzyl group substituted with one or more N-alkylamino groups.

In certain illustrative embodiments, $R^5$ is a phenyl or a benzyl group substituted with one or more —N,N-dialkylamino groups.

In certain illustrative embodiments, $R^5$ is a phenyl or a benzyl group substituted with one or more —N,N-dimethylamino groups.

In certain illustrative embodiments, $R^5$ is a phenyl or a benzyl group substituted with one or more acyl groups.

In certain illustrative embodiments, $R^5$ is a phenyl or a benzyl group substituted with one or more alkyloxycarbonyl groups. groups In certain illustrative embodiments, $R^5$ is a phenyl or a benzyl group substituted with one or more sulfonyl groups.

In certain illustrative embodiments, $R^5$ is a phenyl or a benzyl group substituted with one or more urea groups.

In certain illustrative embodiments, $R^5$ is a phenyl or a benzyl group substituted with one or more —$NO_2$ groups.

In certain illustrative embodiments, $R^5$ is a phenyl or a benzyl group substituted with one or more triazolyl groups.

Illustrative examples of compounds that are encompassed by Formulas I-V and that are useful in the methods of the invention include, but are not limited to:

33 34
3
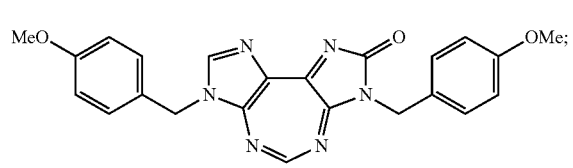
11
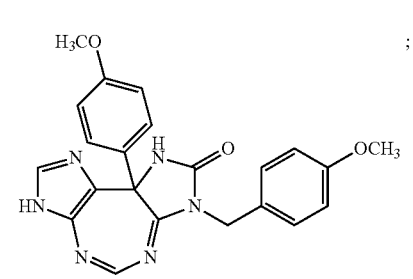
12
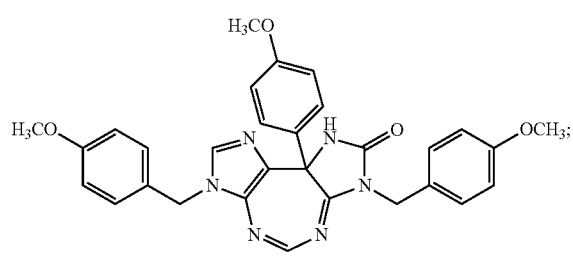
13
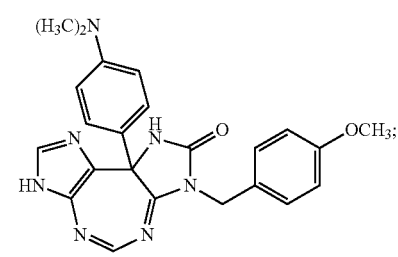
14
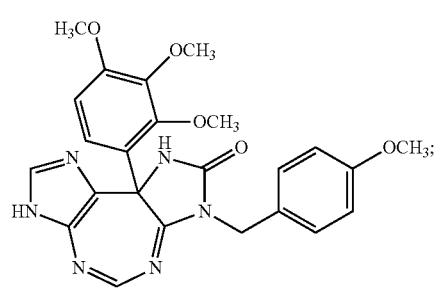
21
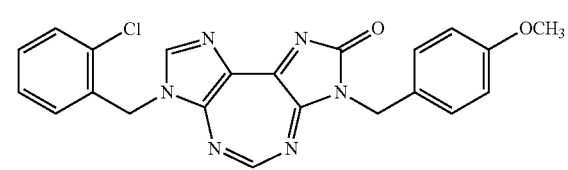
23
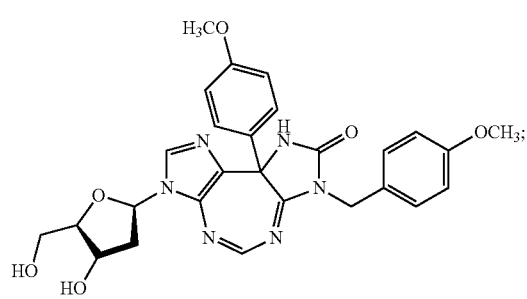
25
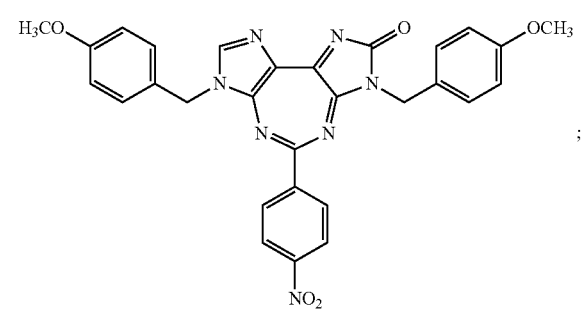
27
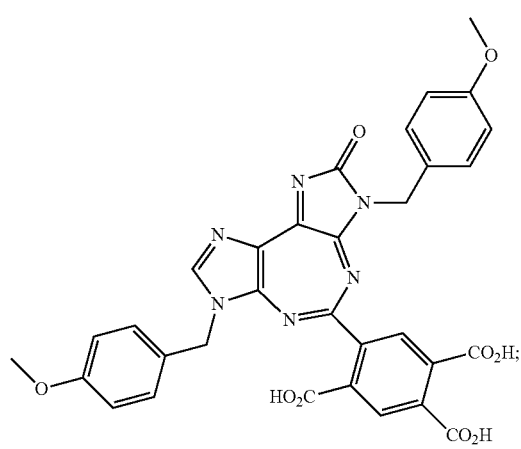
101
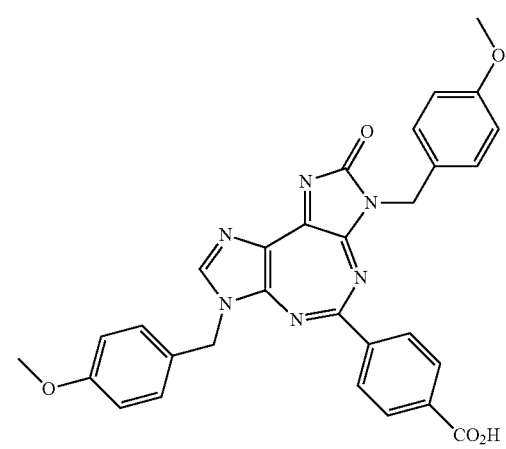

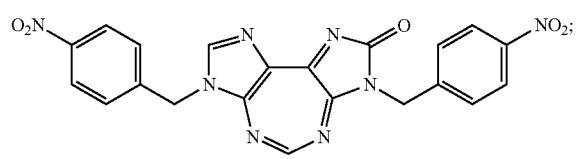
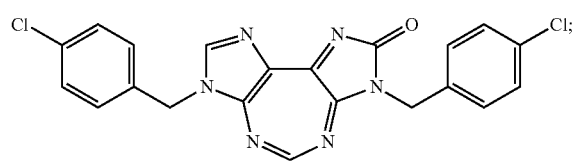
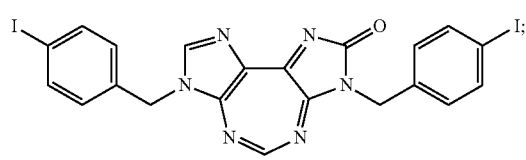
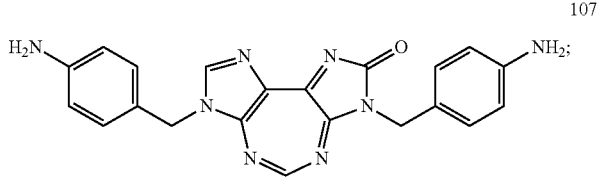
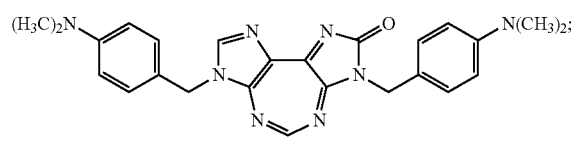
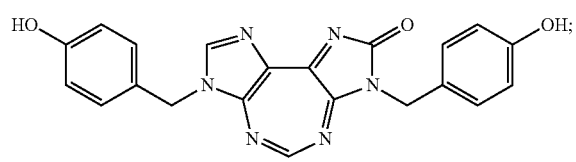
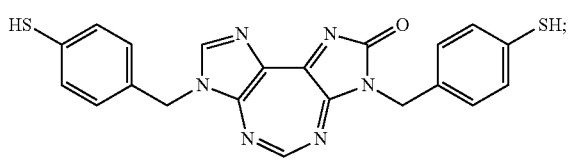
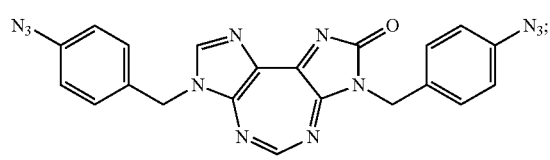
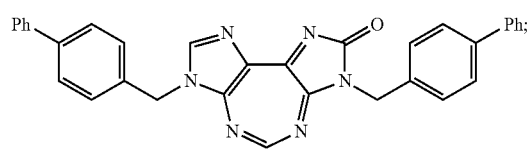
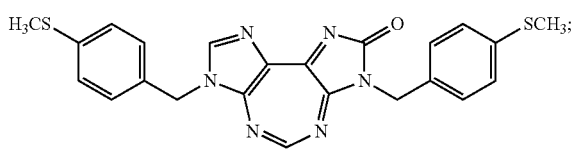
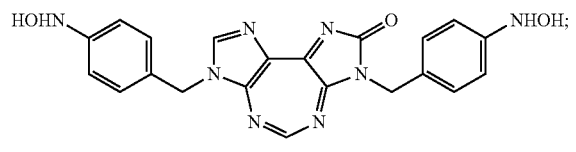
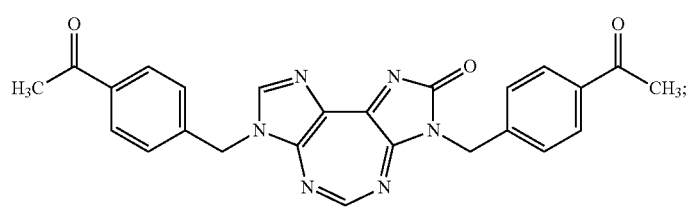

-continued
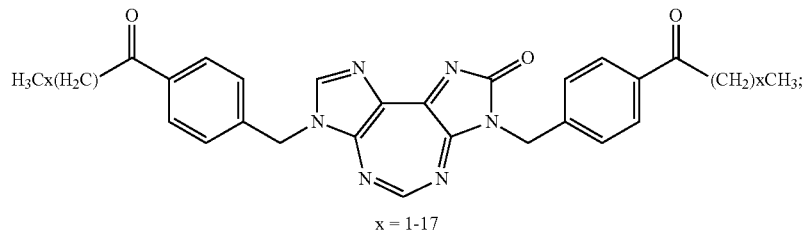
119
x = 1-17
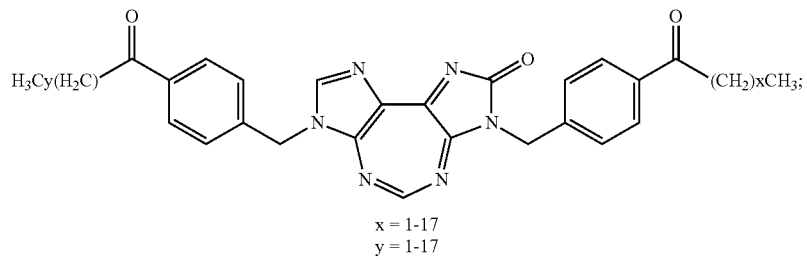
120
x = 1-17
y = 1-17
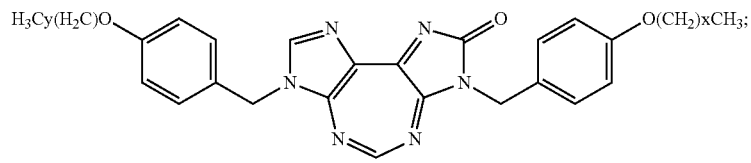
121
x = 1-10
y = 1-10
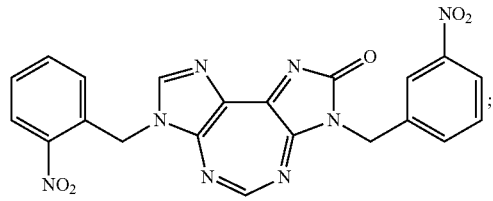
122
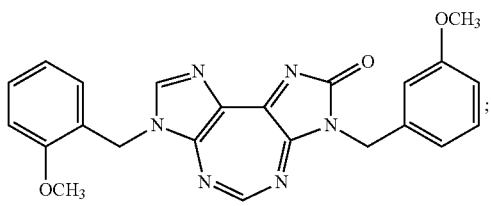
123
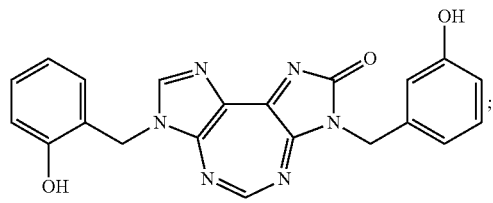
124
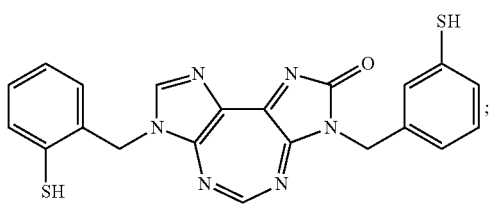
125
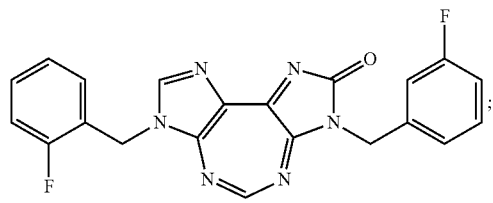
126
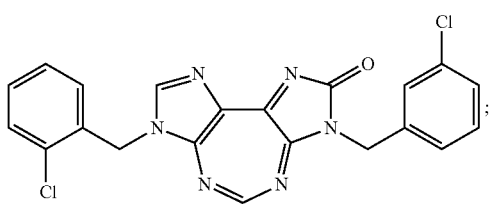
127
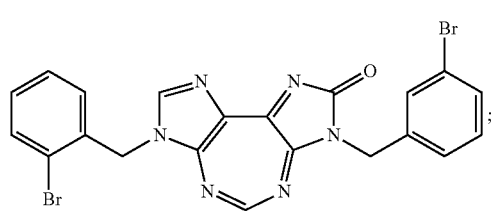
128
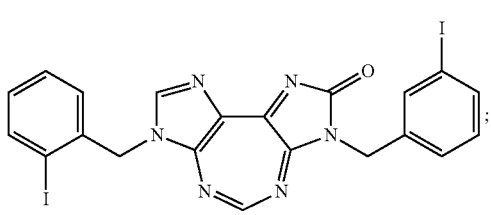
129

-continued
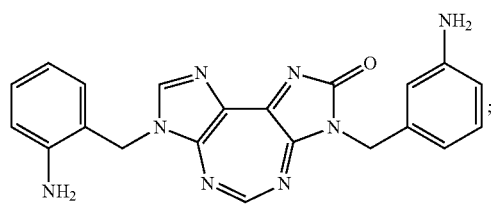
130
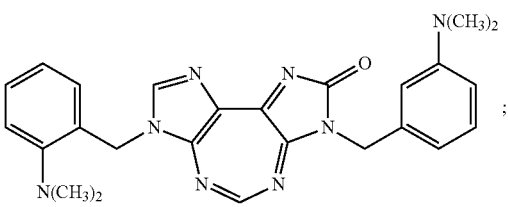
131
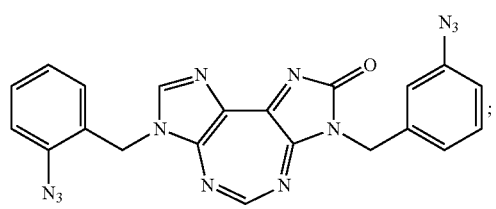
132
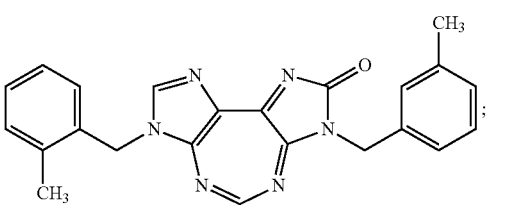
133
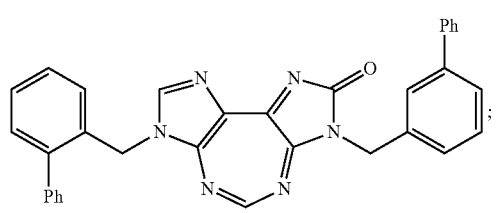
134
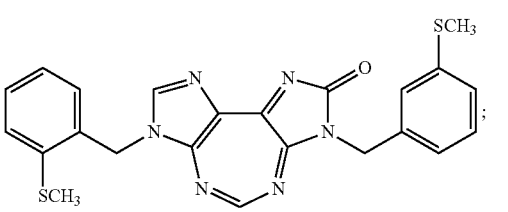
135
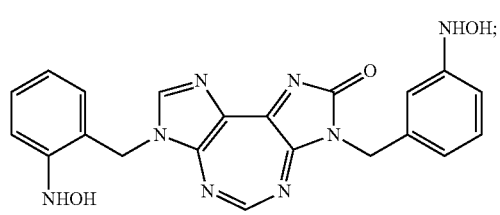
136
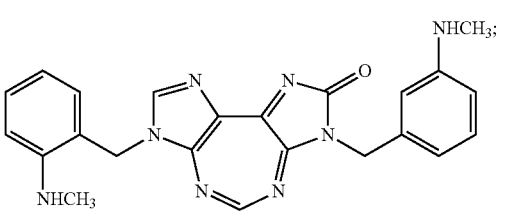
137
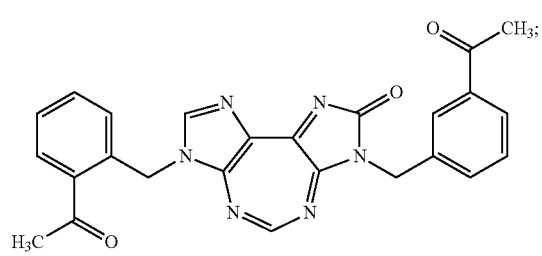
138
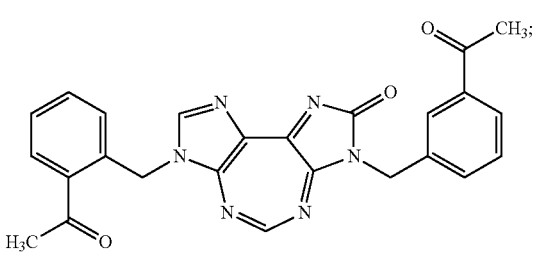
139
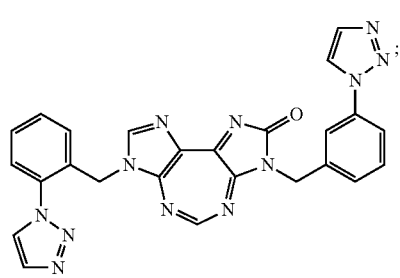
140
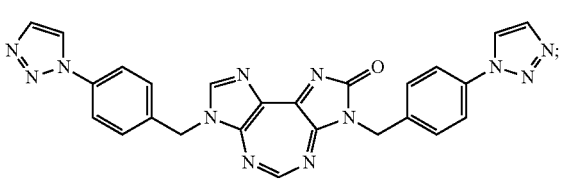
141
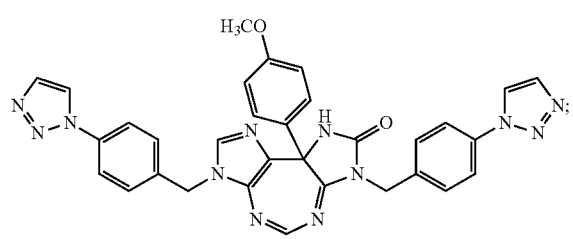
142
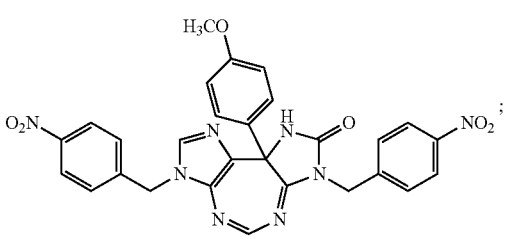
143

-continued
144
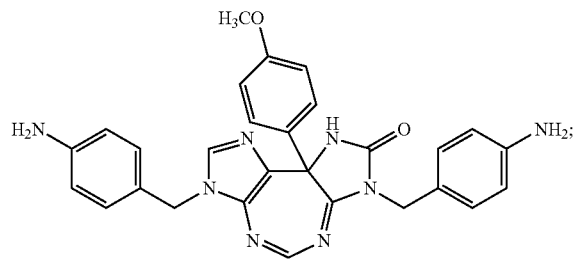
145
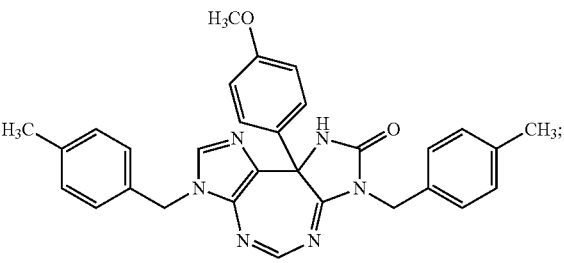
146
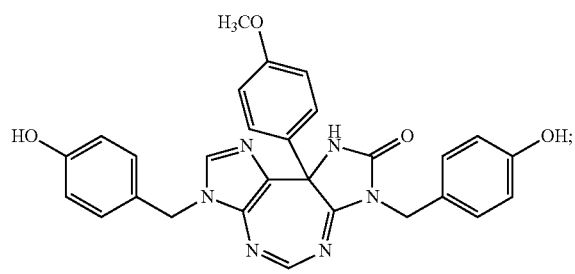
147
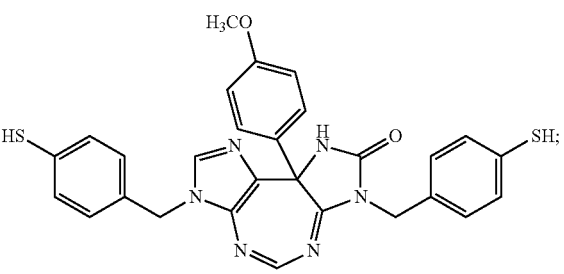
148
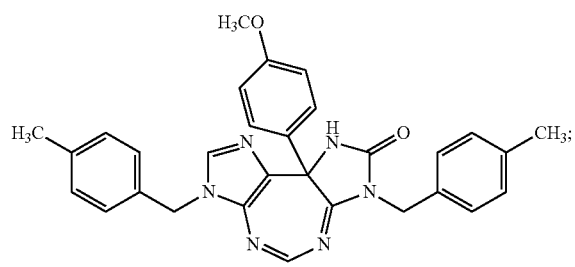
149
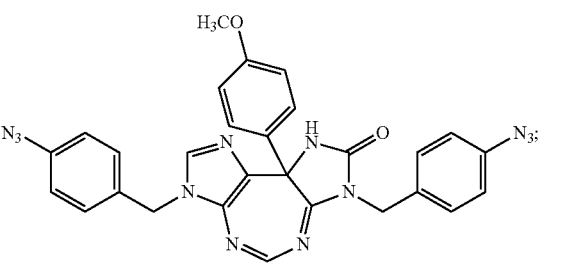
150
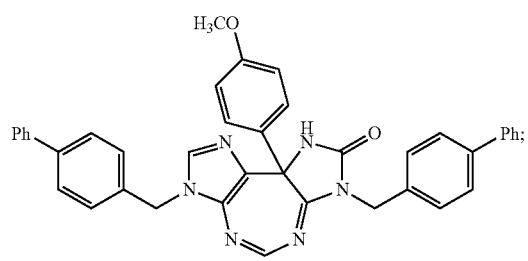
151
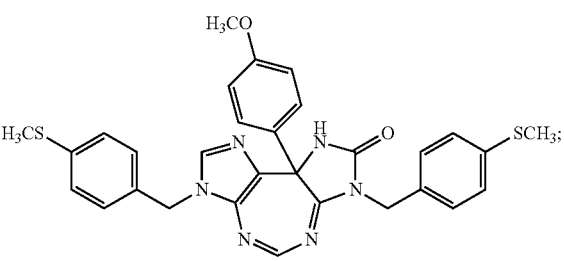
152
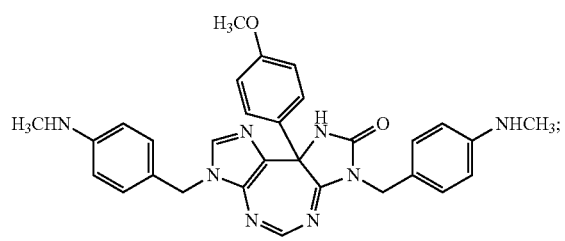
153
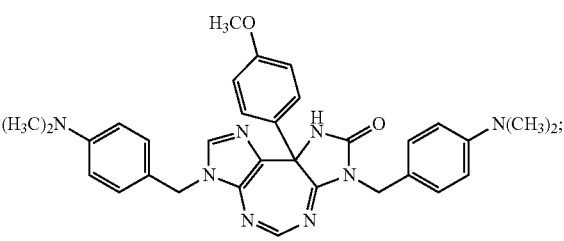
154
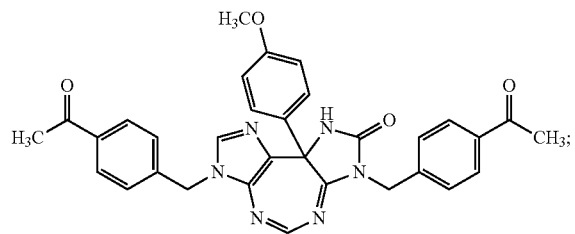
155
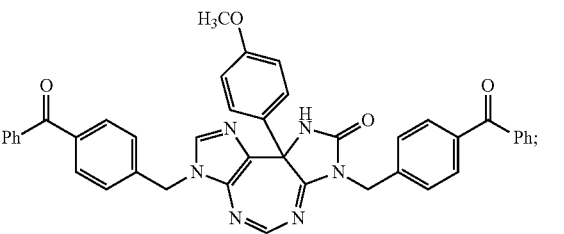

-continued
| | |
|---|---|
| 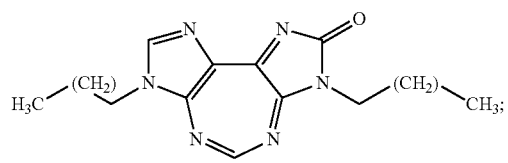 156 | 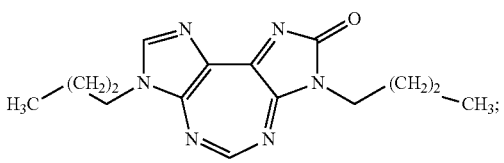 157 |
| 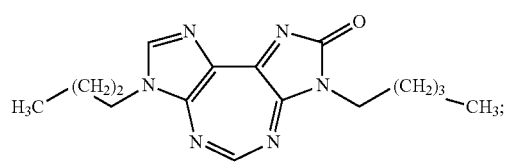 158 | 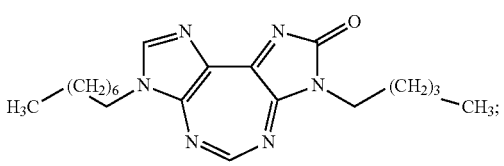 159 |
| 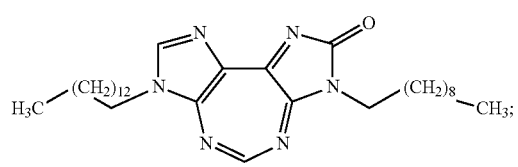 160 | 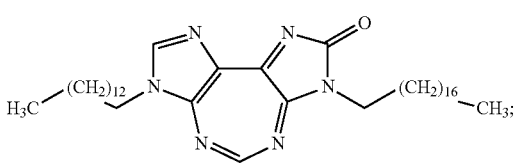 161 |
| 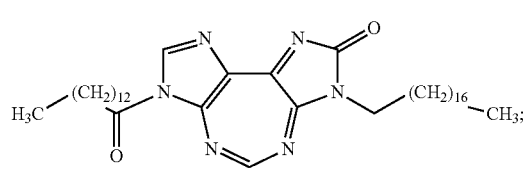 162 | 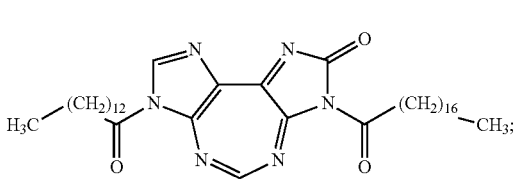 163 |
| 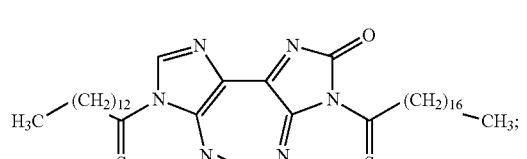 164 | 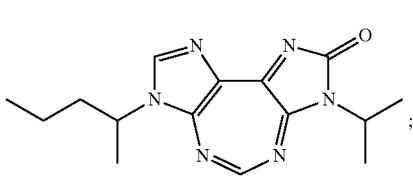 165 |
| 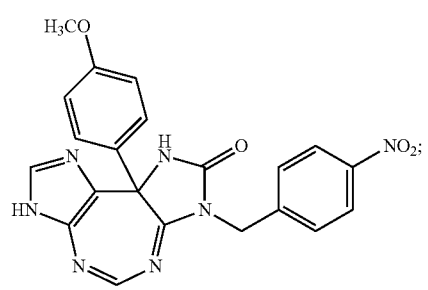 166 | 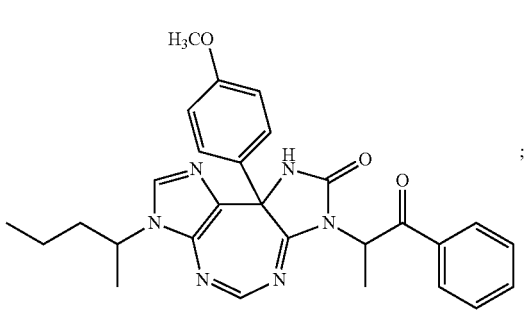 167 |
| 168 | 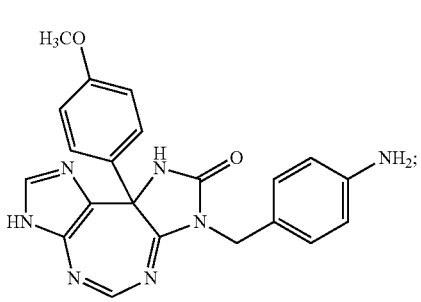 169 |

-continued
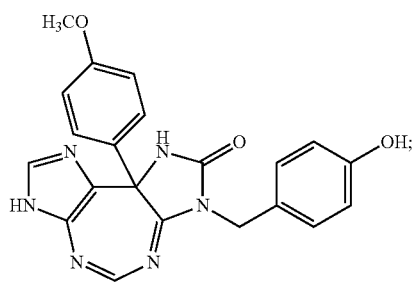
170
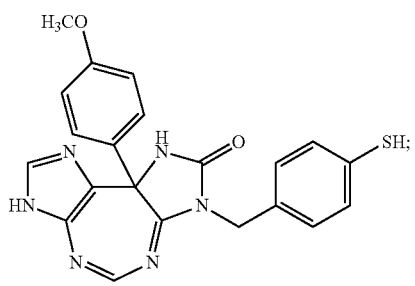
171
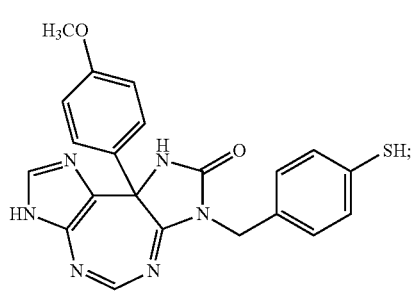
172
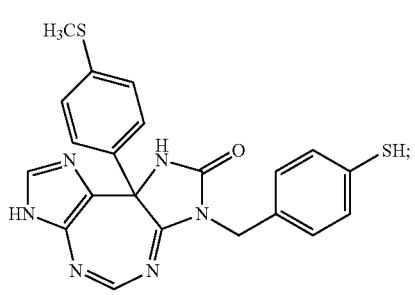
173
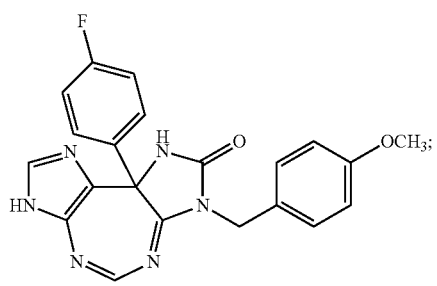
174
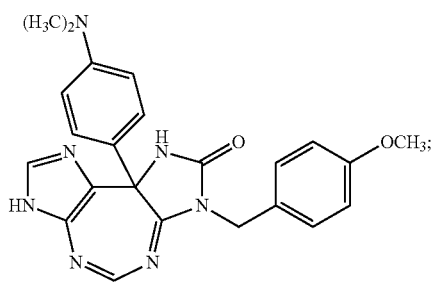
175
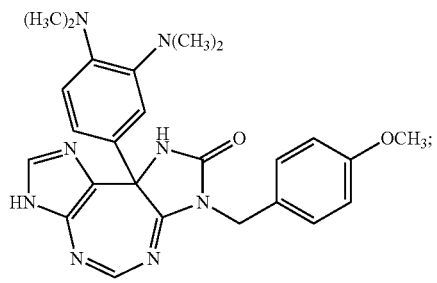
176
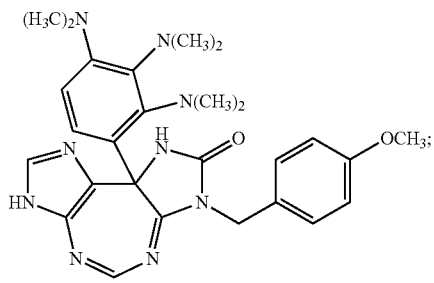
177
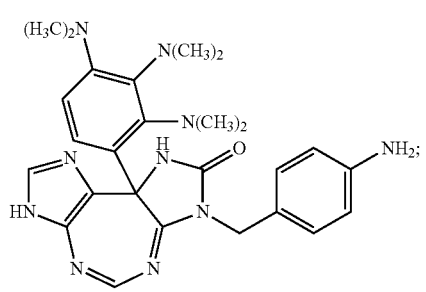
178
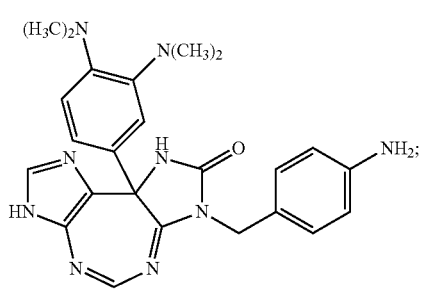
179

-continued
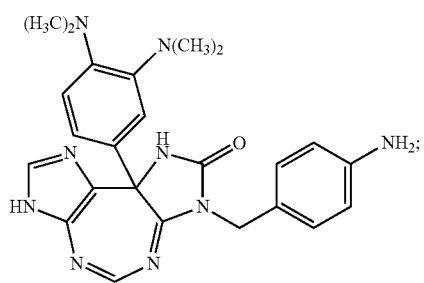
180
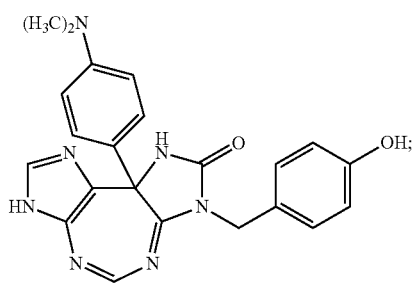
181
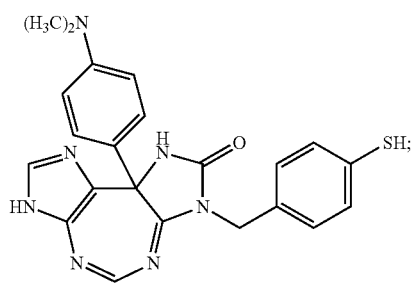
182
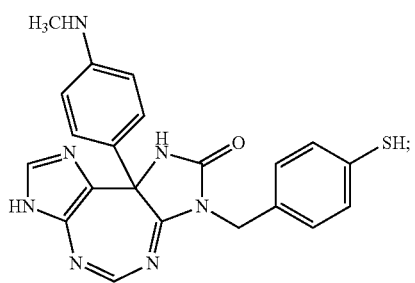
183
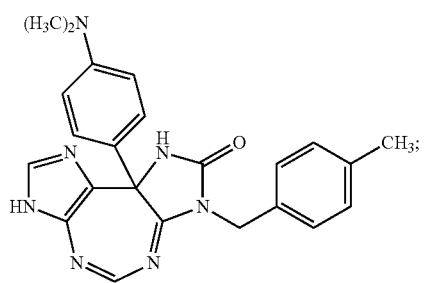
184
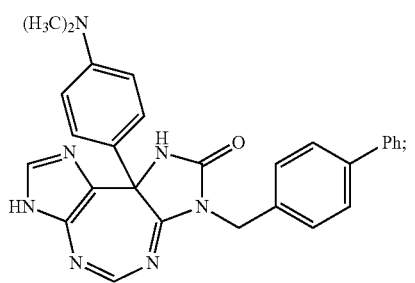
185
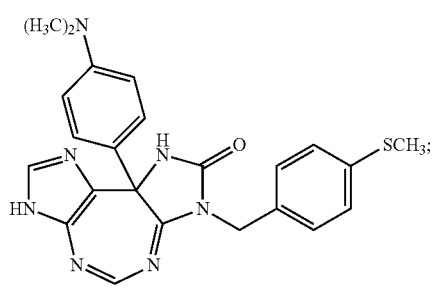
186
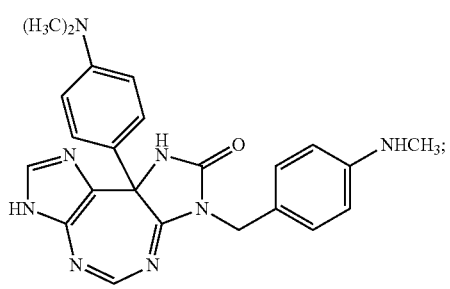
187

-continued

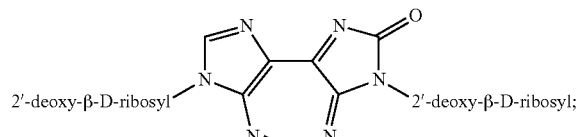
188
2'-deoxy-β-D-ribosyl ... 2'-deoxy-β-D-ribosyl;

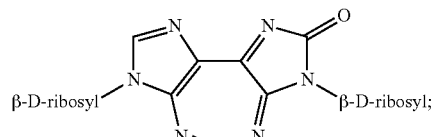
189
β-D-ribosyl ... β-D-ribosyl;

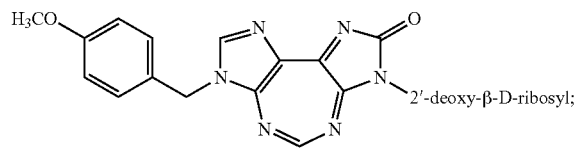
190
2'-deoxy-β-D-ribosyl;

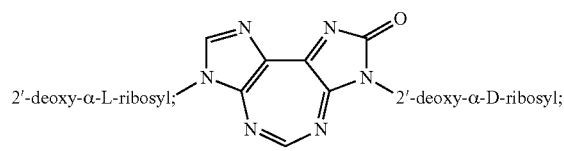
191
2'-deoxy-α-L-ribosyl; ... 2'-deoxy-α-D-ribosyl;

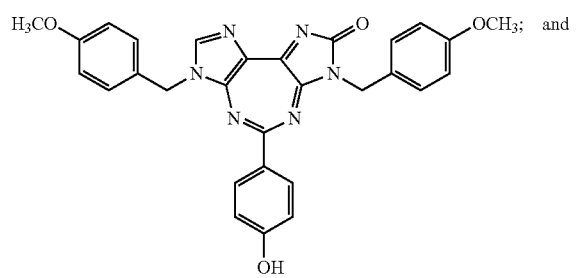
192
and

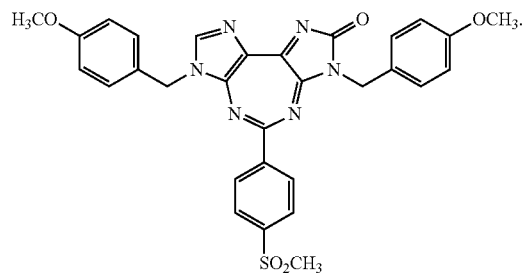
193

It will be understood that above compounds are illustrative only and not intended to limit the scope of the claims to only those compounds.

The compounds of the invention can be synthesized by organic chemistry techniques known to those of ordinary skill in the art, for example, generally as described in the synthesis in Scheme 1 below.

Scheme 1

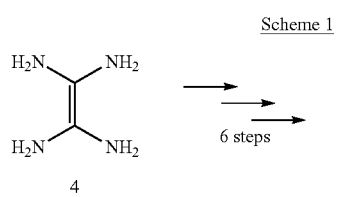

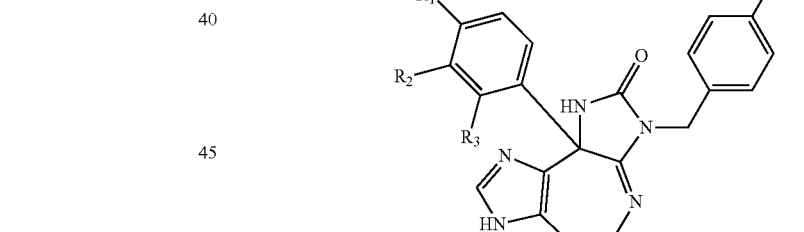

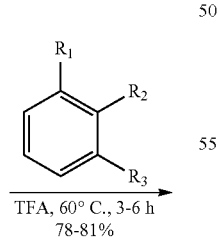

11; $R_1$ = OMe; $R_2$ = $R_3$ = H
13; $R_1$ = N(Me)$_2$; $R_2$ = $R_3$ = H
14; $R_1$ = $R_2$ = $R_3$ = OMe

An examination of the literature revealed that the target 5:7:5 heterocyclic ring system is yet unknown. Scheme 2 illustrates the first entry into such a ring system employing an illustrative representative example 3, containing a removable p-methoxybenzyl (PMB) group attached to each of the two imidazole rings.

Scheme 2
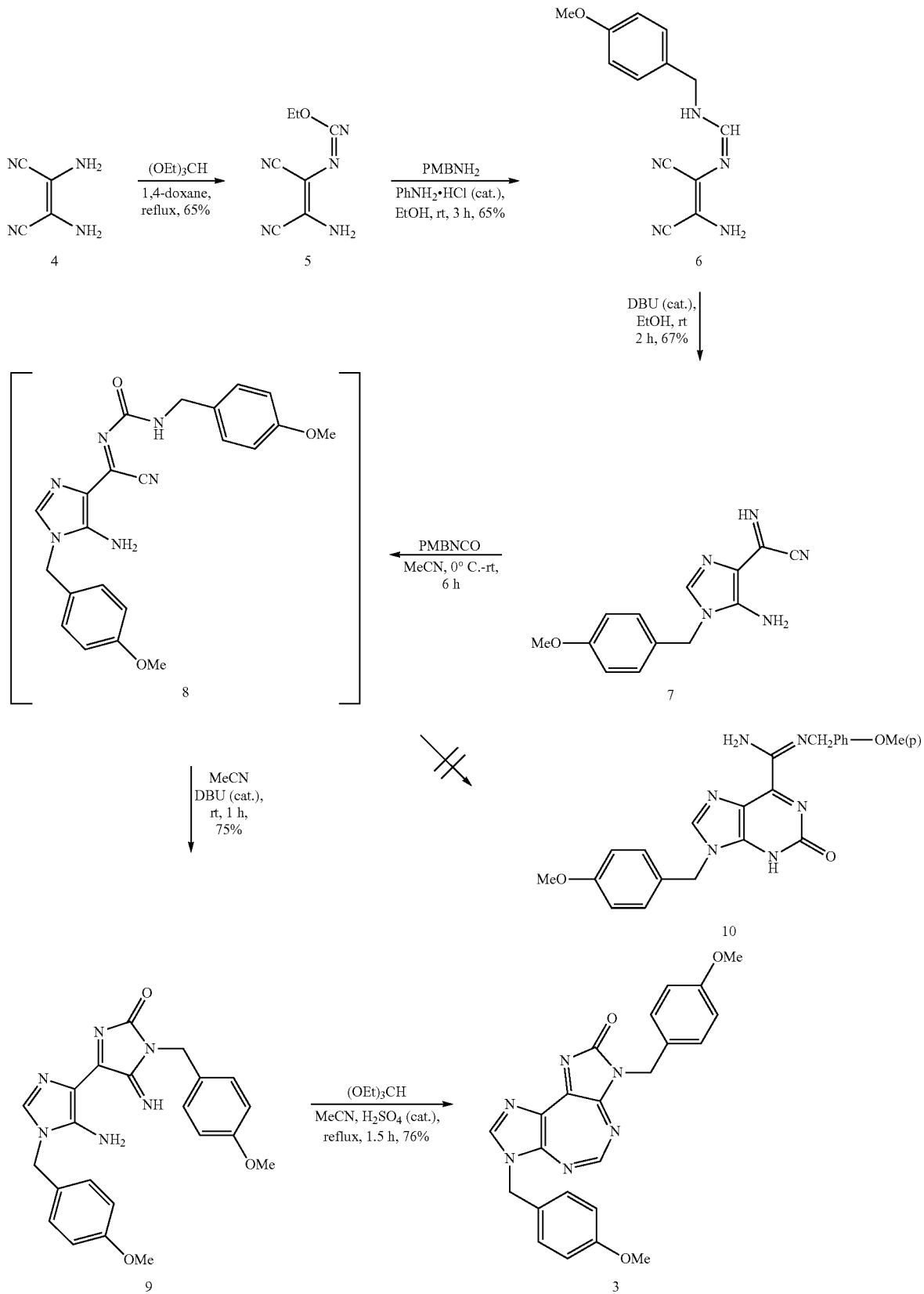

Generally, an illustrative compound of the invention can be synthesized by heating diaminomaleonitrile 4 with triethyl orthoformate in dioxane yielded formimidate 5. (See, e.g., Sun, Z.; Hosmane, R. S. *Synth. Commun.* 2001, 31, 549). The reaction of 5 with p-methoxybenzylamine catalyzed by aniline hydrochloride formed formimidine 6 (See, e.g., Yahya-Zadeh, A.; Booth, B. L. *Synth. Commun.* 2001, 31, 3225), which underwent intramolecular cyclization in the presence of DBU to form imidazole derivative 7. (See, e.g., Yahyazadeh, A.; Sharifi, Z. *Phosphorus, Sulfur, Silicon, Relat. Elem.* 2006, 181, 1339). The treatment of latter with p-methoxybenzyl isocyanate resulted into a mixture of urea 8 and 9. (See, e.g., Dias, A. M.; Cabral, I.; Proenca, M. F.; Booth, B. L. *J. Org. Chem.* 2002, 67, 5546). The complete coversion of 8 into 9 was achieved by treating the mixture with DBU in acetonitrile. (Id.). The reaction of isolated 9 with triethyl orthoformate yielded the target heterocycle 3. In certain embodiments, the reported rearrangement of a compound such as 8 into an oxopurine such as 10 was not observed. In an illustrative embodiment, a rearrangement has been limited to the use of N-tosylisocyanate, but not others. (Id.). This was further corroborated by the facile ring-closure of 9 to form 3. All intermediates and final product were fully characterized by spectroscopic and analytical data. (See Example Section).

The core tricyclic structure of 3 containing 14π electrons is aromatic by the Hückel rule. Nevertheless, with six nitrogen atoms and a conjugated carbonyl group present in the heterocyclic ring system, compound 3 is considerably electrophilic. In order to explore this aspect a little further, compound 3 was reacted with a few carbon and nitrogen nucleophiles. Illustrative examples of the carbon nucleophiles attempted include anisole, N,N-dimethylaniline, and 1,2,3-trimethoxybenzene, all of which contain electron-donating substituent(s) on their aromatic rings. Thus, the reaction of a mixture of 3 (1 mmol), anisole (5 mL), and TFA (10 mL) at 60° C. for 3 h (Scheme 3) formed a novel product 11 which was isolated, purified (81%) and characterised.

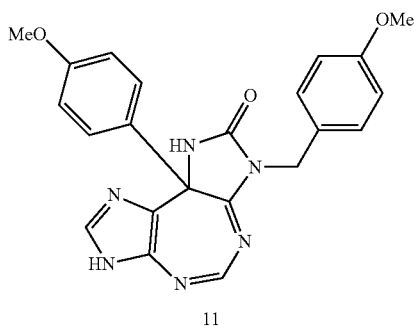

11

In order to illucidate the pathway of formation of 11 from 3, the latter (1 mmol) was treated with a mixture of TFA (10 mL) and anisole (5 mL) 16 at rt for 12 h (Scheme 4), which yielded a mixture of 11 (10%) and 12 (60%) which was found to be an adduct of anisole by spectroscopic and analytical data. Surprisingly, 12 was converted into 11 when heated with TFA at 60° C. for 1 h. This suggests that the reaction proceeds by first addition of anisole, followed by selective cleavage of the N-3 PMB group. As TFA is often used to remove the PMB group from heterocyclic rings, the observed deprotection of one of the imidazole rings under these conditions is not totally surprising. (See, e.g., Miki, Y.; Hachiken, H.; Kashima, Y.; Sugimura, W.; Yanase, N. *Heterocycles* 1998, 48, 1).

Scheme 4

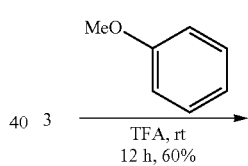

3 → TFA, rt 12 h, 60%

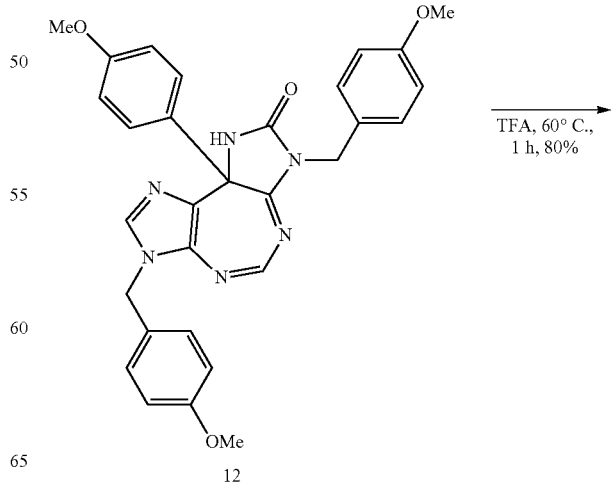

12

→ TFA, 60° C., 1 h, 80%

Scheme 3

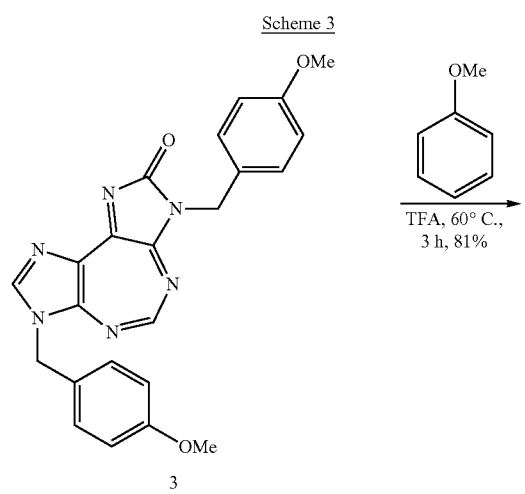

3

-continued

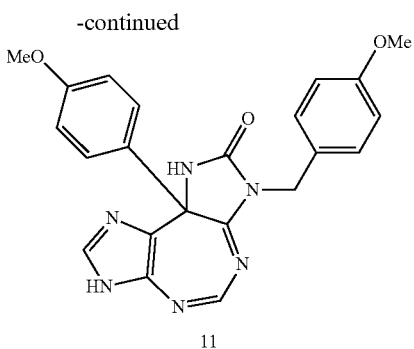

11

The generality of the above reaction was studied using two other electron-rich carbon nucleophiles, including N,N-dimethylaniline and 1,2,3-trimethoxybenzene. Thus, when 3 (1 mmol) was heated separately (Scheme 5) at 60° C. for 6 h with N,N-dimethylaniline (5 mL) or 1,2,3-trimethoxy benzene (5 mL) in TFA (10 mL), compound 13 (78%) or 14 (80%), was formed, respectively.

Scheme 5

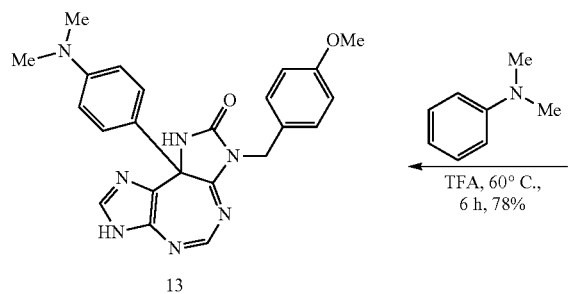

13

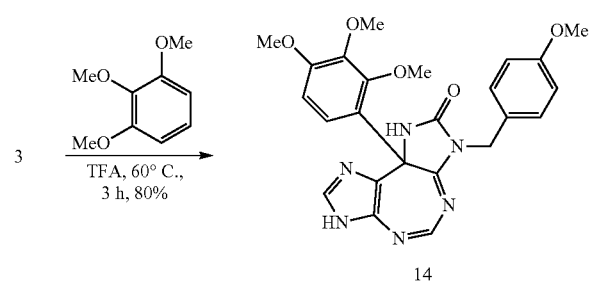

14

In certain illustrative embodiments, the structures of 3 and 11-14 were determined by 1D and 2D NMR experiments (some important peaks and correlations are presented in FIG. 2 with an example of 12; and Tables 1-3), including HMQC, HMBC and DEPT experiments. In the HMBC spectra, H-5 showed the correlations with C-6a and C-11; H-1' showed correlation with C-8, C-3' and C-7'; C-8 showed correlations with H-1'. The addition of anisole/1,2,3-trimethoxybenzene/N,N-dimethylaniline at position 9a was determined by the correlation of H-2"(or/and) and H-6" with C-9a; two-bond coupling enhancement between C-9a and H-9 (N) and H-9 (N) and C-8.

5.3. Therapeutic Uses of the Compounds of the Invention

In accordance with the invention, a composition or formulation comprising a compound of the invention and optionally a pharmaceutically acceptable vehicle, is administered to a mammal, preferably a human, experiencing one or more of the following disorders: conditions caused by uncontrolled cell growth, hyperproliferation of cells, tumor growth, and cancers.

The invention also encompasses methods for treating or preventing lung cancer, pancreatic cancer, leukemia, breast cancer, liver cancer, kidney cancer, ovarian cancer, human glioblastoma and prostate cancer, which comprises administering to a mammal in need of such treatment or prevention a therapeutically or prophylactically effective amount of a composition comprising a compound of Formula I-V, or a pharmaceutically acceptable salt or prodrug thereof, and a pharmaceutically acceptable vehicle.

In certain embodiments, a composition or formulation comprising a compound of Formula I-V is useful in treating or preventing conditions caused by uncontrolled cell growth.

In certain embodiments, a composition or formulation comprising a compound of Formula I-V is useful in killing abnormal or cancerous cells while simultaneously not affecting healthy or normal cells.

In certain embodiments, a composition or formulation comprising a compound of Formula I-V acts as a cytotoxic agent.

In certain embodiments, a composition or formulation comprising a compound of Formula I-V acts as apoptotic agent.

In one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the compositions of the invention are administered to a patient, preferably a human, as a preventative measure against such diseases. As used herein, "prevention" or "preventing" refers to a reduction of the risk of acquiring a given disease or disorder. In a preferred mode, the compositions of the present invention are administered as a preventative measure to a patient.

5.4. Therapeutic/Prophylactic Administration and Compositions and Formulations of the Invention Due to the activity of the compounds of the invention, the compounds are advantageously useful in veterinary and human medicine. As described in Section 5.3 above, the compounds of the invention are useful for the treatment or prevention of conditions caused by uncontrolled cell growth, hyperproliferation of cells, tumor growth, and cancers, for example, lung cancer, pancreatic cancer, leukemia, breast cancer, liver cancer, kidney cancer, human glioblastoma and prostate cancer.

The invention provides methods of treatment and prophylaxis by administration to a patient of a therapeutically effective amount of a composition comprising a compound of the invention. The patient is a mammal, including, but not limited to, an animal such a cow, horse, sheep, pig, chicken, cat, dog, mouse, rat, rabbit, guinea pig, and is more preferably a human.

The present compositions, which comprise one or more compounds of the invention, are preferably administered intravenously or orally.

However, suitable dosage ranges of the compounds of the invention are generally about 0.0001 milligram to 2000 milligrams of a compound of the invention per kilogram body weight. In specific preferred embodiments of the invention, the oral dose is about 0.001 milligram to about 1500 milligrams per kilogram body weight, more preferably about 0.01 milligram to about 1000 milligrams per kilogram body weight, more preferably about 0.1 milligram to about 500 milligrams per kilogram body weight, and yet more preferably about 1 milligram to about 100 milligrams per kilogram body weight.

The compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of the invention can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity of the target of the compounds of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, *Science* 249:1527-1533) may be used.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by A. R. Gennaro.

In another embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

It is preferred that the compositions of the invention be administered orally. Formulations for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to about 200 milligrams of a compound of the invention per kilogram body weight. In specific preferred embodiments of the invention, the oral dose is about 0.01 milligram to about 100 milligrams per kilogram body weight, more preferably about 0.1 milligram to about 50 milligrams per kilogram body weight, more preferably about 0.5 milligram to about 20 milligrams per kilogram body weight, and yet more preferably about 1 milligram to about 10 milligrams per kilogram body weight. In a most preferred embodiment, the oral dose is about 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

In other embodiments, a composition of the invention for oral administration includes about 0.001 milligram to about 2000 milligrams of a compound of the invention, more preferably about 0.01 milligram to about 1000 milligrams of a compound of the invention, more preferably about 0.1 milligram to about 500 milligrams of a compound of the invention, and yet more preferably about 1 milligram to about 200 milligrams of a compound of the invention.

Suitable dosage ranges for parenteral, for example, intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

In other embodiments, a composition of the invention for parenteral, for example, intravenous administration includes about 0.001 milligram to about 2000 milligrams of a compound of the invention, more preferably about 0.01 milligram to about 1000 milligrams of a compound of the invention, more preferably about 0.1 milligram to about 500 milligrams of a compound of the invention, and yet more preferably about 1 milligram to about 200 milligrams of a compound of the invention.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for treating depression, MS, incontinence, or IBS. The compounds of the invention may also be demonstrated to be effective and safe using animal model systems.

Other methods will be known to the skilled artisan and are within the scope of the invention.

EXAMPLES

The compounds of the invention showed pharmacological efficacy in treating or preventing various disorders.

General.

The $^1$H and $^{13}$C NMR spectra were recorded on a JEOL-400 NMR spectrometer, operating at 400 MHZ for $^1$H, and 100 MHz for $^{13}$C NMR. Thin layer chromatography was performed on Merck Kieselgel 60 $F_{254}$ (0.2 mm thickness). Flash column chromatography was performed using 32-63 mesh silica gel. Melting points were determined on a Thomas Hoover capillary melting point apparatus and are uncorrected. The high resolution mass spectra were recorded either at the Mass Spectral Analysis Service, Department of Chemistry, The Johns Hopkins University, Baltimore, Md. Anhydrous solvents were purchased and used without further drying and alcohols were dried over sodium metal, distilled, and stored over molecular sieves.

Example 1

Synthesis of ethyl (Z)—N-(2-amino-1,2-dicyanovinyl)formimidate[1] (5)

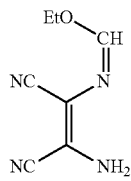

A mixture of diaminomaleonitrile (4, 6.0 g, 55.5 mmol, 1 equiv) and triethyl orthoformate (9.2 mL, 55.5 mmol, 1 equiv) in dioxane (80 mL) was heated at reflux in a flask fitted with a short Vigreux column, a distillation head, a condenser, and a receiver. Ethanol mixed with 1,4-dioxane was collected continuously until the temperature in the distillation head reached 99-100° C. (approximately 20 min). The clear brown liquid in the distillation pot was allowed to cool overnight. The reaction mixture was diluted with hot diethyl ether, filtered to remove the dark brown solid impurity, and left to cool overnight to give 5 as colorless needles (6 g, 65%). IR (KBr): 3309 (N—H str.), 2247 (CN str.), 2207 (CN str.), 1636 (C=N str.), 1608, 1256 (C—O str.), 810 cm$^{-1}$. $^1$H NMR (400 MHz, CDCl$_3$): δ=1.35 (t, J=7.3 Hz, 3H, CH$_3$), 4.25 (q, J=7.3 Hz, 2H, CH$_2$), 4.66 (brs, 2H, D$_2$O-exchangable NH$_2$), 7.97 (s, 1H, CH).

Synthesis of (4-methoxybenzyl)-(Z)—N-(2-amino-1,2-dicyanovinyl)formimidine (6)

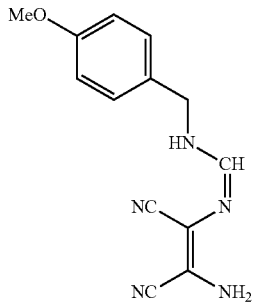 [SMILES: COc1ccc(CN/C=N\C(C#N)=C(/N)C#N)cc1]

4-methoxybenzyl amine (0.92 mL, 6.70 mmol, 1.1 equiv) was added to a suspension of 5 (1 g, 6.09 mmol, 1 equiv) in dry EtOH which contained aniline hydrochloride (0.02 g). The mixture was stirred at room temperature until TLC showed that all the formimidate had disappeared (~3 h) and the pale yellow solid was obtained by filtration, washed with diethyl ether and dried to give 6 (1.2 g, 65%). mp: 96-98° C., IR (KBr): 3309 (N—H str.), 2225 (CN str.), 2206 (CN str.), 1632 (C=N str.), 1591, 1511, 1247 (C—O str.) $^1$H NMR (400 MHz, d$_6$-DMSO): δ=3.72 (s, 3H, OCH$_3$), 4.44 (d, J=4.5 Hz, 2H, CH$_2$), 6.11 (s, 2H, D$_2$O-exchangable NH$_2$), 6.89 (d, J=8.2 Hz, 2H, Ar—H), 7.26 (d, J=8.2 Hz, 2H, Ar—H), 7.70 (d, J=2.3 Hz, 1H, CH), 8.10 (brs, 1H, D$_2$O-exchangable NH). $^{13}$C NMR (100 MHz, d$_6$-DMSO): δ=43.4, 55.6, 106.8, 114.2, 115.7, 116.8, 117.6, 129.7, 131.1, 150.8, 158.9. HRMS (FAB) Calcd for C$_{14}$H$_{14}$N$_4$O, 254.1168 (M$^+$); observed m/z 255.1115 (M+H)$^+$.

Synthesis of 5-amino-1-(4-methoxybenzyl)-4-cyanoformimidoylimidazole (7)

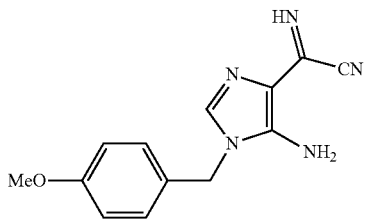 [SMILES: COc1ccc(Cn2cnc(C(=N)C#N)c2N)cc1]

To a suspension of 6 (2.0 g) in dry EtOH (10 mL), DBU was added (1 drop). The reaction mixture was stirred 2 h at room temperature under nitrogen atmosphere until starting material was disappeared (TLC). The precipitated product was filtered, washed with diethyl ether and dried under vacuum to afford 7 as off-white solid (1.35 g, 67%). mp: 92-94° C., IR (KBr): 3290 (N—H str.), 3122 (N—H str.), 2218 (CN str.), 1629 (C=N str.), 1549, 1515 (C—O str.), 1254, 810 cm$^{-1}$. $^1$H NMR (400 MHz, d$_6$-DMSO): δ=3.72 (s, 3H, OCH$_3$), 5.03 (s, 2H, CH$_2$), 6.76 (brs, 2H, D$_2$O-exchangable NH$_2$), 6.91 (d, J=8.2 Hz, 2H, Ar—H), 7.22 (d, J=8.2 Hz, 2H, Ar—H), 7.30 (s, 1H, Imid-H), 10.87 (s, 1H, D$_2$O-exchangable NH). $^{13}$C NMR (100 MHz, d$_6$-DMSO): δ=45.7, 55.7, 114.1, 114.6, 116.7, 128.8, 129.5, 132.8, 143.5, 144.7, 159.4. HRMS (FAB) Calcd for C$_{13}$H$_{13}$N$_5$O, 255.1120 (M$^+$); observed m/z 256.1113 (M+H)$^+$.

Synthesis of 4-(1-(4-methoxybenzyl)-5-amino-1H-imidazol-4-yl)-1-(4-ethoxybenzyl)-5-imino-1H-imidazol-2(5H)-one (9)

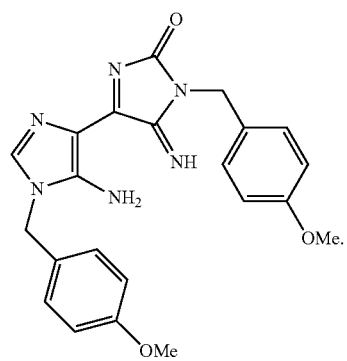 [SMILES: COc1ccc(CN2C(=N)C(c3ncn(Cc4ccc(OC)cc4)c3N)=NC2=O)cc1]

To a suspension of 7 (1.35 g, 5.29 mmol, 1 equiv) in dry MeCN (10 mL), 4-methoxybenzyl isocyanate was added (2.16 mL, 15.87 mmol, 3 equiv) under nitrogen atmosphere at 0° C. The reaction mixture was stirred at rt for 6 h until starting material was disappeared (TLC). The yellow precipitate was filtered, washed with diethyl ether and dried under vacuum to afford the mixture of (Z)-1-(4-methoxybenzyl)-3-

((1-(4-methoxybenzyl)-5-amino-1H-imidazol-4-yl)(cyano) methylene) urea (8) and 9 as yellow solid. Further, 2-5 drops of DBU were added to a suspension of 8 and 9 and the reaction mixture was stirred for 1 h. The deep yellow precipitate was filtered, washed with diethyl ether and dried under vacuum to afford 9 as yellow solid (1.6 g, 75%). mp: decomposed >215-217° C., IR: 3195 (N—H str.), 3131 (N—H str.), 1702 (C=O), 1643, 1513, 1249, 773 cm$^{-1}$. $^1$H NMR (400 MHz, d$_6$-DMSO): δ=3.70 (s, 3H, OCH$_3$), 3.72 (s, 3H, OCH$_3$), 4.62 (s, 2H, CH$_2$), 5.11 (s, 2H, CH$_2$), 6.85 (d, J=8.2 Hz, 2H, Ar—H), 6.93 (d, J=8.2 Hz, 2H, Ar—H), 7.21 (d, J=8.2 Hz, 2H, Ar—H), 7.25 (d, J=8.2 Hz, 2H, Ar—H), 7.73 (s, 1H, Imid-H), 7.90 (brs, 2H, D$_2$O-exchangable NH$_2$), 9.77 (s, 1H, D$_2$O-exchangable NH). $^{13}$C NMR (100 MHz, d$_6$-DMSO): δ=41.7, 45.9, 55.6, 55.7, 114.3, 114.7, 128.2, 129.4, 129.5, 130.2, 139.5, 152.2, 157.6, 158.9, 159.5, 160.1, 167.3. HRMS (FAB) Calcd for C$_{22}$H$_{22}$N$_6$O$_3$, 418.1753 (M$^+$); observed m/z 419.1824 (M+H)$^+$.

Synthesis of 3,7-Dihydro-3,7-bis[(4-methoxyphenyl) methyl]-2H-diimidazo[4,5-d:4',5'-f][1,3]diazepin-2-one (3)

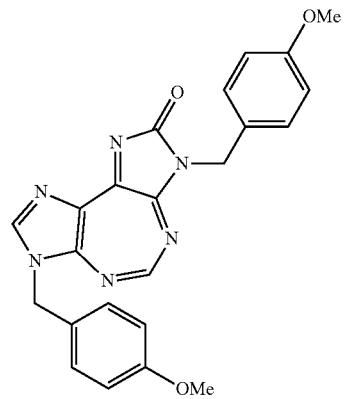 [SMILES: COc1ccc(Cn2c3ncnc4c(ncn4Cc4ccc(OC)cc4)c-3nc2=O)cc1]

To a suspension of 9 (1.0 g, 2.39 mmol, 1 equiv) in MeCN (10 mL), triethyl orthoformate (2.8 g, 19.13 mmol, 8 equiv) was added followed by 2 drops of sulfuric acid. The reaction mixture was heated at reflux for 1.5 h until starting material was disappeared (TLC). The precipitated product was filtered, washed with diethyl ether and dried under vacuum to afford 3 as pale yellow solid (0.77 g, 76%). mp: 175-177° C., IR: 1737 (C=O), 1610, 1589, 1251, 1176 cm$^{-1}$. $^1$H NMR (400 MHz, d$_6$-DMSO): δ=3.69 (s, 3H, OCH$_3$), 3.70 (s, 3H, OCH$_3$), 5.08 (s, 2H, CH$_2$), 5.51 (s, 2H, CH$_2$), 6.85 (d, J=8.2 Hz, 2H, Ar—H), 6.89 (d, J=8.2 Hz, 2H, Ar—H), 7.29 (d, J=8.2 Hz, 2H, Ar—H), 7.33 (d, J=8.2 Hz, 2H, Ar—H), 8.75 (s, 1H, Ar—C=N—H), 8.92 (s, 1H, Imid-H). $^{13}$C NMR (100 MHz, d$_6$-DMSO): δ=43.4, 47.0, 55.6, 55.7, 114.4, 114.6, 128.5, 128.8, 129.2, 129.7, 129.8, 148.9, 150.3, 156.3, 159.2, 159.5, 160.2, 166.3. HRMS (FAB) Calcd for C$_{23}$H$_{20}$N$_6$O$_3$, 428.1597 (M$^+$); observed m/z 429.1667 (M+H)$^+$.

Synthesis of 1,3,7,9b-Tetrahydro-9b-(4-methoxyphenyl)-3-[(4-methoxyphenyl)methyl]-2H-diimidazo[4,5-d:4',5-f][1,3]diazepin-2-one (11)

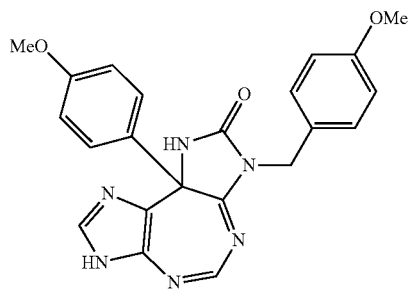 [SMILES: COc1ccc(CN2C(=O)NC3(c4ccc(OC)cc4)C2=NC=Nc2[nH]cnc23)cc1]

To a stirred suspension of 3 (0.43 g, 1 mmol) in anisole (5 mL), TFA (10 mL, dropwsie) was added. The reaction mixture was heated at 60° C. for 3 h. TFA was evaporated on rotary evaporator after the disappearance of starting material (TLC) and excess of sodium bicarbonate was added. The reaction mixture was extracted with EtOAc (30×3 mL), washed with brine, dried (anhyd. Na$_2$SO$_4$) and adsorbed over silica and purified through column chromatography to afford 11 as yellowish white solid (0.34 g, 81%). mp: 223-225° C., IR: 1743 (C=O str.), 1619, 1513, 1249 (C—O str.) NMR (400 MHz, d$_6$-DMSO): δ=3.67 (s, 3H, OCH$_3$), 3.71 (s, 3H, OCH$_3$), 4.63 (dd, J=15.1, 18.3 Hz, 2H, CH$_2$), 6.68 (d, J=8.6 Hz, 2H, Ar—H), 6.80 (d, J=9.16 Hz, 2H, Ar—H), 6.86 (d, J=8.7 Hz, 2H, Ar—H), 7.19 (d, J=8.6 Hz, 2H, Ar—H), 7.53 (s, 1H, Ar—CH=N—), 7.87 (s, 1H, Imid-H), 9.82 (brs, 1H, D$_2$O-exchangable NH), $^{13}$C NMR (100 MHz, d$_6$-DMSO): δ=42.9, 55.6, 55.7, 64.6, 114.4, 114.5, 121.1, 127.7, 129.0, 129.4, 134.8, 137.5, 145.9, 154.3, 155.8, 159.1, 159.7. HRMS (FAB) Calcd for C$_{22}$H$_{20}$N$_6$O$_3$, 416.1597 (M$^+$); observed m/z 417.1669 (M+H)$^+$.

Synthesis of 1,3,7,9b-Tetrahydro-9b-(4-methoxyphenyl)-3,7-bis[(4-methoxyphenyl)methyl]-2H-diimidazo[4,5-d:4',5-f][1,3]diazepin-2-one (12)

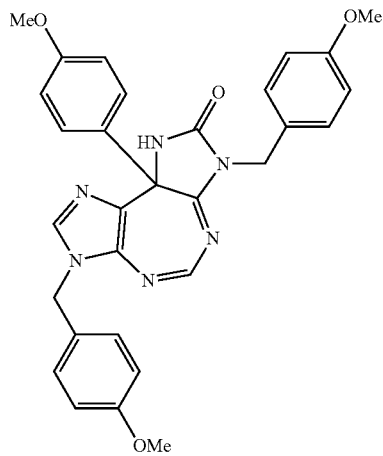 [SMILES: COc1ccc(CN2C(=O)NC3(c4ccc(OC)cc4)C2=NC=Nc2c3ncn2Cc2ccc(OC)cc2)cc1]

To a stirred suspension of 3 (0.43 g, 1 mmol) in anisole (5 mL), TFA (10 mL, dropwsie) was added and the reaction mixture was stirred at rt for 12 h. TFA was evaporated on rotary evaporator after the disappearance of starting material (TLC) and excess of sodium bicarbonate was added. The reaction mixture was extracted with EtOAc (30×3 mL), washed with brine, dried (anhyd. Na$_2$SO$_4$) and adsorbed over silica and purified through column chromatography to afford 12 (0.32 g, 60%, yellowish solid) and 11 (0.042 g, 10%). mp: 95-97° C., IR: 1754 (C=O str.), 1612, 1512, 1250 (C—O str.) cm$^{-1}$. $^1$H NMR (400 MHz, CDCl$_3$): δ=3.68 (s, 3H, OCH$_3$), 3.77 (s, 3H, OCH$_3$), 3.77 (s, 3H, OCH$_3$), 4.72 (s, 2H, CH$_2$), 5.13 (q, J=14.2 Hz, 2H, CH$_2$), 6.61 (d, J=8.6 Hz, 2H, Ar—H), 6.72 (d, J=8.6 Hz, 2H, Ar—H), 6.79-6.83 (m, 4H, Ar—H), 7.08 (d, J=8.6 Hz, 2H, Ar—H), 7.33 (d, J=8.6 Hz, 2H, Ar—H), 7.65 (s, 1H, Ar—CH=N—), 7.69 (s, 1H, Imid-H), 9.47 (brs, 1H, D$_2$O-exchangable NH), $^{13}$C NMR (100 MHz, CDCl$_3$): δ=43.4, 46.9, 55.3, 55.4, 64.2, 114.0, 114.1, 114.3, 121.0, 127.4, 128.4, 129.0, 129.9, 134.4, 138.3, 146.6, 154.6, 156.2, 159.2, 159.4, 159.6. HRMS (FAB) Calcd for C$_{30}$H$_{28}$N$_6$O$_4$, 536.2172 (M$^+$); observed m/z 537.2235 (M+H)$^+$.

Synthesis of 1,3,7,9b-Tetrahydro-9b-(4-N,N-dimethylaminophenyl)-3-[(4-methoxyphenyl)methyl]-2H-diimidazo[4,5-d:4',5'-f][1,3]diazepin-2-one (13)

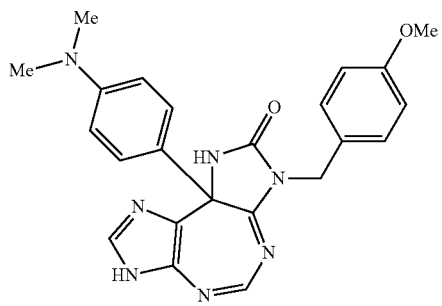 [SMILES: COc1ccc(CN2C(=O)NC3(c4ccc(N(C)C)cc4)C2=NC=Nc2[nH]cnc23)cc1]

To a stirred suspension of 3 (0.43 g, 1 mmol) in N,N-dimethylaniline (5 mL), TFA (10 mL, dropwsie) was added. The reaction mixture was heated at 60° C. for 6 h. TFA was evaporated on rotary evaporator after the disappearance of starting material (TLC) and excess of sodium bicarbonate was added. The reaction mixture was extracted with EtOAc (30×3 mL), washed with brine, dried (anhyd. Na$_2$SO$_4$) and adsorbed over silica and purified through column chromatography to afford 13 as yellowish white solid (0.33 g, 78%); mp: decomposed >225° C., IR: 1730 (C=O str.), 1610, 1525, 1248 (C—O str.) cm$^{-1}$. $^1$H NMR (400 MHz, d$_6$-DMSO): δ=2.81 (s, 6H, N(CH$_3$)$_2$), 3.71 (s, 3H, OCH$_3$), 4.62 (dd, J=15.1, 18.3 Hz, 2H, CH$_2$), 6.52 (d, J=9.2 Hz, 2H, Ar—H), 6.56 (d, J=9.2 Hz, 2H, Ar—H), 6.85 (d, J=8.72 Hz, 2H, Ar—H), 7.20 (d, J=8.72 Hz, 2H, Ar—H), 7.50 (s, 1H, Ar—CH=N—), 7.83 (s, 1H, Imid-H), 9.68 (brs, 1H, D$_2$O-exchangable NH), $^{13}$C NMR (100 MHz, d$_6$-DMSO): δ=40.4 (visible in DEPT 135), 42.8, 55.6, 64.8, 112.4, 114.4, 121.3, 124.4, 127.1, 129.1, 129.4, 134.7, 137.2, 145.9, 150.7, 154.7, 155.8, 159.1. HRMS (FAB) Calcd for C$_{23}$H$_{23}$N$_7$O$_2$, 429.1913 (M$^+$); observed m/z 430.1980 (M+H)$^+$.

Synthesis of 1,3,7,9b-Tetrahydro-9b-(2,3,4-trimethoxyphenyl)-3-[(4-methoxyphenyl)methyl]-2H-diimidazo[4,5-d:4',5'-f][1,3]diazepin-2-one (14)

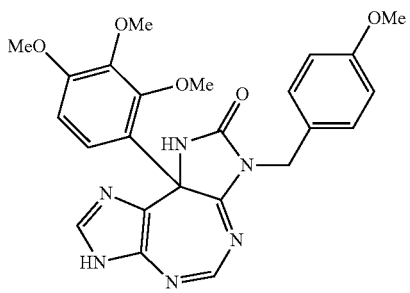 [SMILES: COc1ccc(CN2C(=O)NC3(c4ccc(OC)c(OC)c4OC)C2=NC=Nc2[nH]cnc23)cc1]

To a stirred suspension of 3 (0.43 g, 1 mmol) in 1,2,3-trimethoxybenzene (5 mL), TFA (10 mL, dropwsie) was added. The reaction mixture was heated at 60° C. for 3 h. TFA was evaporated on rotary evaporator after the disappearance of starting material (TLC) and excess of sodium bicarbonate was added. The reaction mixture was extracted with EtOAc (30×3 mL), washed with brine, dried (anhyd. Na$_2$SO$_4$) and adsorbed over silica and purified through column chromatography to afford 14 as yellowish white solid (0.38 g, 80%); mp: decomposed >225° C. IR: 1734 (C=O str.), 1620, 1514, 1247 (C—O str.) cm$^{-1}$. $^1$H NMR (400 MHz, d$_6$-DMSO): δ=3.52 (s, 3H, OCH$_3$), 3.69 (s, 6H, OCH$_3$), 4.60 (dd, J=15.1, 18.3 Hz, 2H, CH$_2$), 5.80 (J=8.7 Hz, 1H, Ar—H), 6.50 (J=8.7 Hz, 1H, Ar—H), 6.85 (d, J=8.7 Hz, 2H, Ar—H), 7.22 (d, J=8.7 Hz, 2H, Ar—H), 7.50 (s, 1H, Ar—CH=N—), 7:85 (s, 1H, Imid-H), 9.40 (brs, 1H, D$_2$O-exchangable NH). $^{13}$C NMR (100 MHz, d$_6$-DMSO): δ=42.9, 55.6, 56.3, 60.7, 60.8, 63.4, 106.7, 114.2, 120.0, 122.0, 122.8, 129.1, 129.9, 134.9, 137.2, 142.0, 146.0, 152.6, 154.2, 154.7, 156.6, 159.1. HRMS (FAB) Calcd for C$_{24}$H$_{24}$N$_6$O$_5$, 476.1808 (M$^+$); observed m/z 477.1875 (M+H)$^+$.

Reaction of 3 with Phenol in TFA: Formation of 1,3,7,9b-Tetrahydro-9b-(o-hydroxyphenyl)-3-[(4-methoxyphenyl)methyl]-2H-diimidazo[4,5-d:4',5'-f][1,3]diazepin-2-one (Ortho Isomer)) and 1,3,7,9b-Tetrahydro-9b-(p-hydroxyphenyl)-3-[(4-methoxyphenyl)methyl]-2H-diimidazo[4,5-d:4',5'-f][1,3]diazepin-2-one (Para Isomer):

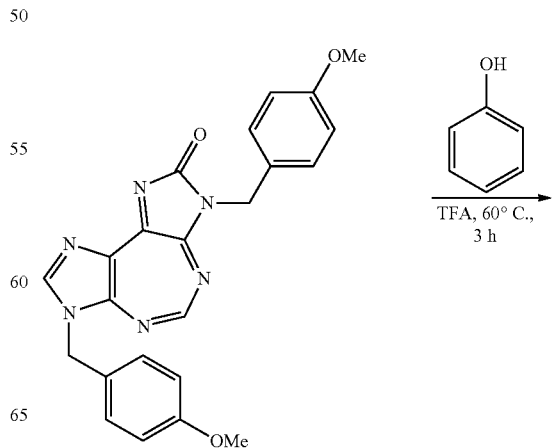

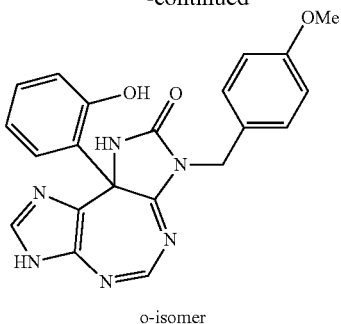

o-isomer

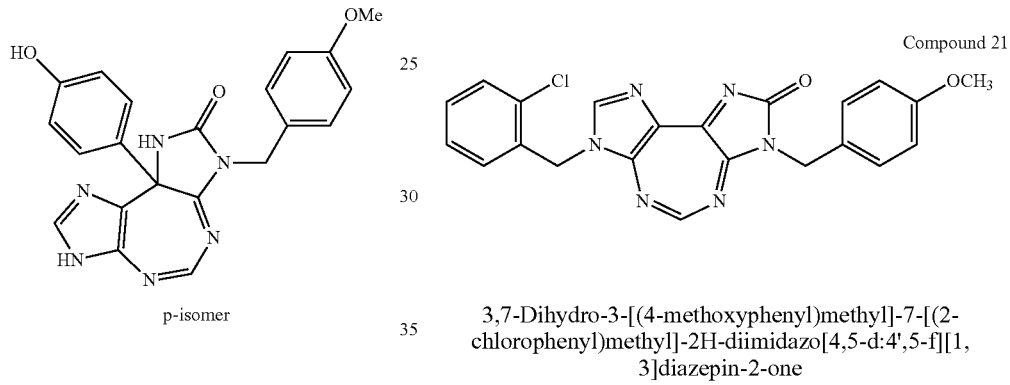

p-isomer

To a stirred suspension of 3 (0.43 g, 1 mmol) in phenol (5 mL), TFA (10 mL, dropwsie) was added. The reaction mixture was heated at 60° C. for 3 h. TFA was evaporated on rotary evaporator after the disappearance of starting material (TLC) and excess of sodium bicarbonate was added. The reaction mixture was extracted with EtOAc (30×3 mL), washed with brine, dried (anhyd. Na$_2$SO$_4$) afford mixture of o and p isomers (0.37 g, 79%) and were not separated.

Reaction of 3 with Aniline in TFA:

To a stirred suspension of 3 (0.43 g, 1 mmol) in aniline (5 mL), TFA (10 mL, dropwsie) was added. The reaction mixture was heated at 60° C. for 2 h. The multiple spots (more than 8) appeared on TLC and were not separated.

Reaction of 3 with Nitrobenzene in TFA:

To a stirred suspension of 3 (0.43 g, 1 mmol) in nitobenzene (5 mL), TFA (10 mL, dropwsie) was added. The reaction mixture was heated at 60° C. for 12 h. The starting material remained unchanged.

Synthesis of Compound 21: an Analogue of Compound 3 with an Ortho-Chlorophenyl Substituent at the 7-Position Compound 21

3,7-Dihydro-3-[(4-methoxyphenyl)methyl]-7-[(2-chlorophenyl)methyl]-2H-diimidazo[4,5-d:4',5-f][1,3]diazepin-2-one Synthetic Scheme 4

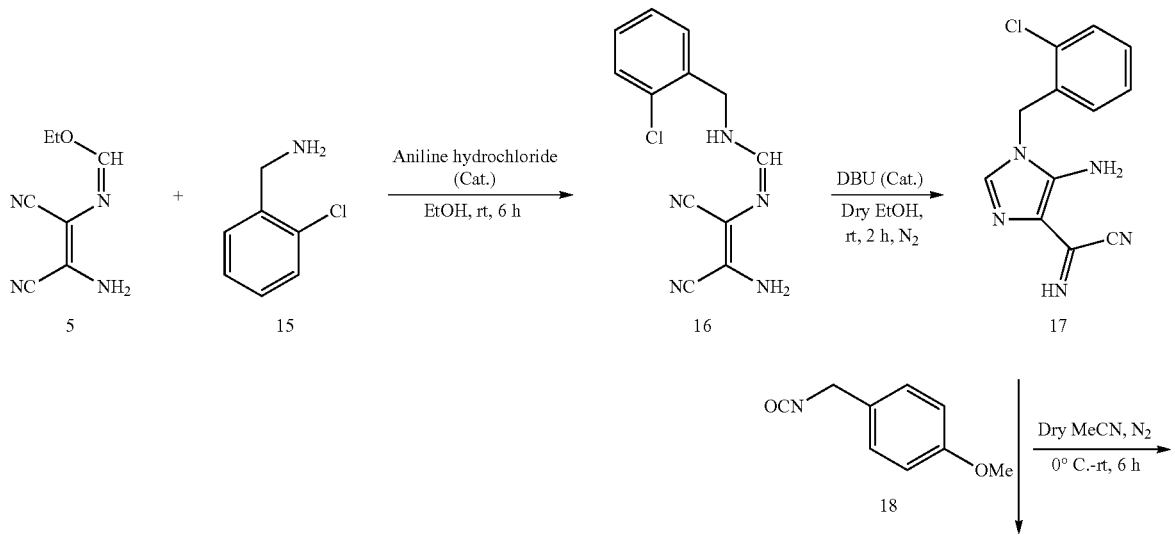

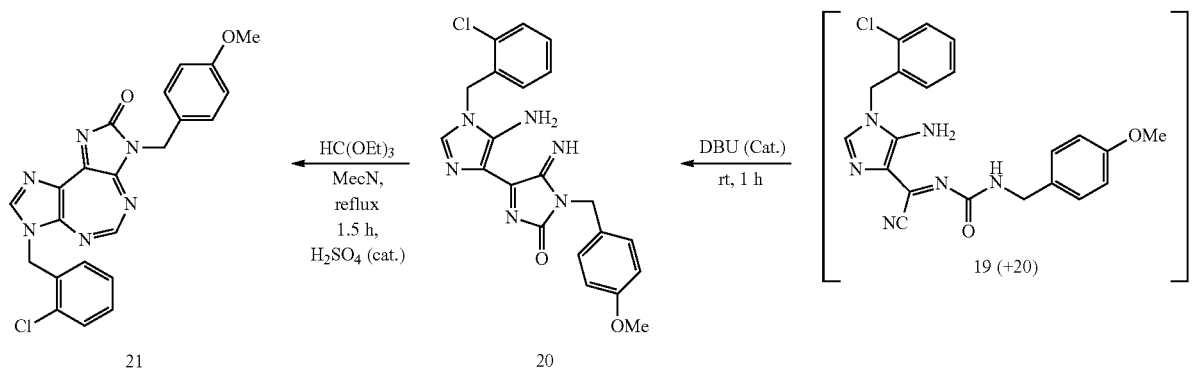
Synthesis of Compound 23 an Analogue of Compound 3 with a 2'-Deoxyribosyl Substituent at the 7-Position
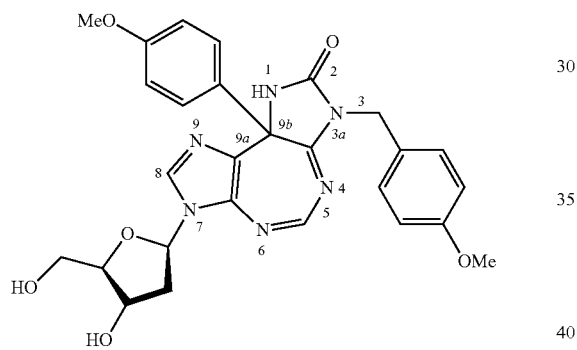
1,3,7,9b-Tetrahydro-9b-(4-methoxyphenyl)-3-[(4-methoxyphenyl)methyl]-7-(2'-deoxy-β-D-erythro-pentofuranosyl)-2H-diimidazo[4,5-d:4',5'-f][1,3]diazepin-2-one
Synthetic Scheme 5
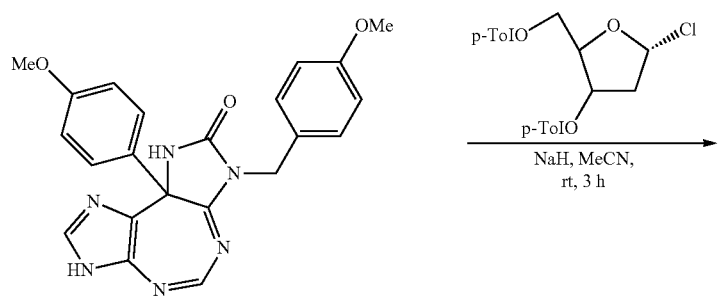

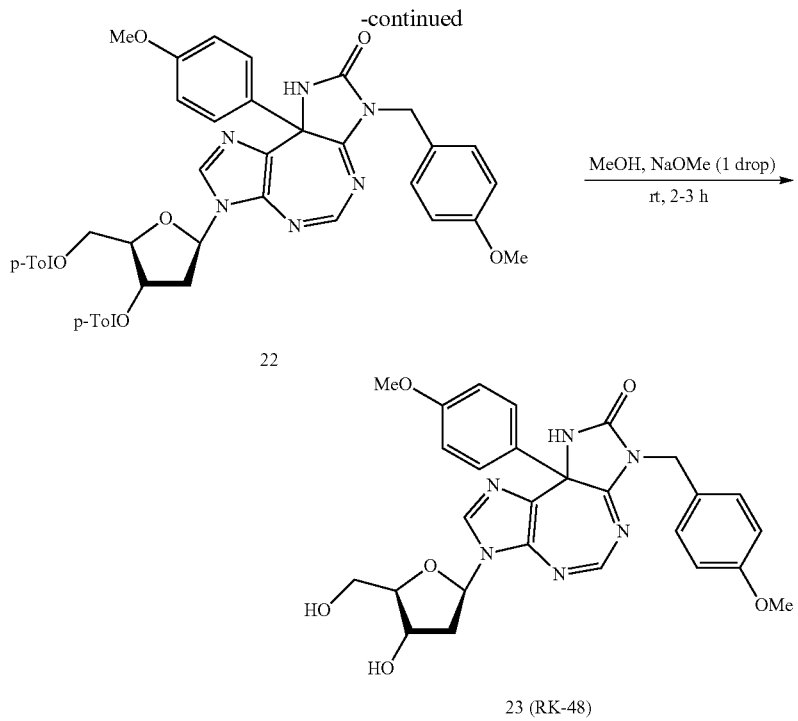

(2-Chlorobenzyl)-(Z)—N-(2-amino-1,2-dicyanovinyl)formimidine (16)

o-Chlorobezylamine (15, 0.77 mL, 6.39 mmol, 1.05 equiv) was added to a suspension of imidate 5 (1 g, 6.09 mmol, 1 equiv) in dry EtOH which contained aniline hydrochloride (0.02 g). The mixture was stirred at room temperature until TLC (1:1 EtOAc/hexane) showed that all the formimidate had disappeared (~6 h) and the pale yellow solid was obtained by filtration, washed with diethyl ether and dried to give pure 16 (1.2 g, 73%). $^1$H NMR (400 MHz, $d_6$-DMSO): δ=4.57 (d, J=5.9 Hz, 2H, CH$_2$), 6.10 (s, 2H, NH$_2$), 7.29-7.31 (m, 2H, Ar—H), 7.42-7.44 (m, 2H, Ar—H), 7.74 (d, J=3.7 Hz, 1H, CH), 8.16 (d, J=4.6 Hz, 1H, NH).

5-Amino-1-(2-chlorobenzyl)-4-cyanoformimidoylimidazole (17)

To a suspension of 16 (1.0 g) in dry EtOH (5 mL), DBU was added (1 drop). The reaction mixture was stirred 2 h at room temperature under nitrogen atmosphere until starting material was disappeared (TLC). The precipitated product was filtered, washed with diethyl ether and dried under vacuum to afford the pure product 17 as off-white solid (0.69 g, 69%). IR: 3290 (N—H str.), 2360 (CN str.), 1631 (C=N str.), 1554, 754 (C—Cl str.) cm$^{-1}$. $^1$H NMR (400 MHz, $d_6$-DMSO): δ=5.19 (s, 2H, CH$_2$), 6.74-6.76 (m, 1H, Ar—H), 6.82 (brs, 2H, NH$_2$), 7.24 (s, 1H, Imid-H), 7.31-7.36 (m, 2H, Ar—H), 7.51-7.54 (m, 1H, Ar—H), 10.97 (s, 1H, NH).

4-(1-(2-Chlorobenzyl)-5-amino-1H-imidazol-4-yl)-1-(4-methoxybenzyl)-5-imino-1H-imidazol-2(5H)-one (20)

To a suspension of 17 (1.0 g, 3.86 mmol, 1 equiv) in dry MeCN (10 mL), 4-methoxybenzyl isocyanate was added (0.94 mL, 5.79 mmol, 1.5 equiv) under nitrogen atmosphere. The reaction mixture was stirred 6 h until starting material was disappeared (TLC). The yellow precipitate was filtered, washed with diethyl ether and dried under vacuum to afford the mixture of 19 and 20 as a yellow solid (1.2 g). Further, 1 drop of DBU was added to a suspension of the mixture in acetonitrile, and the reaction mixture was stirred for 1 h. The deep yellow precipitate was filtered, washed with diethyl ether and dried under vacuum to afford 20 as a yellow solid (0.8 g). IR: 3218 (N—H str.), 1702 (C=O str.), 1649 (C=N, str.), 1598, 1443, 1247 (C—O str.), 753 (C—Cl str.) $^1$H NMR (400 MHz, $d_6$-DMSO): δ=3.71 (s, 3H, OCH$_3$), 4.64 (s, 2H, CH$_2$), 5.27 (s, 2H, CH$_2$), 6.79-6.82 (m, 1H, Ar—H), 6.86 (d, J=8.7 Hz, 2H, Ar—H), 7.23 (d, J=8.7 Hz, 2H, Ar—H), 7.31-7.39 (m, 2H, Ar—H), 7.53-7.55 (m, 1H, Ar—H), 7.63 (s, 1H, Imid-H), 7.99 (brs, 2H, NH$_2$ D$_2$O-exchangable), 9.78 (s, 1H, NH D$_2$O-exchangable).

3,7-Dihydro-3-[(4-methoxyphenyl)methyl]-7-[(2-chlorophenyl)methyl]-2H-diimidazo[4,5-d:4',5'-f][1,3]diazepin-2-one (21)

To a suspension of 20 (3.5 g, 8.29 mmol, 1 equiv) in MeCN (30 mL), triethyl orthoformate (6.2 mL, 41.46 mmol, 5 equiv) was added followed by 4 drops of sulfuric acid. The reaction mixture was heated at reflux for 1.5 h until starting material was disappeared (TLC). The precipitated product was filtered, washed with diethyl ether and dried under vacuum to afford the pure product 21 (RK-12) as a pale yellow solid (3 g, 85%). IR: 1745 (C=O str.), 1621, 1586, 1248, 1171, 759 (C—Cl str.) cm$^{-1}$. $^1$H NMR (400 MHz, $d_6$-DMSO): δ=3.71 (s, 3H, OCH$_3$), 5.09 (s, 2H, CH$_2$), 5.68 (s, 2H, CH$_2$), 6.86 (d, J=8.7 Hz, 2H, Ar—H), 6.98-6.99 (m, 1H, Ar—H), 7.25-7.27 (m, 1H, Ar—H), 7.30 (d, J=8.7 Hz, 2H, Ar—H), 7.34-7.38 (m, 1H, Ar—H), 7.53-7.55 (m, 1H, Ar—H), 8.70 (s, 1H, Ar—C=N—H), 8.86 (s, 1H, Imid-H). MS (ESI+ve) m/z: 433.2 (M+H)$^+$, 455.1 (M+Na)$^+$.

1,3,7,9b-Tetrahydro-9b-(4-methoxyphenyl)-3-[(4-methoxyphenyl)methyl]-7-[(2'-deoxy-4',5'-bis(O-p-toluoyl)-β-D-erythropentofuranosyl)]-2H-diimidazo[4,5-d:4',5'-f][1,3]diazepin-2-one (22)

To a suspension of 11 (0.2 g, 0.48 mmol, 1 equiv) in dry acetonitrile (10 mL), sodium hydride (60% suspension, 40 mg, 1.2 mmol, 2.5 equiv) was added and the mixture was stirred at rt under nitrogen atmosphere for 30 min. 2-Deoxy-3,5-di-O-p-toluoyl-α-D-erythropentofuranosyl chloride (186 mg, 0.48 mmol, 1 equiv) was added portionwise over a period of 30 min. After the addition is complete, the reaction mixture was stirred for 2 h. It has then filtered and evaporated under reduced pressure. The residue was purified by column chromatography on a silica gel to afford a pure off-white solid (0.25 g, 68%). mp: 100-101° C., $^1$H NMR (400 MHz, d$_6$-DMSO): δ=2.37 (s, 3H, OCH$_3$), 2.42 (s, 3H, OCH$_3$), 2.72-2.83 (m, 2H), 3.68 (s, 3H, OCH$_3$), 3.77 (s, 3H, OCH$_3$), 4.57-4.71 (m, 5H, 2H+3H), 5.68-5.72 (m, 1H), 6.42 (m, 1H), 6.66-6.84 (m, 5H), 7.20-7.25 (m, 7H), 7.66-7.95 (m, 6H), MS (ESI+ve) m/z: 769 (M+H)

1,3,7,9b-Tetrahydro-9b-(4-methoxyphenyl)-3-[(4-methoxyphenyl)methyl]-7-[(2'-deoxy-β-D-erythropentofuranosyl)]-2H-diimidazo[4,5-d:4',5'-f][1,3]diazepin-2-one (23)

To a solution of 22 (0.25 g) in MeOH (10 mL), sodium methoxide (1 drop) was added at rt. The reaction mixture was stirred for 2-3 h. After the completion of reaction (TLC), reaction mixture was adsorbed over silica gel and purified by column chromatography to afford a pure white solid (100 mg, 58%); mp: 130-132° C., IR: 1763 (C=O str.), 1621, 1513, 1252. (C—O str.), 1171 cm$^{-1}$. $^1$H NMR (400 MHz, d$_6$-DMSO): δ=3.40-3.60 (m, 2H), 3.67 (s, 3H, OCH$_3$), 3.72 (s, 3H, OCH$_3$), 3.78-3.82 (m, 2H), 4.01-4.05 (m, 1H), 4.30-4.33 (m, 1H), 4.62 (s, 2H, CH$_2$), 4.92-4.96 (m, 1H, D$_2$O-exchangable OH), 5.25-5.28 (m, 1H, D$_2$O-exchangable OH), 6.20 (m, 1H), 6.68-6.69 (m, 2H, Ar—H), 6.80-6.81 (m, 2H, Ar—H), 6.86-6.89 (m, 2H, Ar—H), 7.19-7.23 (m, 2H, Ar—H), 7.58 (s, 1H, Ar—CH=N—), 8.21 (d, J=8.2 Hz, 1H, Imid-H), 9.87 (s, 1H, D$_2$O-exchangable NH), MS (ESI+ve) m/z: 533 (M+H)$^+$.

Synthesis of Compound 25: An Analogue of RK-33 with a Para-nitrophenyl Substituent at the 5-Position Compound 25

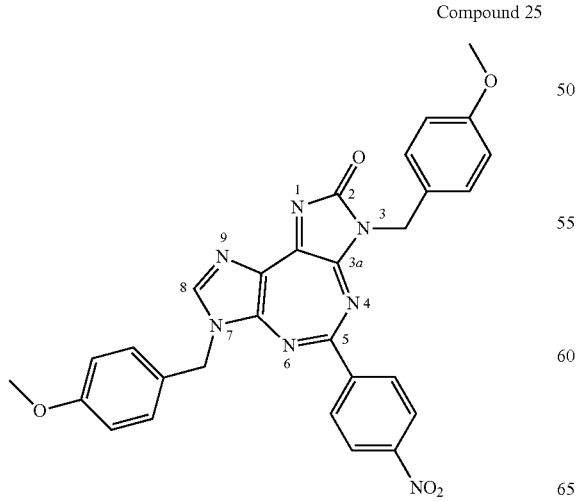

3,7-Dihydro-3,7-bis[(4-methoxyphenyl)methyl]-5-(4-nitrophenyl)-2H-diimidazo[4,5-d:4',5'-f][1,3]diazepin-2-one (25) (AK-104)

Synthesis of 3,7-Dihydro-3,7-bis[(4-methoxyphenyl)methyl]-5-(4-nitrophenyl)-2H-diimidazo[4,5-d:4',5'-f][1,3]diazepin-2-one (25)

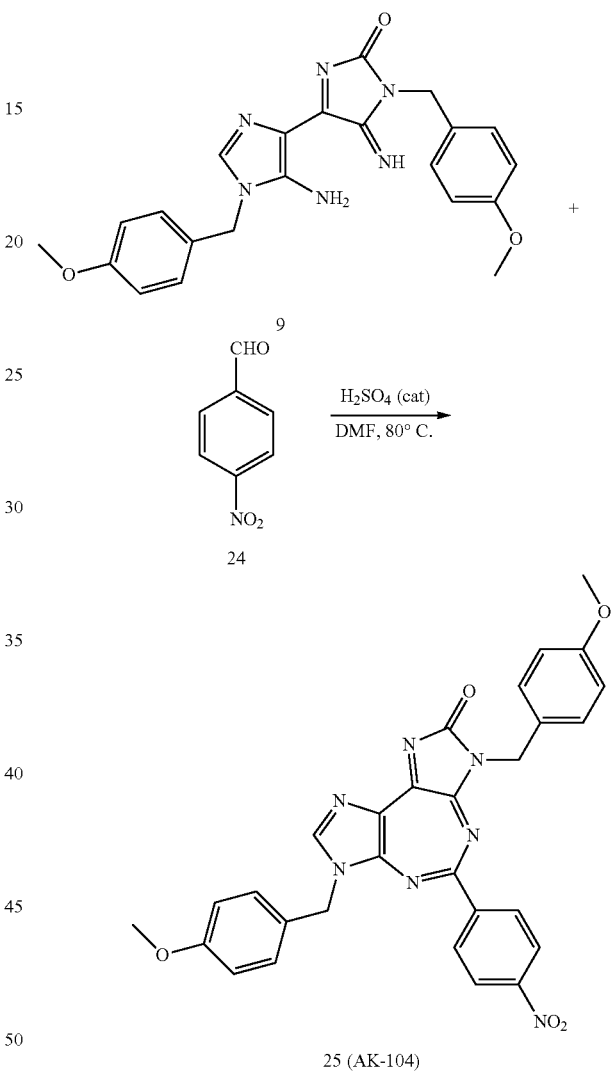

25 (AK-104)

To a solution of 9 (150 mg, 0.36 mmol, 1.0 equi.) in DMF (1 mL) was added 4-nitrobenzaldehyde (24) (60 mg, 0.395 mmol, 1.1 equi.) and heated at 80° C. for 6 h. Reaction mixture was cooled and water was added to form a precipitate. The precipitate was filtered and washed with water. The residue was then dried and recrystalised from 1:1 ethanol and CHCl$_3$ for get the pure compound 25 (80 mg, 40%). $^1$H NMR (400 MHz, DMSO-D6): δ=3.65 (s, 6H, 2×OCH$_3$), 5.19 (s, 2H, CH), 5.62 (s, 2H, CH$_2$), 6.86 (dd, J=8.4 Hz, 12.0 Hz, 2H, Ar—H), 7.37 (d, J=8.4 Hz, 13.0 Hz, 2H, Ar—H), 8.37 (d, J=8.8 Hz, 2H, Ar—H), 8.78 (d, J=8.8 Hz, 2H, Ar—H), 8.97 (s, 1H, Imid-H). MS (ESI) m/z 550 (M+H)$^+$.

Synthesis of Compound 27: An Analogue of Compound 3 with a 2,4,5-Tricarboxyphenyl Substituent at the 5-Position Compound 27

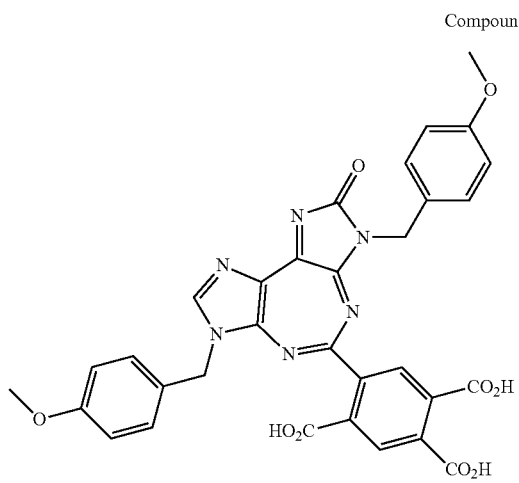

3,7-Dihydro-3,7-bis[(4-methoxyphenyl)methyl]-5-(2,4,5-tricarboxyphenyl)-2H-diimidazo[4,5-d:4',5'-j][1,3]diazepin-2-one (27) (AK-119)

Synthesis of 3,7-Dihydro-3,7-bis[(4-methoxyphenyl)methyl]-5-(2,4,5-tricarboxyphenyl)-2H-diimidazo[4,5-d:4',5'-f][1,3]diazepin-2-one (27)

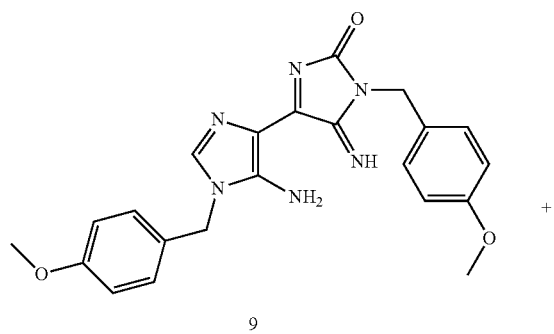

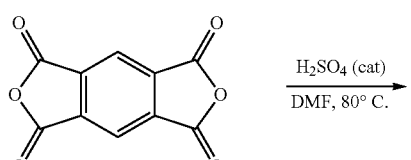

27 (AK-119)

To a solution of 9 (150 mg, 0.36 mmol, 1.0 equi.) in DMF (3 mL) was added 1,2,4,5-benzenetetracaroxylic dianhydride (26) (400 mg, 1.83 mmol, 5.1 equi.) and heated at 80° C. for 15 h. Reaction mixture was cooled and water was added to form a precipitate. The precipitate was filtered and washed with water to obtain the product 27 (150 mg, 65%). $^1$H NMR (400 MHz, DMSO-D6): $\delta$=3.66 (s, 6H, 2×OCH$_3$), 5.06 (s, 2H, CH), 5.48 (s, 2H, CH), 6.82 (dd, J=8.4 Hz, 12.0 Hz, 4H, Ar—H), 7.35 (d, J=8.4 Hz, 13.0 Hz, 4H, Ar—H), 7.93 (s, 1H, Ar—H), 7.94 (s, 1H, Ar—H), 8.94 (s, 1H, Imid-H). MS (ESI) m/z 637 (M+H)$^+$.

6.1.1. Results

Without being limited by theory, it is believed that the compound of the invention down regulate the expression of DDX3, a member of the DEAD box RNA helicase family.

It has now been surprisingly found that the compounds of the invention can kill cancer cells but not affect normal cells at the concentration of the drug used.

The immunoblot analyses were performed to show the DDX3 levels in the respective cell lines. Also it can kill prostate cancer cell line (PC-3) and human glioblastoma cell line (U87).

Purpose: The CellTiter One Solution Assay (Promega) is a colorimetric method for determining the number of viable cells in proliferation or cytotoxicity assays. The One Solution contains MTS compound and an electron coupling reagent PES. The MTS compound is bioreduced by cells into a colored formazan product that is soluble in tissue culture medium. The quantity of formazan product as measured by the amount of 490 nm absorbance is directly proportional to the number of living cells in culture.

1. 25,000 cells were seeded in 24 well plate in duplicate for each concentration of drug.

2. 24 hours after seeding, we replaced the medium with drug containing fresh medium. Cells were incubated with drug for 72 hrs. After completion of the treatment drug containing media was replaced with MTS reagent. Culture medium "no-cell" control was used as a negative control at the same time.

3. Absorbance at 490 nm (450-540 nm) was measured using a plate reader. The absorbance values were subtracted from "no-cell" control, which yield the corrected absorbance.

Results

QRT-PCR of DDX3 levels in a series of immortalized normal breast cell lines (1-2) and breast cancer cell lines (3-7) are illustrated in FIG. 1. The breast cancer cell lines are in the order of aggressive phenotype. Immunoblot analysis for DDX3 expression in the identical cell lines as above. QRT-PCR of DDX3 levels in different grades of human breast carcinoma samples. Immunostaining for DDX3 levels in normal human breast sections and in breast carcinoma sample.

Tumor growth rate in the mammary fat pad of SCID mice (preclinical breast cancer model) using wild type and DDX3 knockdown MDA-MB-231 cells is illustrated in FIG. 2. Cross section of lungs of animals injected orthotopically (mammary fat pad) with MDA-MB-231 and MDA-MB-231-shDDX3 cells. Note that the lungs from MDA-MB-231-shDDX3 injected animals showed no tumor formation as compared to the wild type cells (black arrows points to lung metastasis).

MTS assays of MCF 10A cells (immortalized normal breast cell line) incubated with Compound 3 are illustrated in FIG. 3. X-axis indicates concentration of drug used. The cells were incubated for three days (fresh drug was added daily) following which cell viability was determined.

MTS assays of MCF 10A cells (immortalized normal breast cell line) incubated with Compound 3 are illustrated in FIG. 4. X-axis indicates concentration of drug used. The cells were incubated for three days (fresh drug was added daily) following which cell viability was determined.

Figure 5:
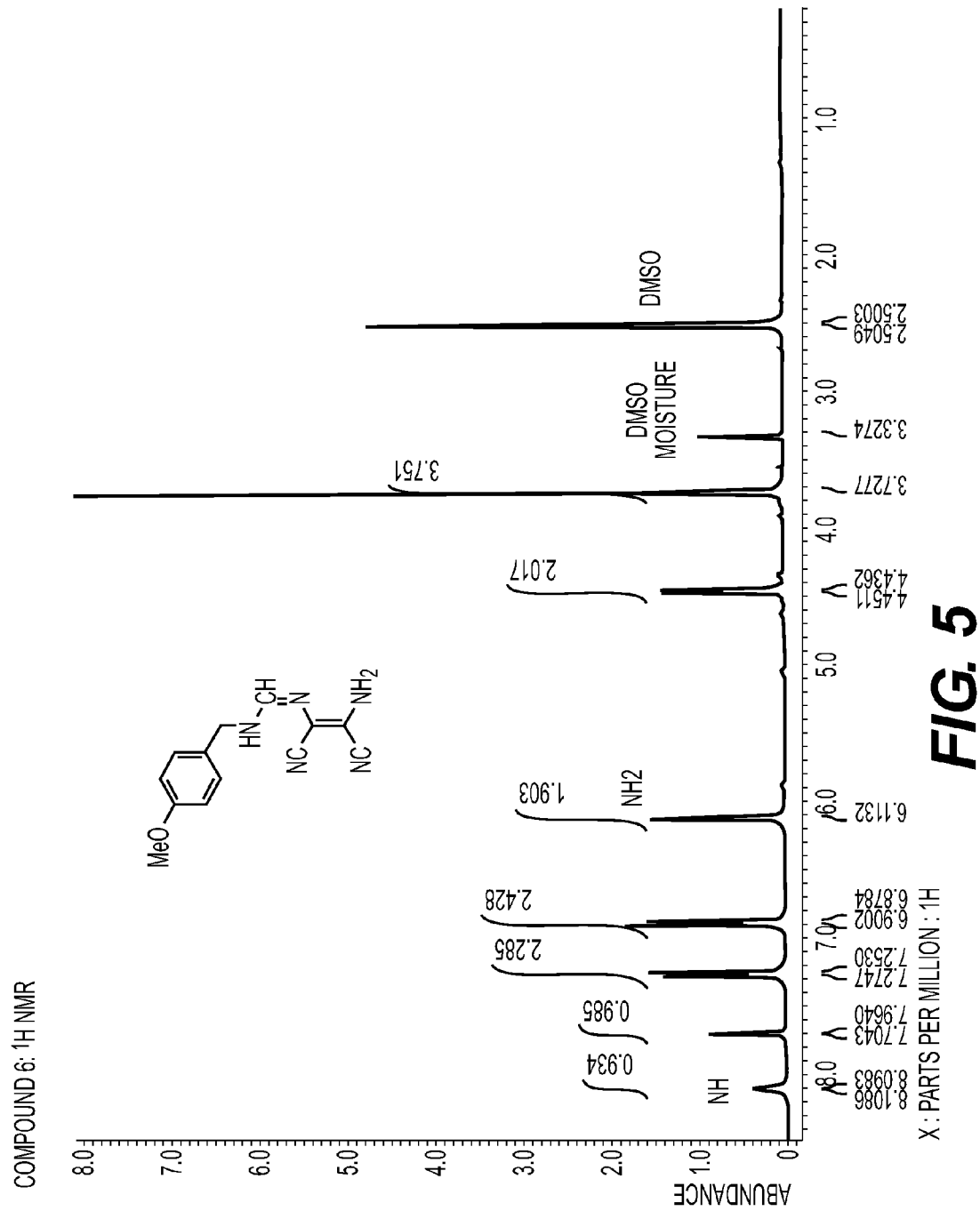
FIG. 5 illustrates $^1$H NMR (δ, DMSO-d$_6$, J in Hz in parentheses) data of compound 6.

MTS assays of MCF-7 cells (breast cancer cell line) incubated with Compound 3 are illustrated in FIG. 5. X-axis indicates concentration of drug used. The cells were incubated for three days (fresh drug was added daily) following which cell viability was determined.

Figure 6:
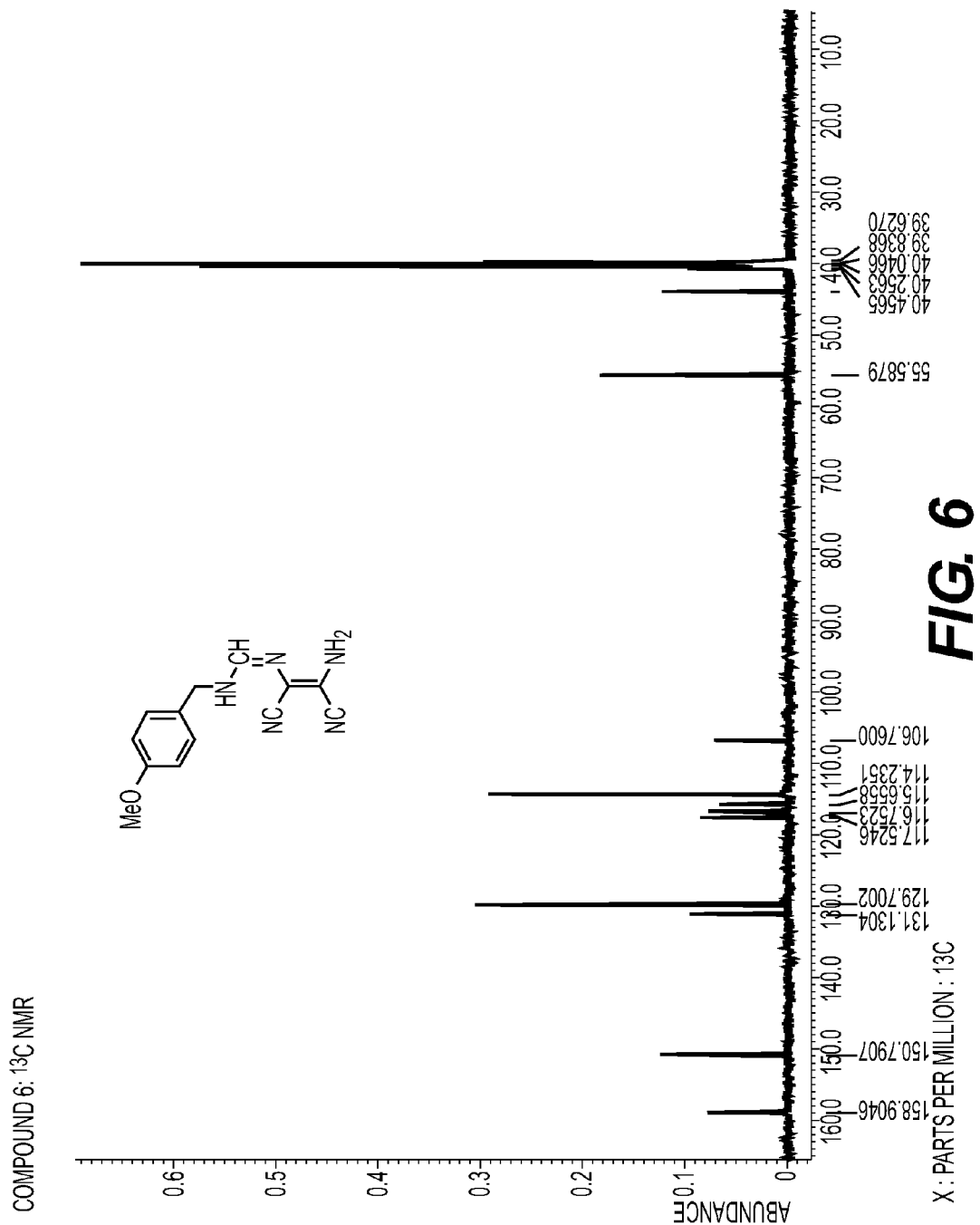
FIG. 6 illustrates $^{13}$C NMR (δ, DMSO-d$_6$) data of compound 6.

MTS assays of MDA-MB-468 cells (breast cancer cell line) incubated with Compound 3 are illustrated in FIG. 6. X-axis indicates concentration of drug used. The cells were incubated for three days (fresh drug was added daily) following which cell viability was determined.

Figure 7:
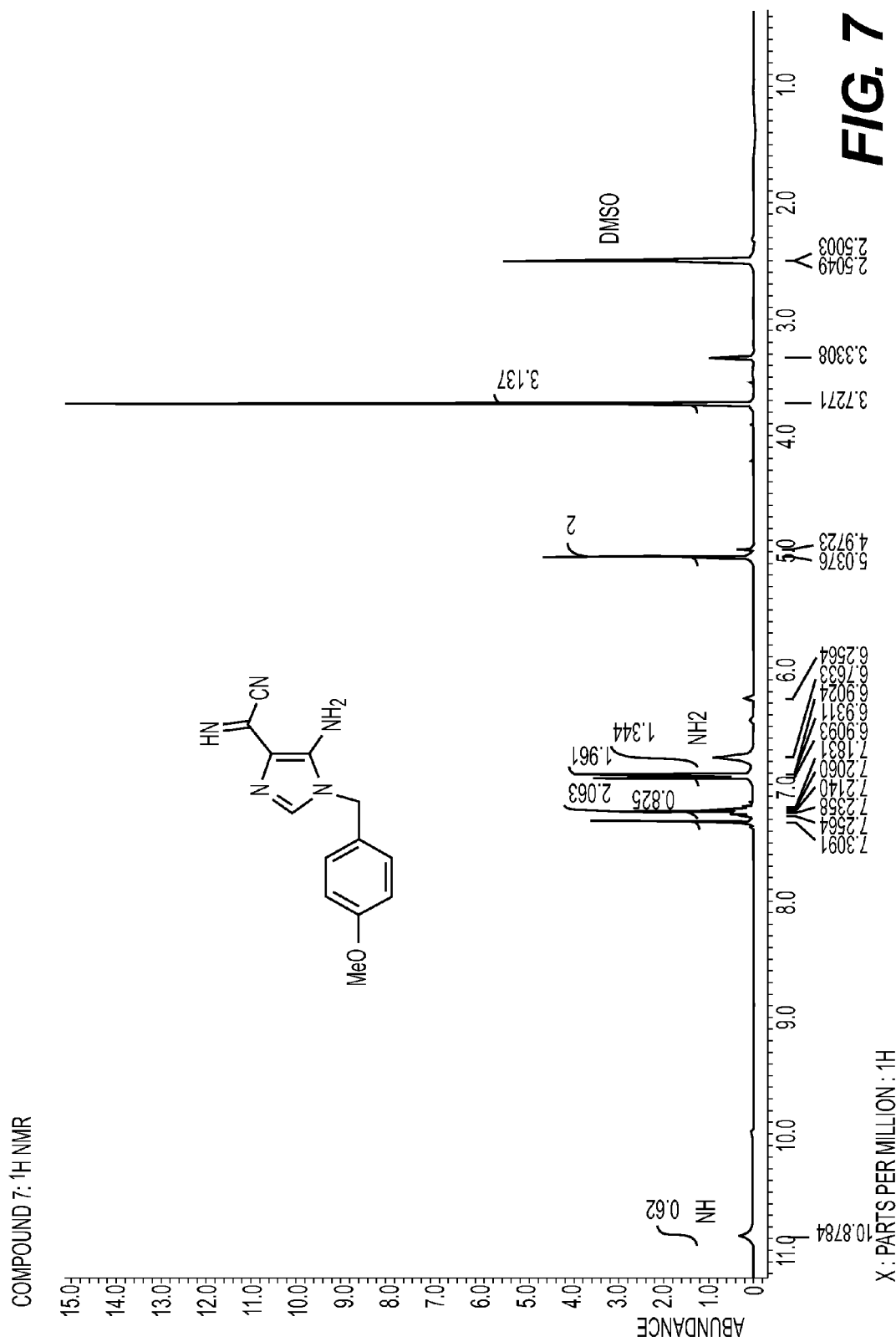
FIG. 7 illustrates $^1$H NMR (δ, DMSO-d$_6$, J in Hz in parentheses) data of compound 7.

MTS assays of MDA-MB-231 cells (breast cancer cell line) incubated with Compound 3 are illustrated in FIG. 7. X-axis indicates concentration of drug used. The cells were incubated for three days (fresh drug was added daily) following which cell viability was determined.

Figure 8:
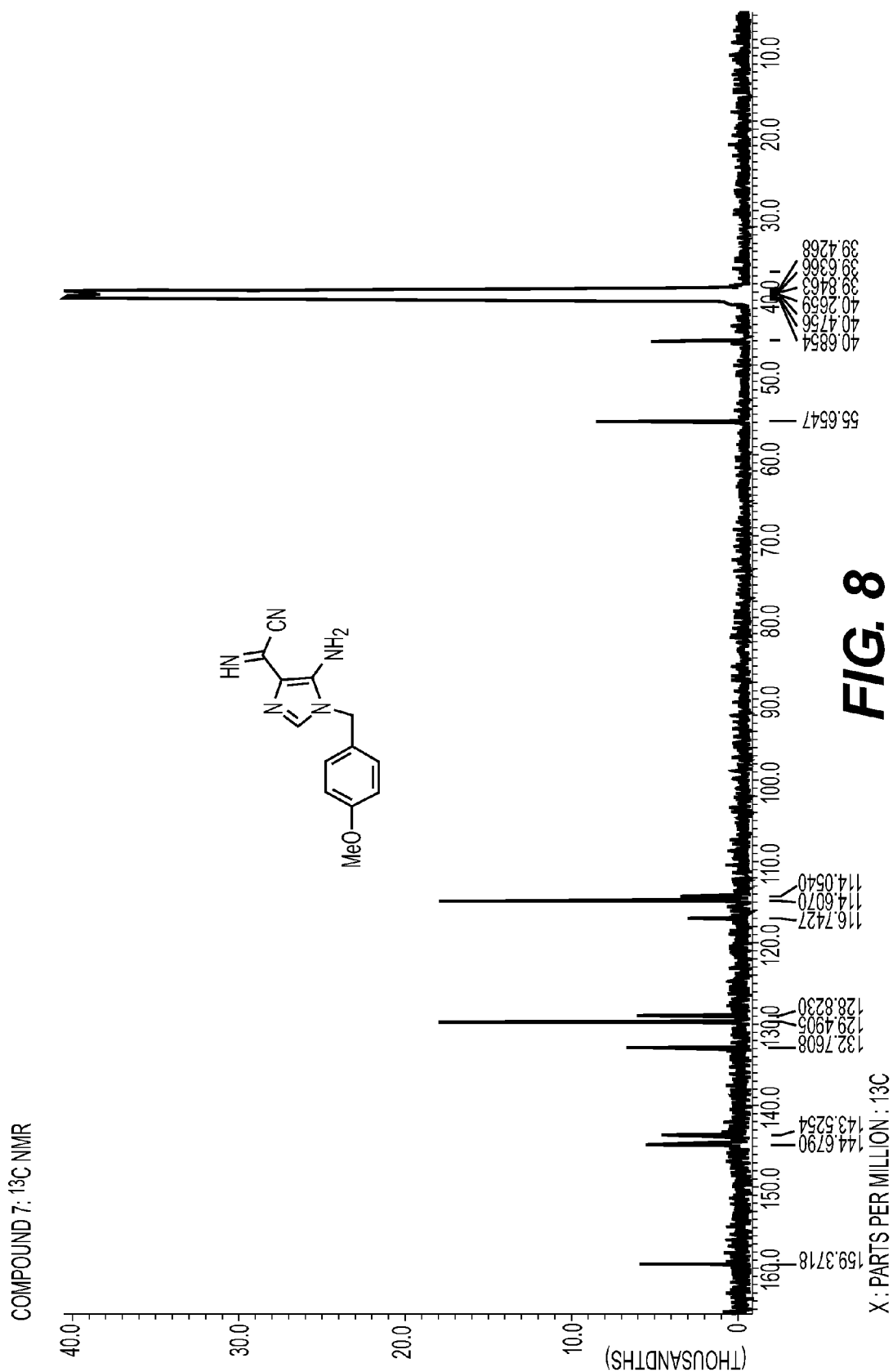
FIG. 8 illustrates $^{13}$C NMR (δ, DMSO-d$_6$) data of compound 7.

MTS assays of HL60T cells (leukemia cell line) incubated with Compound 3 are illustrated in FIG. 8. X-axis indicates concentration of drug used. The cells were incubated for three days (fresh drug was added daily) following which cell viability was determined.

Figure 9:
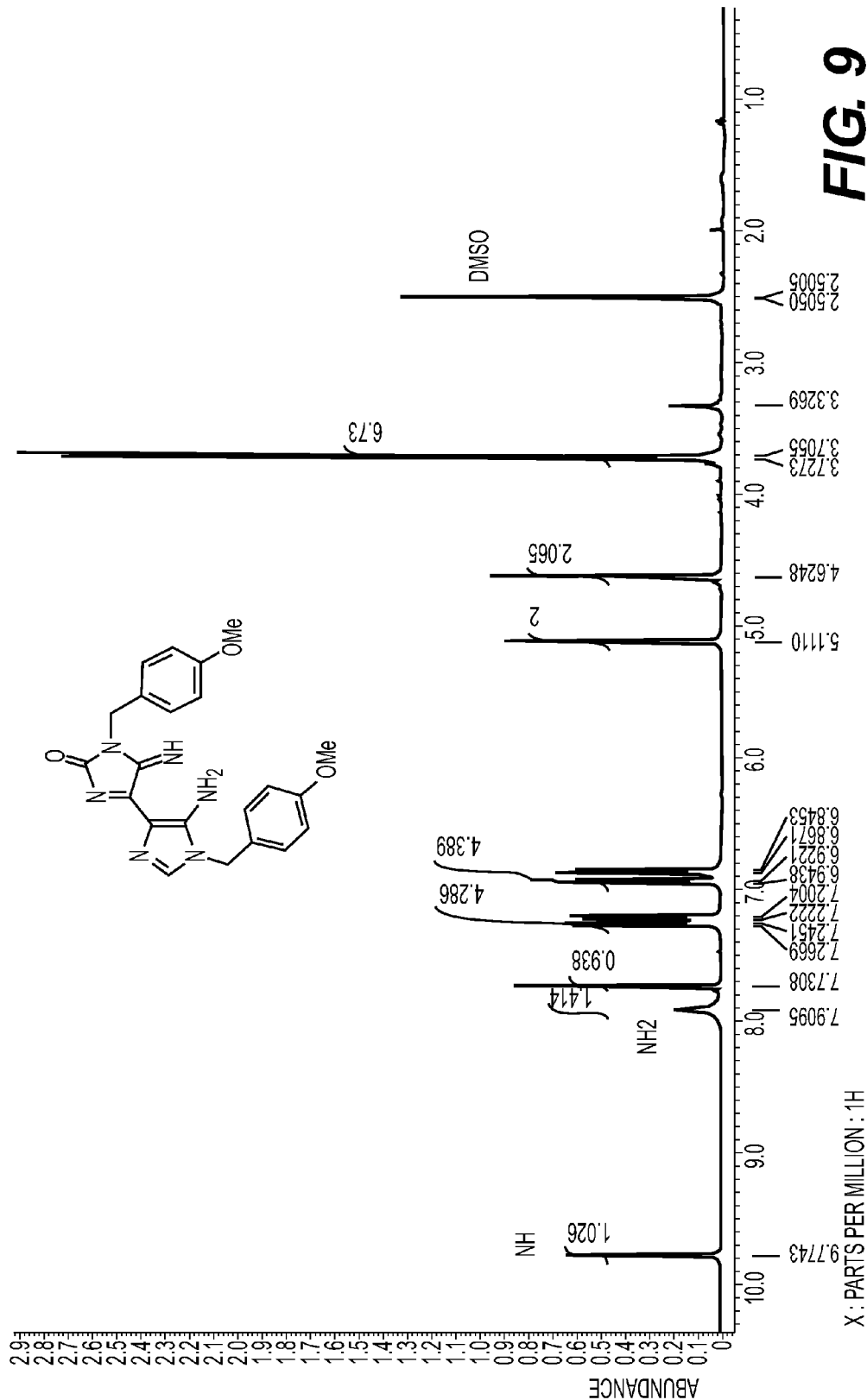
FIG. 9 illustrates $^1$H NMR (δ, DMSO-d$_6$, J in Hz in parentheses) data of illustrative compound 9.

MTS assays of HNT34 cells (leukemia cell line) incubated with Compound 3 are illustrated in FIG. 9. X-axis indicates concentration of drug used. The cells were incubated for three days (fresh drug was added daily) following which cell viability was determined.

Figure 10:
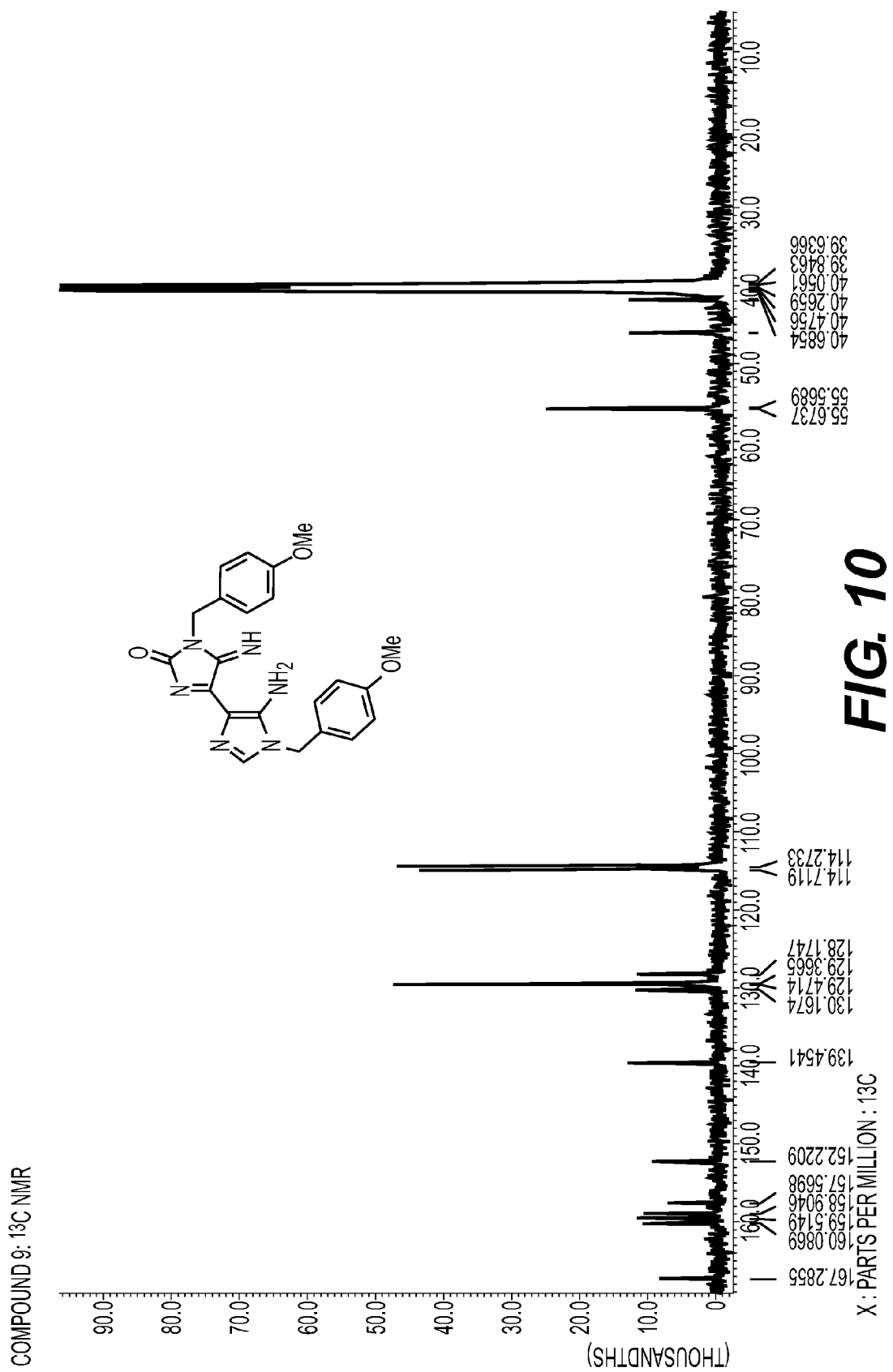
FIG. 10 illustrates $^{13}$C NMR (δ, DMSO-d$_6$) data of illustrative compound 9.
Figure 11:
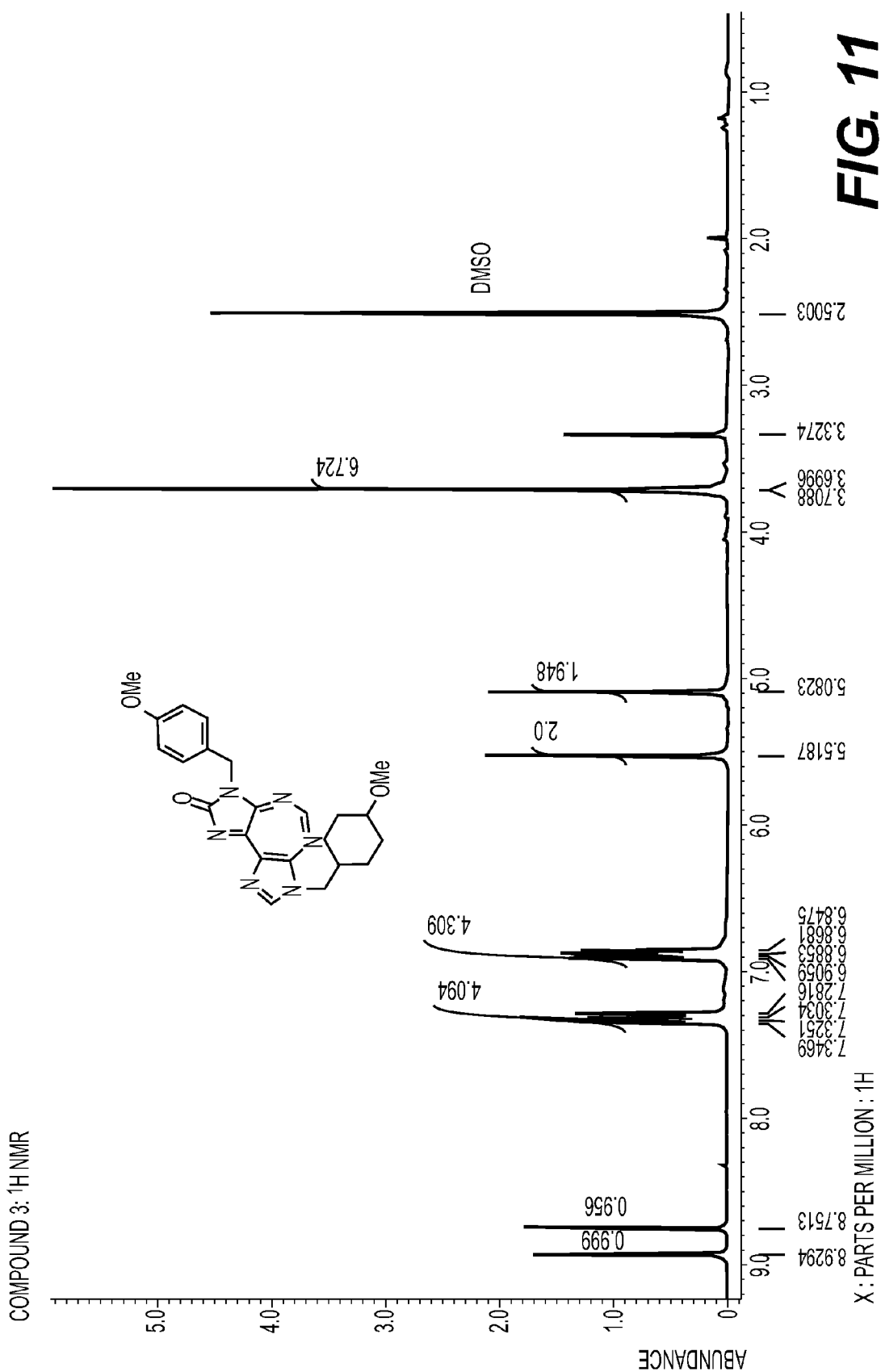
FIG. 11 illustrates $^1$H NMR (δ, DMSO-d$_6$, J in Hz in parentheses) data of illustrative compound 3.
Figure 12:
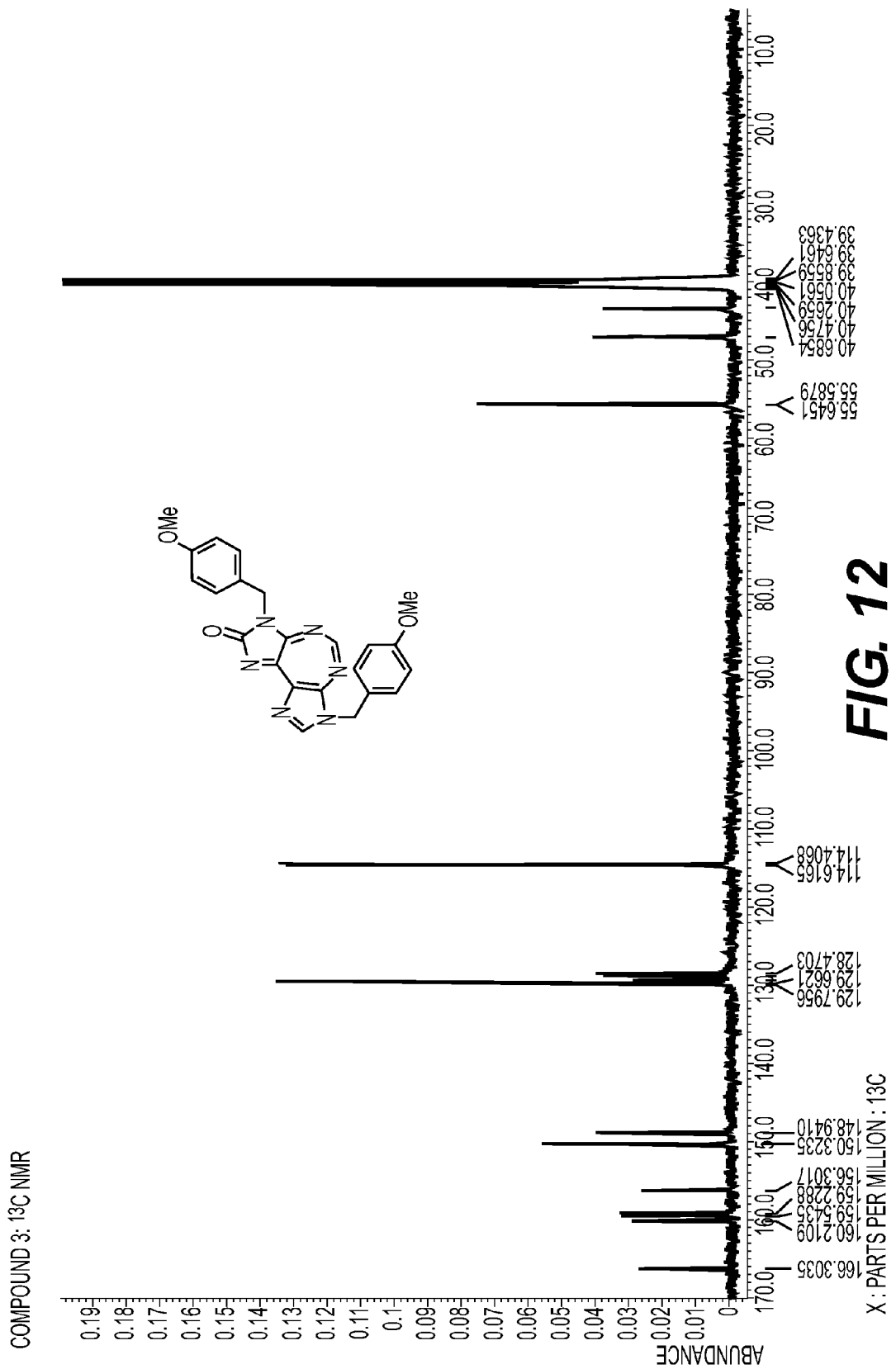
FIG. 12 illustrates $^{13}$C NMR (δ, DMSO-d$_6$) data of illustrative compound 3.
Figure 13:
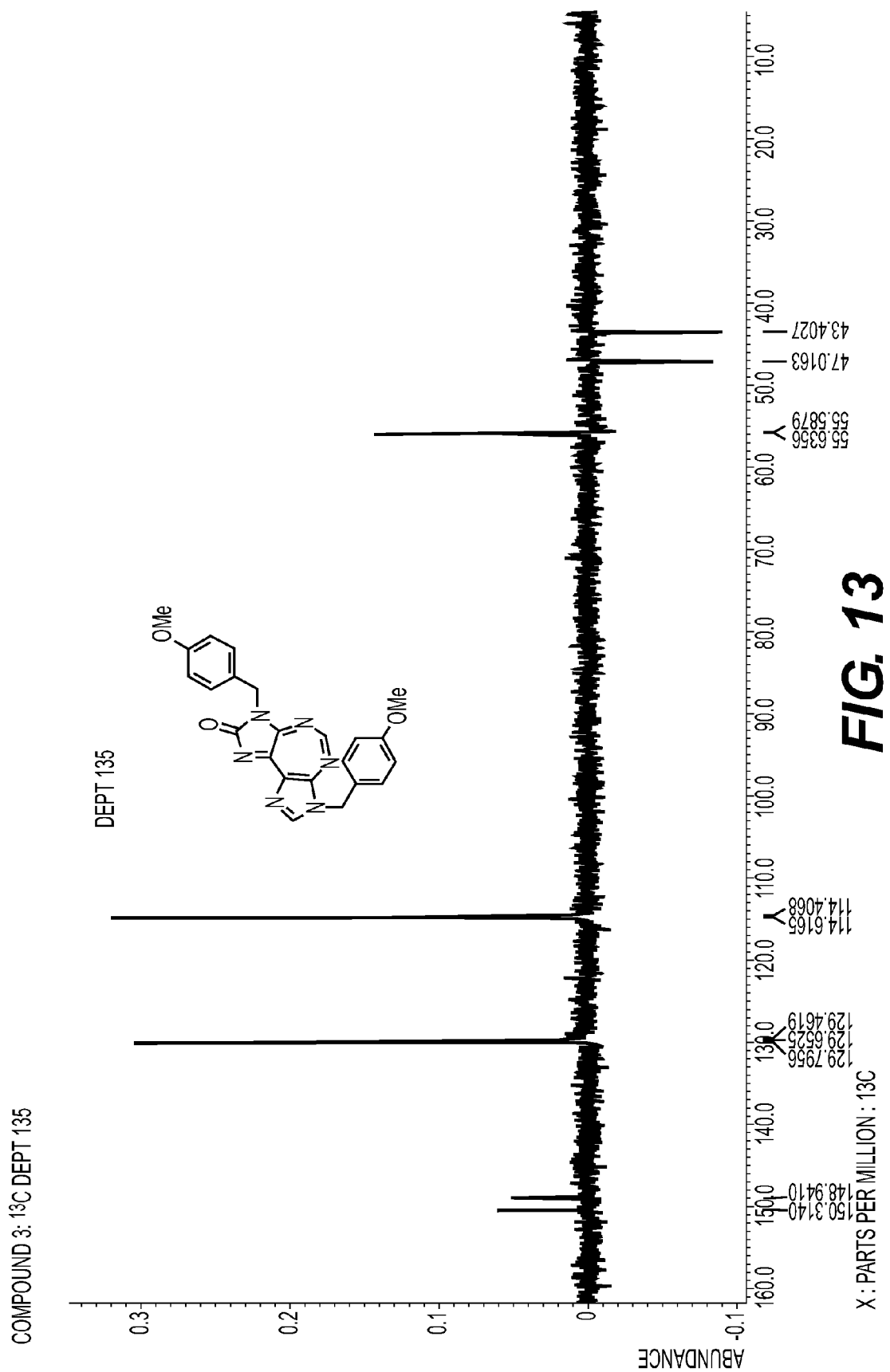
FIG. 13 illustrates $^{13}$C NMR DEPT 135 (δ, DMSO-$d_6$) data of illustrative compound 3.
Figure 14:
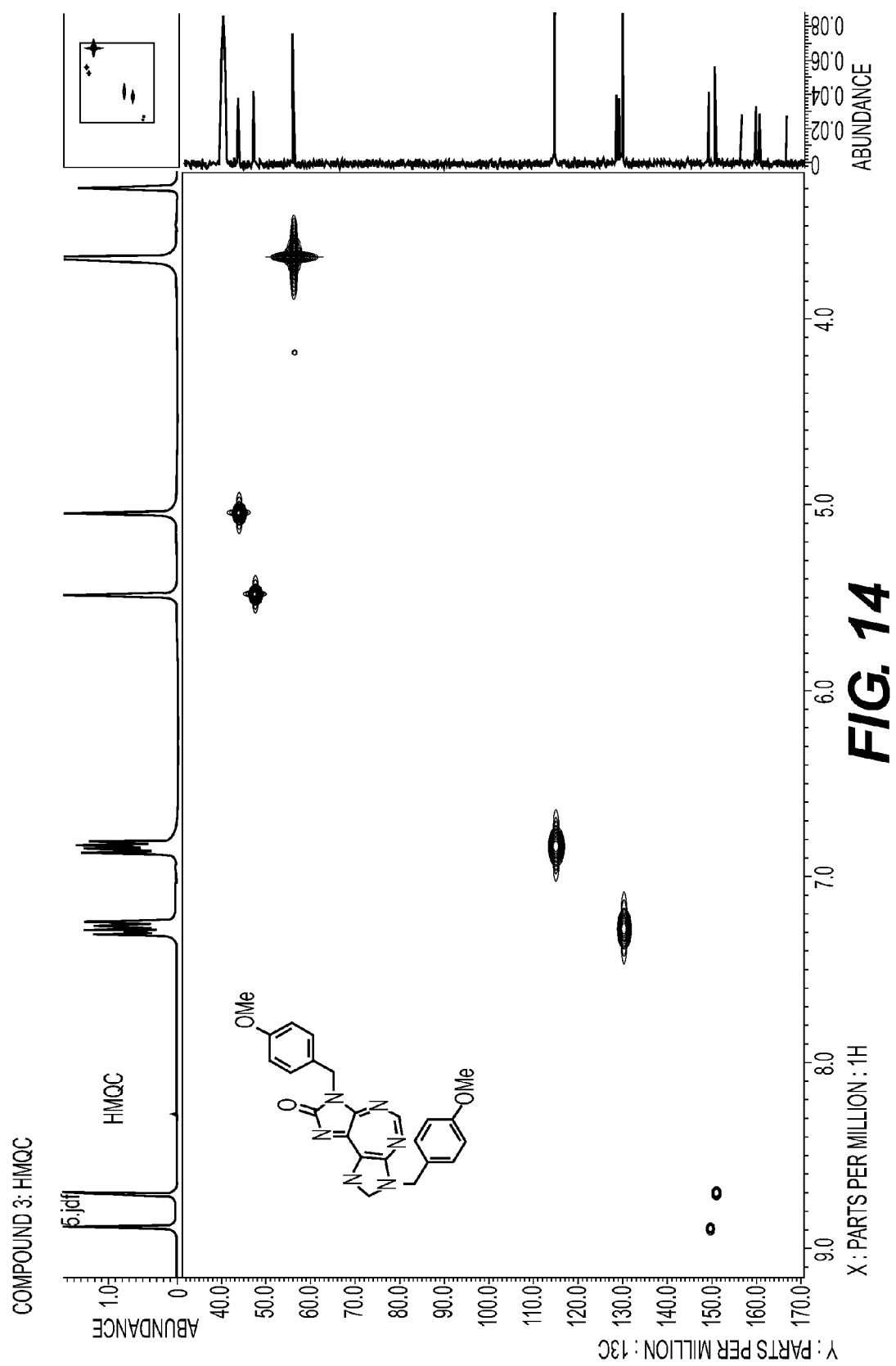
FIG. 14 illustrates HMQC NMR (δ, DMSO-$d_6$) data of illustrative compound 3.
Figure 15:
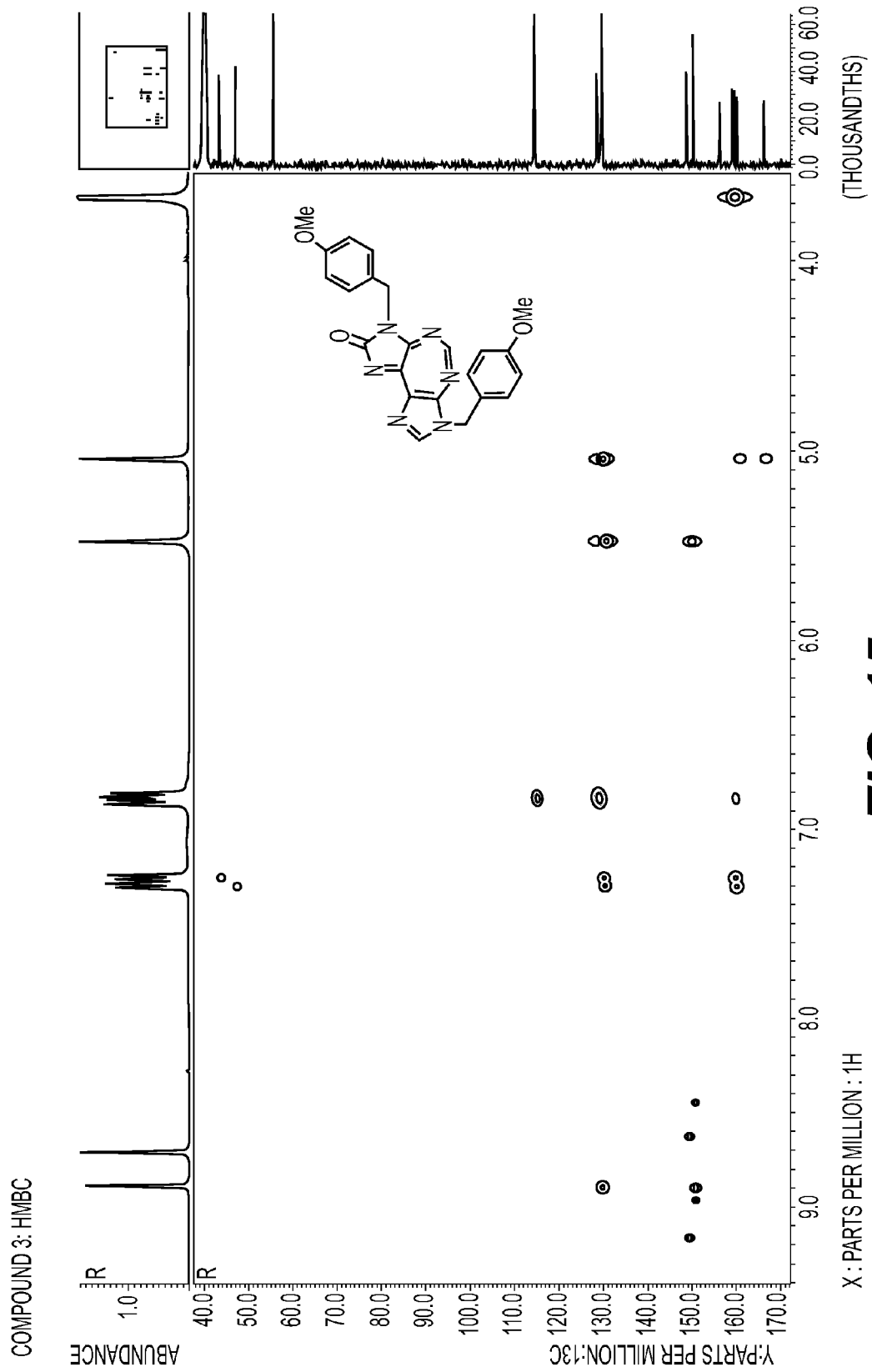
FIG. 15 illustrates HMBC NMR (δ, DMSO-$d_6$) data of illustrative compound 3.
Figure 16:
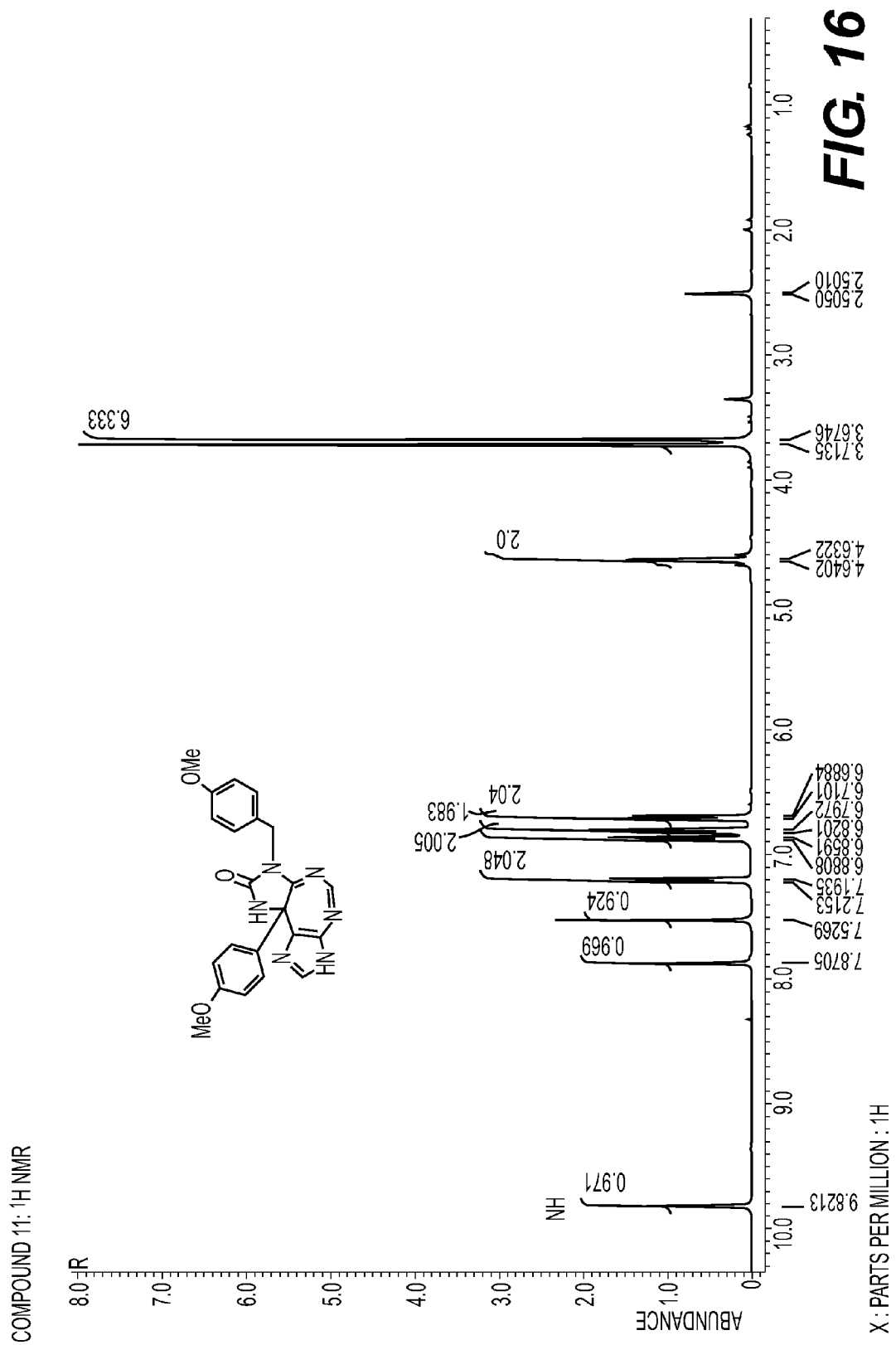
FIG. 16 illustrates $^1$H NMR (δ, DMSO-$d_6$, J in Hz in parentheses) data of illustrative compound 11.
Figure 17:
FIG. 17 illustrates $^{13}$C NMR (δ, DMSO-$d_6$) data of illustrative compound 11.
Figure 18:
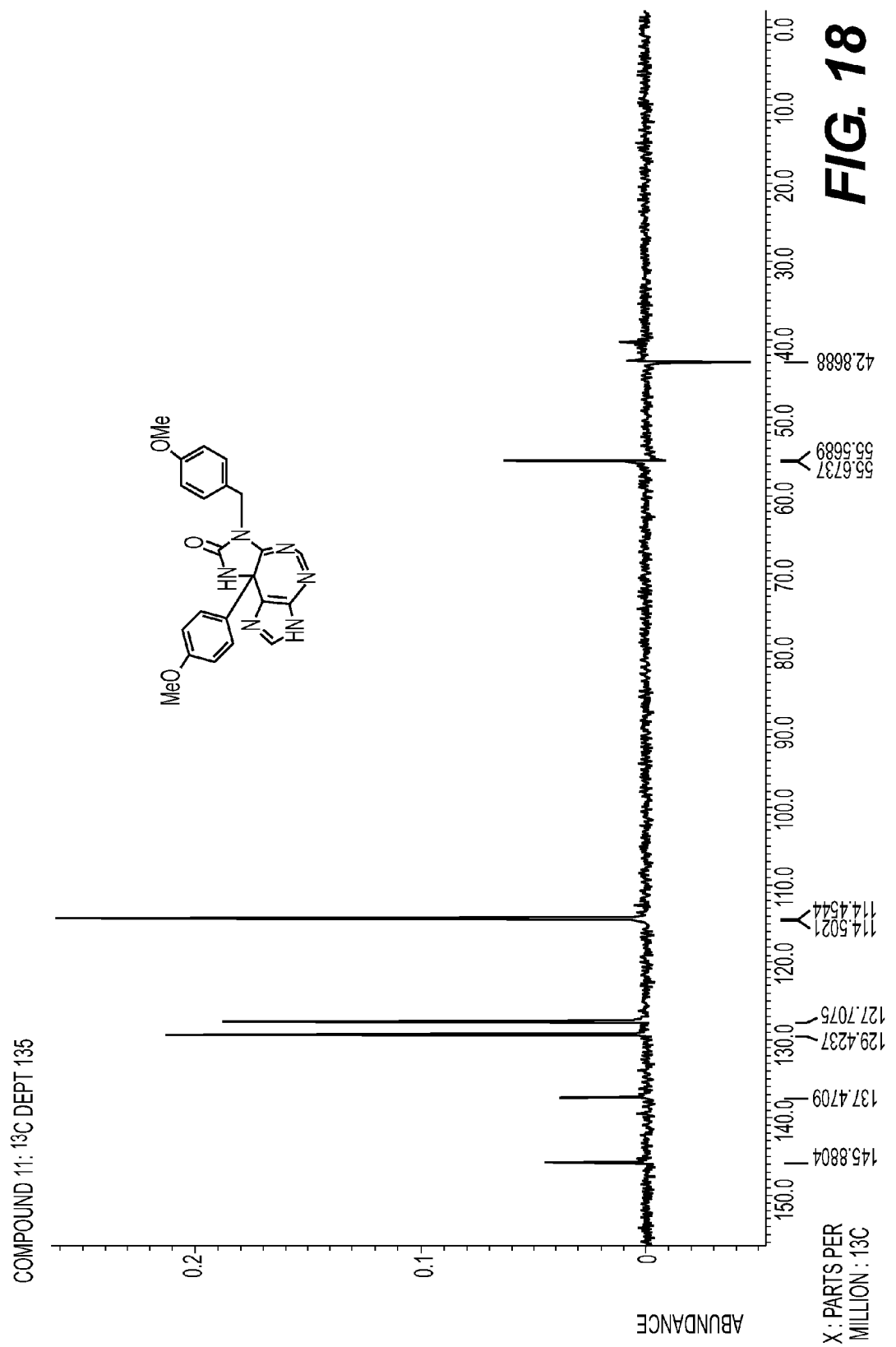
FIG. 18 illustrates $^{13}$C NMR DEPT 135 (δ, DMSO-$d_6$) data of illustrative compound 11.
Figure 19:
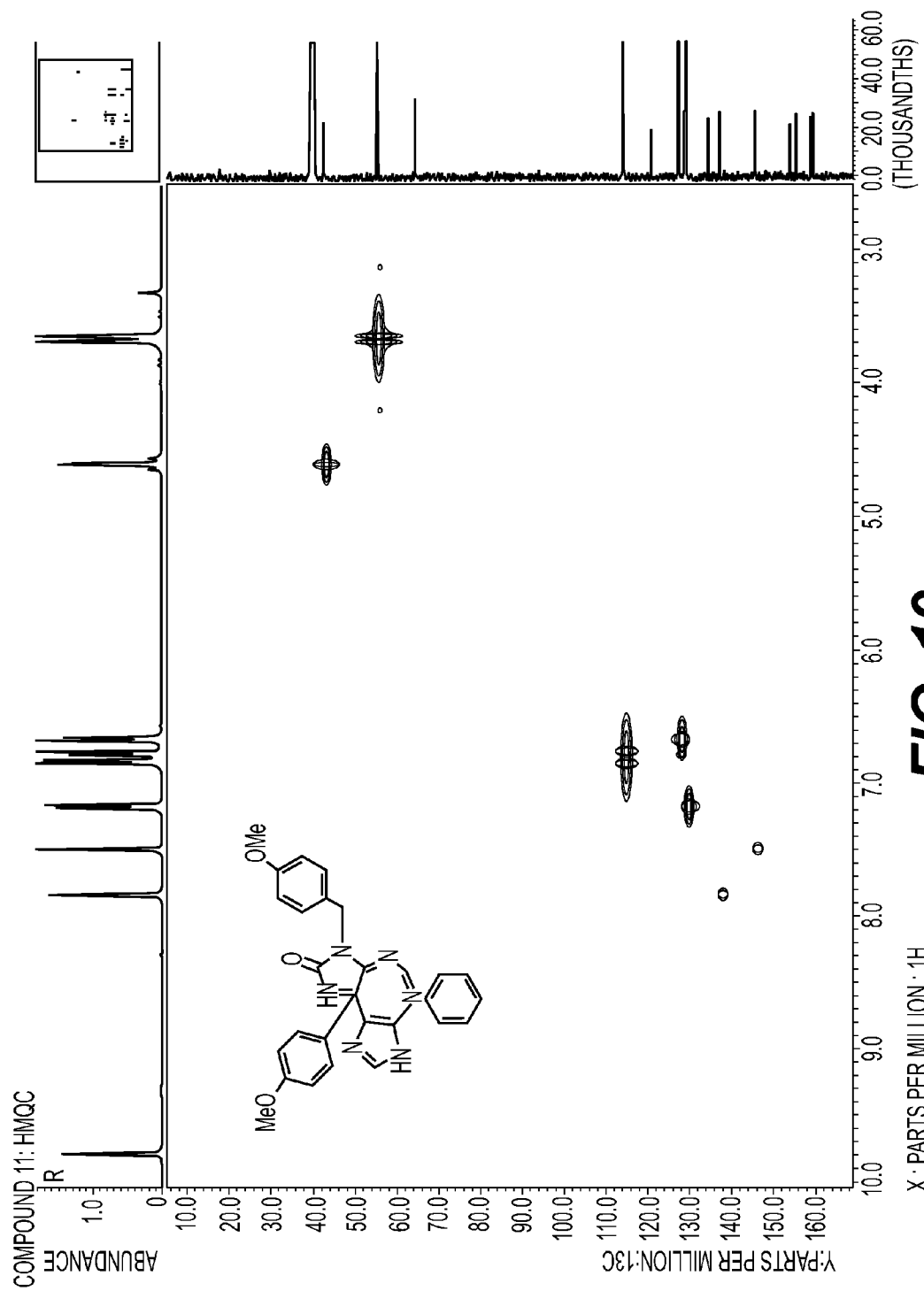
FIG. 19 illustrates HMQC NMR (δ, DMSO-$d_6$) data of illustrative compound 11.
Figure 20:
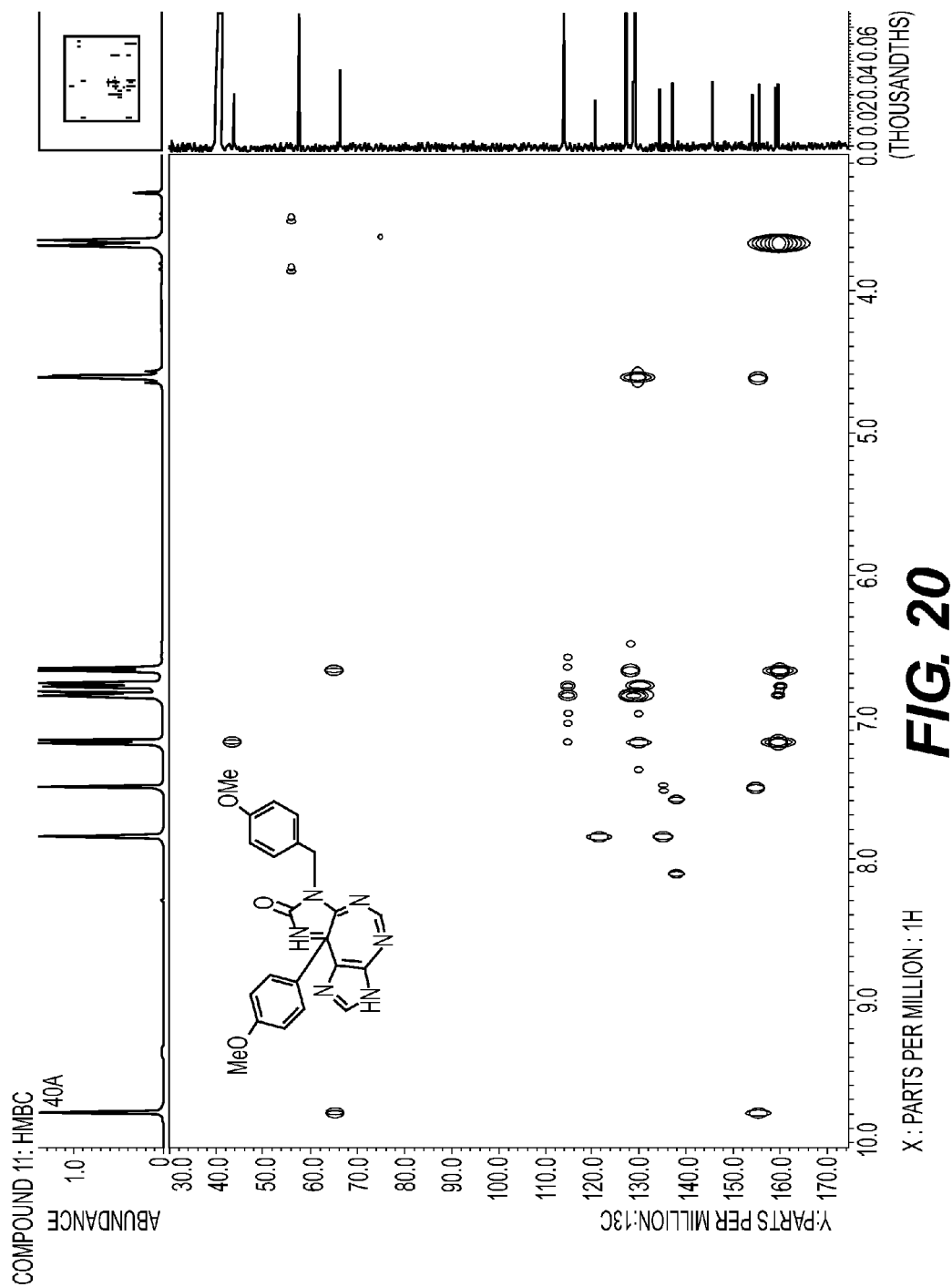
FIG. 20 illustrates HMBC NMR (δ, DMSO-$d_6$) data of illustrative compound 11.
Figure 21:
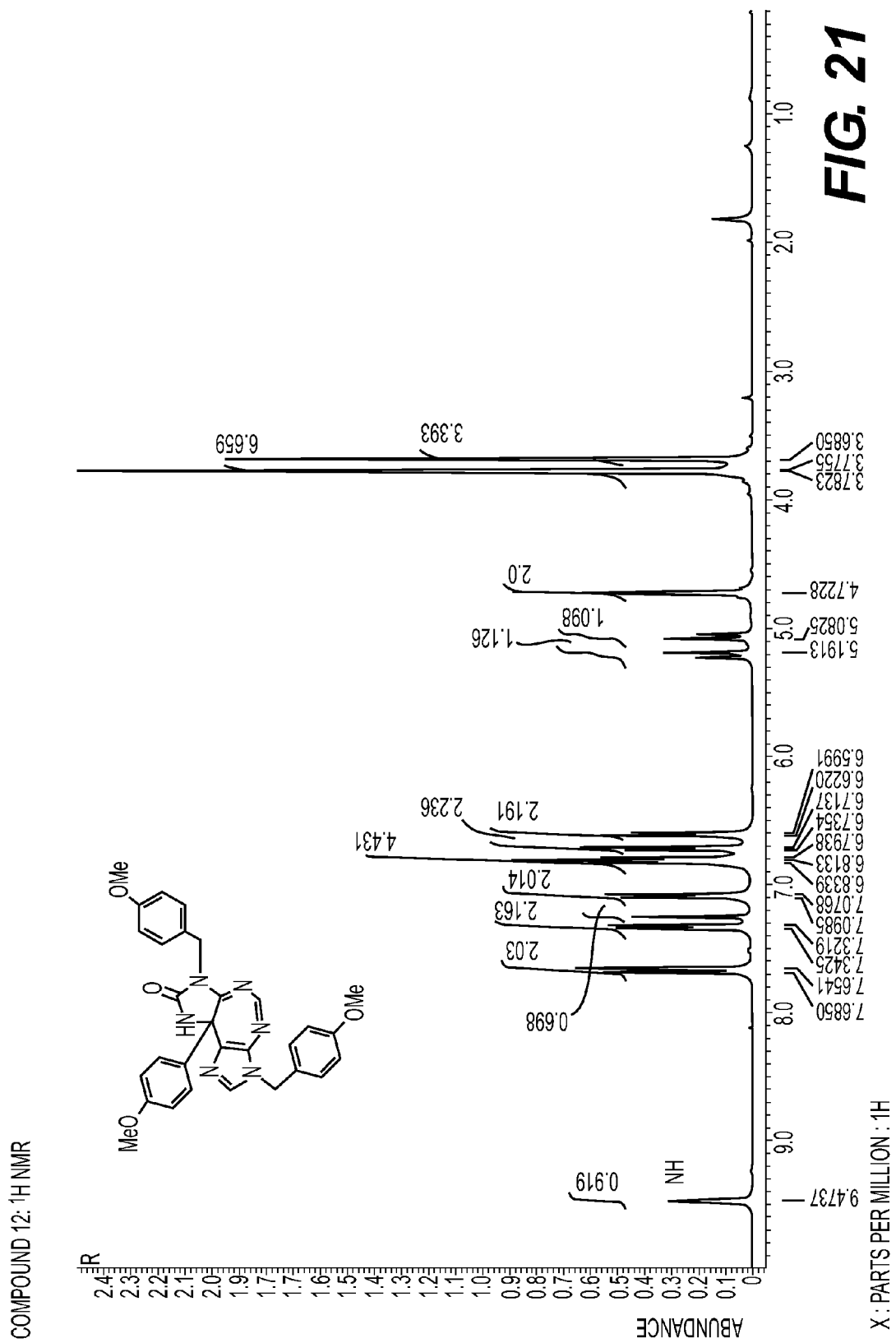
FIG. 21 illustrates $^1$H NMR (δ, DMSO-$d_6$, J in Hz in parentheses) data of illustrative compound 12.
Figure 22:
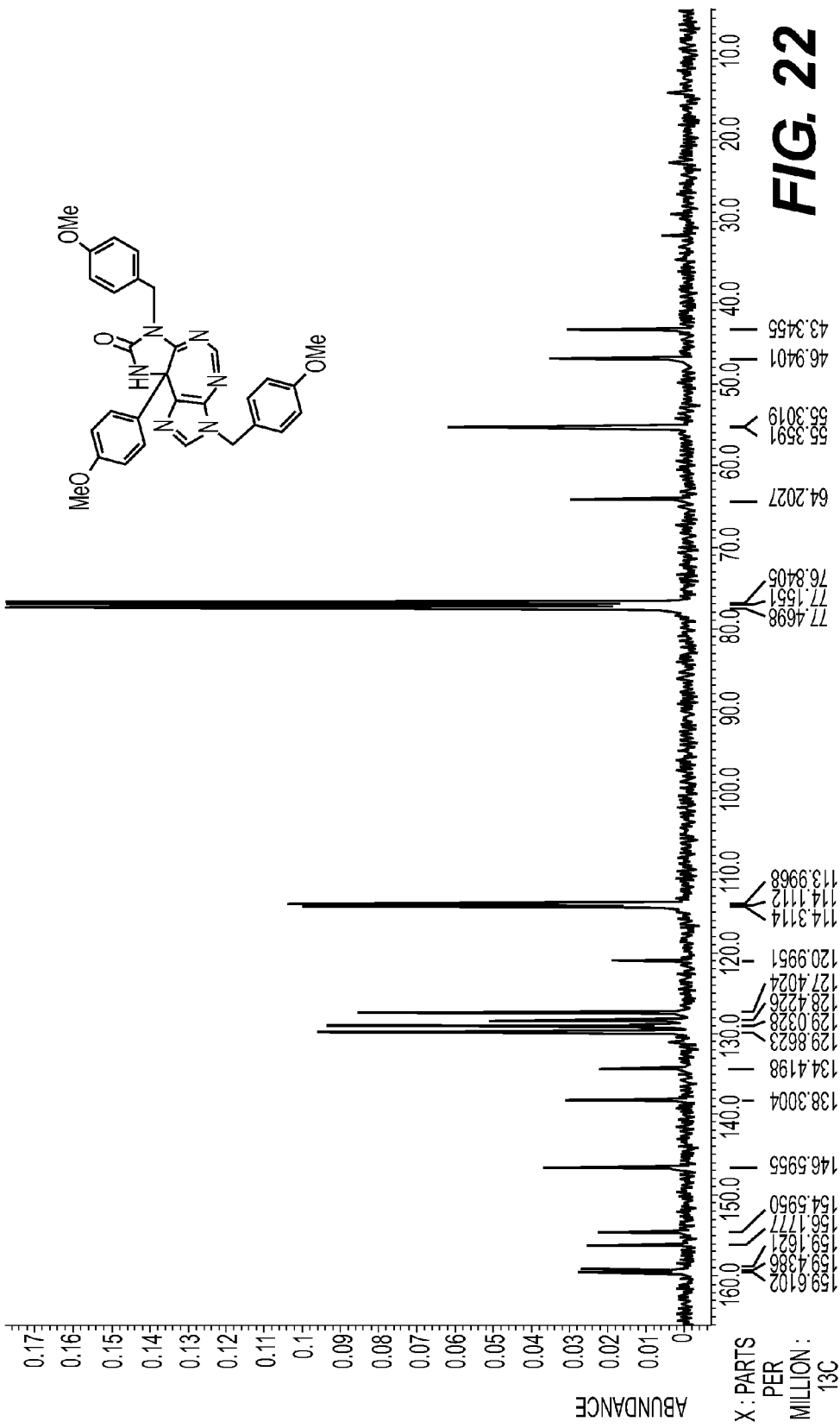
FIG. 22 illustrates $^{13}$C NMR (δ, DMSO-$d_6$) data of illustrative compound 12.
Figure 23:
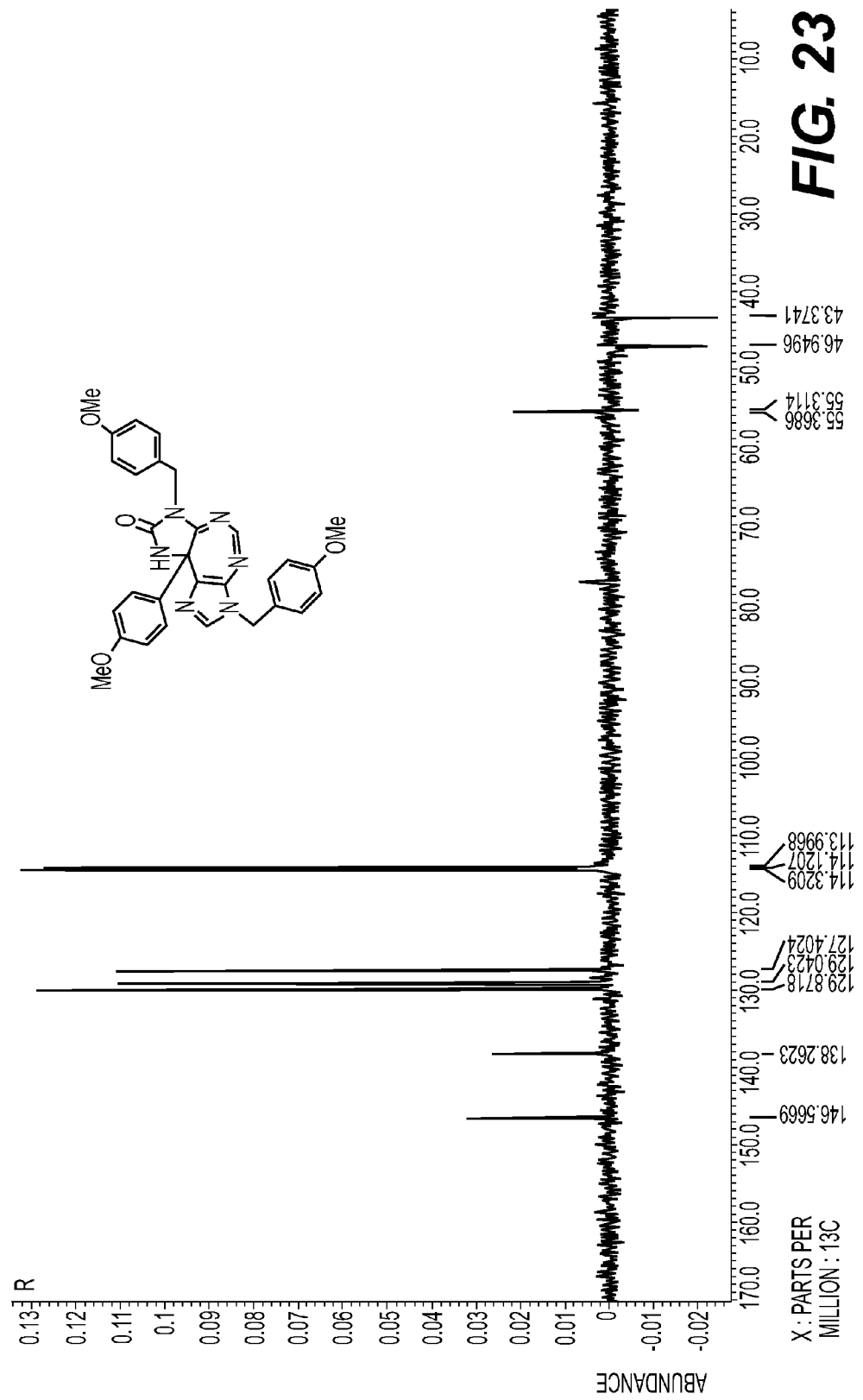
FIG. 23 illustrates $^{13}$C NMR DEPT 135 (δ, DMSO-$d_6$) data of illustrative compound 12.
Figure 24:
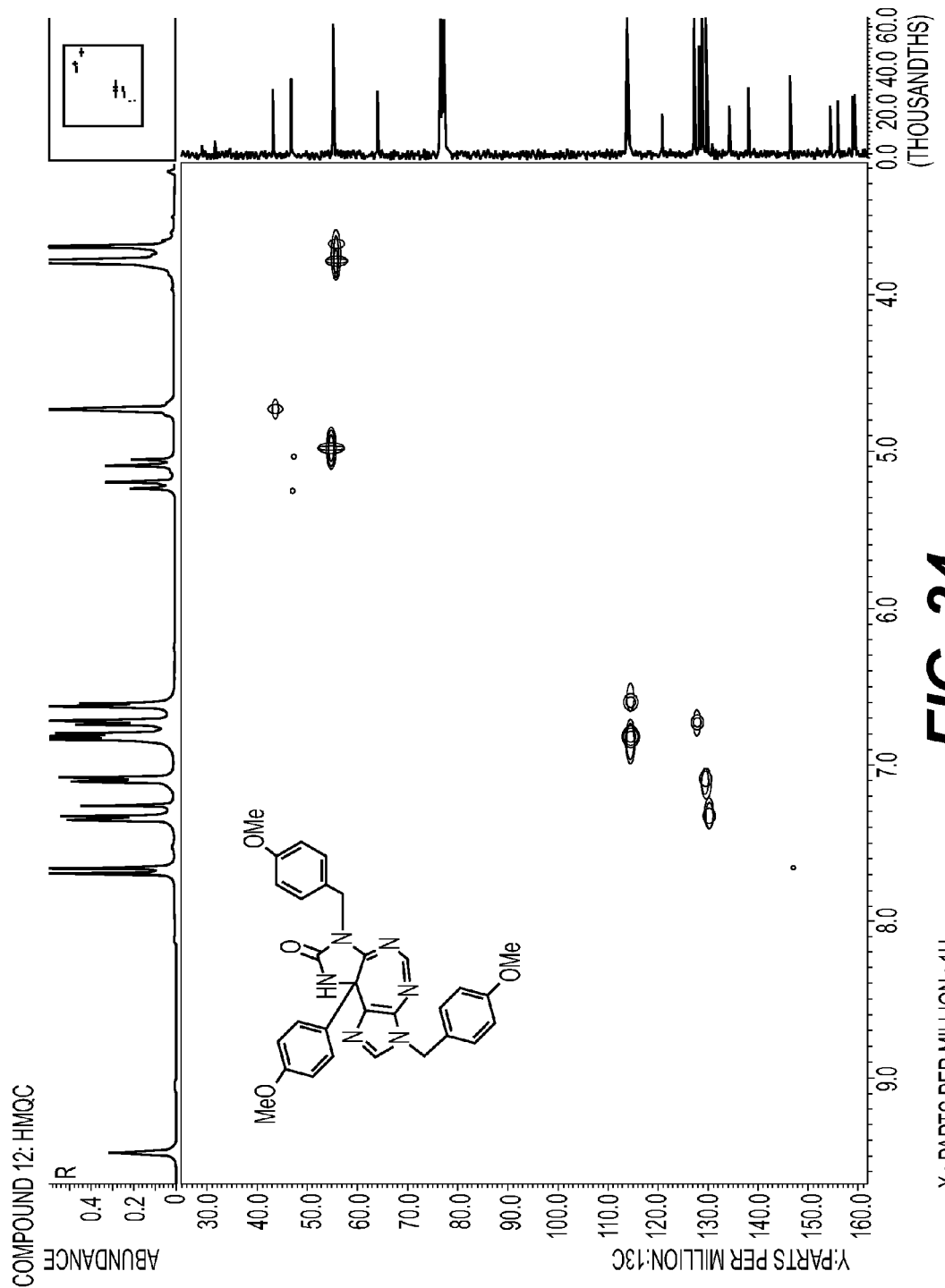
FIG. 24 illustrates HMQC NMR (δ, DMSO-$d_6$) data of illustrative compound 12.
Figure 25:
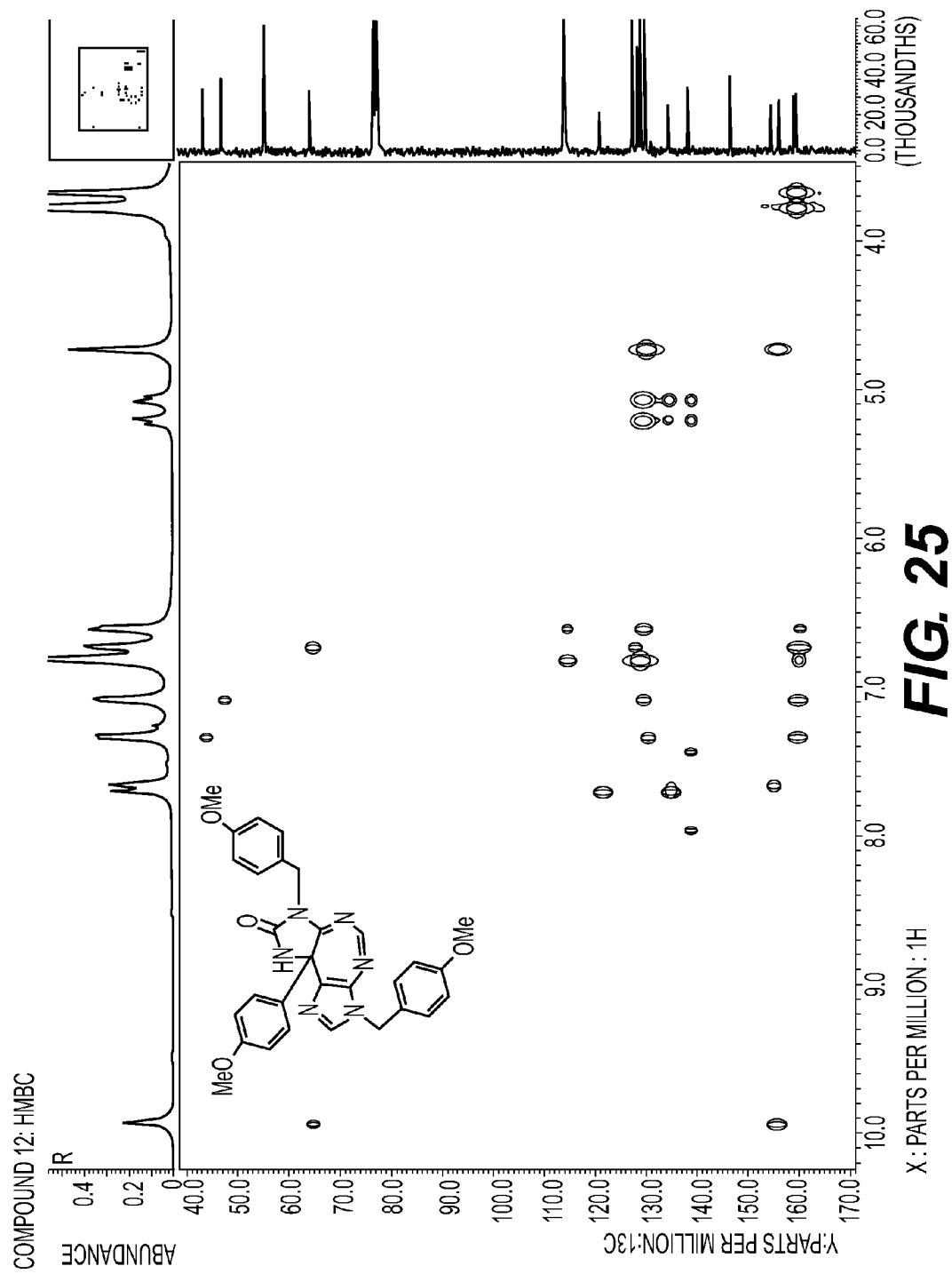
FIG. 25 illustrates HMBC NMR (δ, DMSO-$d_6$) data of illustrative compound 12.
Figure 26:
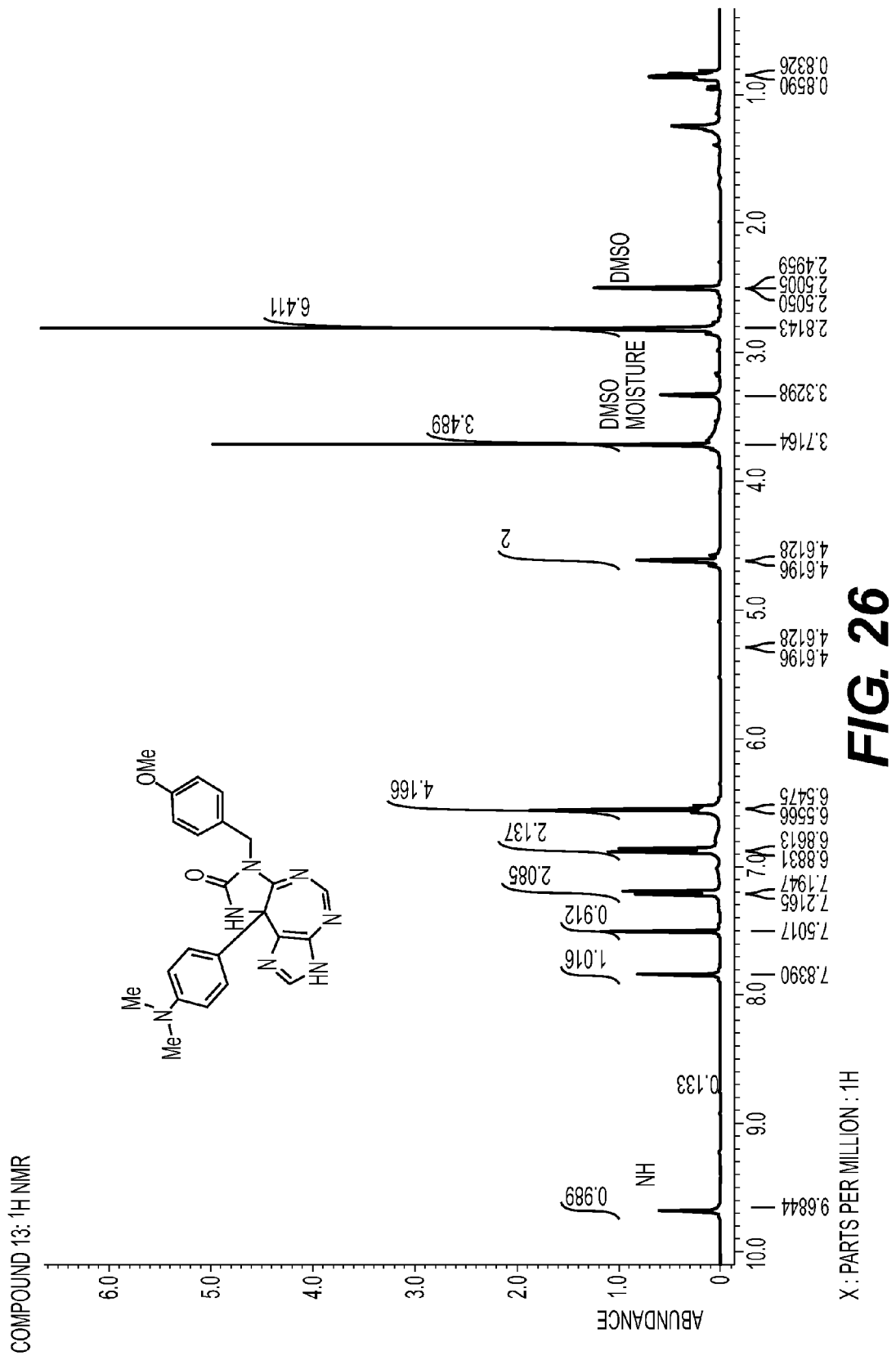
FIG. 26 illustrates $^1$H NMR (δ, DMSO-$d_6$, J in Hz in parentheses) data of illustrative compound 13.
Figure 27:
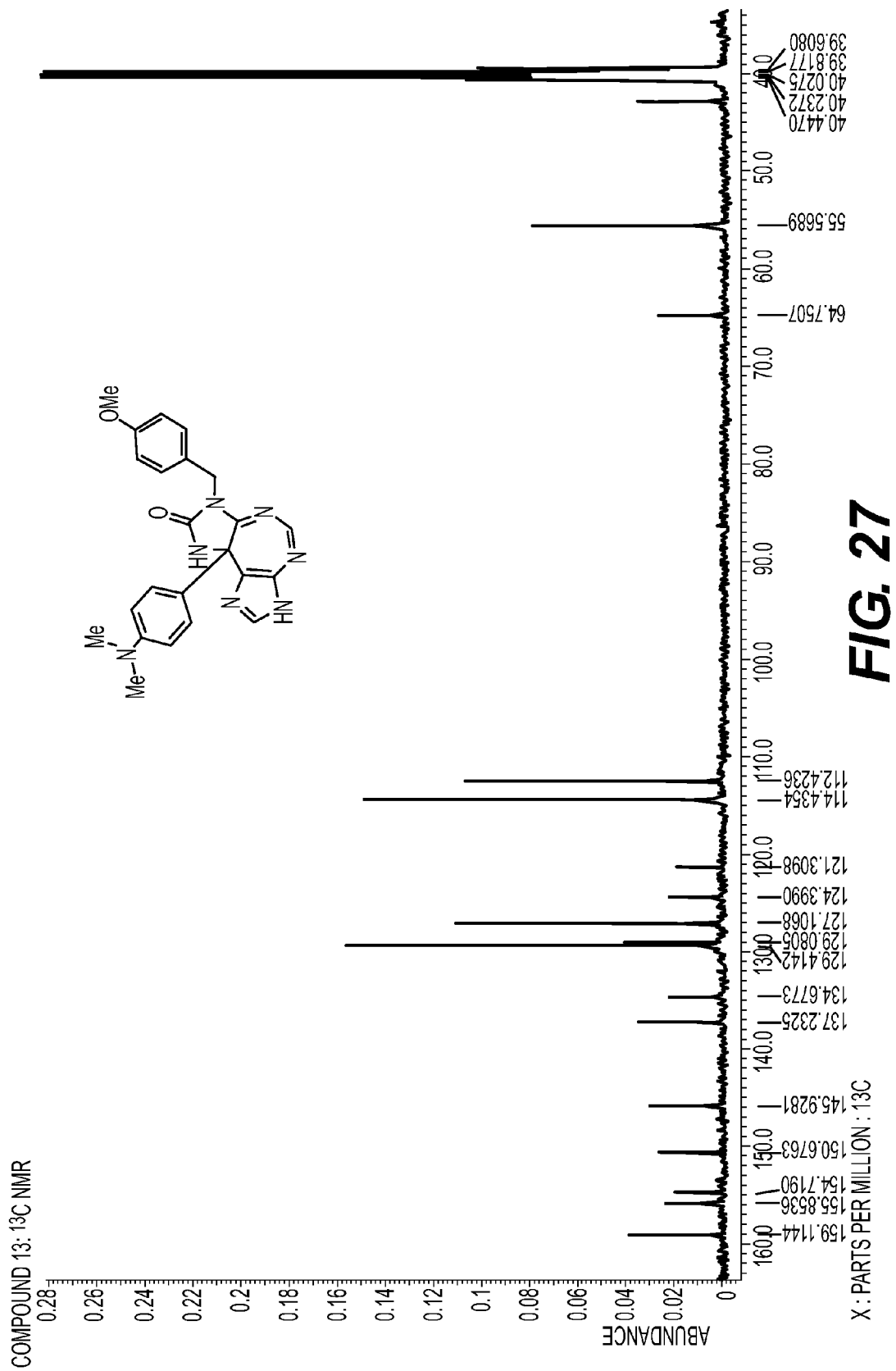
FIG. 27 illustrates $^{13}$C NMR (δ, DMSO-$d_6$) data of illustrative compound 13.
Figure 28:
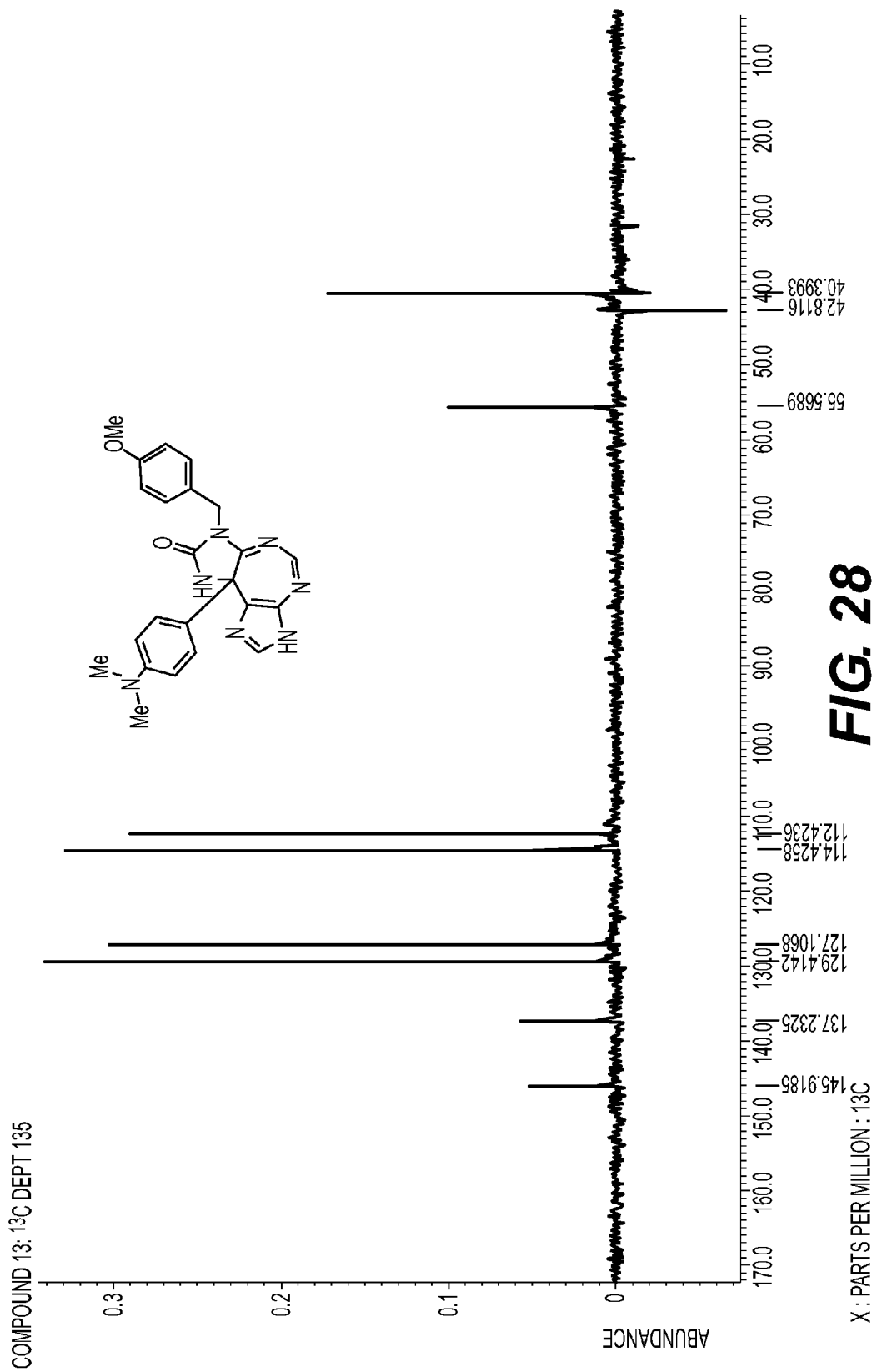
FIG. 28 illustrates $^{13}$C NMR DEPT 135 (δ, DMSO-$d_6$) data of illustrative compound 13.
Figure 29:
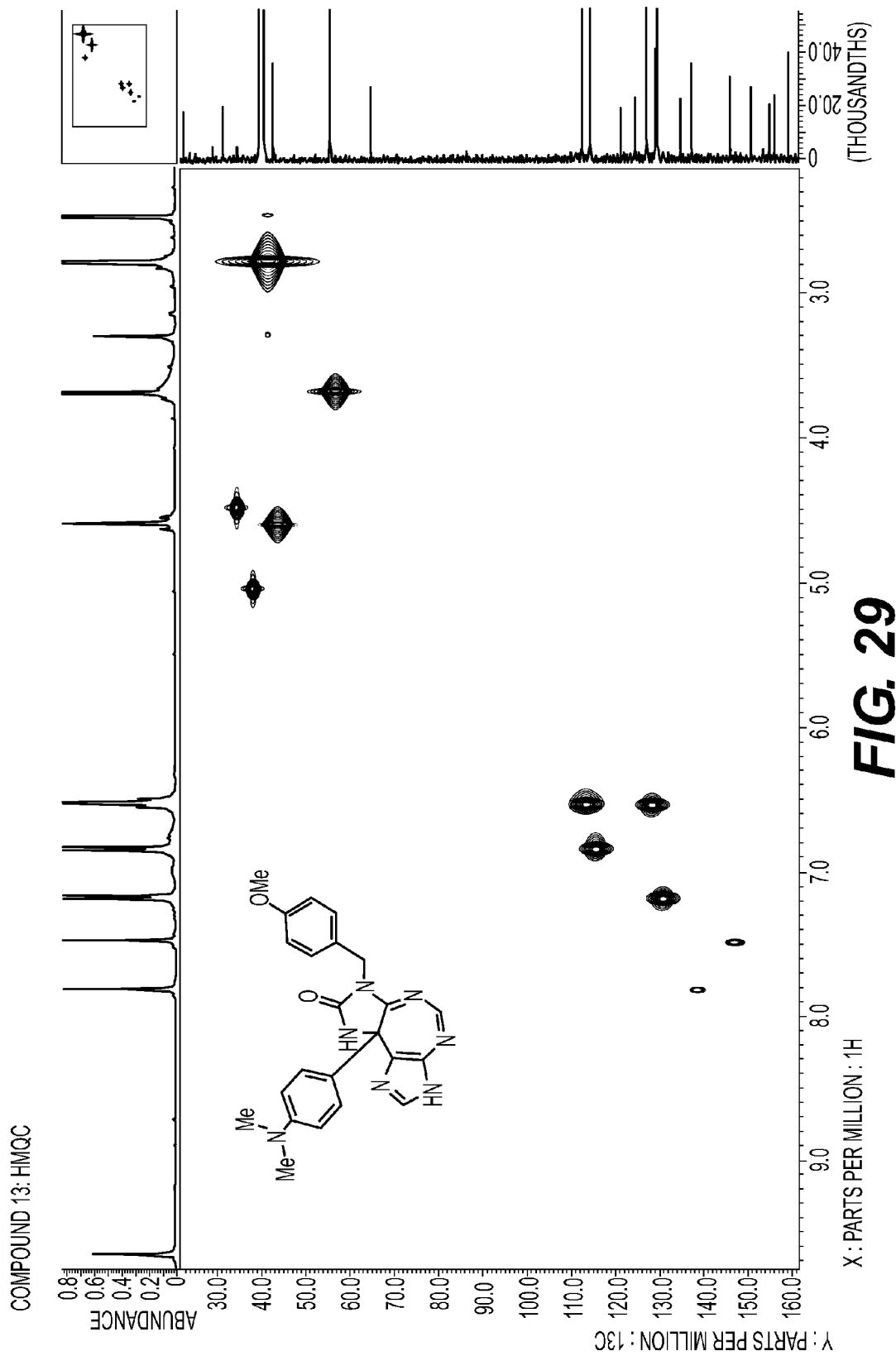
FIG. 29 illustrates HMQC NMR (δ, DMSO-$d_6$) data of illustrative compound 13.
Figure 30:
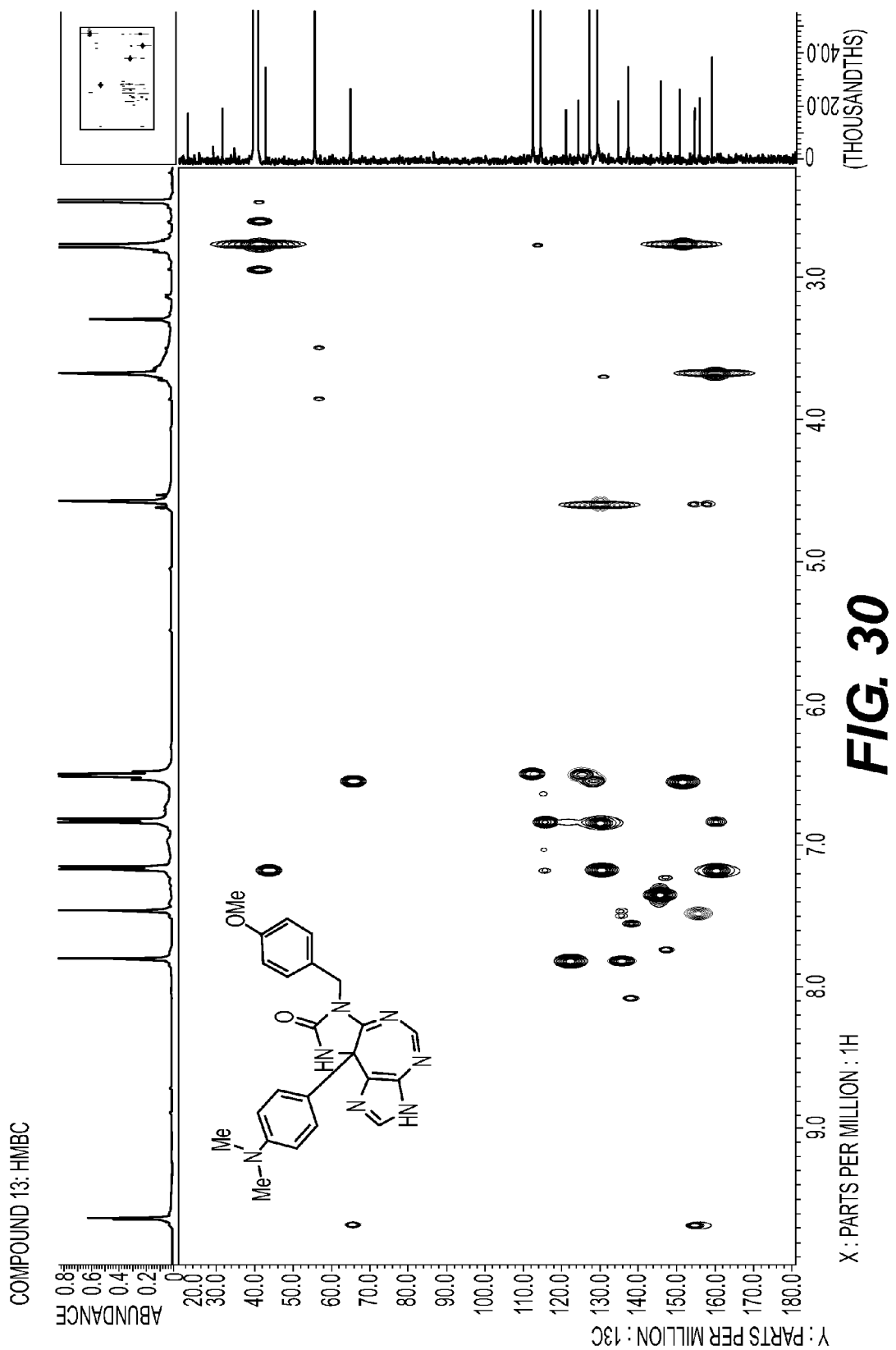
FIG. 30 illustrates HMBC NMR (δ, DMSO-$d_6$) data of illustrative compound 13.
Figure 31:
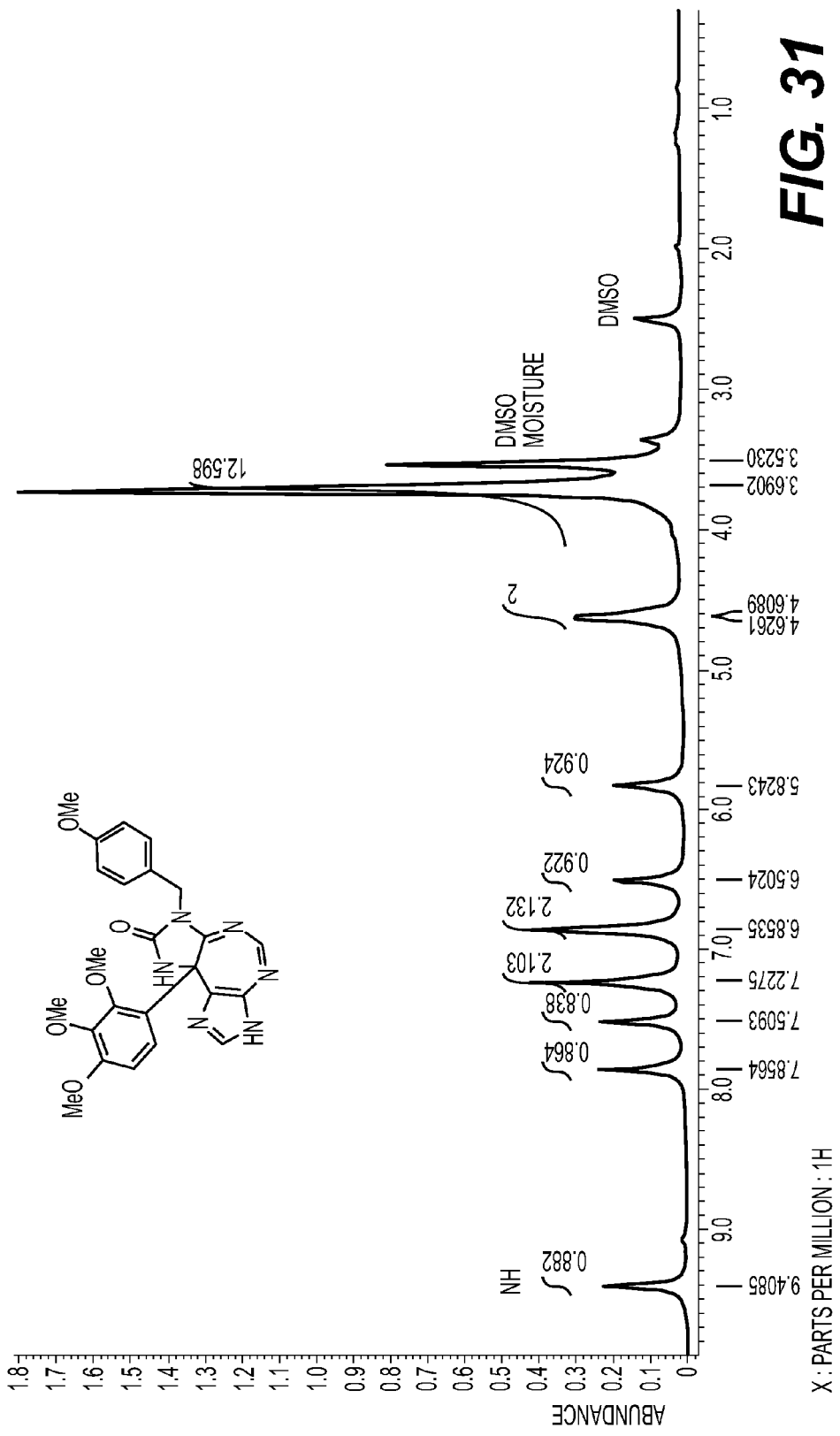
FIG. 31 illustrates $^1$H NMR (δ, DMSO-$d_6$, J in Hz in parentheses) data of illustrative compound 14.
Figure 32:
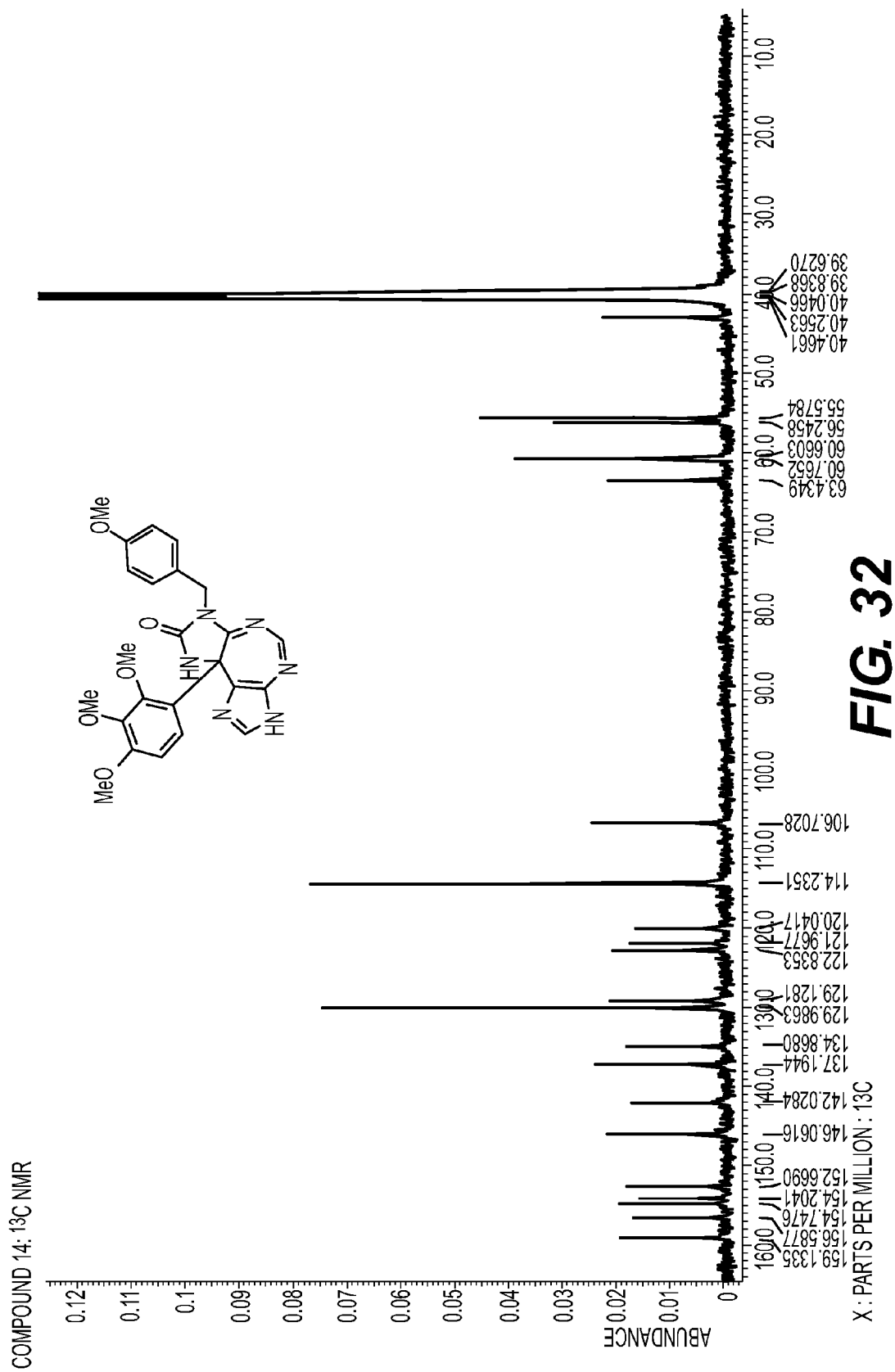
FIG. 32 illustrates $^{13}$C NMR (δ, DMSO-$d_6$) data of illustrative compound 14.
Figure 33:
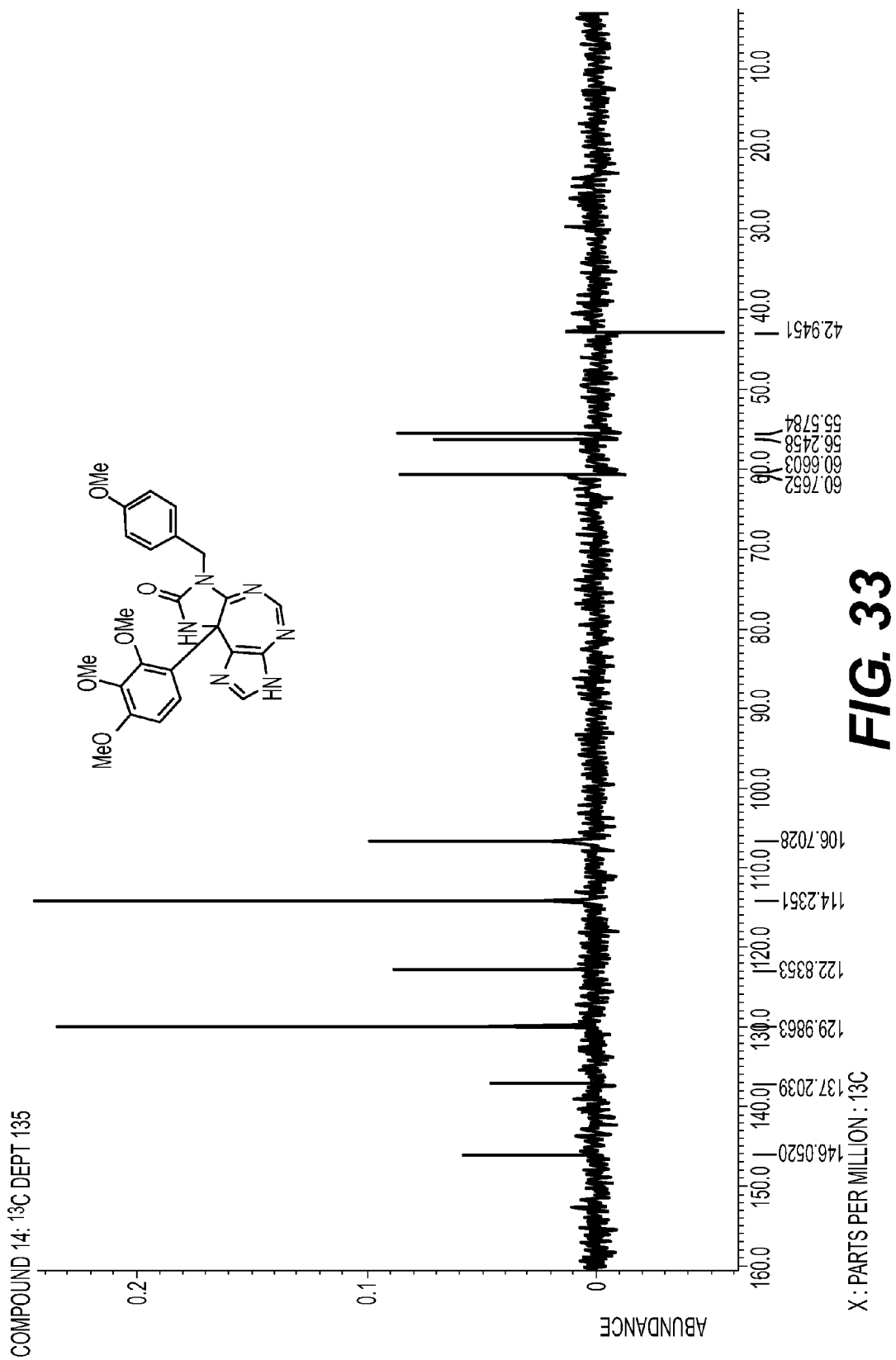
FIG. 33 illustrates $^{13}$C NMR DEPT 135 (δ, DMSO-$d_6$) data of illustrative compound 14.
Figure 34:
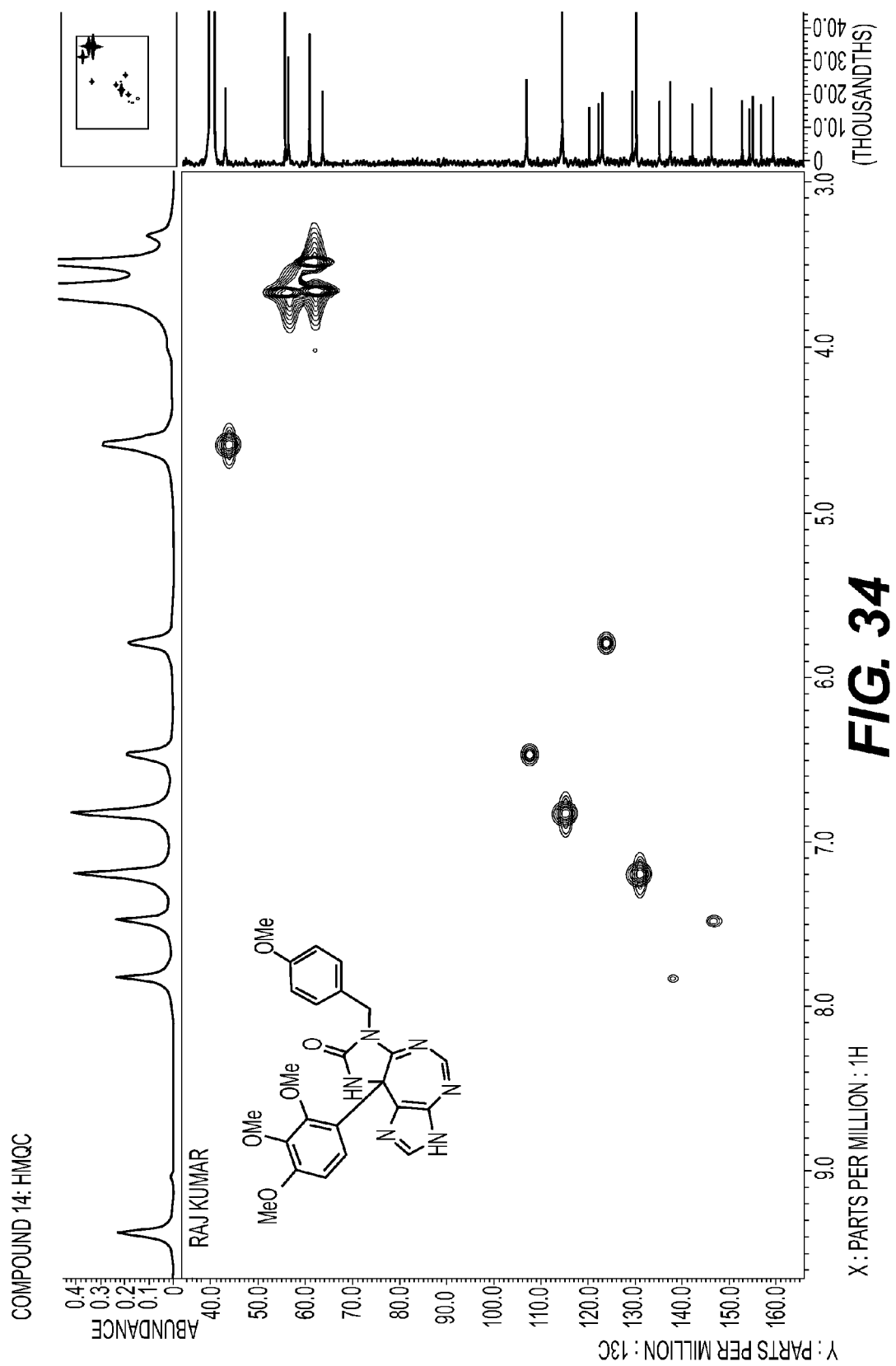
FIG. 34 illustrates HMQC NMR (δ, DMSO-$d_6$) data of illustrative compound 14.
Figure 35:
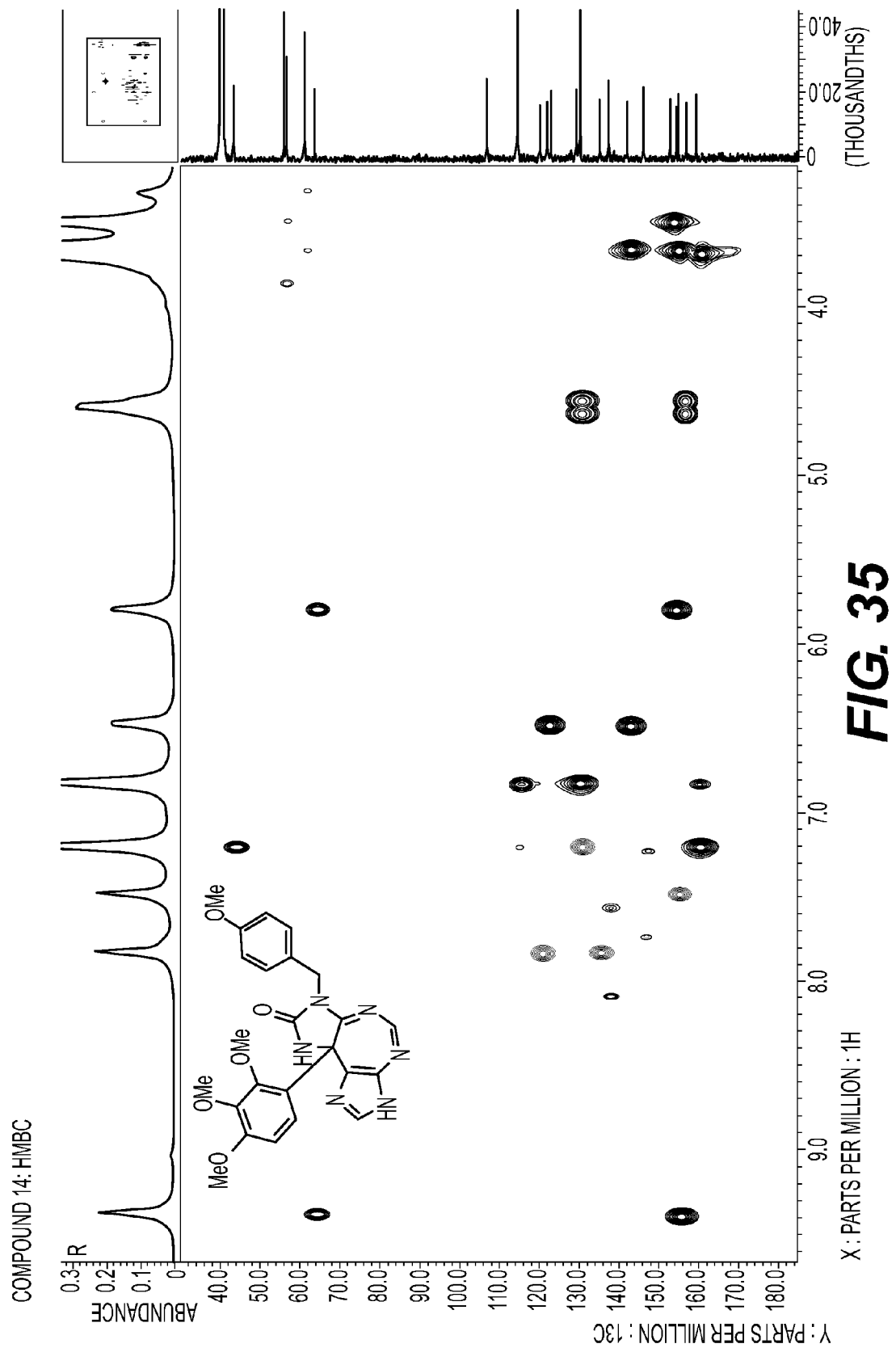
FIG. 35 illustrates HMBC NMR (δ, DMSO-$d_6$) data of illustrative compound 14.
Figure 36:
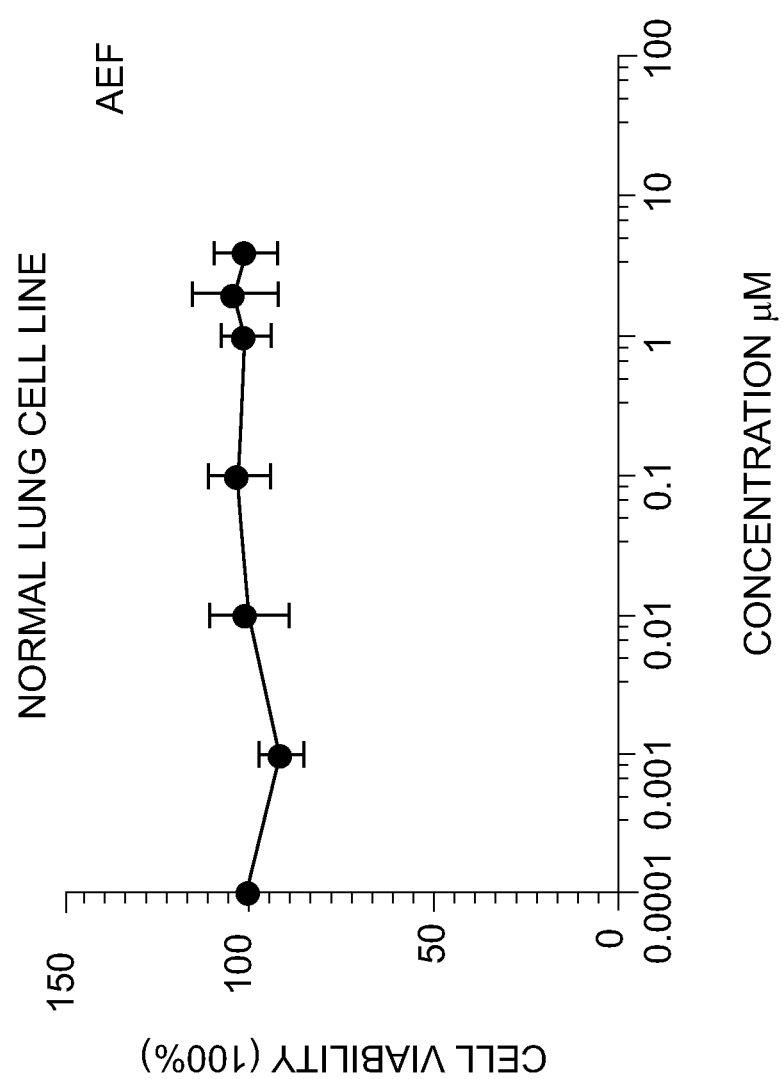
FIG. 36 illustrates normal lung cell lines when contacted with illustrative compound of the invention compound 3.
Figure 37:
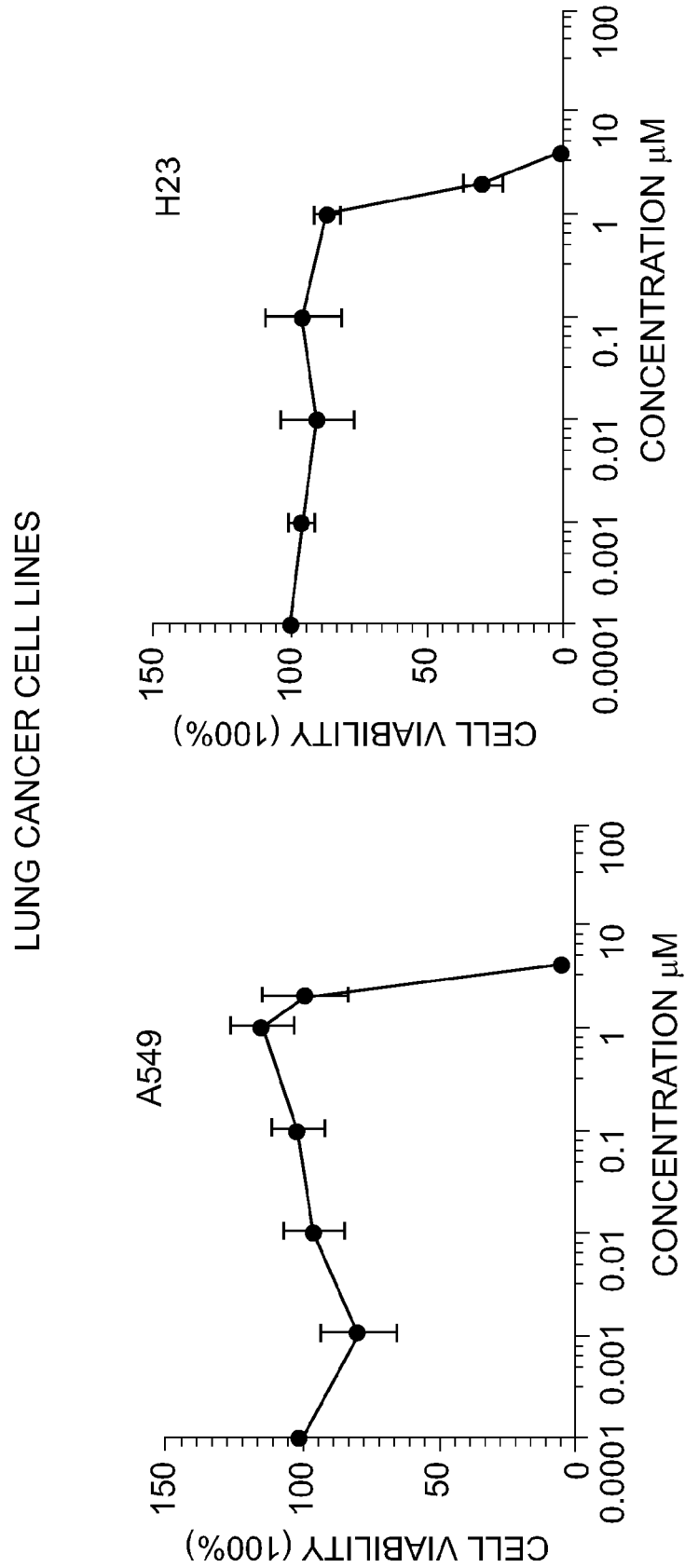
FIG. 37 illustrates lung cancer cell lines when contacted with illustrative compound of the invention compound 3.
Figure 38:
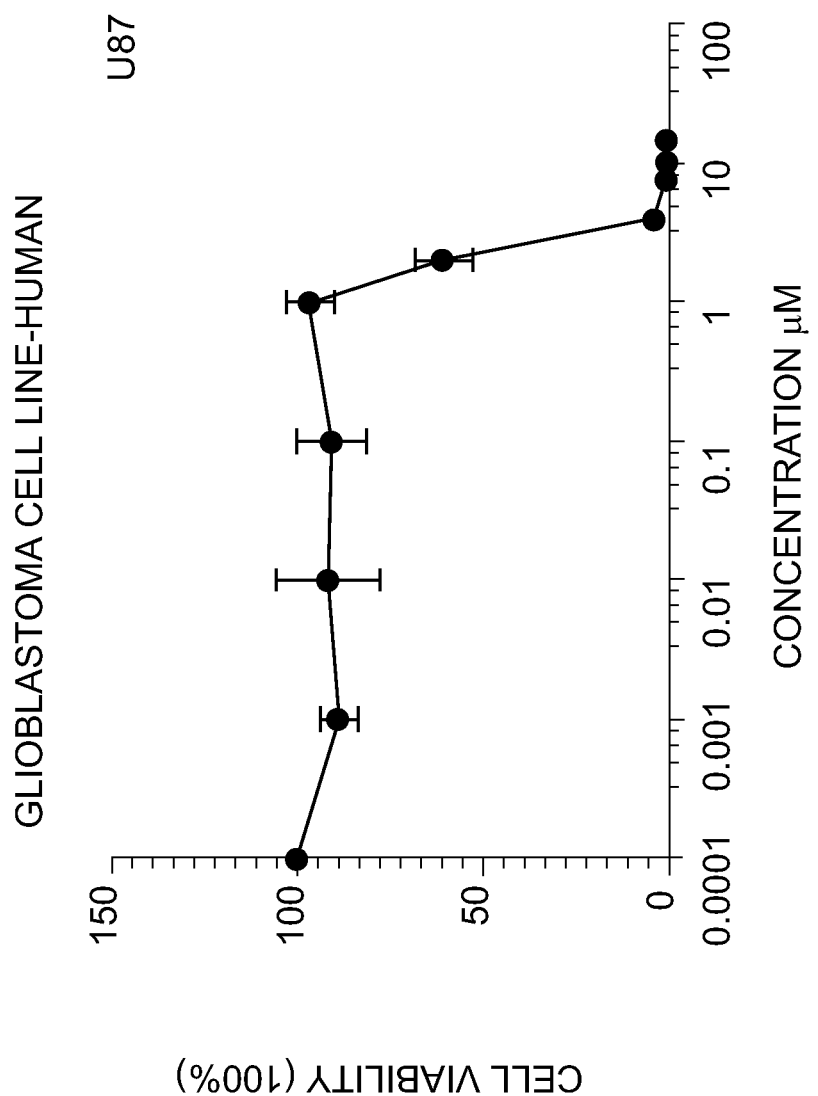
FIG. 38 illustrates glioblastoma human cell lines when contacted with illustrative compound of the invention compound 3.
Figure 39:
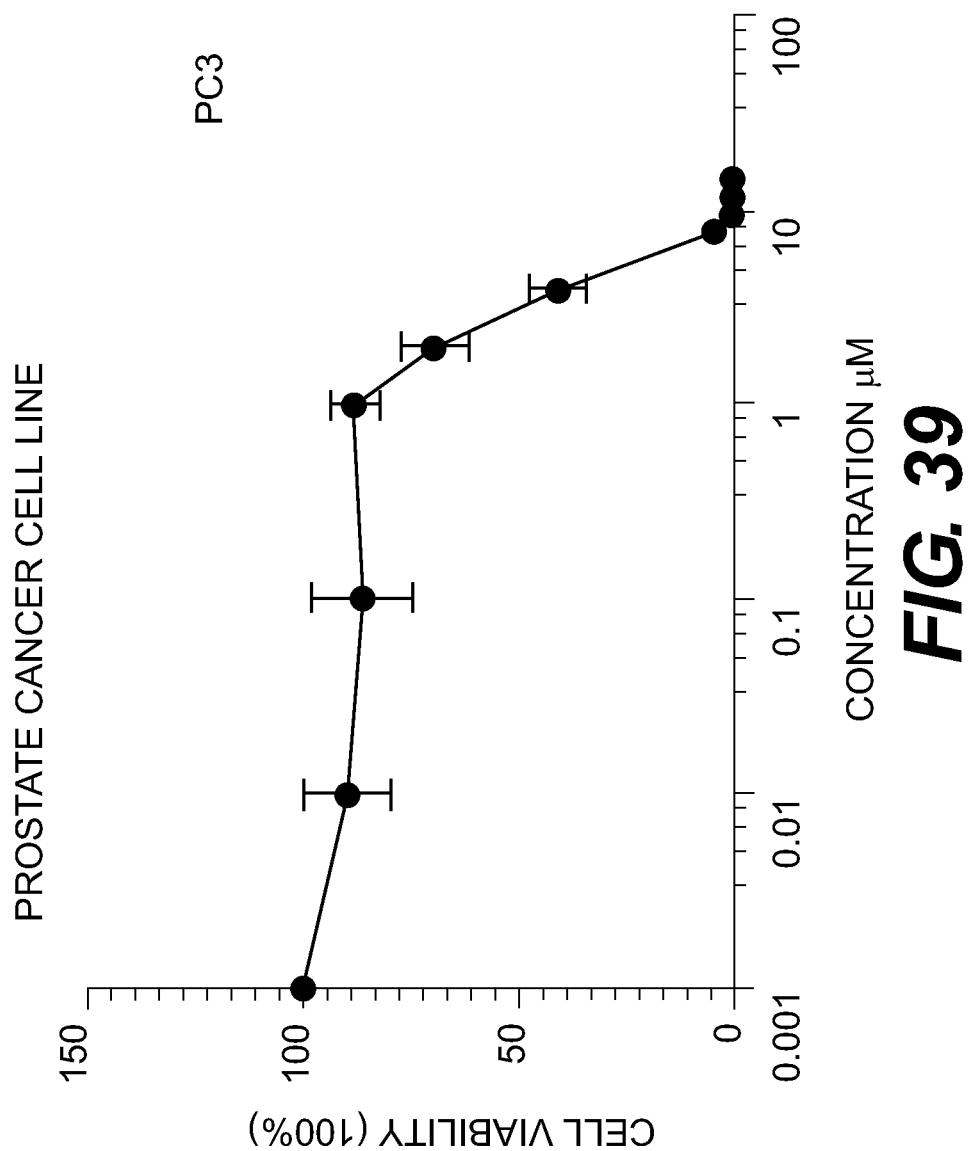
FIG. 39 illustrates prostate cancer cell lines when contacted with illustrative compound of the invention compound 3.
Figure 40:
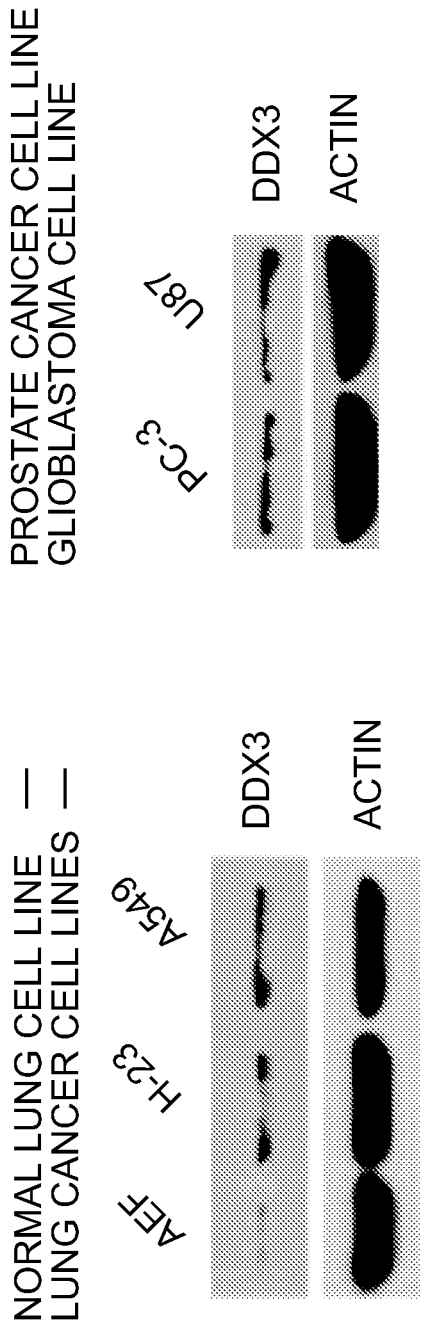
FIG. 40 illustrates immunoblast analyses for DDX-3 expression in lung, prostate, and glioblastoma cell lines.
Figure 41:
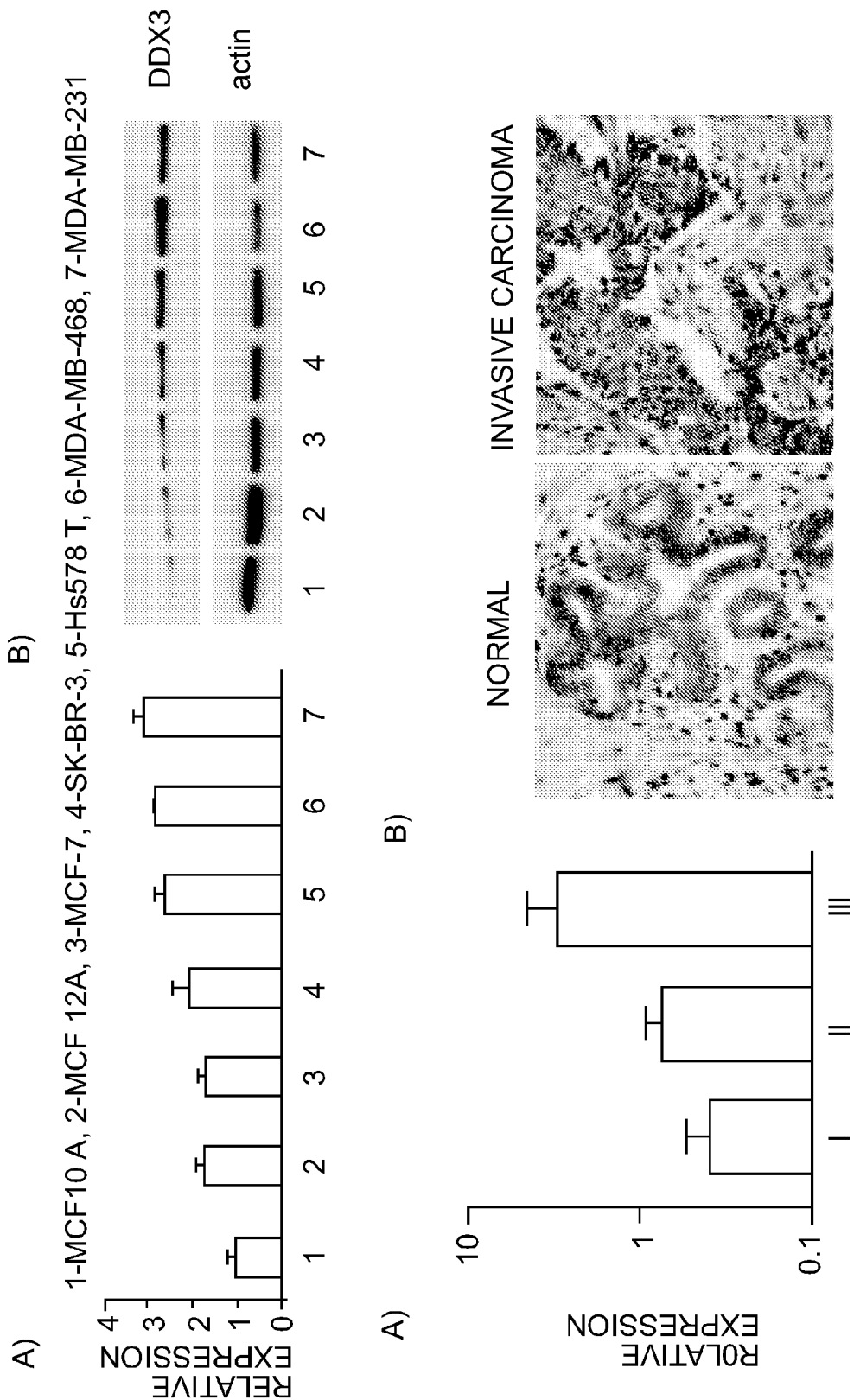
FIG. 41: Top panel: A) QRT-PCR of DDX3 levels in a series of immortalized normal breast cell lines (1-2) and breast cancer cell lines (3-7). The breast cancer cell lines are in the order of aggressive phenotype. Top panel: B) Immunoblot analysis for DDX3 expression in the identical cell lines as above. Bottom panel: A) QRT-PCR of DDX3 levels in different grades of human breast carcinoma samples. Bottom panel: B) Immunostaining for DDX3 levels in normal human breast sections and in breast carcinoma sample.
Figure 43:
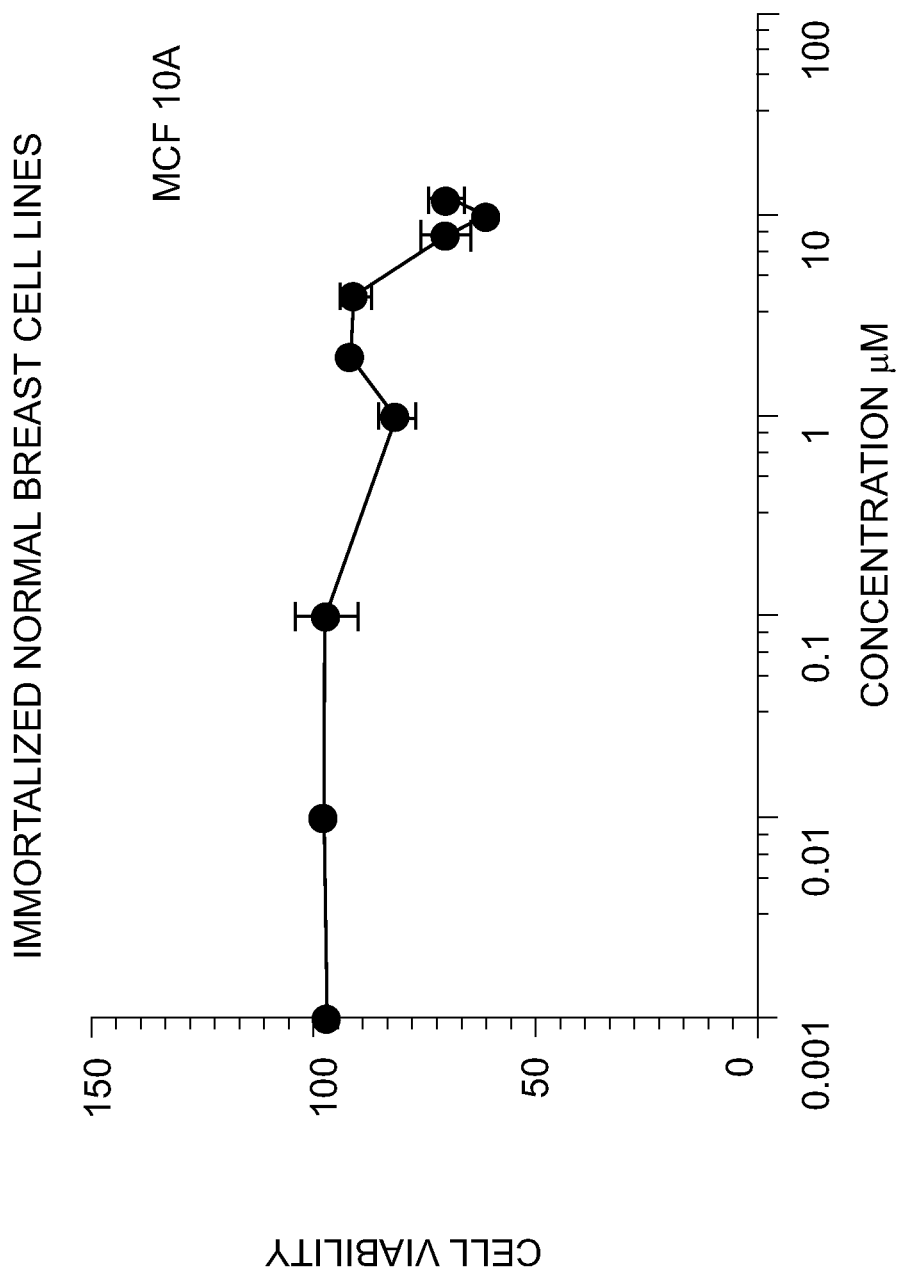
FIG. 43: MTS assays of MCF 10A cells (immortalized normal breast cell line) incubated with Compound 3 drug. X-axis indicates concentration of drug used. The cells were incubated for three days (fresh drug was added daily) following which cell viability was determined.
Figure 44:
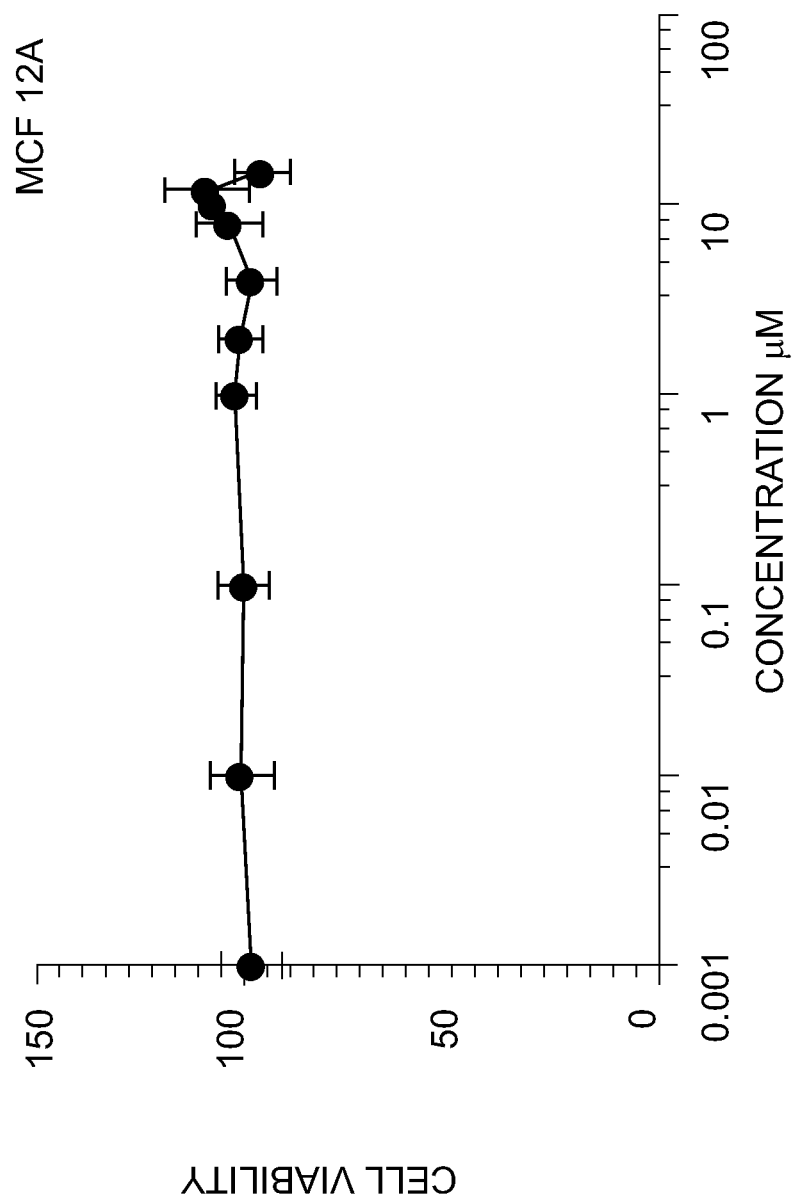
FIG. 44: MTS assays of MCF 10A cells (immortalized normal breast cell line) incubated with Compound 3 drug. X-axis indicates concentration of drug used. The cells were incubated for three days (fresh drug was added daily) following which cell viability was determined.
Figure 45:
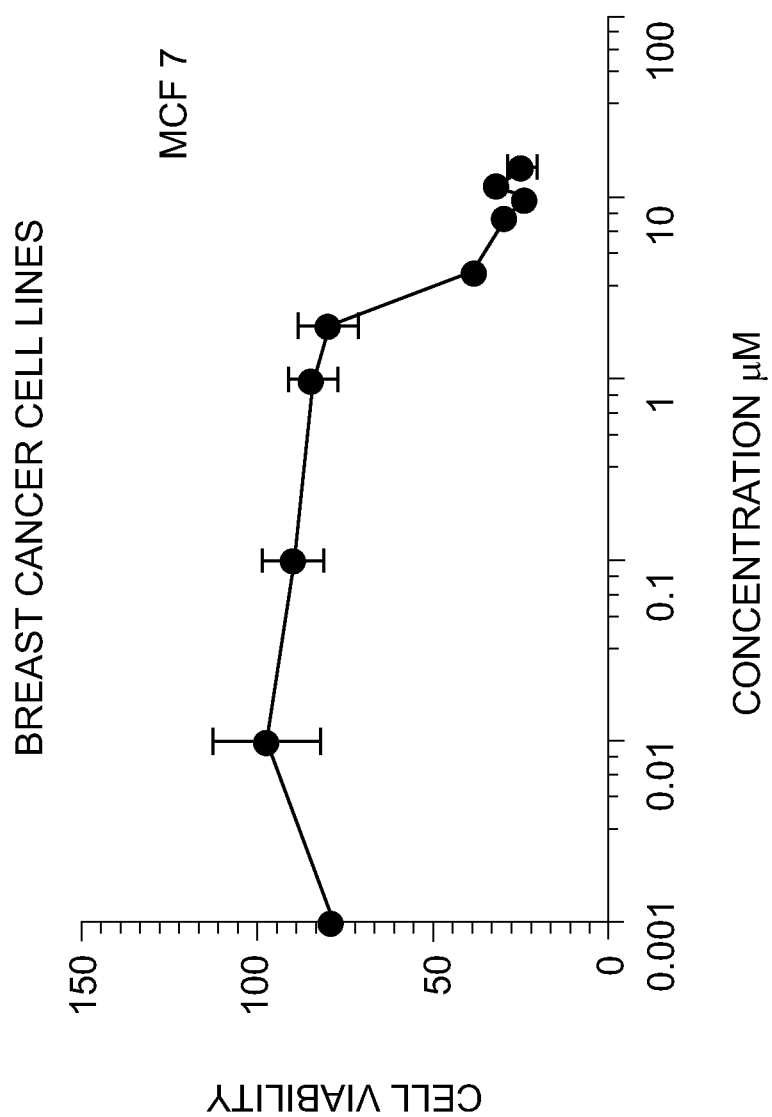
FIG. 45: MTS assays of MCF-7 cells (breast cancer cell line) incubated with Compound 3 drug. X-axis indicates concentration of drug used. The cells were incubated for three days (fresh drug was added daily) following which cell viability was determined.
Figure 46:
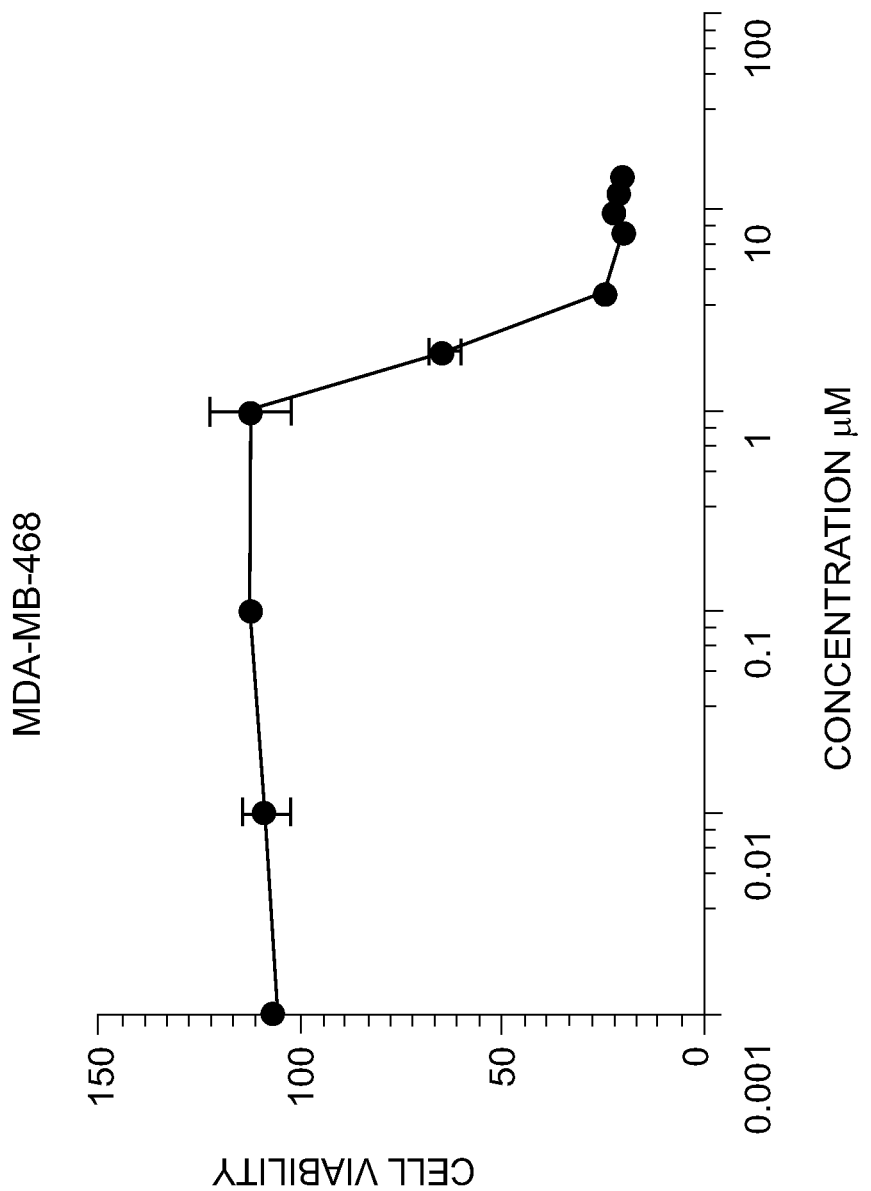
FIG. 46: MTS assays of MDA-MB-468 cells (breast cancer cell line) incubated with Compound 3 drug. X-axis indicates concentration of drug used. The cells were incubated for three days (fresh drug was added daily) following, which cell viability was determined.
Figure 47A:
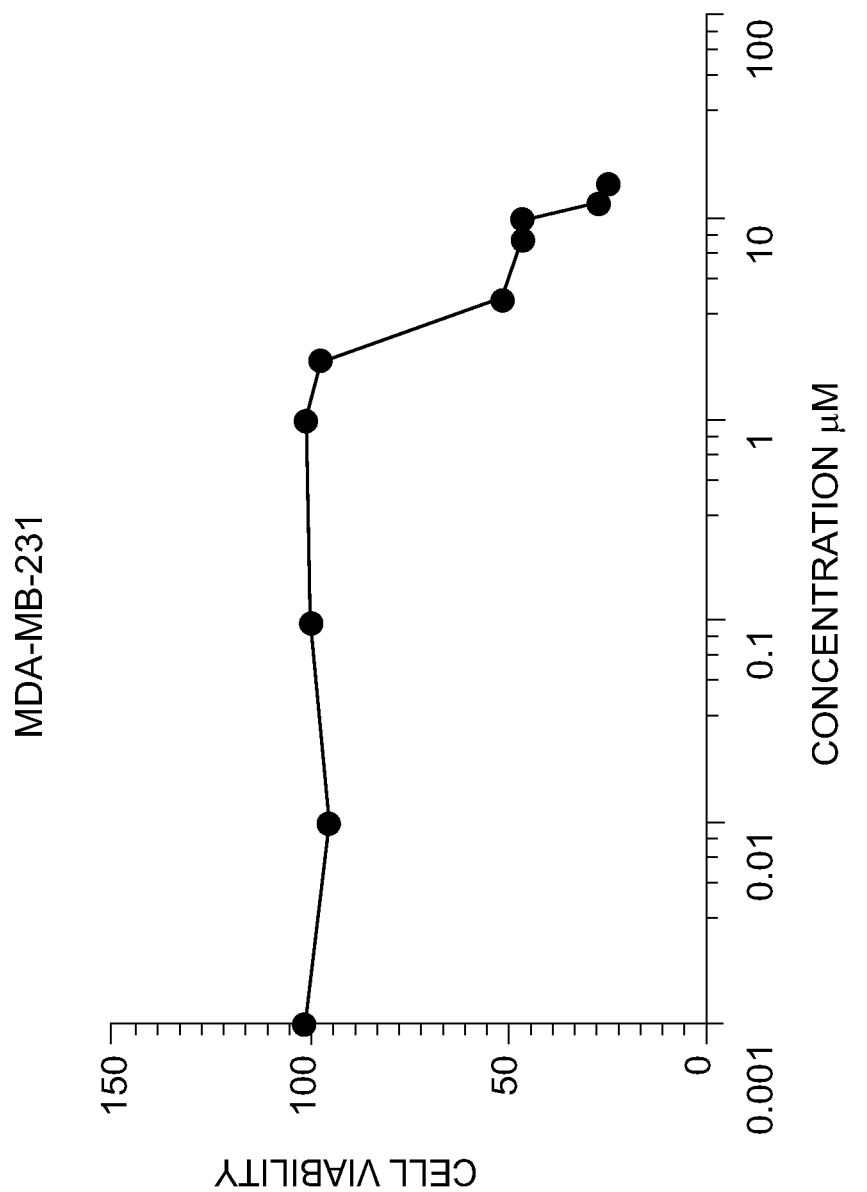
FIG. 47: MTS assays of MDA-MB-231 cells (breast cancer cell line) incubated with Compound 3 drug. X-axis indicates concentration of drug used. The cells were incubated for three days (fresh drug was added daily) following which cell viability was determined.
Figure 47B:
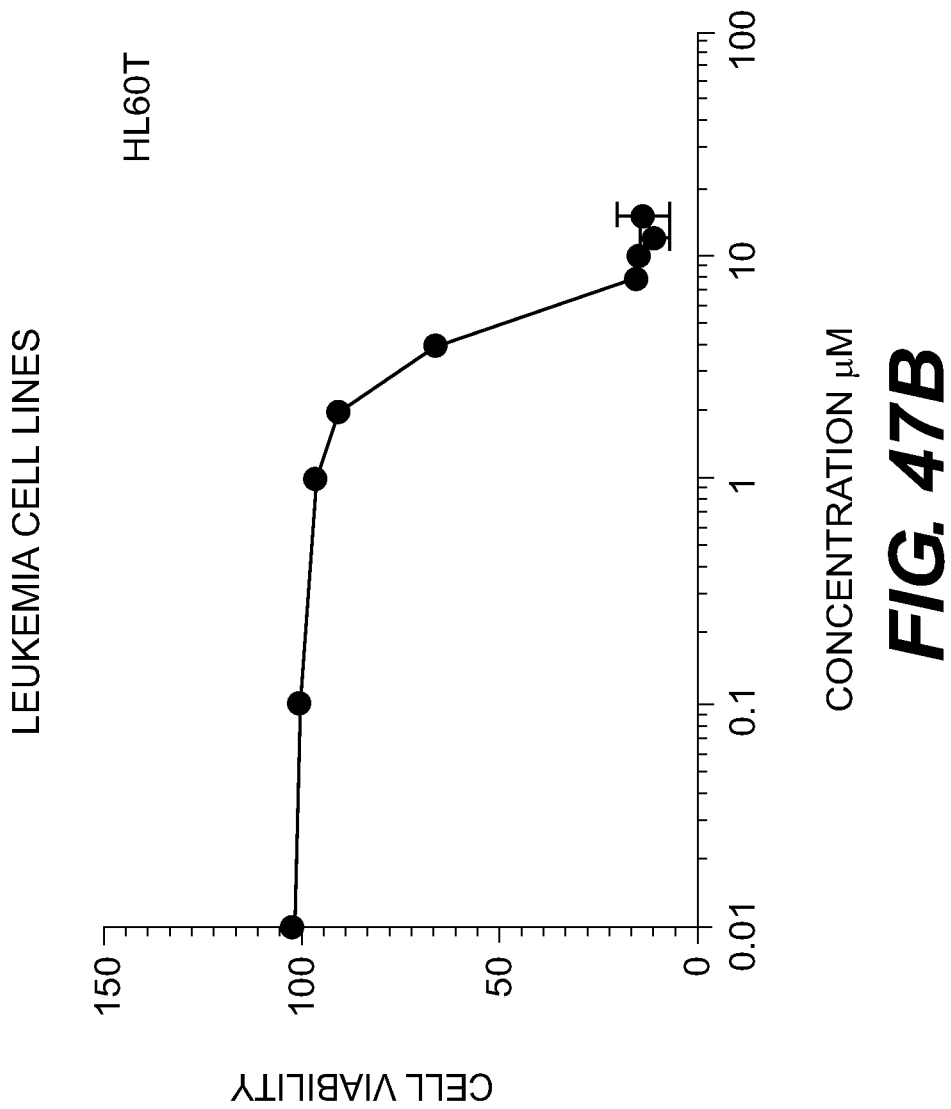
Figure 48:
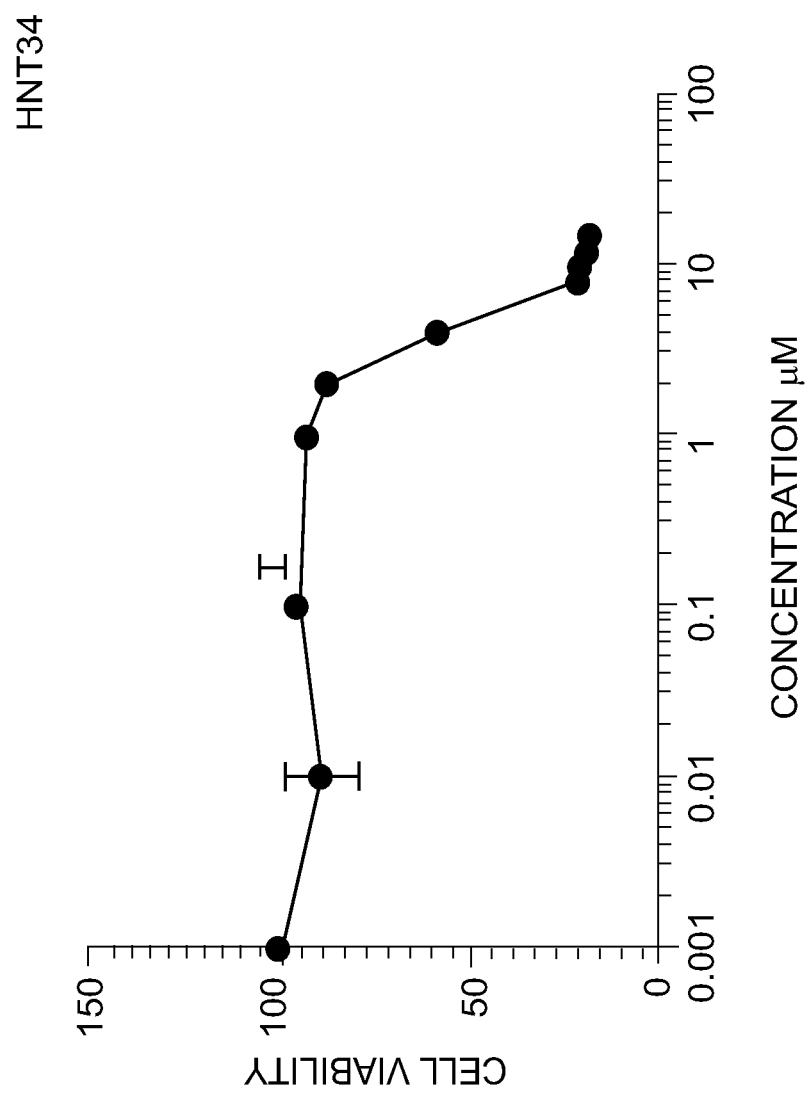
FIG. 48: MTS assays of HL60T cells (leukemia cell line) incubated with Compound 3 drug. X-axis indicates concentration of drug used. The cells were incubated for three days (fresh drug was added daily) following which cell viability was determined.
Figure 49:
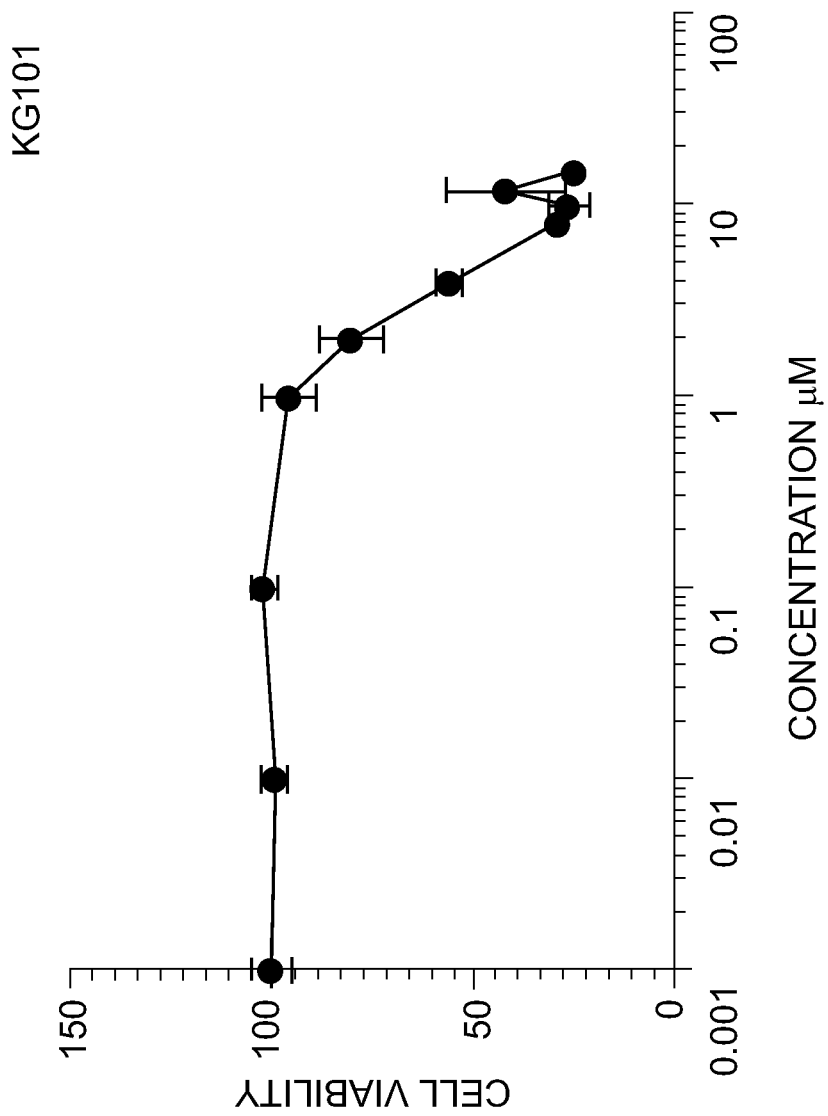
FIG. 49: MTS assays of HNT34 cells (leukemia cell line) incubated with Compound 3 drug. X-axis indicates concentration of drug used. The cells were incubated for three days (fresh drug was added daily) following which cell viability was determined.
Figure 50:
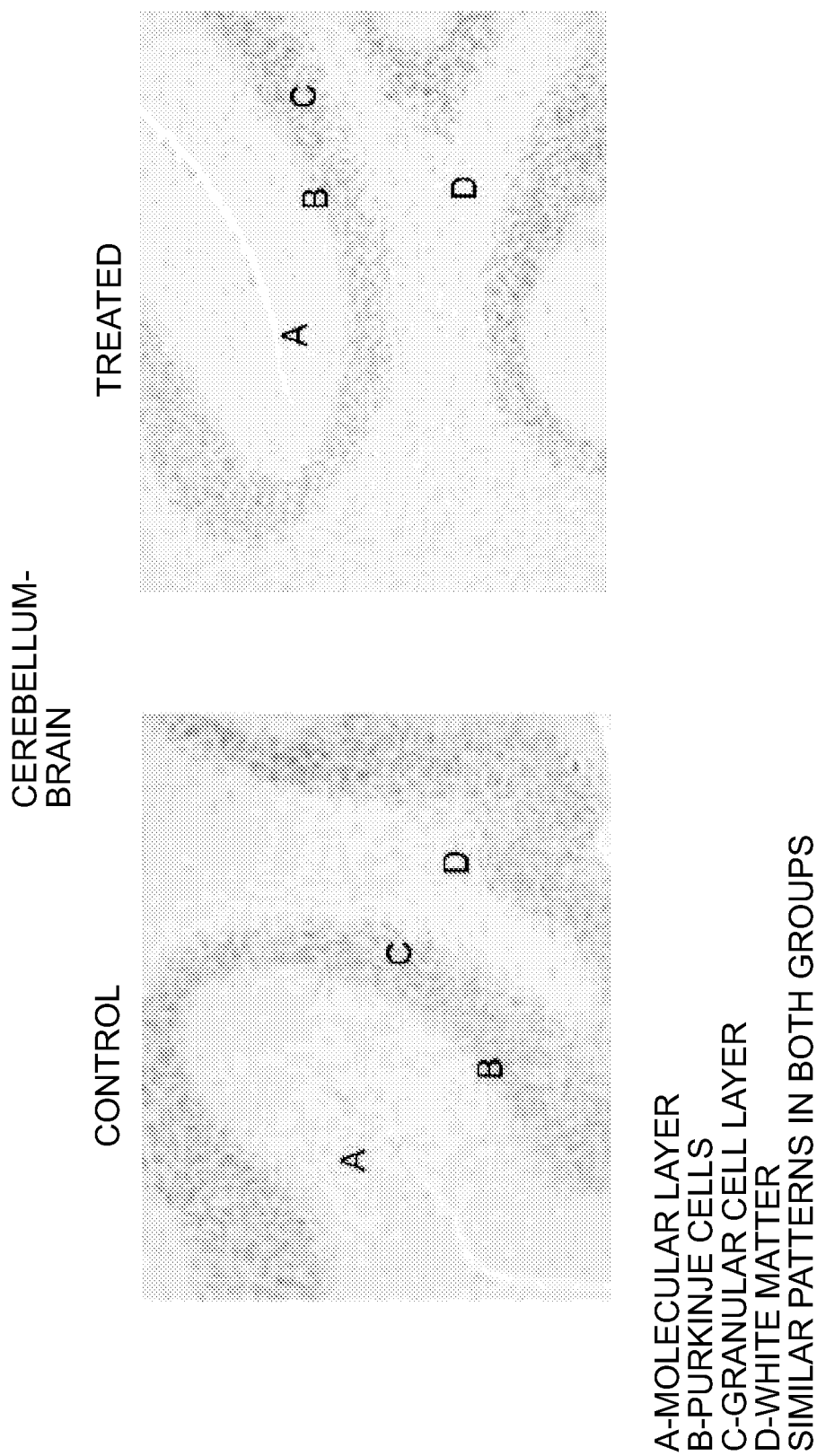
FIG. 50: MTS assays of KG101 cells (leukemia cell line) incubated with Compound 3 drug. X-axis indicates concentration of drug used. The cells were incubated for three days (fresh drug was added daily) following which cell viability was determined.
Figure 51:
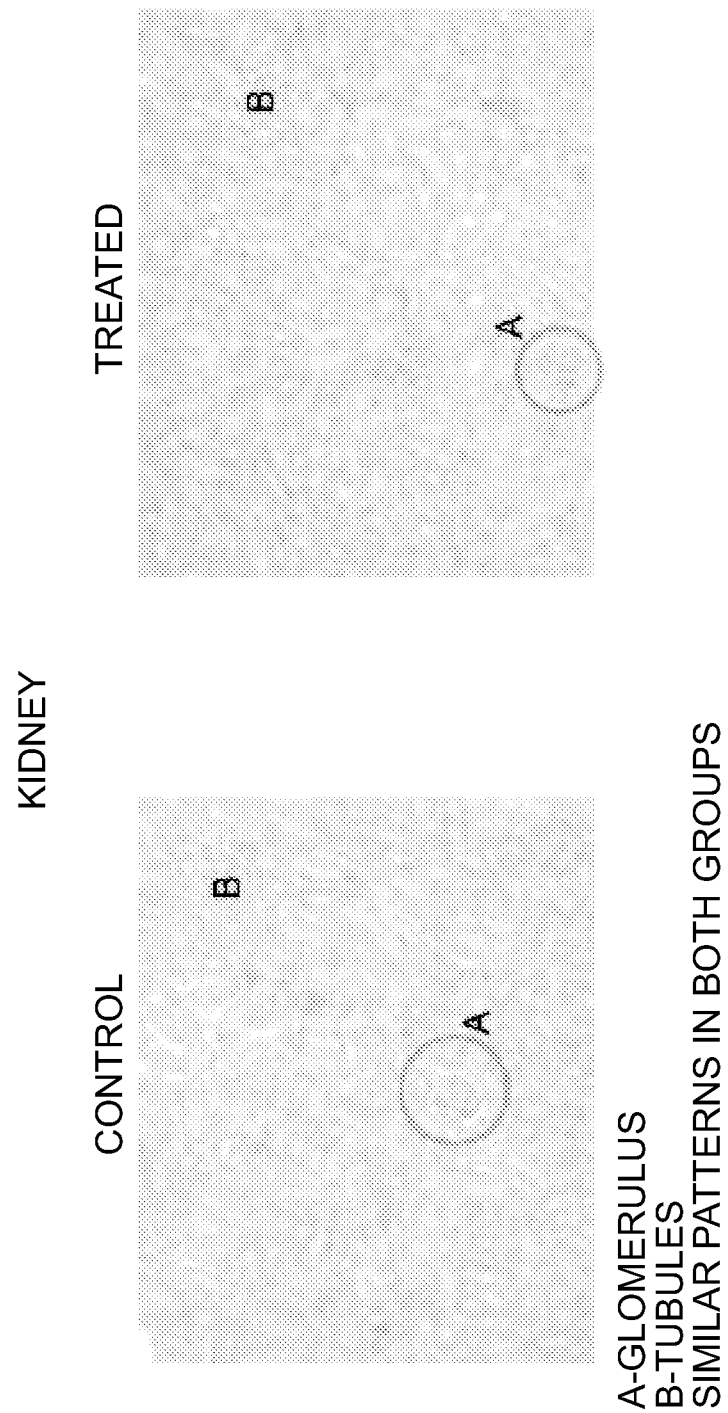
FIGS. 51-54 illustrate Toxicity studies of Compound 3 in SCID mouse. Data shown is that of 500 μM of RK-33 drugs that were injected twice daily for four weeks. Following that the drug was injected once a week for three weeks. At the end of the experiment the animals were sacrificed and histopathology performed. The range of drug dose tested was from 500 to 100 μM.
Figure 52:
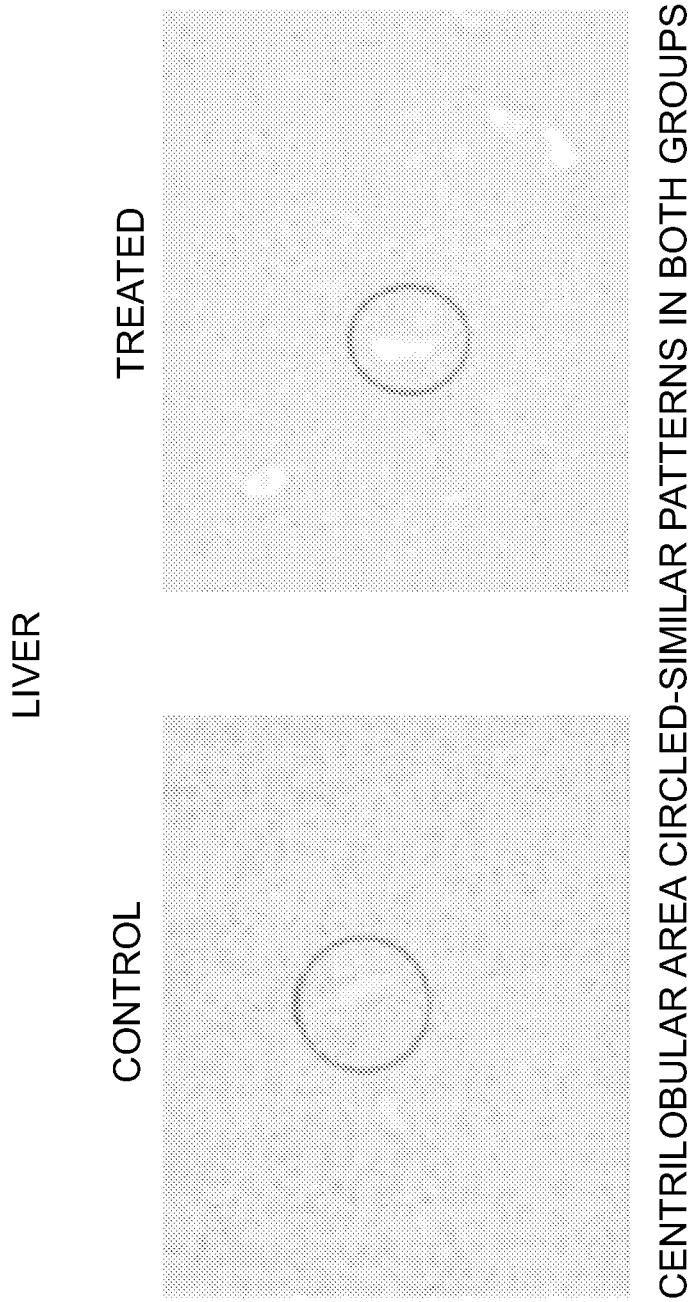
Figure 53:
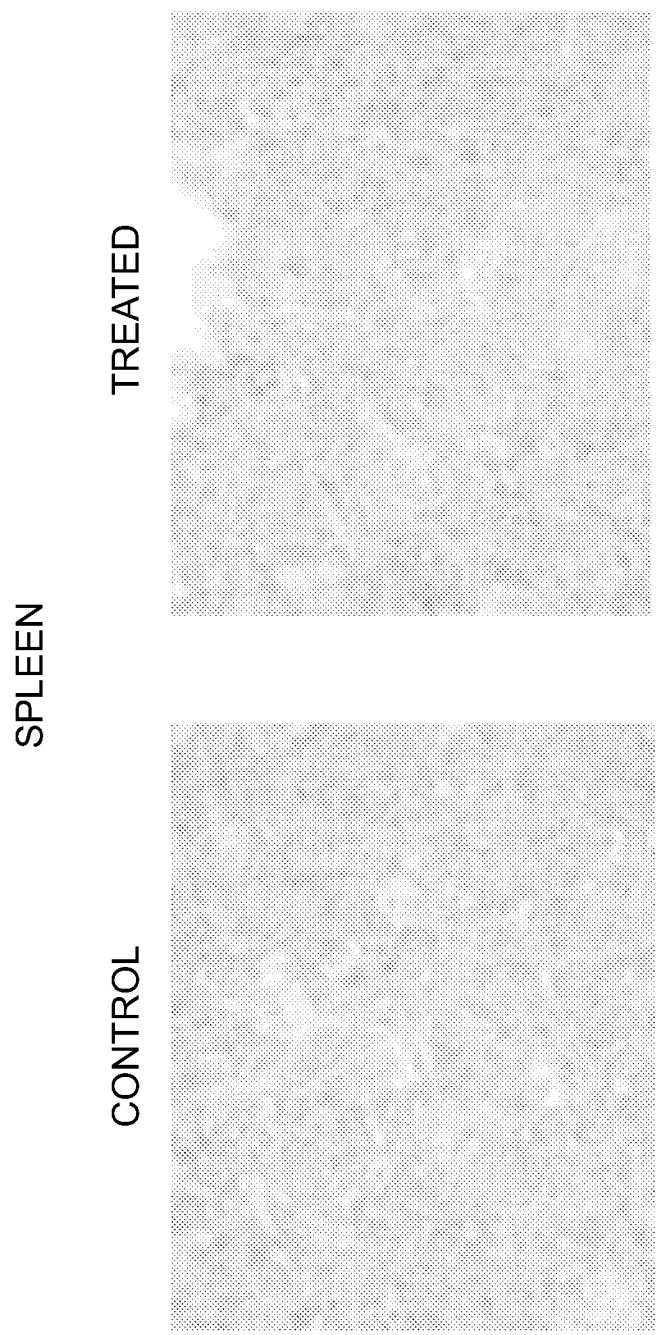
Figure 54:
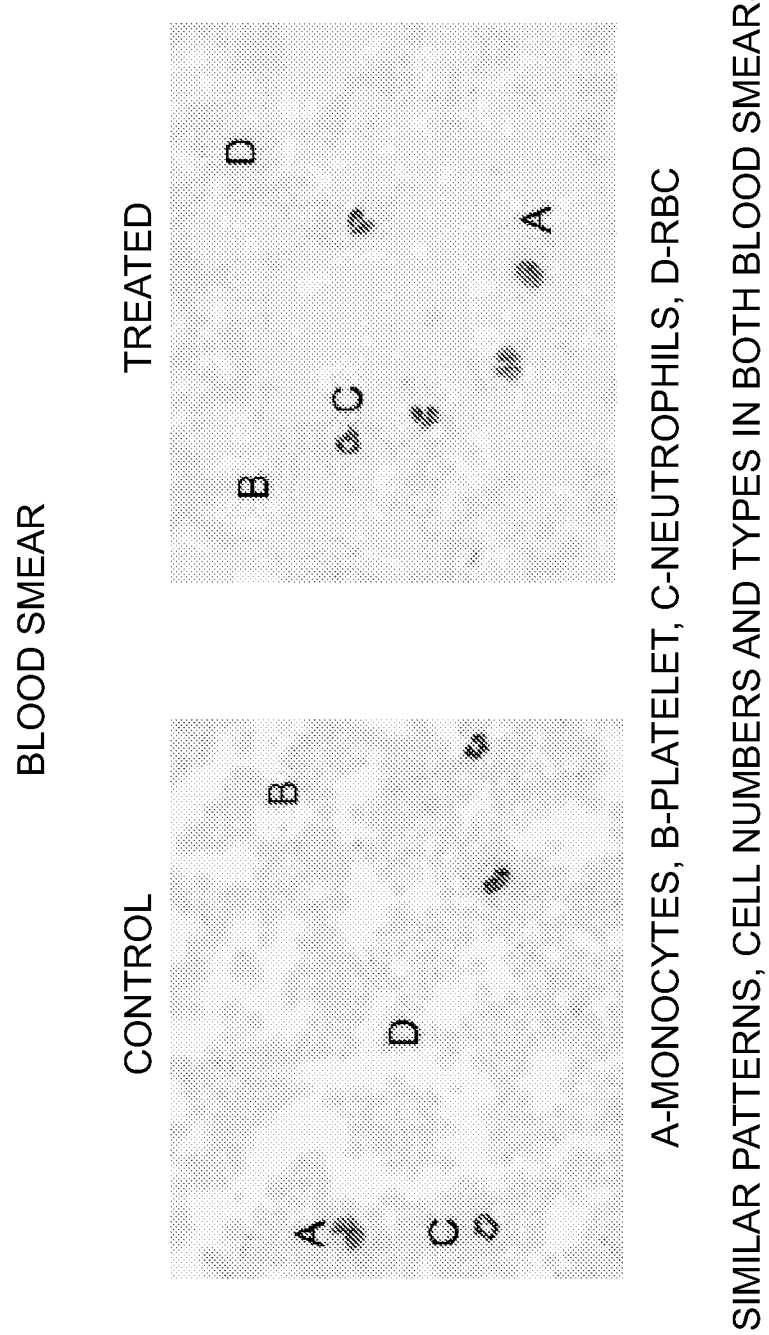

MTS assays of KG101 cells (leukemia cell line) incubated with Compound 3 are illustrated in FIG. 10. X-axis indicates concentration of drug used. The cells were incubated for three days (fresh drug was added daily) following which cell viability was determined.

Toxicity studies of Compound 3 were conducted in SCID mouse. Data shown is that of 500 μM of Compound 3 drugs that were injected twice daily for four weeks. Following that the drug was injected once a week for three weeks. At the end of the experiment the animals were sacrificed and histopathology performed. The range of drug dose tested was from 500 to 100 μM.

The results confirm that the illustrative compounds of the invention were successful in killing cancer cell lines while at the same time not affecting normal cells.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A compound of Formula (I):

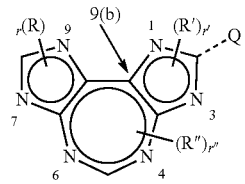

(I) or pharmaceutically acceptable salts and prodrugs thereof, wherein:

R, R', and R" are each independently a hydrogen; hydroxyl; substituted or unsubstituted: cyclic or acyclic alkyl group, cyclic or acyclic alkenyl group, cyclic or acyclic alkynyl group, aryl group, alkylaryl group, arylalkyl group, benzyl group, cyclic or acyclic heteroalkyl group, heteroaryl group; —C(O)R$^3$; —C(S)R$^3$; —S(O)$_2$R$^3$; —C(O)NR$^3$R$^4$; —C(S)NR$^3$R$^4$; —C(S)YR$^3$; —C(O)YR$^3$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; or ribose or deoxyribose sugars substituted with one or more halogens;

When Q is present, _____ represents a double bond and Q is O, NH, or S;

Y is O or S;

R$^3$ and R$^4$ are independently a hydrogen; hydroxyl; substituted or unsubstituted: cyclic or acyclic alkyl group, cyclic or acyclic alkenyl group, cyclic or acyclic alkynyl group, aryl group, alkylary group, aryalkyl group, heteroaryl group, heterocycloalkyl group; and r, r', and r" are each independently an integer from 1 to 3.

2. The compound of claim 1, wherein R is a substituted benzyl.

3. The compound of claim 1, wherein R' is a substituted benzyl.

4. The compound of claim 1, wherein R" is a substituted phenyl.

5. The compound of claim 1, wherein R and R' are each a substituted benzyl.

6. The compound of claim 1, wherein R is cyclic or acyclic alkyl; aryl; heterolkyl; or heteroaryl.

7. The compound of claim 1, wherein R' is cyclic or acyclic alkyl; aryl; heterolkyl; or heteroaryl.

8. The compound of claim 6, wherein the cyclic or acyclic alkyl; aryl; heteroalkyl; heteroaryl are substituted.

9. The compound of claim 7, wherein the cyclic or acyclic alkyl aryl; heteroalkyl; and heteroaryl are substituted.

10. The compound of claim 1, wherein R" is hydrogen, R is a substituted benzyl, and R' is a substituted benzyl.

11. The compound of claim 1, wherein R" is hydrogen, R is p-methoxybenzyl, and R' is p-methoxy-benzyl.

12. The compound of claim 1, selected from the group consisting of:
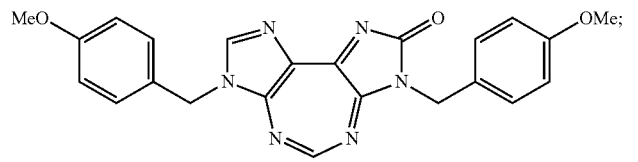 [SMILES: COc1ccc(Cn2c3ncnc4c(ncn4Cc4ccc(OC)cc4)c-3nc2=O)cc1]
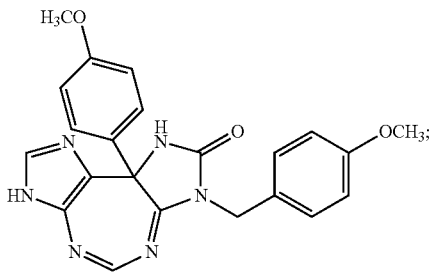
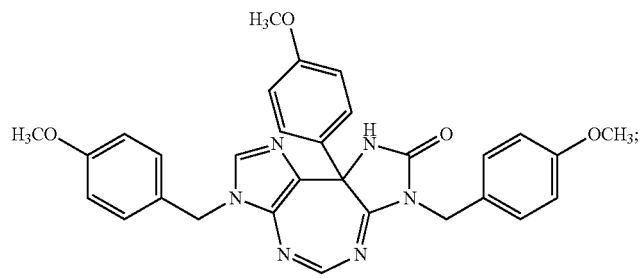
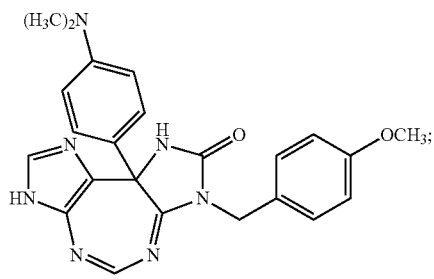
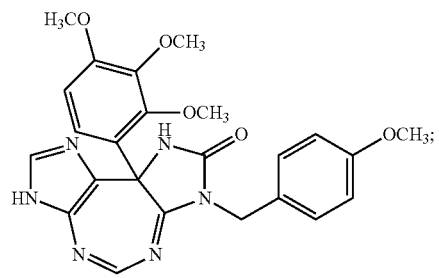
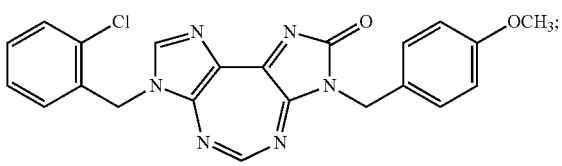
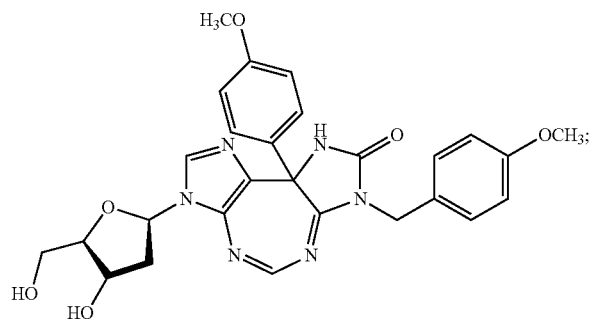
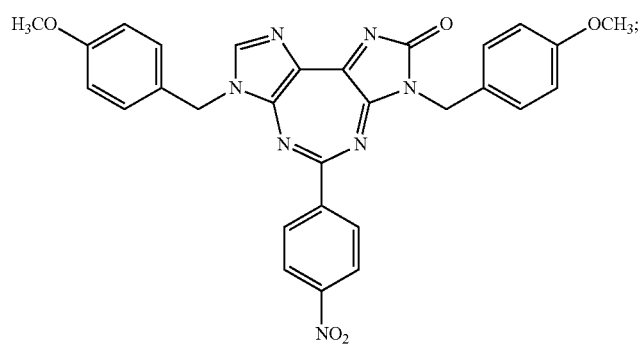
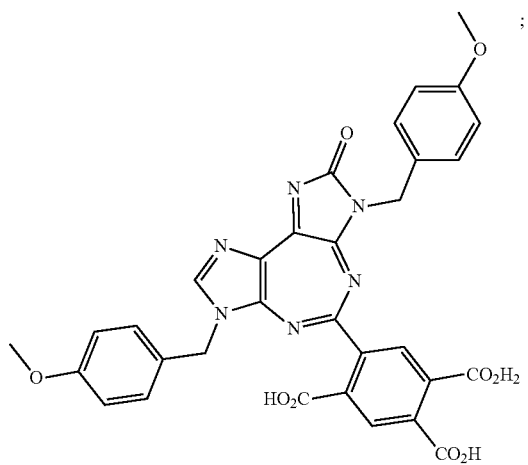

-continued
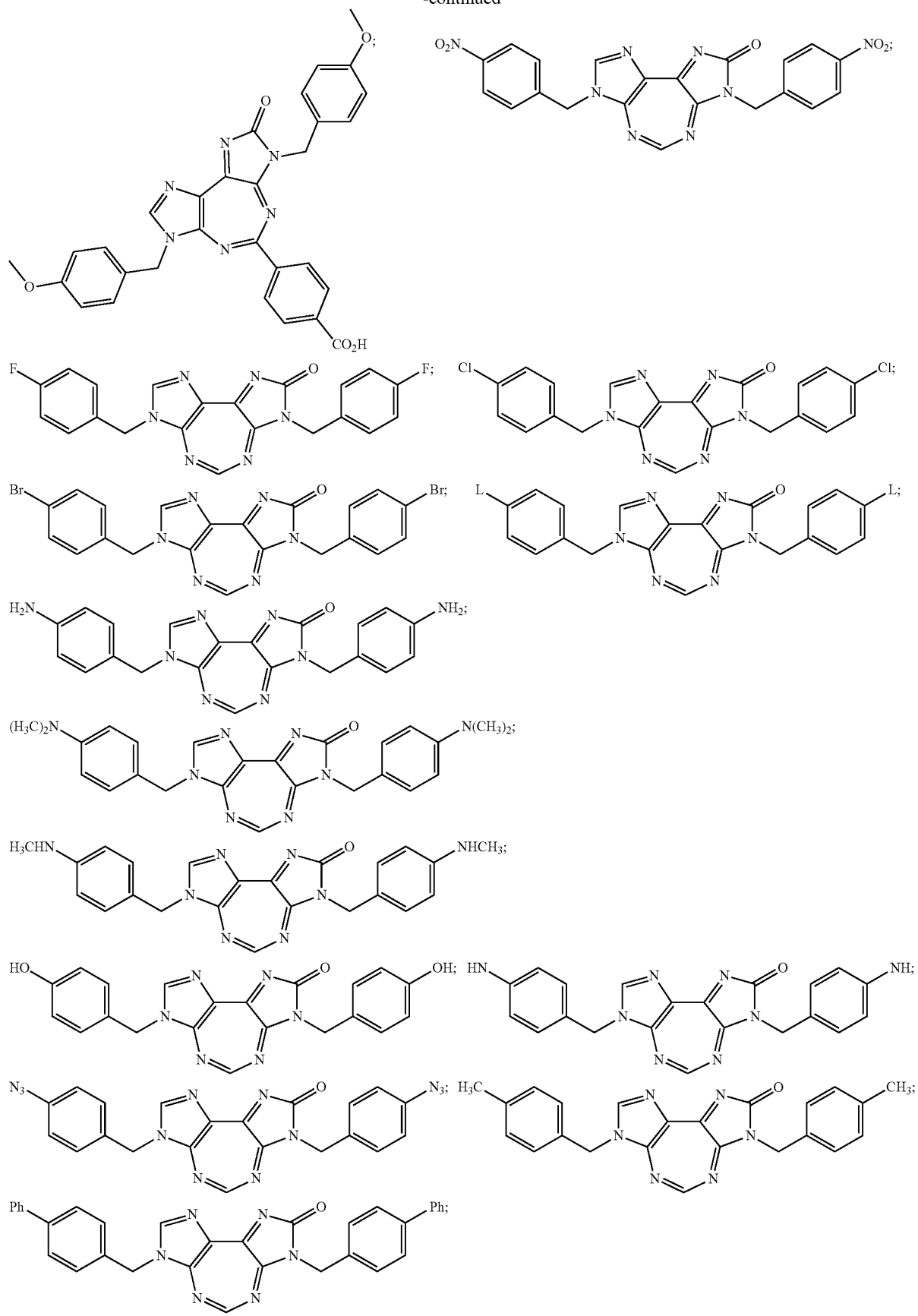

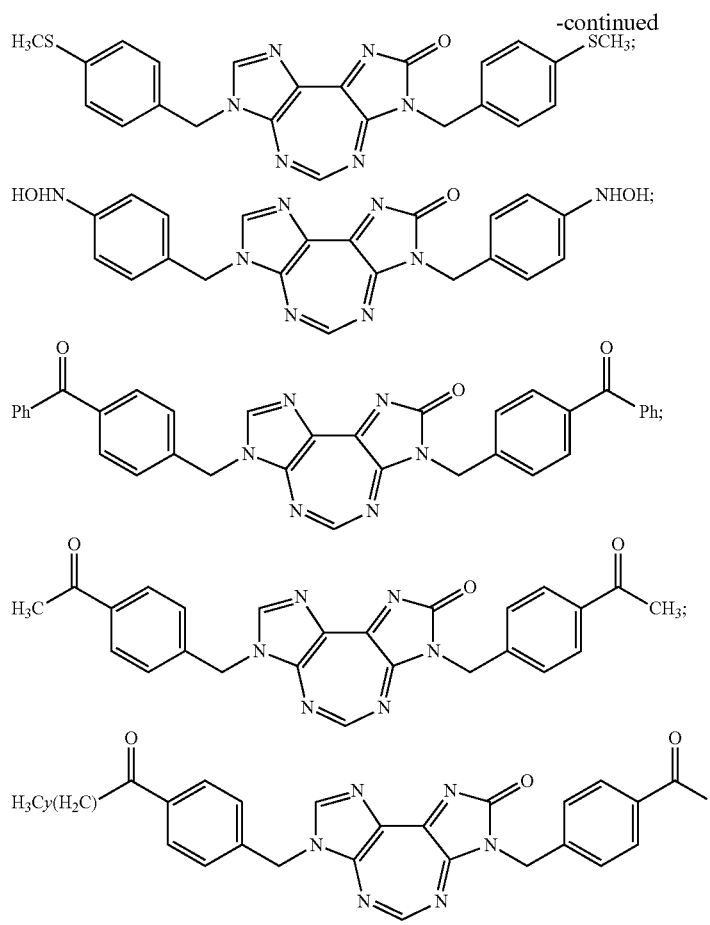
wherein x and y are integers from 1-17;
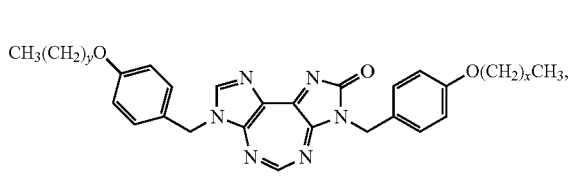
wherein x and y are integers from 1-10;
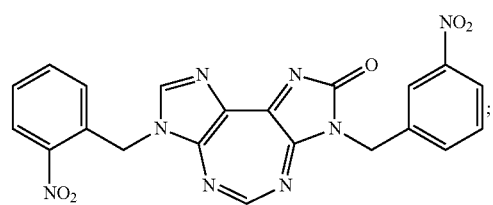
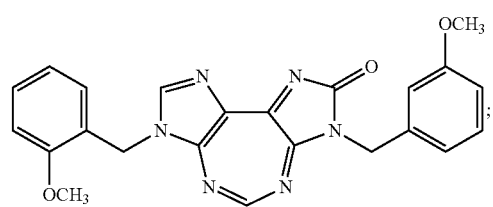
-continued
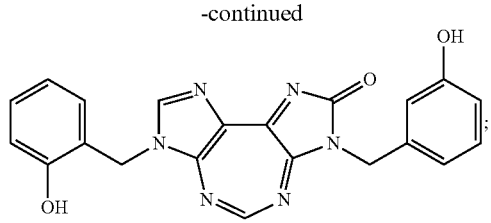
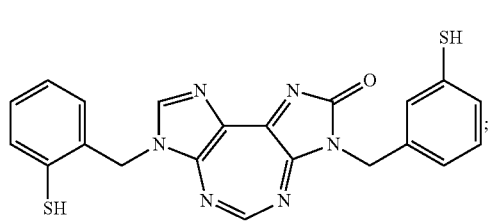
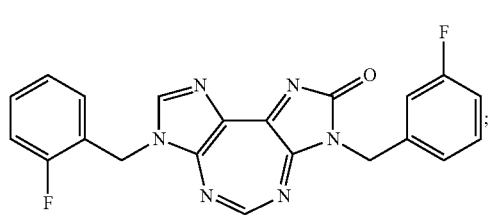

85
-continued
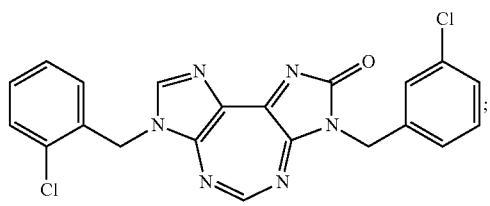
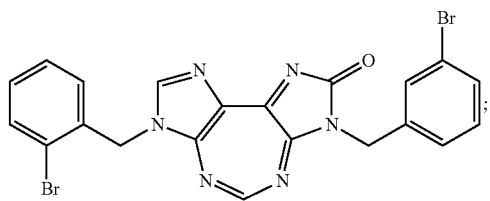
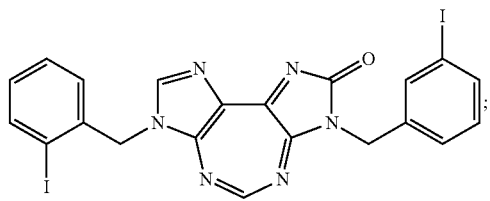
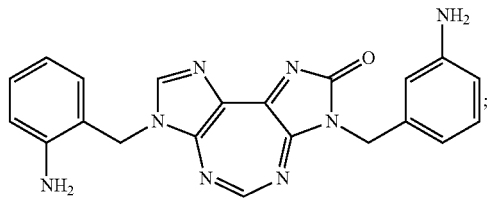
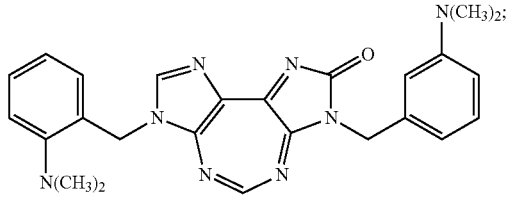
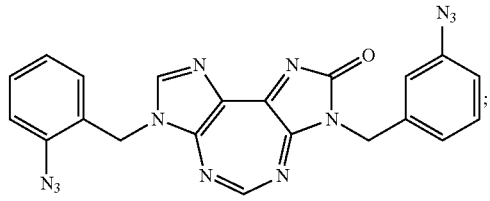
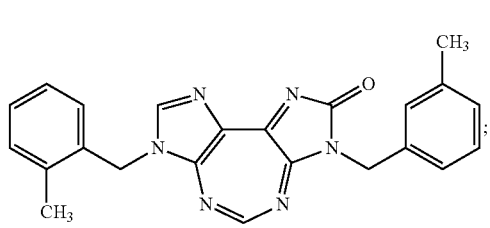
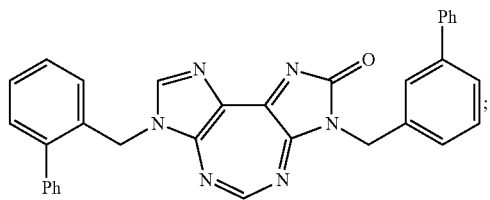
86
-continued
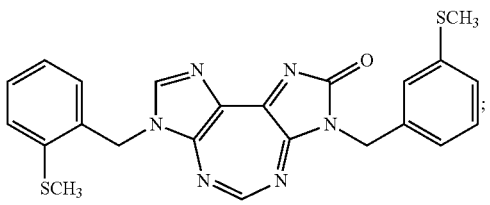
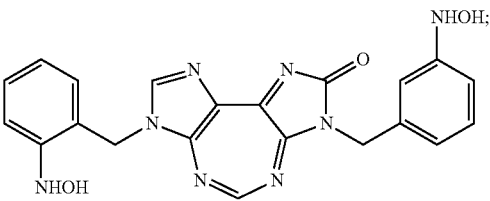
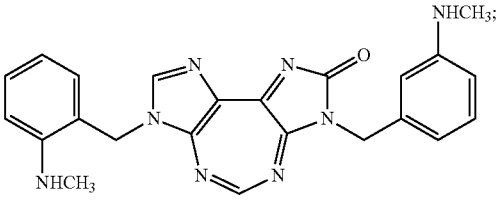
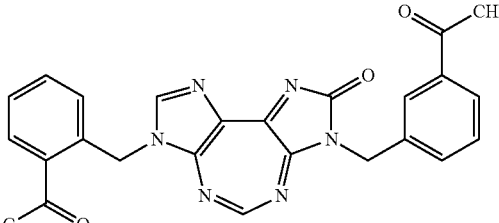
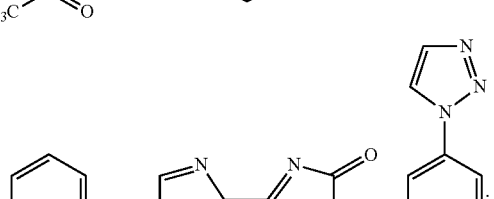
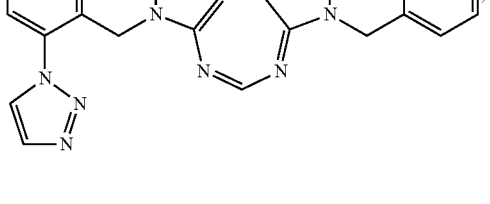
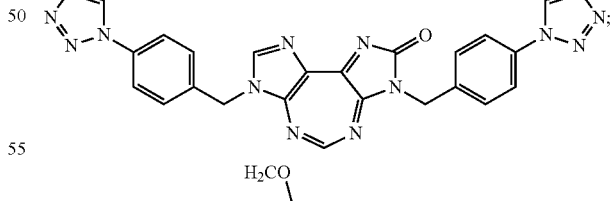
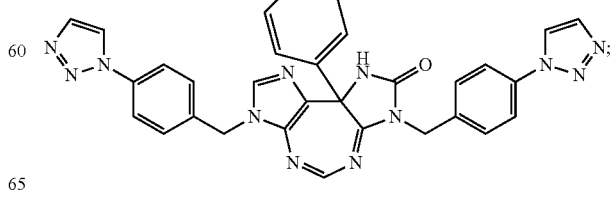

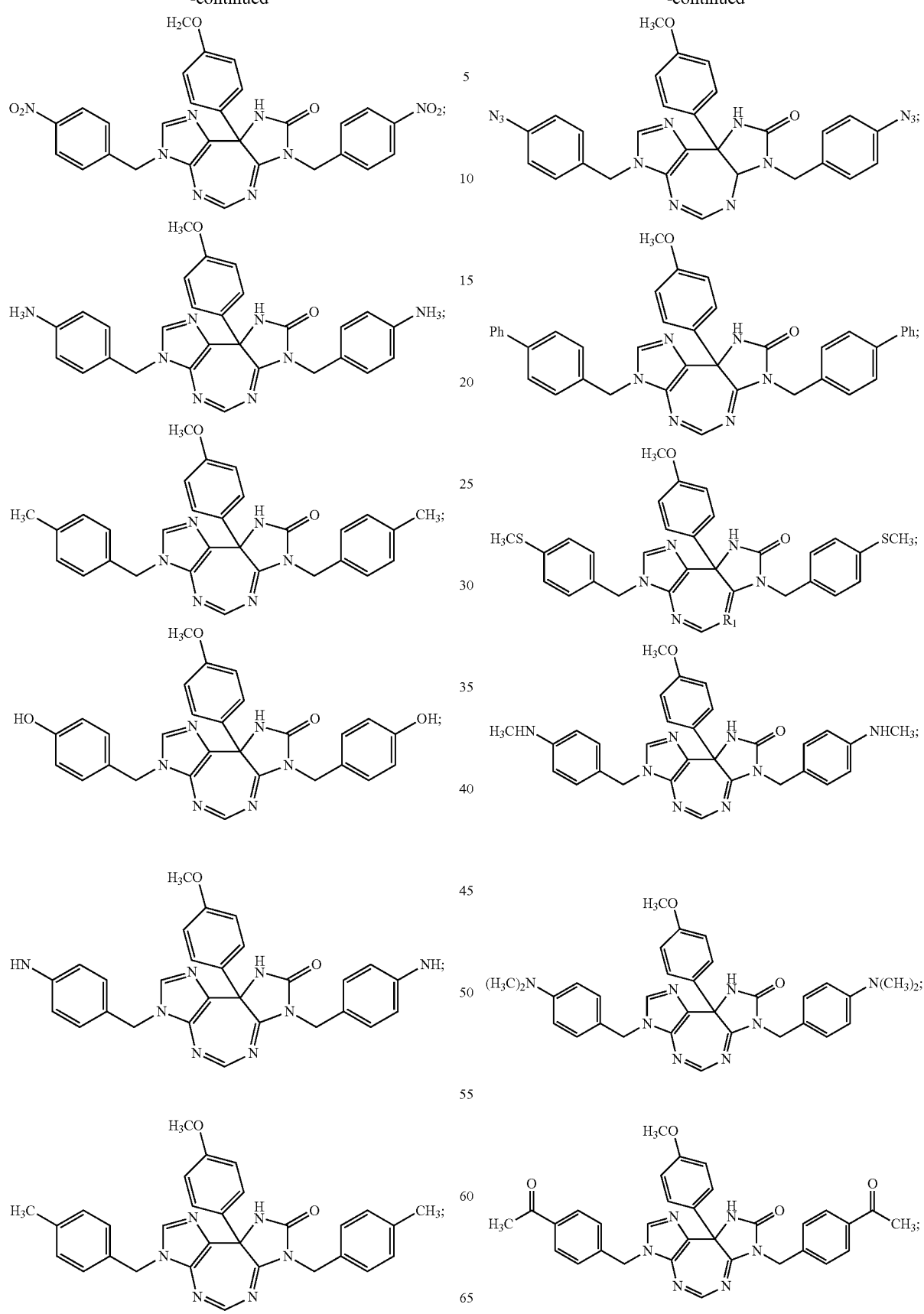

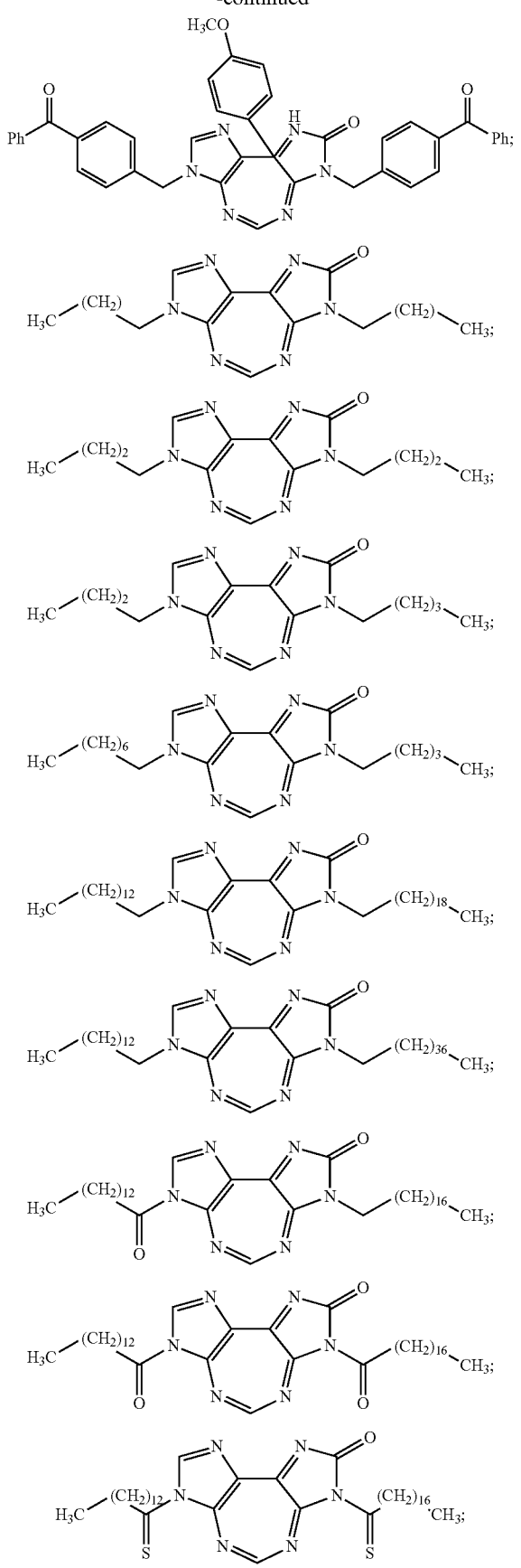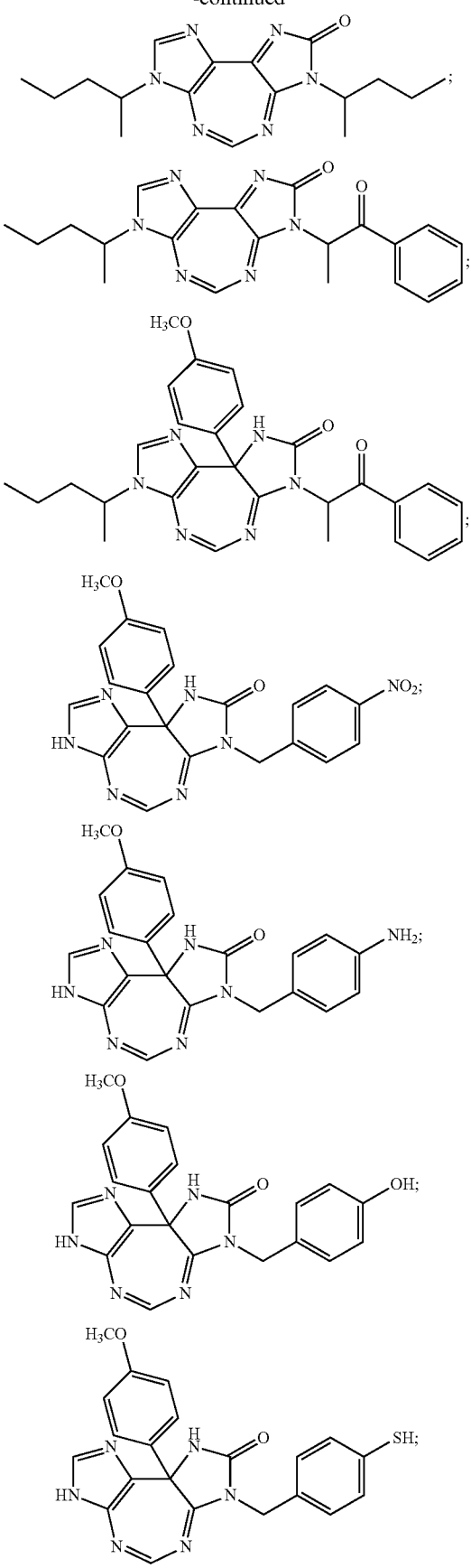

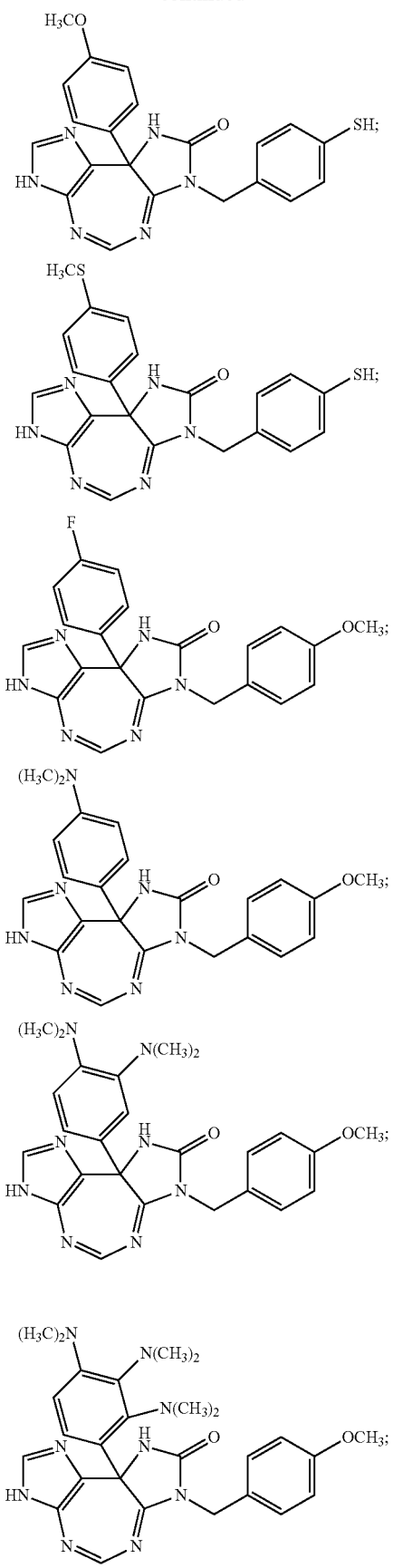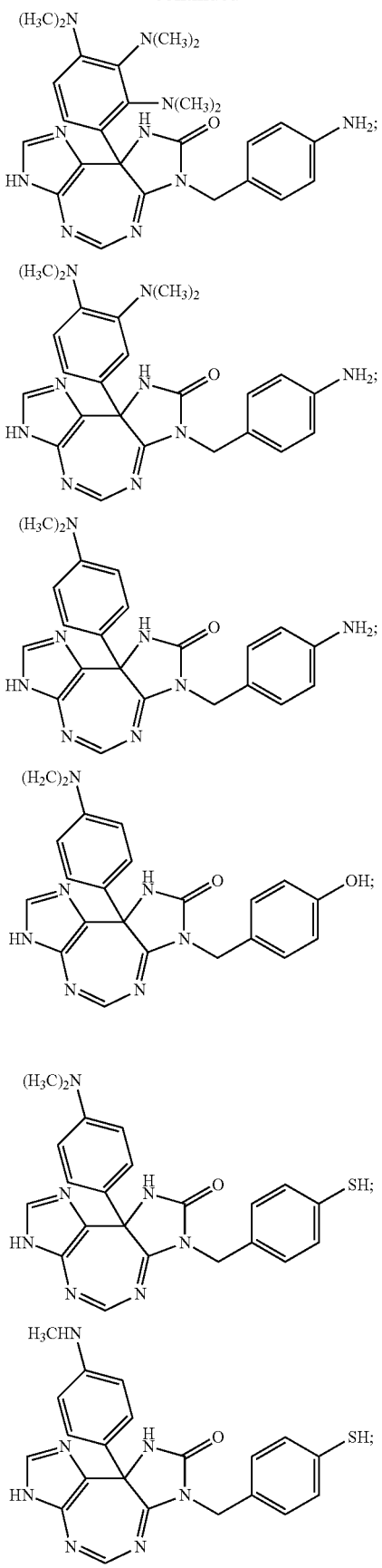

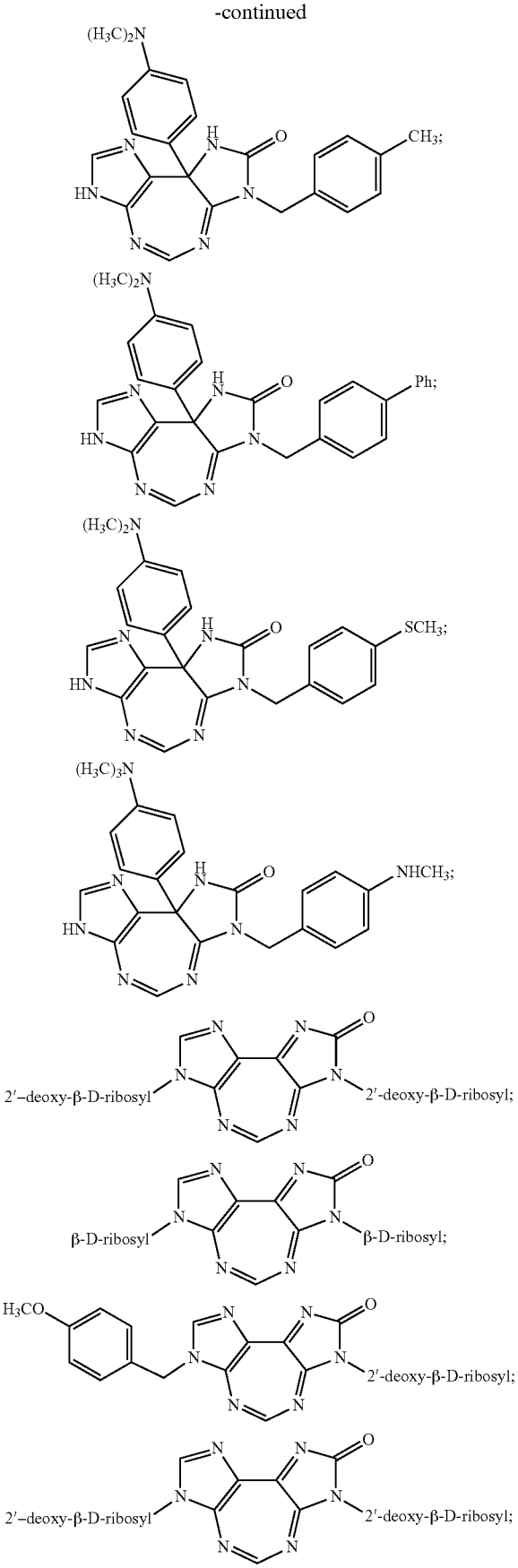

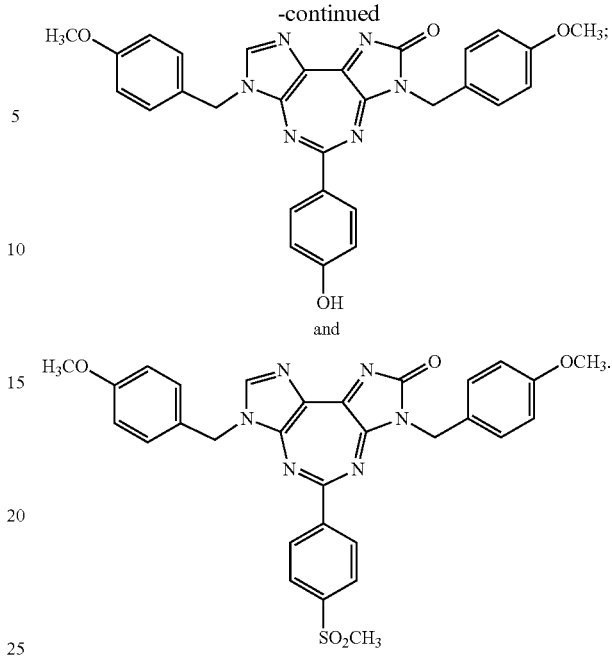

13. The compound of claim 1, wherein R is covalently bonded to the 7-position.

14. The compound of claim 1, wherein R' is covalently bonded to the 3-position.

15. The compound of claim 1, wherein R" is a substituted phenyl.

16. The compound of claim 15, wherein the substituted phenyl is p-methoxyphenyl.

17. The compound of claim 1, wherein R is hydrogen, R' is p-methoxybenzyl and R" is p-methoxy-phenyl.

18. The compound of claim 1, wherein R is hydrogen, R' is p-methoxybenzyl and R" is p-methoxy-phenyl and R' is substituted on the 3 position, R" is substituted on the 9(b) position and Q is oxygen.

19. A composition comprising a compound of claim 1 and a pharmaceutically acceptable carrier.

20. A method for treating breast cancer comprising administering to a mammal in need thereof a composition comprising a therapeutically acceptable compound of claim 1.

21. The compound of claim 1 that is

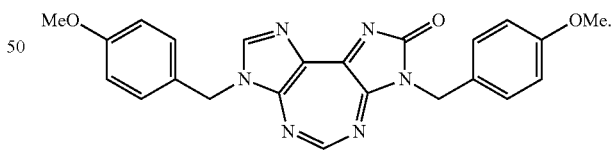

22. The composition of claim 19, wherein at least one of R, R', and R" is a substituted benzyl.

23. The composition of claim 19, wherein R and R' are each a substituted benzyl.

24. The composition of claim 19, wherein at least one of R and R' is cyclic or acyclic alkyl; aryl; heteroalkyl; or heteroaryl, wherein the cyclic or acyclic alkyl, aryl, heteroalkyl or heteroaryl is optionally substituted.

25. The composition of claim 19, wherein R" is hydrogen, R is a substituted benzyl, and R' is a substituted benzyl.

26. The composition of claim 19, wherein R" is hydrogen, R is p-methoxybenzyl, and R' is p-methoxy-benzyl.

27. The composition of claim 19, wherein R is hydrogen, R' is 3-(p-methoxybenzyl) and R" is 9(b)-(p-methoxy-phenyl) and Q is oxygen.
28. The composition of claim 19, wherein the compound is selected from the group consisting of
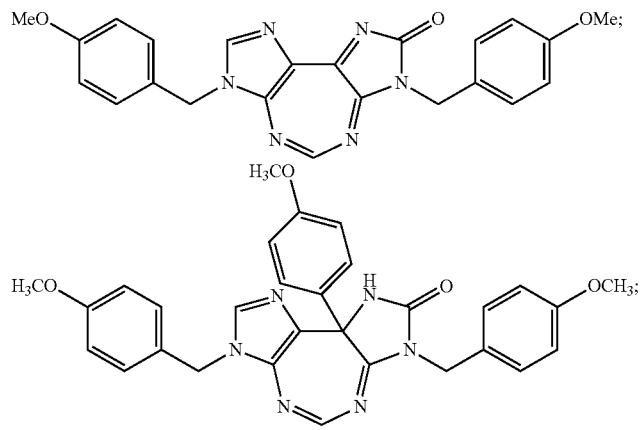
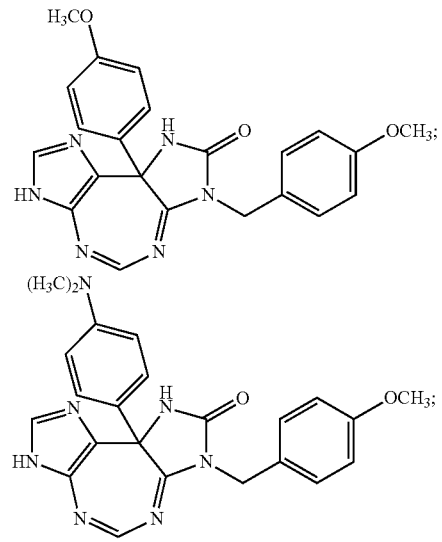
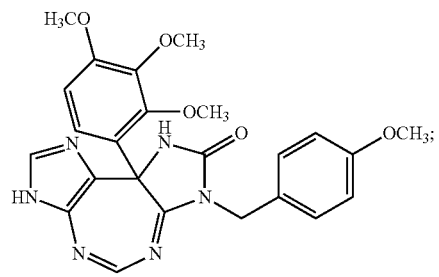
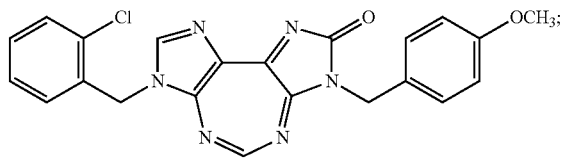
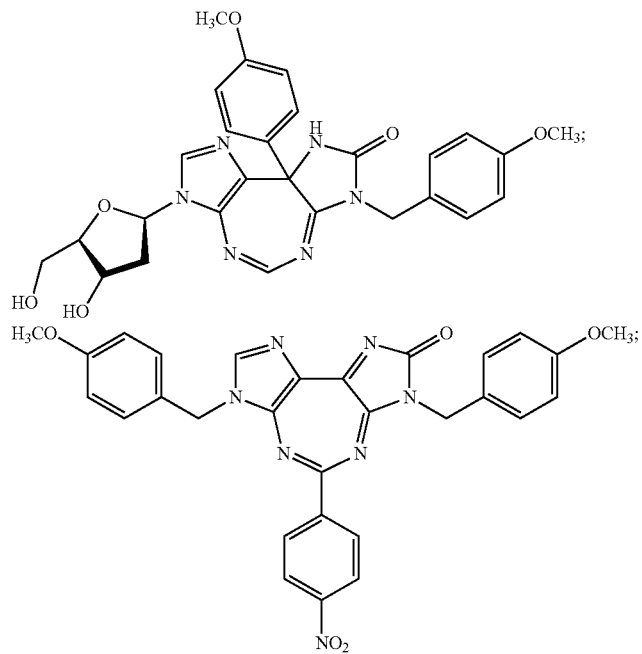

-continued
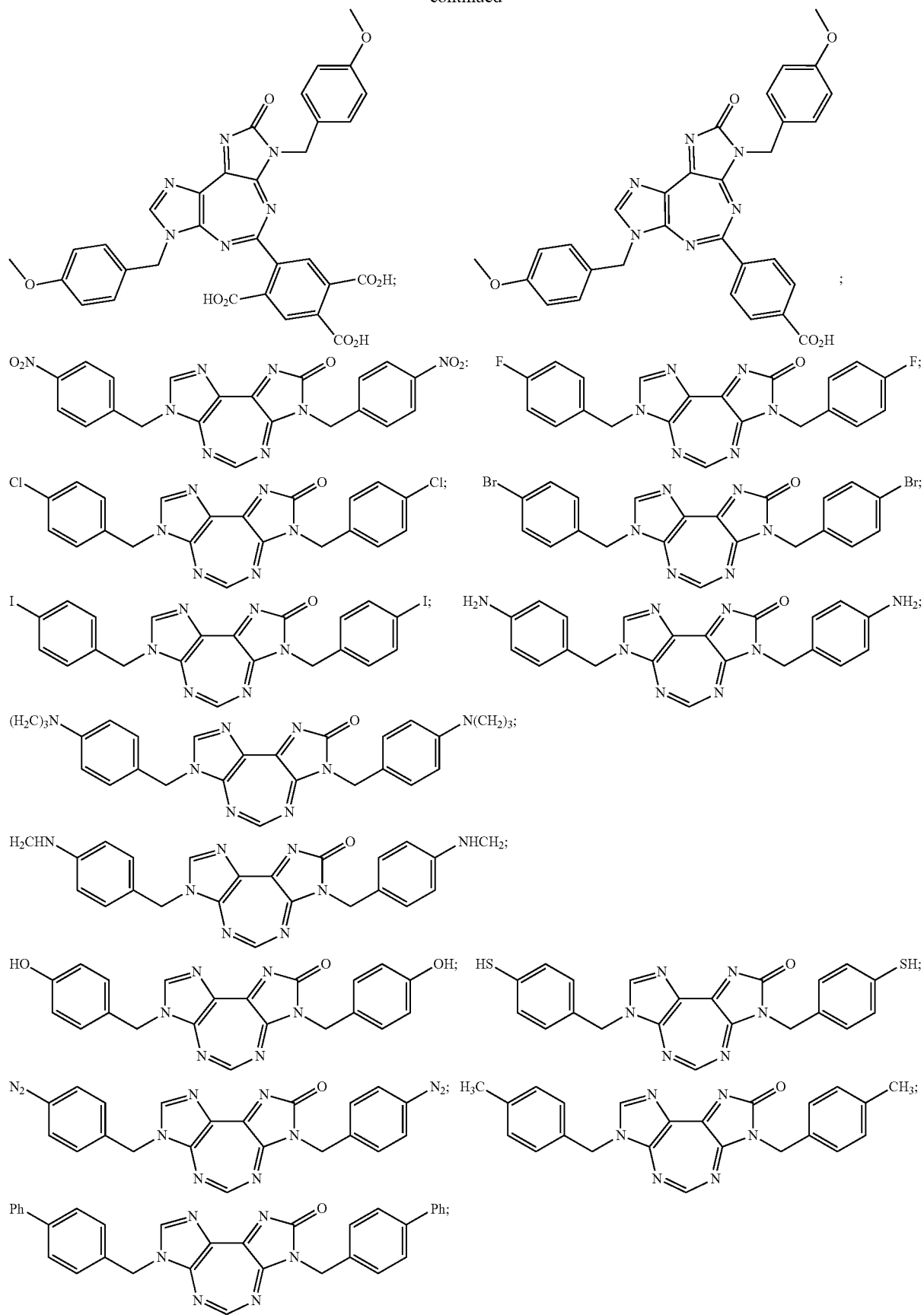

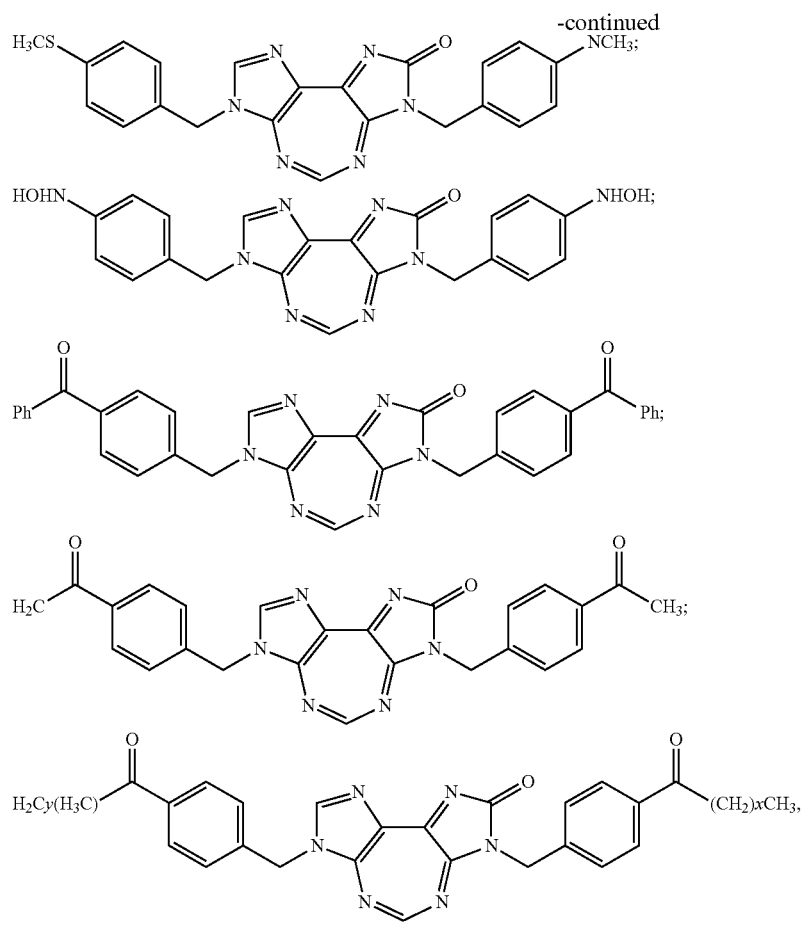
wherein x and y are integers from 1-17;
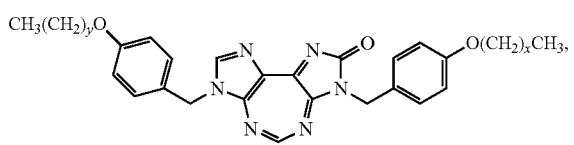
wherein x and y are integers from 1-10;
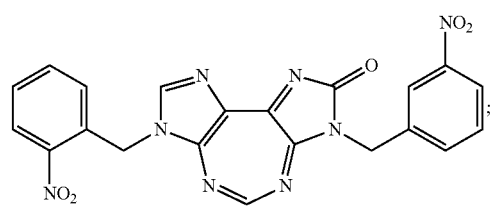
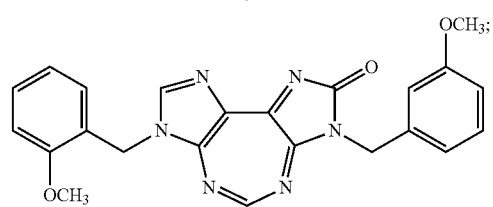
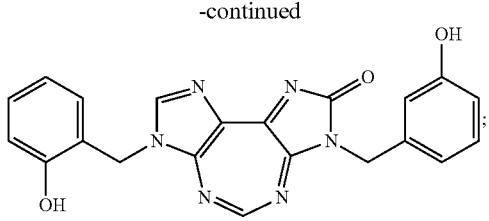
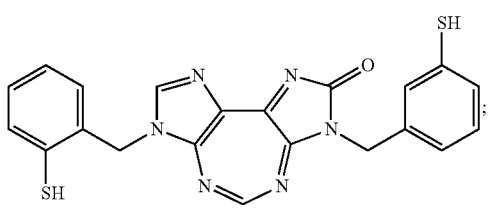
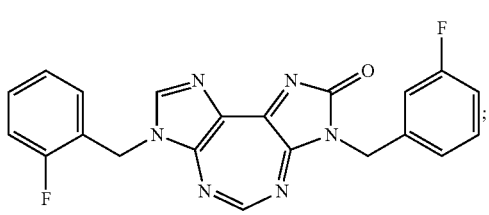

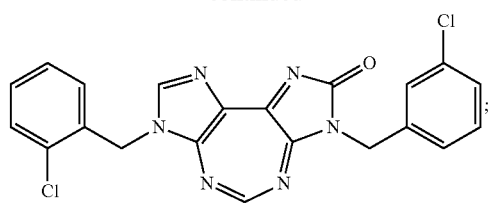
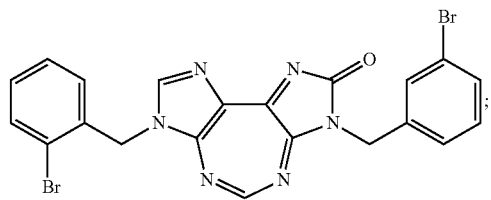
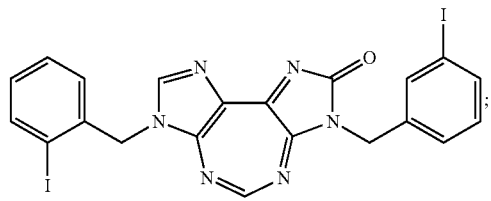
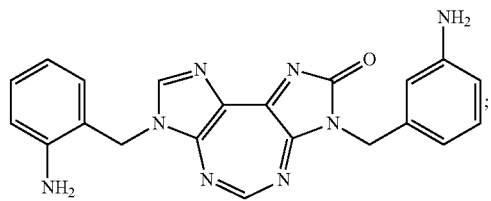
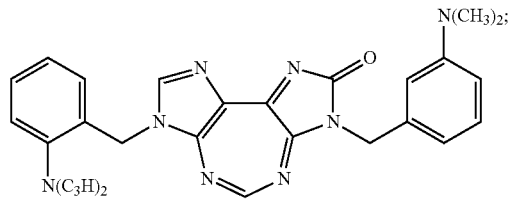
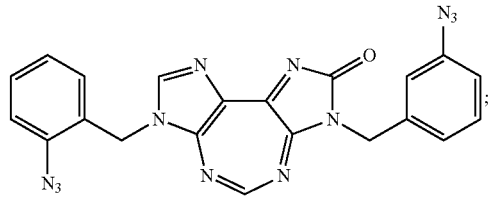
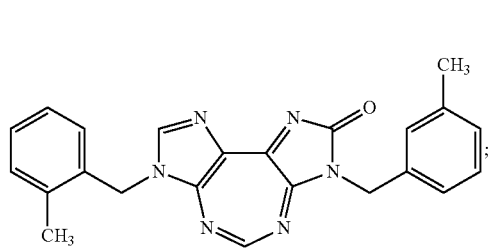
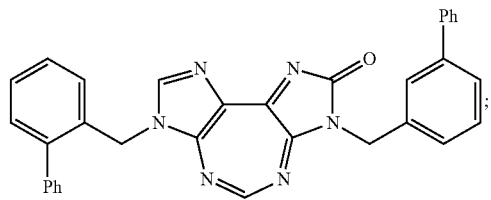
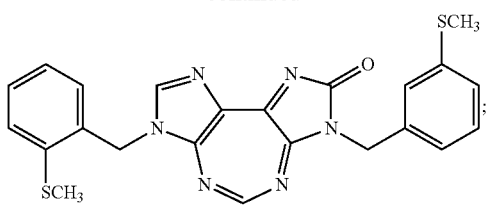
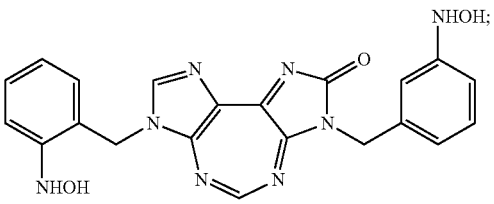
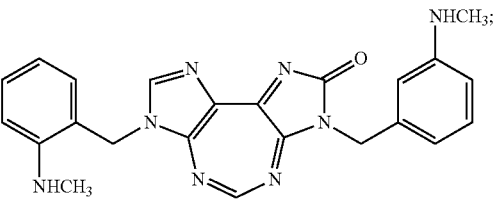
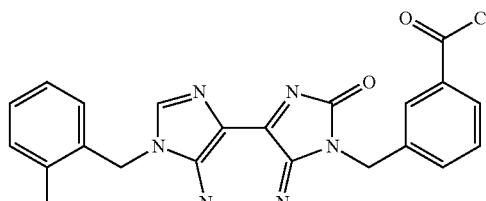
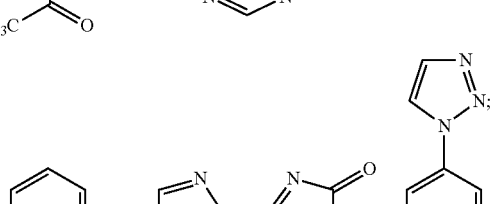
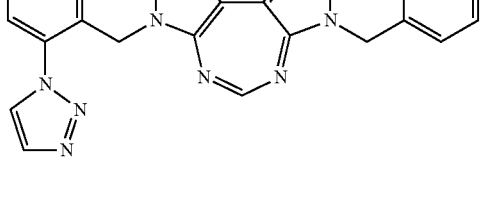
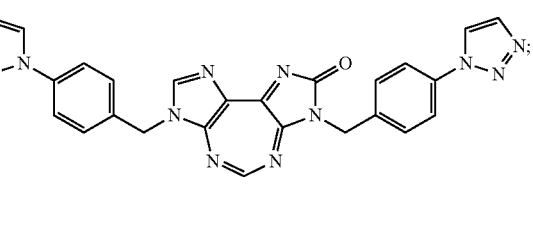
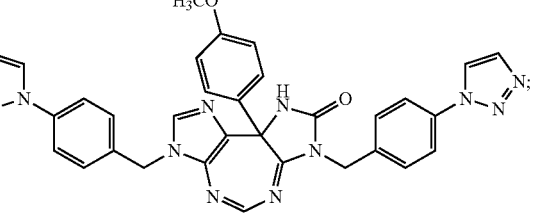

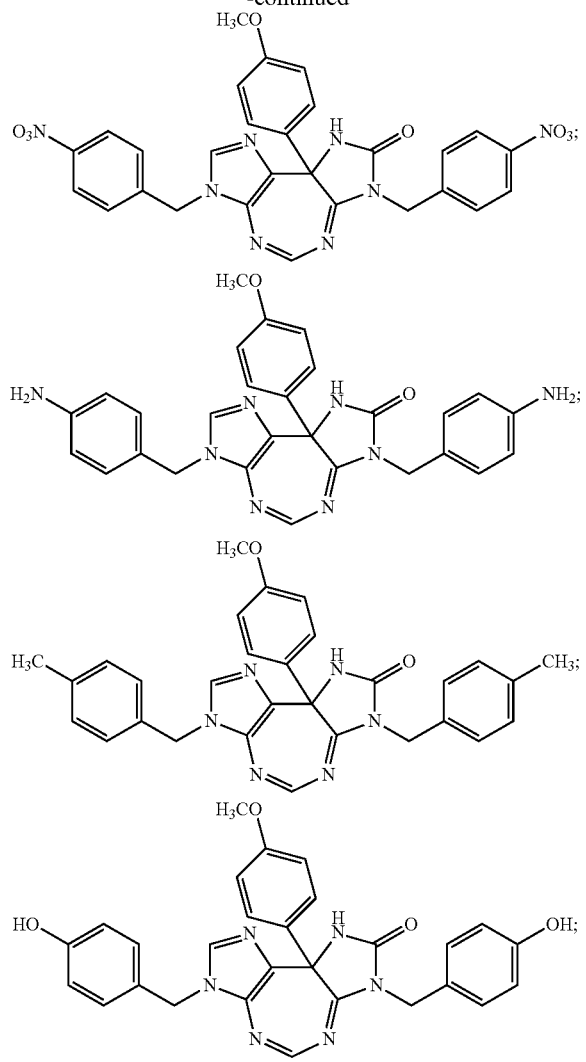
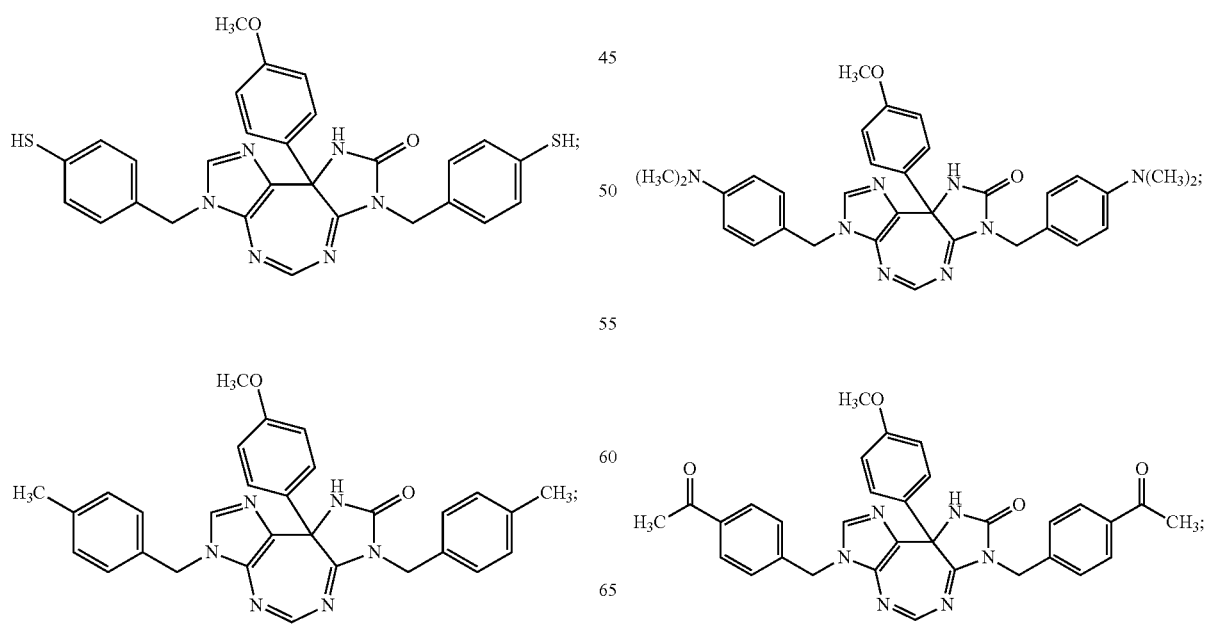

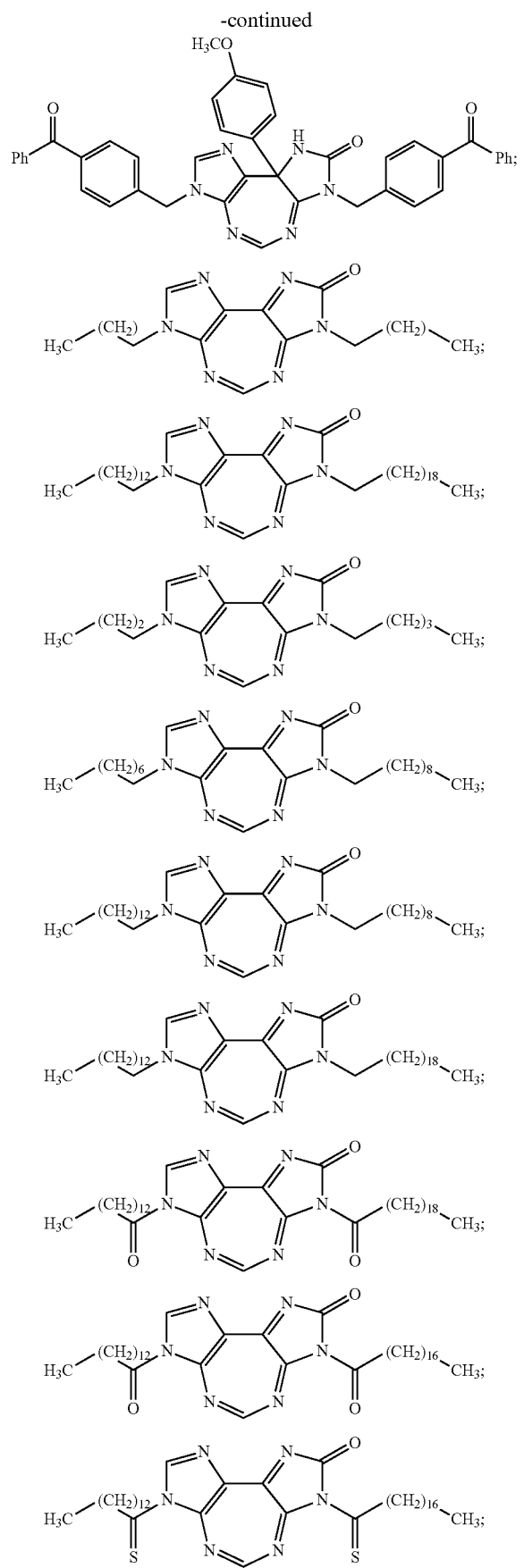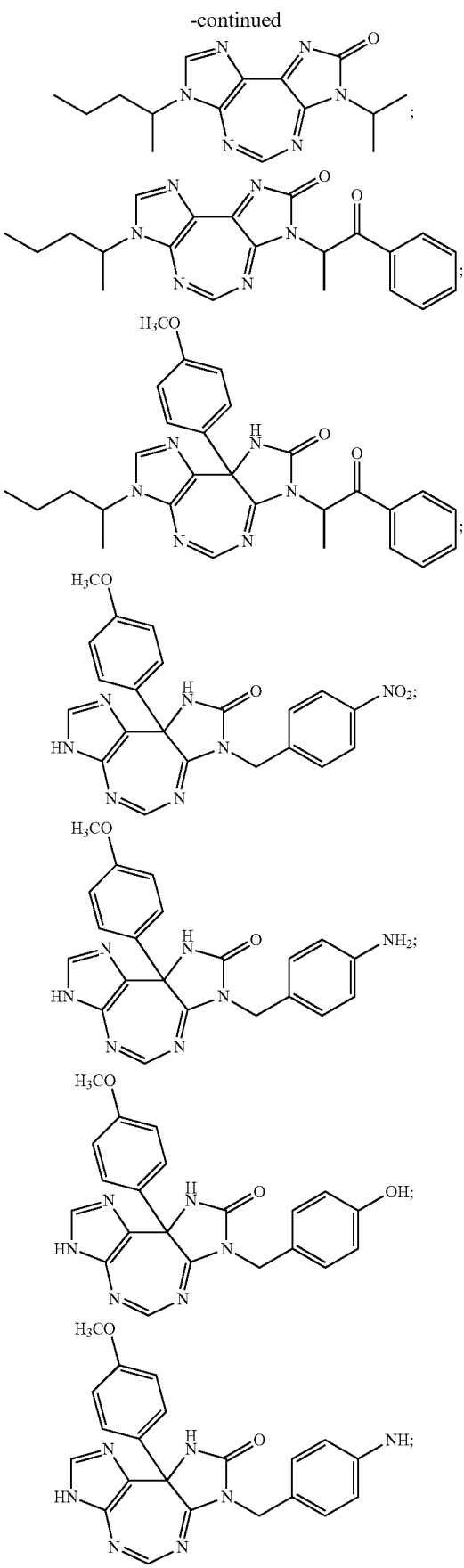

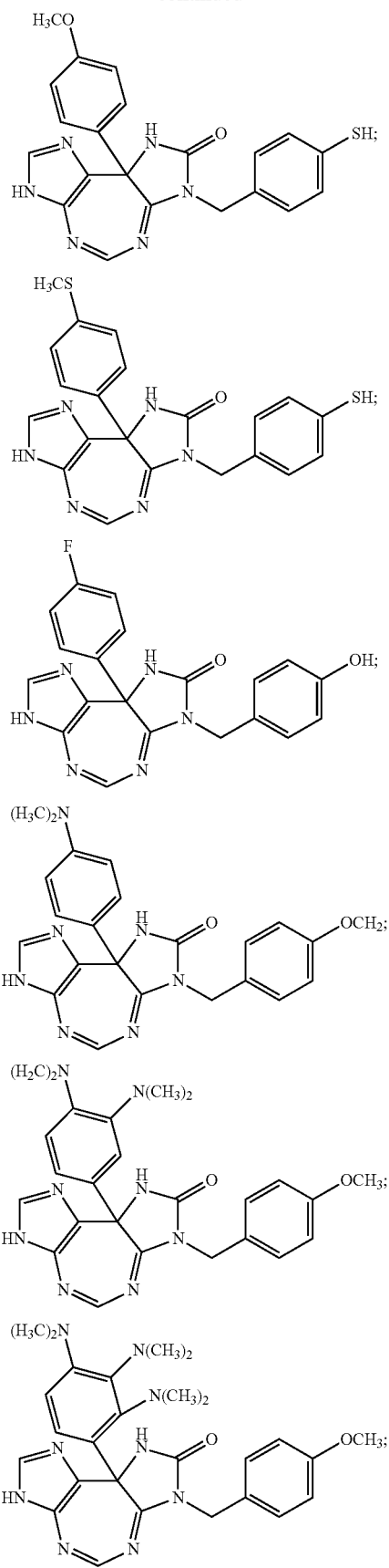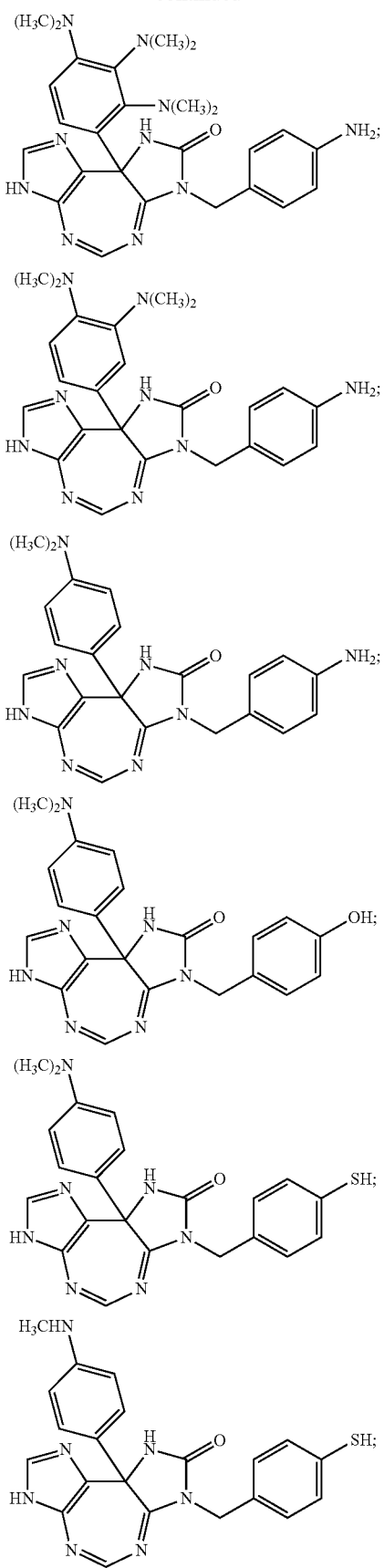

109

-continued

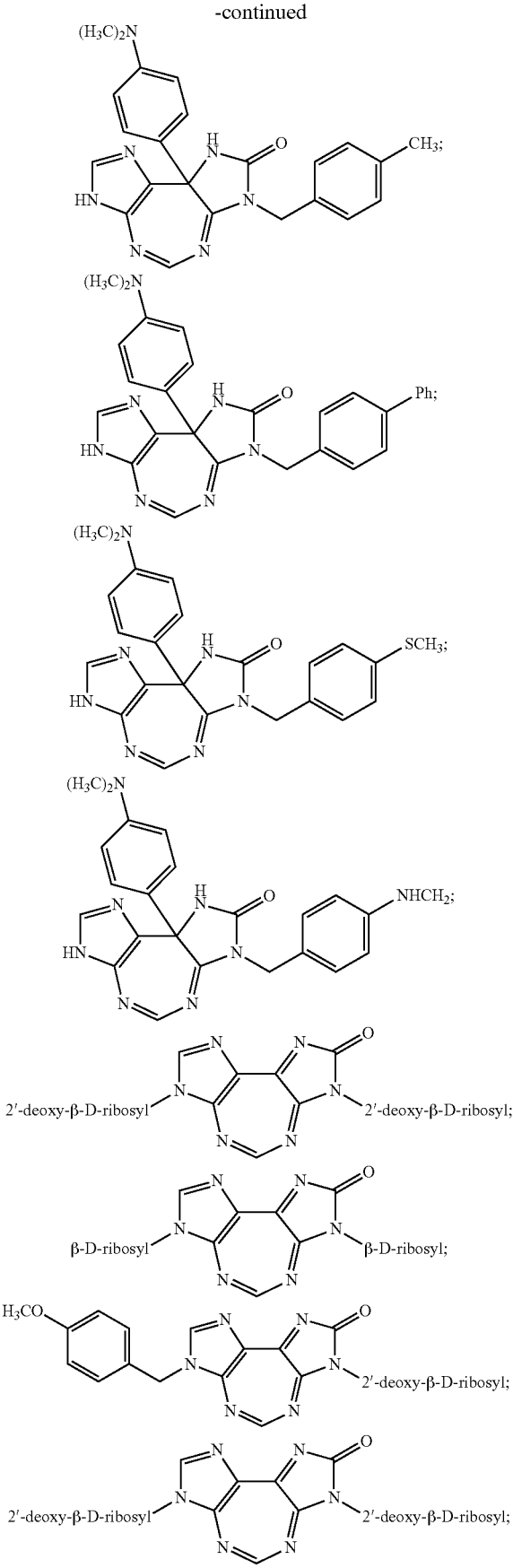

110

-continued

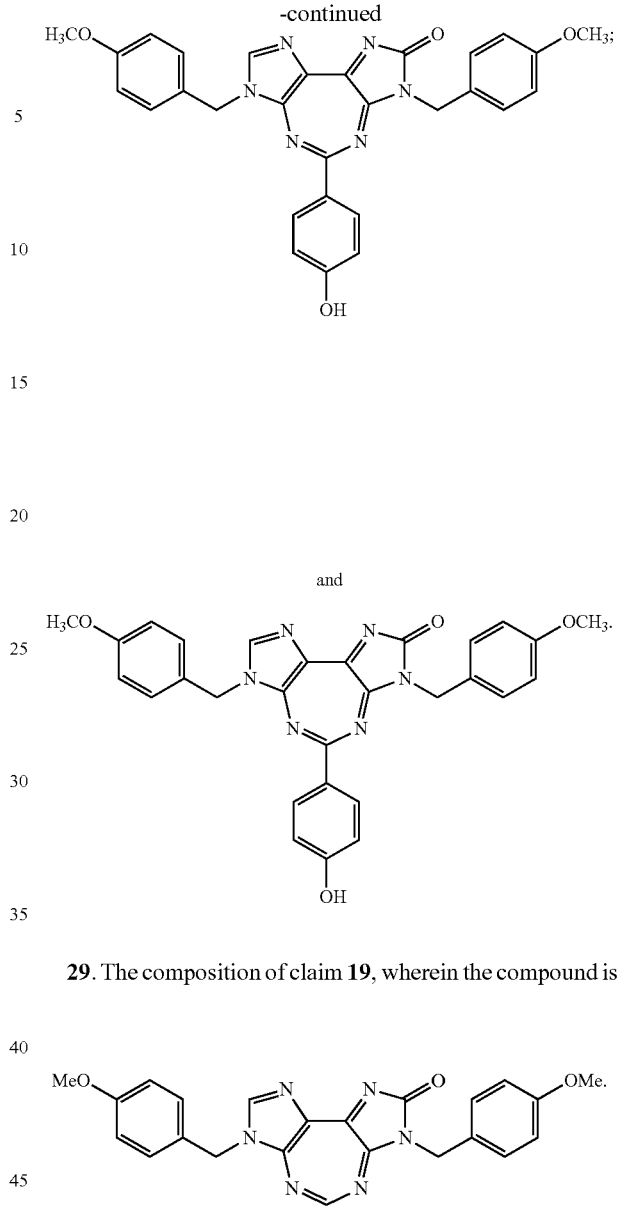

29. The composition of claim 19, wherein the compound is

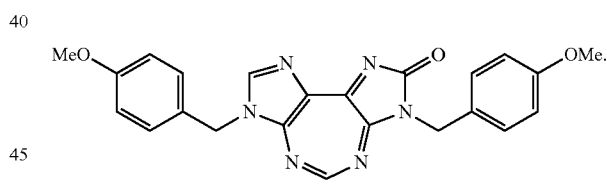

30. The method of claim 20, wherein at least one of R, R', and R" is a substituted benzyl.

31. The method of claim 20, wherein R and R' are each a substituted benzyl.

32. The method of claim 20, wherein at least one of R and R' is cyclic or acyclic alkyl; aryl; heteroalkyl; or heteroaryl, wherein the cyclic or acyclic alkyl, aryl, heteroalkyl or heteroaryl is optionally substituted.

33. The method of claim 20, wherein R" is hydrogen, R is a substituted benzyl, and R' is a substituted benzyl.

34. The method of claim 20, wherein R" is hydrogen, R is p-methoxybenzyl, and R' is p-methoxy-benzyl.

35. The method of claim 20, wherein R is hydrogen, R' is 3-(p-methoxybenzyl) and R" is 9(b)-(p-methoxy-phenyl) and Q is oxygen.

36. The composition of claim 19, wherein the compound is selected from the group consisting of
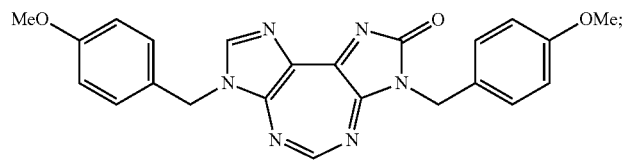 [SMILES: COc1ccc(Cn2c3ncnc4c(ncn4Cc4ccc(OC)cc4)c-3nc2=O)cc1]
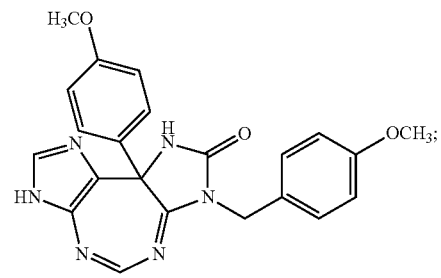
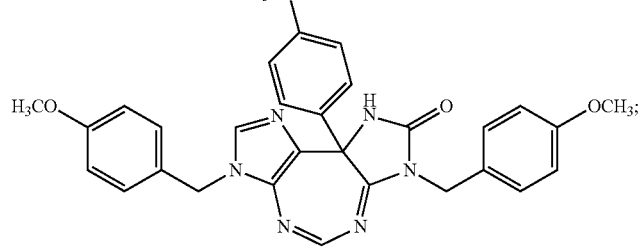
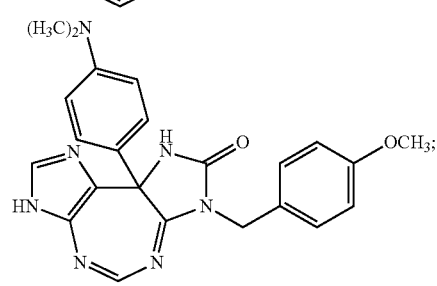
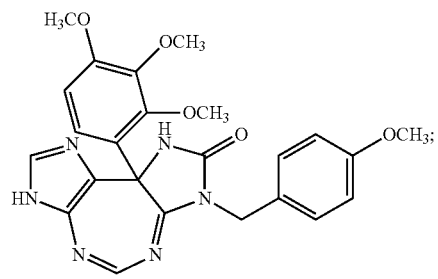
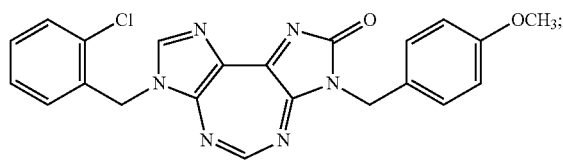
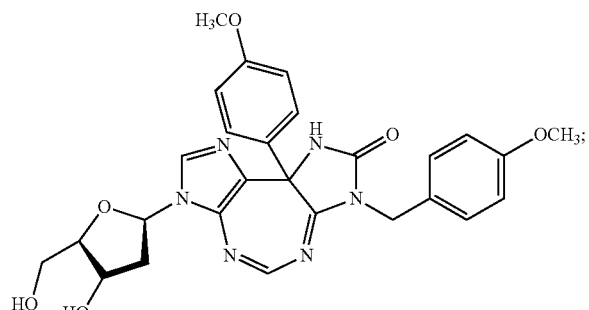
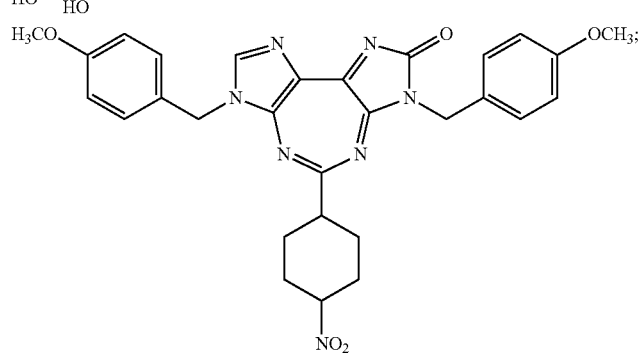

113 114
-continued
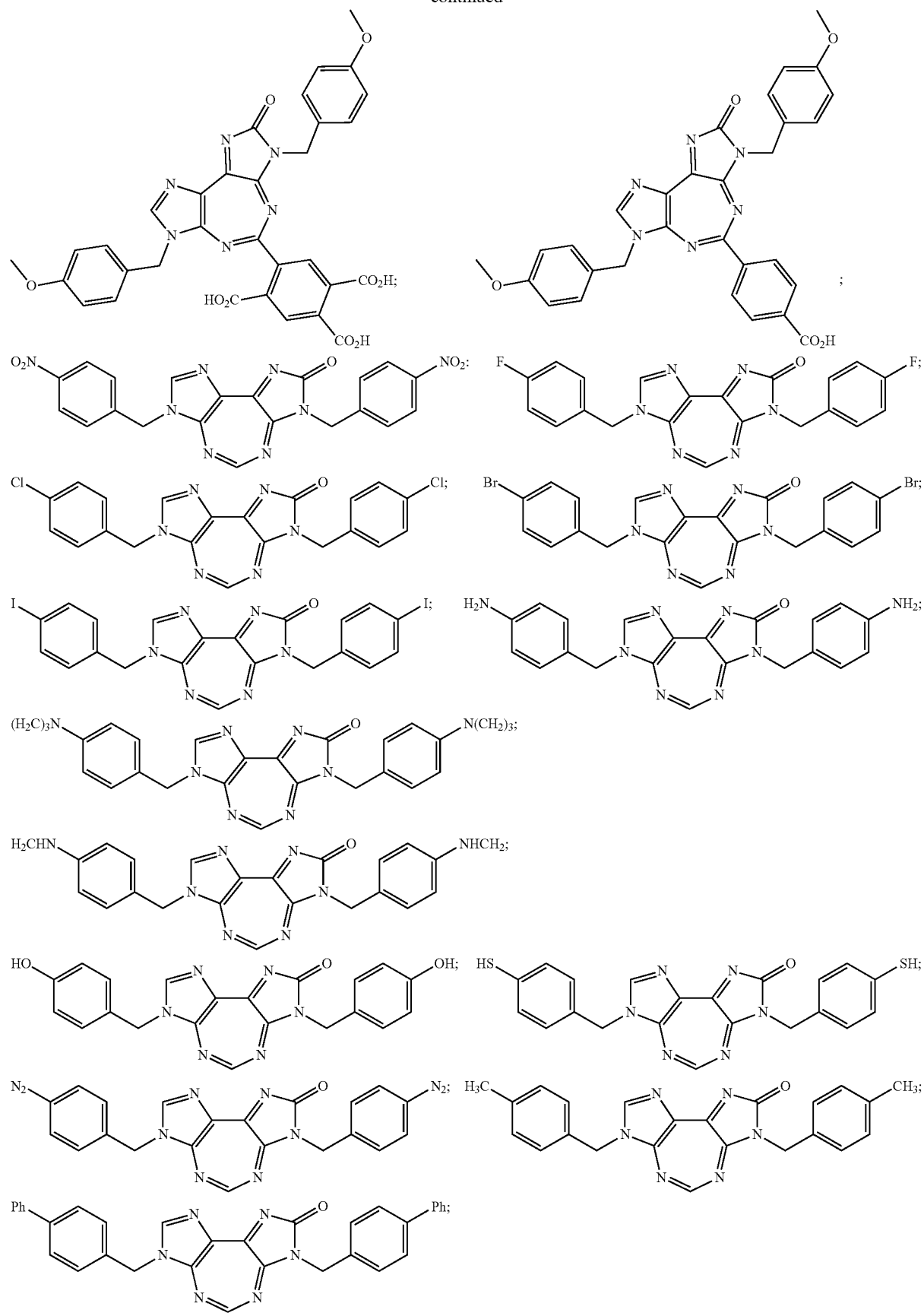

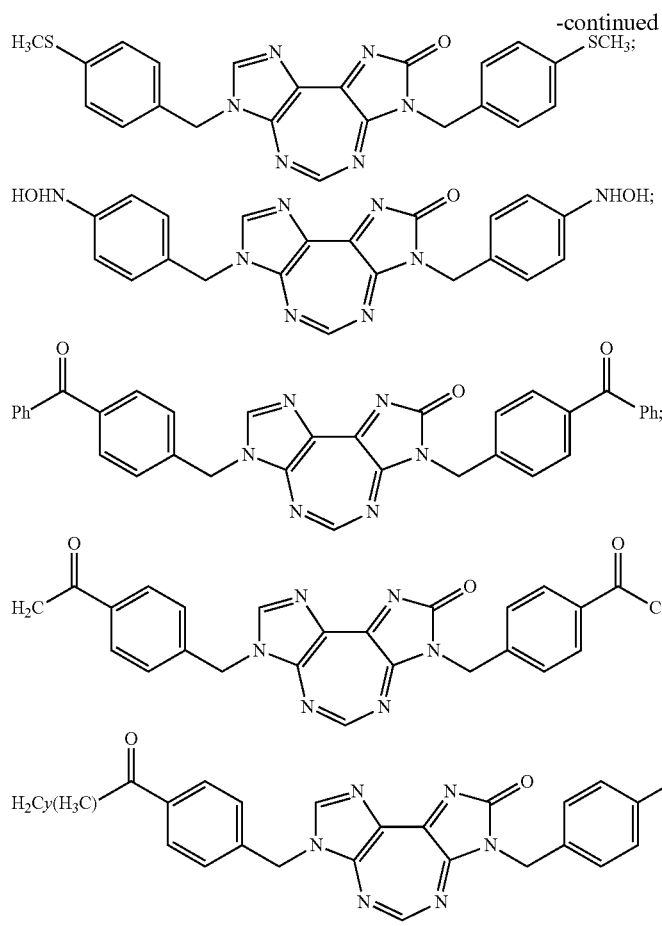
wherein x and y are integers from 1-17;
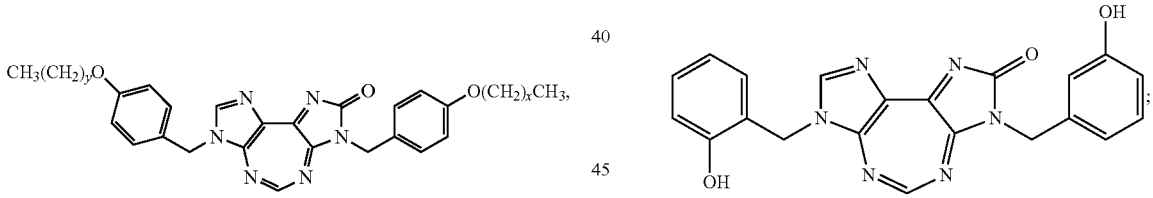
wherein x and y are integers from 1-10;
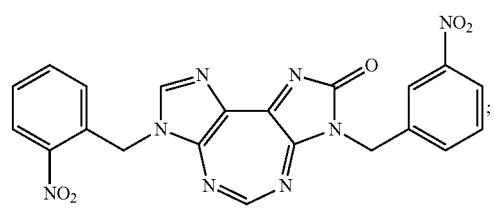
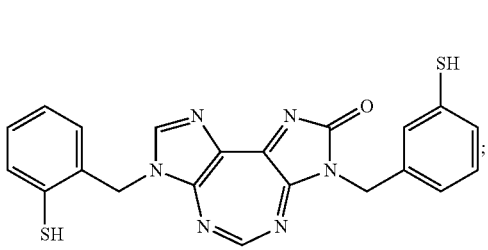
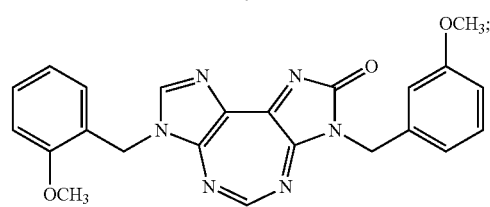
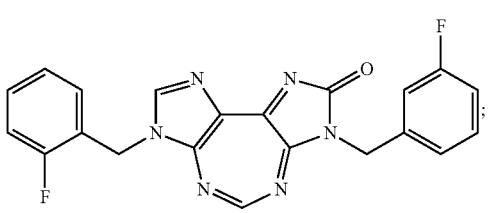

117
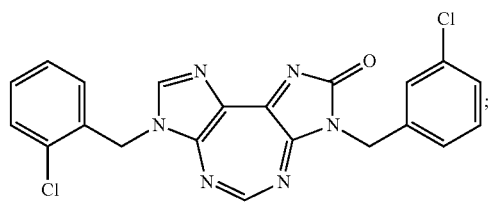
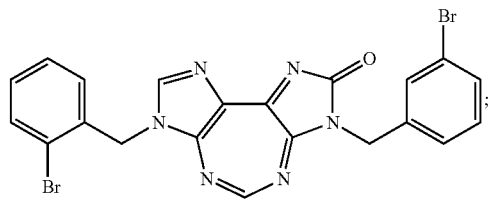
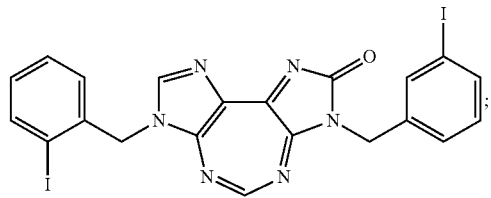
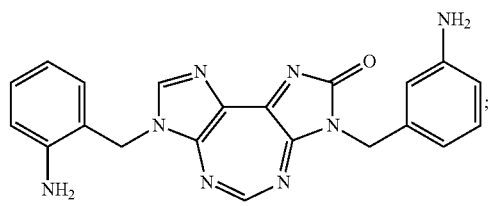
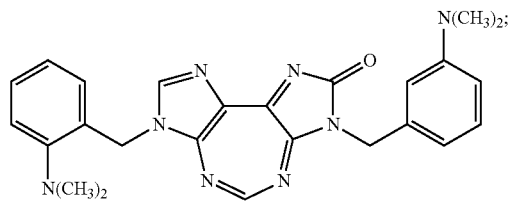
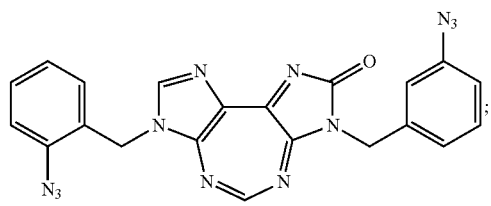
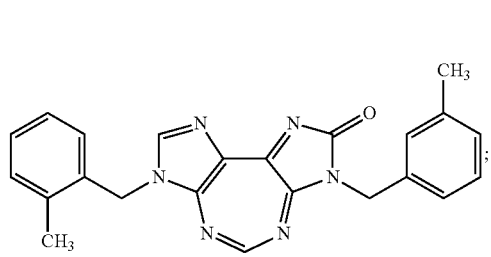
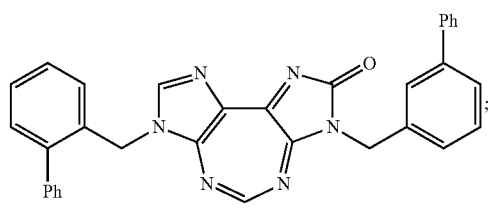
118
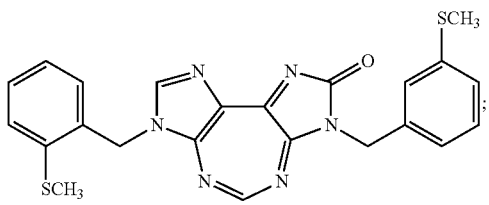
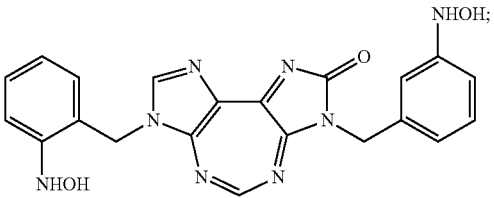
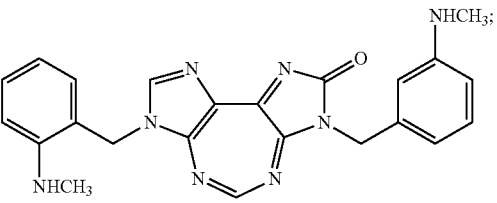
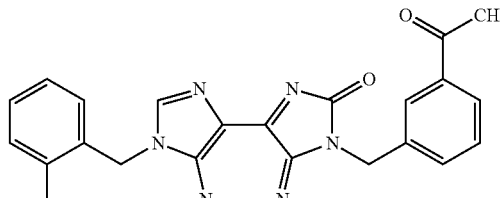
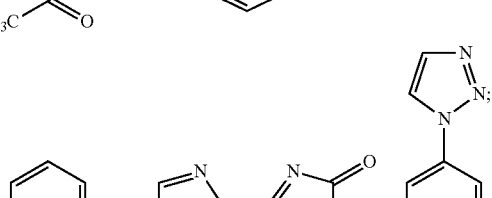
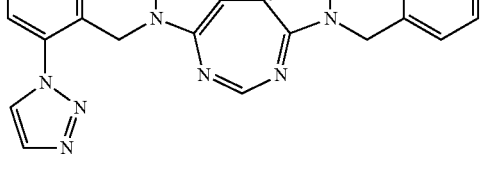
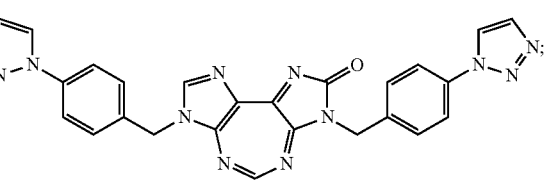
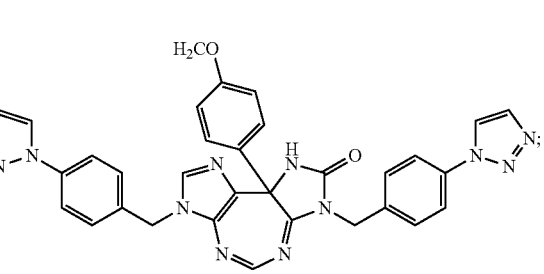

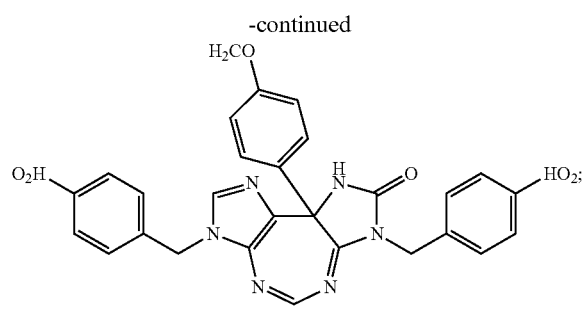
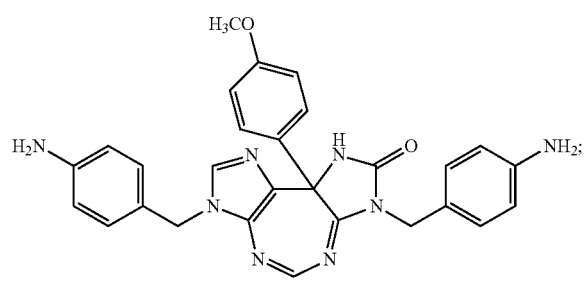
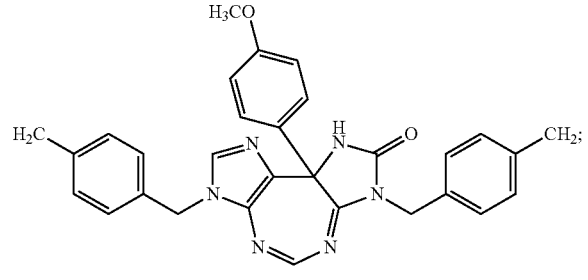
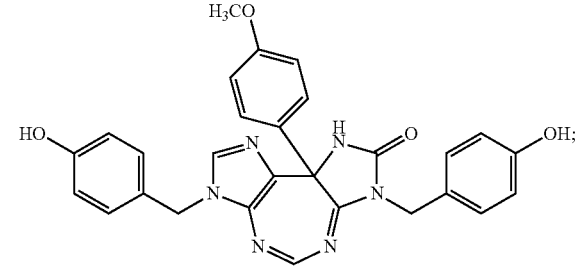
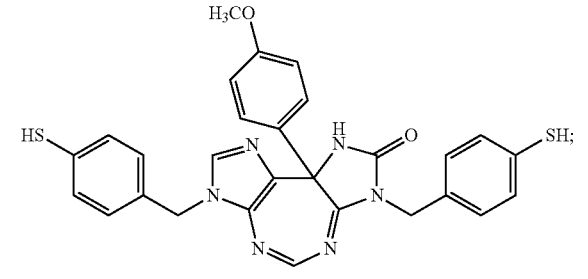
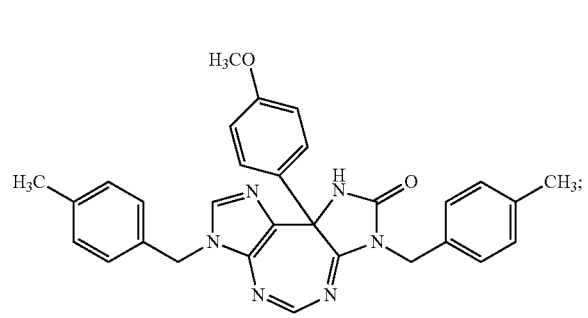
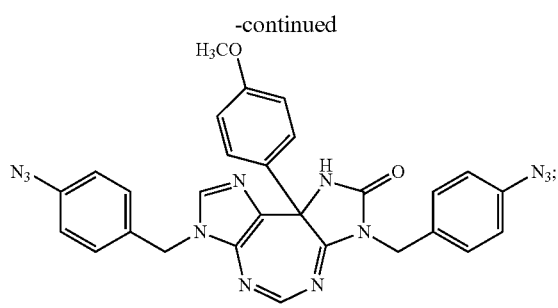
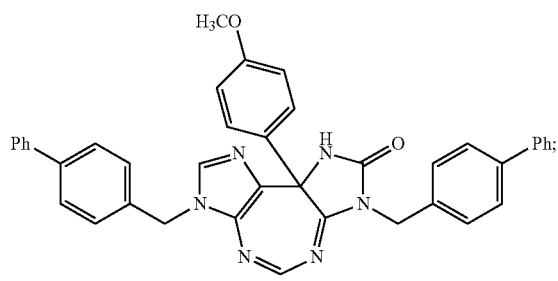
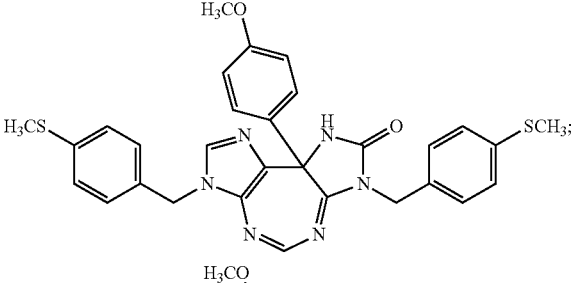
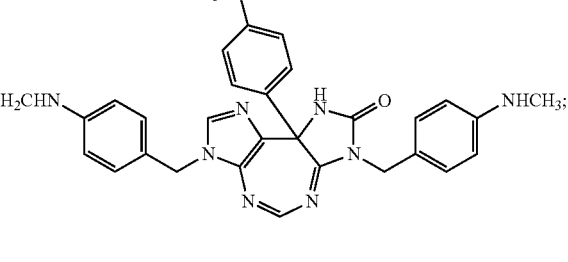
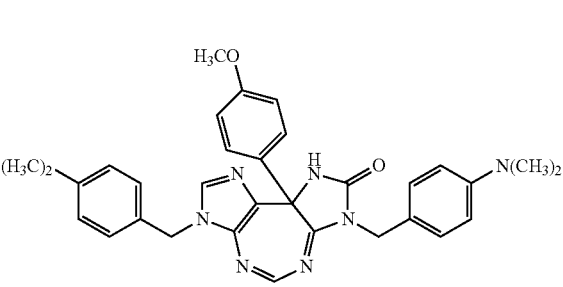
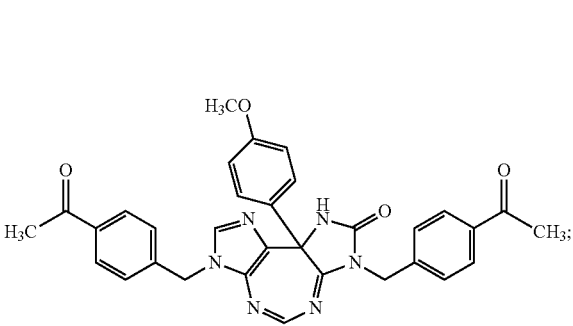

121
-continued
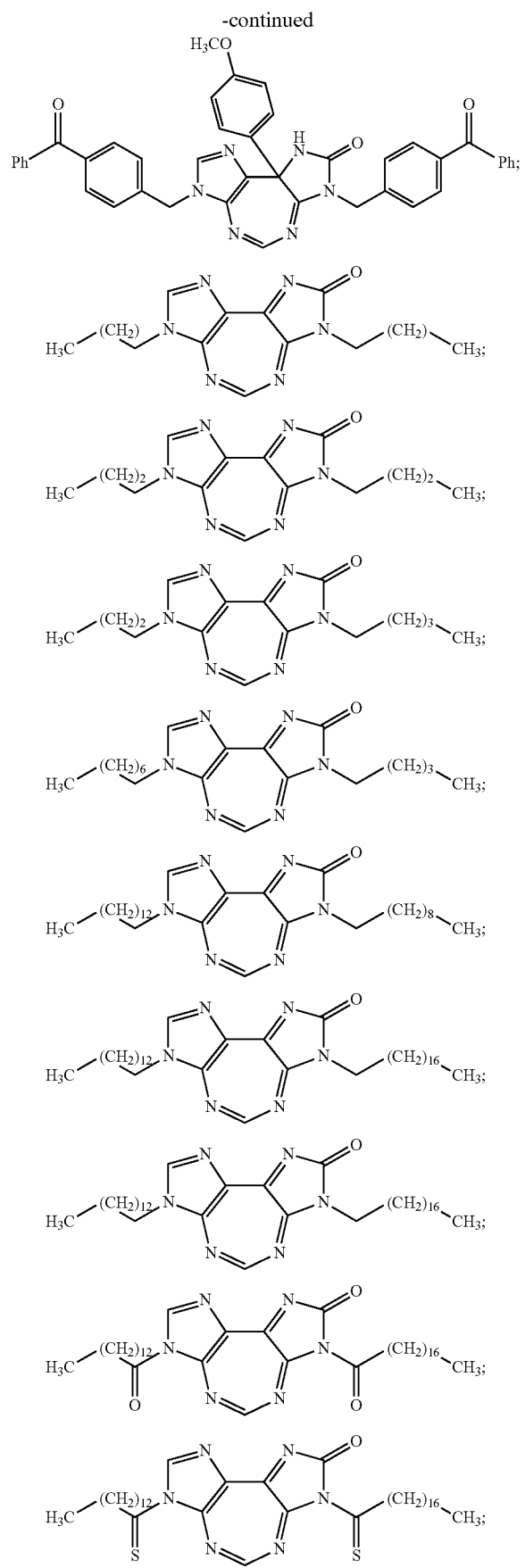
122
-continued
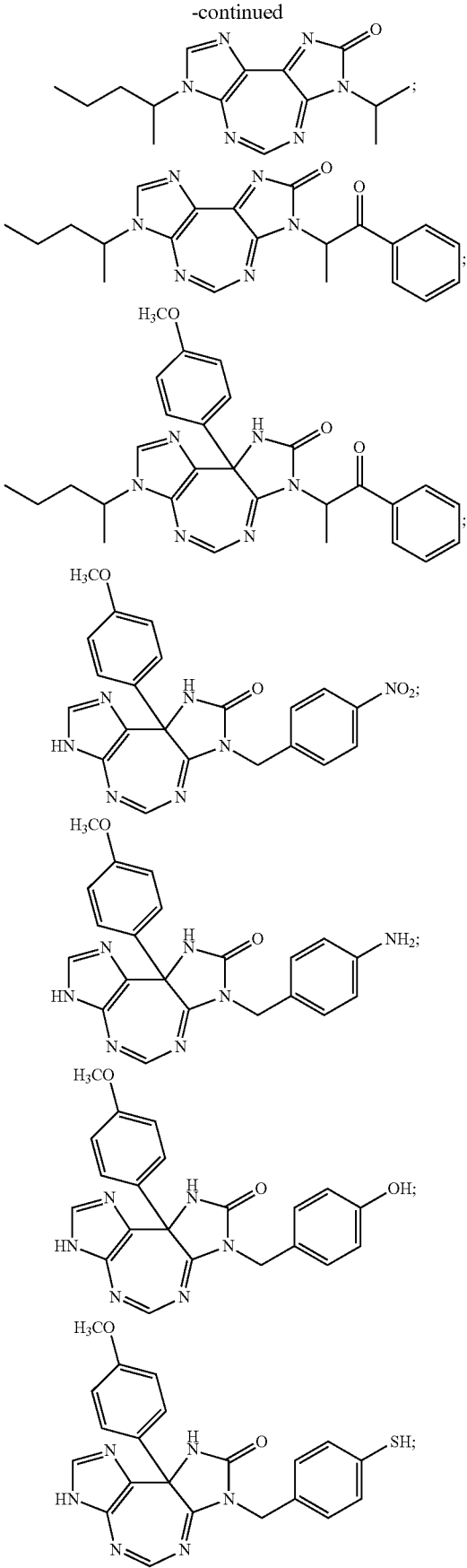

123
-continued
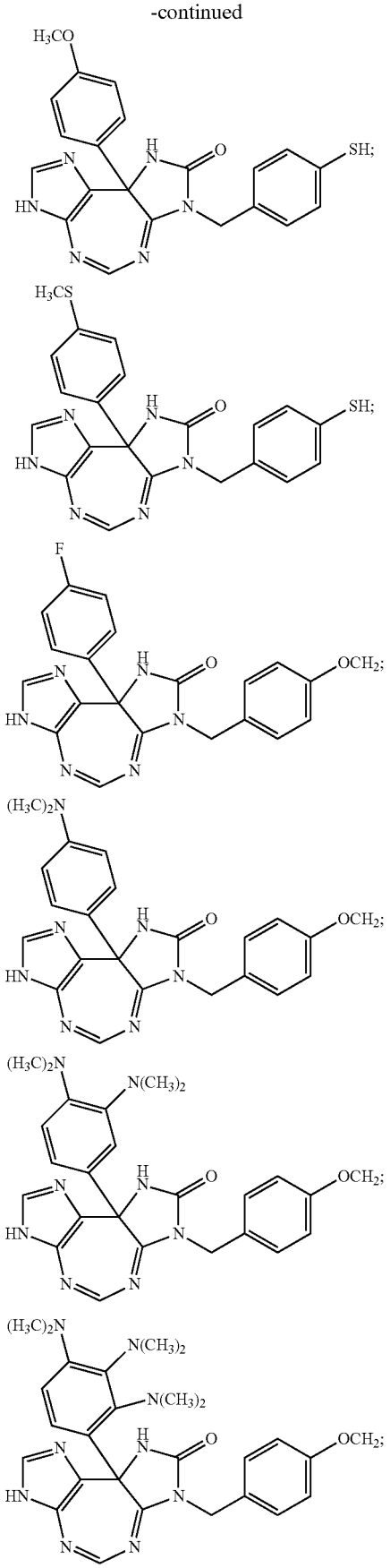
124
-continued
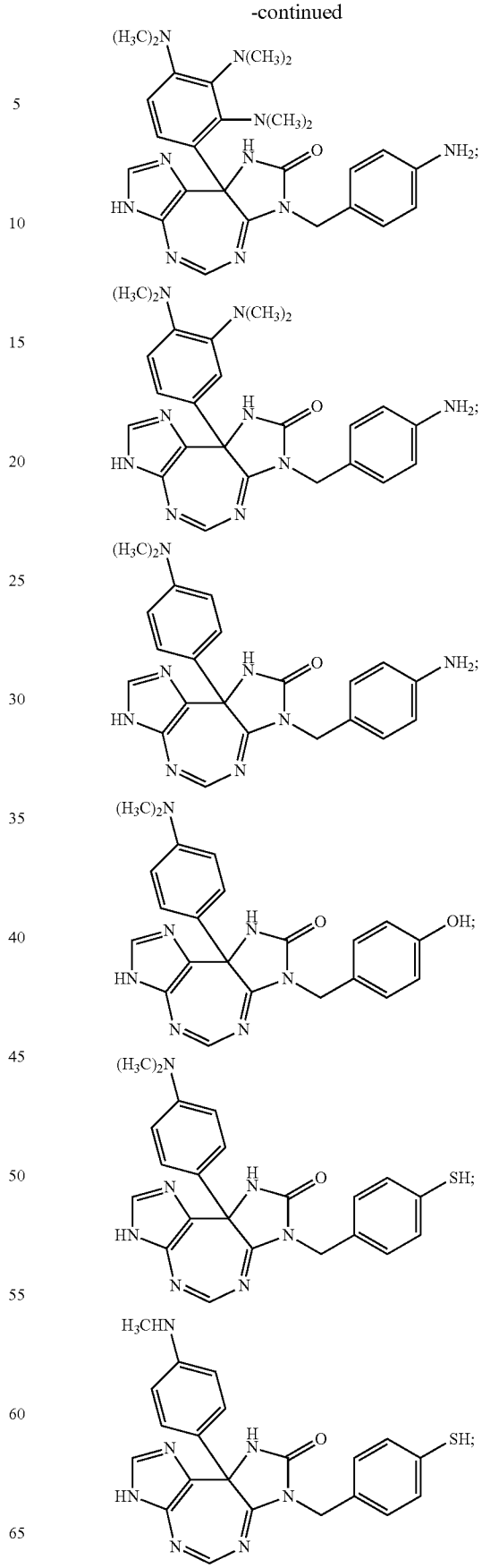

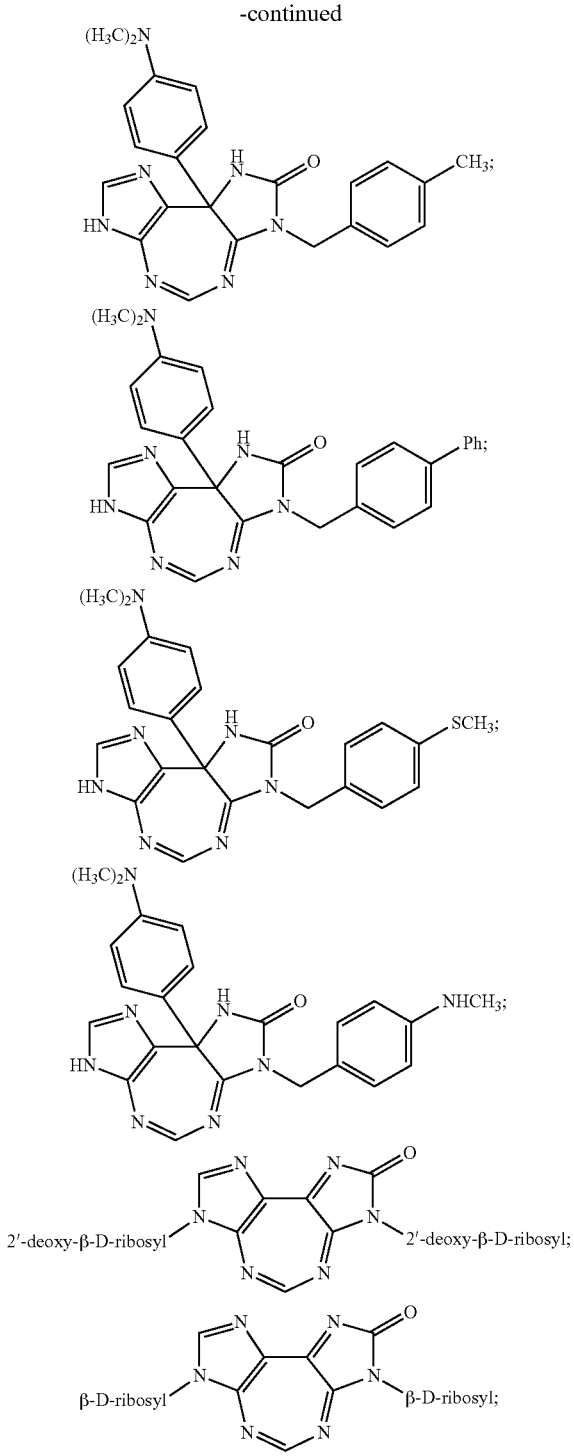
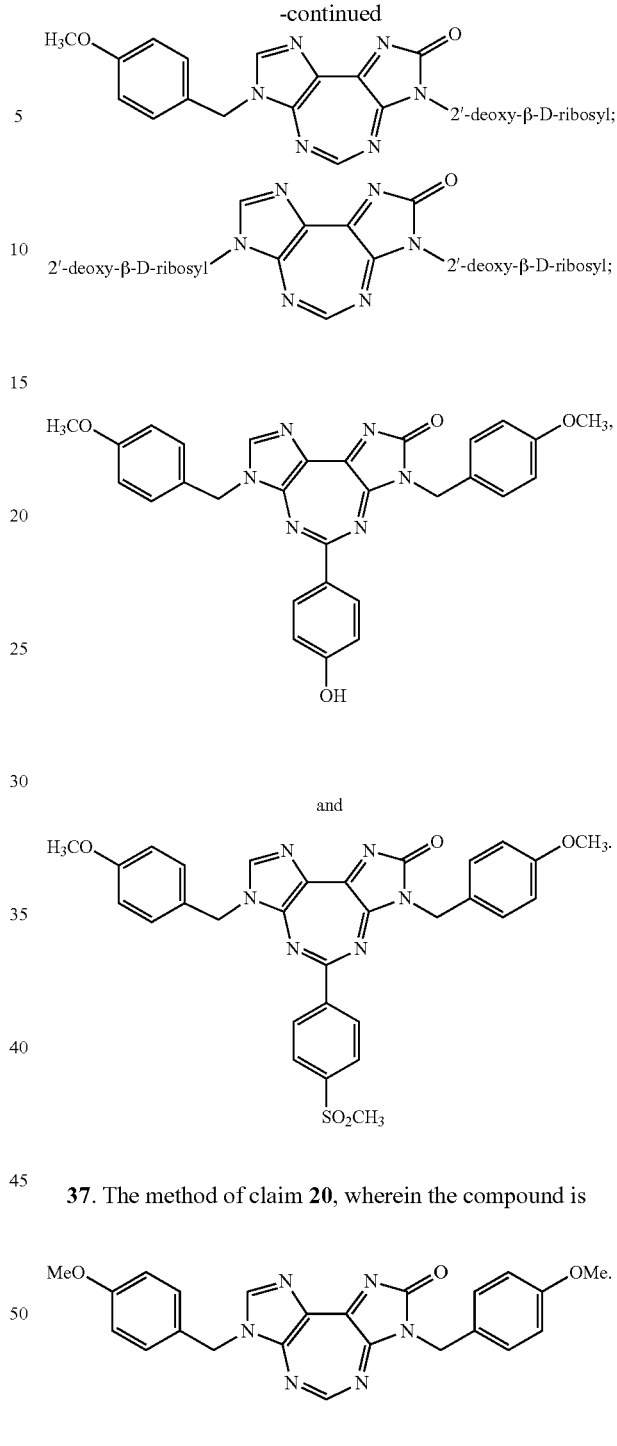
37. The method of claim 20, wherein the compound is
* * * * *